United States Patent
Ryazanov

(10) Patent No.: US 7,087,427 B2
(45) Date of Patent: Aug. 8, 2006

(54) MAMMALIAN ALPHA-KINASE PROTEINS, NUCLEIC ACIDS AND DIAGNOSTIC AND THERAPEUTIC USES THEREOF

(75) Inventor: Alexey Ryazanov, Princeton, NJ (US)

(73) Assignee: University of Medicine & Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/832,292

(22) Filed: Apr. 10, 2001

(65) Prior Publication Data

US 2002/0177205 A1    Nov. 28, 2002

Related U.S. Application Data

(63) Continuation-in-part of application No. 09/632,131, filed on Aug. 3, 2000.

(51) Int. Cl.
*C12N 15/85* (2006.01)
*C07H 21/04* (2006.01)

(52) U.S. Cl. .................. 435/325; 435/194; 435/183; 435/320.1; 435/252.3; 536/23.1; 536/23.2; 536/23.7; 530/350

(58) Field of Classification Search ................ 435/194, 435/183, 320.1, 252.3; 536/23.1, 23.2, 23.7; 530/350
See application file for complete search history.

(56) References Cited

FOREIGN PATENT DOCUMENTS

WO    WO 00/40614    *    7/2000

* cited by examiner

*Primary Examiner*—Richard Hutson
(74) *Attorney, Agent, or Firm*—Klauber & Jackson

(57) ABSTRACT

The present invention provides novel mammalian alpha-kinase proteins: melanoma alpha-kinase (MK), heart alpha-kinase (HK), kidney alpha-kinase (KK), skeletal muscle alpha-kinase (SK), and lymphocyte alpha-kinase (LK). In particular, a novel kinase type is herein provided, characterized by the presence of an alpha-kinase catalytic domain and an ion channel domain. Isolated nucleic acids of the alpha-kinases MK, HK, KK, SK and LK are provided. Methods for making the novel alpha-kinases, cells that express the alpha-kinases and methods for treating an animal in need of either increased or decreased activity of the alpha-kinases are provided.

7 Claims, 34 Drawing Sheets

```
                                 I
human EF2K   122  GEWLDDEVLIKMASQPFGRGAMRECFRTKKLSNFLHAQ----------------------QWKGASNYVAKRYIEPVD
C. e. EF2K   108  KQWTEDIVDVRLHPDSFARGAMRECYRLKKCSKHGTSQ----------------------DW--SSNYVAKRYICQVD
MHCK A       570  NKWIRLSMKLKVERKPFAEGALREAYHTVSLGVGTDENYPLGTTTKLFPPIEMISPISKNNEAMTQLKNGTKFVLKLYKKEAE
MHCK B       130  AQWTCTATLVKVEPVPFAEGAFRKAYHTLDLSKSGA-------------------------------SGRYVSKIGKK--
FC-AN09        1  IVCVSIEKTPFAKGSCRTAHKLKDWSQP--------------------------------------DQGLVGKFSTNKK-
consensus         **w**o*o**FGRo*****************************************oV*K*******

III                              IV
human EF2K   178  ----RDVYFEDVRLQMEAKLWGEEYNRHKPPKQVDIMQMCIIELKDR----PGKPLF-HLEHYIEGKYIKYNSNSGFVRDDNI
C. e. EF2K   162  ----RRVLFDDVRLQMDAKLWAEEYNRYNPPRKIDIVQMCVIEMIDV----KGSPLY-HLEHFIEGKYIKYNSNSGFVSNAA-
MHCK A       653  QQASRELYFEDVKMQMVCRDWGNKFNQKKPPKKIEFLMSWVVELIDRSPSSNGQPILCSIEPLLVGEFKKNNSNYGAVLTN--
MHCK B       177  -PTPRPSYFEDVKMQMIAKKWADKYNSFKPPKKIEFLQSCVLEFVDRTSSD----LICGAEPYVEGQYRKYNNNSGFVSNDE-
FC-AN09       42  --TTRDSYFTDVLMQTFCAKWAEKFNEAKPPKPITFLPSYVYELTDHPPPY---PV-CGGEPFTEGDYKKHNNNSGYVSSDA-
consensus         ****R**oF*DV*oQ*****W*****oN***PPK*o*oo****ooEo*D*******E*oo*G*o*K*N*N*G*V******

V                                                     VI
human EF2K   252  RLTPQAFSHFTFERSGHQLIVDIQGVGDLYTDPQIHTETGTDFGDGNLGVRGMALFFYSHACNRICESMGLAPFDLSPRERD
C. e. EF2K   235  RLTPQAFSHFTFERSGHQMMVDIQGVGDLYTDPQIHTVVGTDYGDGNLGTRGMALFFHSHRCNDICETMDLSNFELSPPELE
MHCK A       734  RSTPQAFSHFTYELSNKQMIVDIQGVDDLYTDPQIHTPDGKGFGLGNLGKAGINKFITTHKCNAVCALLDL-DVKLG----
MHCK B       254  RNTPQSFSHFTYEHSNHIQLLIDIQGVGDHYTDPQIHTYDGVGFGIGNLGQKGFEKFLDTHKCNAICQYINLQSIN-----
FC-AN09      118  RNTPQSFSHFSYELSNHELLIVDIQGVNDFYTDPQIHTKSGEGFGENLGETGFHKFLQTHKCNPVCDFLKLKPIN------
consensus         R*TPQ*FSHF*oE*S****ooooDIQGV*DoYTDPQIHTGoG*GNLG**Go*Fo**H*CN*oC**o*Lo*****

VII
human EF2K   335  AVNQNTKLLQSAKT--ILRGTEEKCGS
C. e. EF2K   318  ATEVAMEVAAKQKKSCIVPPTVFEARR
MHCK A       811  ---GVLSGNNKKQ-LQQGTMVMPDI
MHCK B       330  ------PKSEKSDC---GTVPRPDL
FC-AN09      194  ------QSKKA--LLRGTLPVVQL
consensus         *******K*****T*********
```

```
human eEF-2K   257  AFSHFTFERSGHQMVVDIQGVGDLYTDPQIHTVVGTDYGDNLGTRGMA          306
C.elegans eEF-2K 240 AFSHFTFERSGHQLIVVDIQGVGDLYTDPQIHTEKGTDFGDNLGVRGMA          289
mouse eEF-2K   256  AFSHFTFERSGHQMVVDIQGVGDLYTDPQIHTVVGTDYGDNLGTRGMA          305
MHCK A         739  AFSHFTYELSNKQMIVVDIQGVDDLYTDPQIHTPDGKGFGLGNLLGKAGIN        788

E.........A.......R..N.K..T........
human eEF-2K   307  LFEHSHRCNDICETMDLSNFELSPPEIEATEVAMEVAAKQKKSCIVPPTV         354
C.elegans eEF-2K 290 LFEYSHACNRICQSMGLTPFDLSPREQDAVNQSTRLLQSAKT--ILRGTE        339
mouse eEF-2K   306  LFEHSHRCNDICETMDLSNFELSPPEIEATEVAMEVAAKQKKSCIVPPTV         353
MHCK A         789  KFITHKCNAVCALLDL                                          805

V..G......---........-RP...........
human eEF-2K   355  FEARRNRISSECVHVEHGISMDQLRKKTL---NQSTDLSAKSHNEDCV          400
C.elegans eEF-2K 340 EKCGSPRIRTLSSS---RPPLL--LRLSENSGDENMSDVTFDSLPSSSA         386
mouse eEF-2K   354  FEARRNRISSECVHVEHGISMDQLRKKTL---NQSTDLSAKSHNEDCV          399

.S.....AS...HL...E........G....
human eEF-2K   401  CPECIPVVEQTCEPCSEDEEEDYPRSEKSGNSQKSRRSMSISTRSS            449
C.elegans eEF-2K 387 TPHSQKLDH-LHWPVFGDLDNMGPRDHDRMDNHRDSENSGDSGYPSEKRS        436
mouse eEF-2K   400  CPECIPVVEQTCEPCSEDEEEDYPRSEKSGNSQKSRRSMSISTRSS            448

-E.............---..--YS.-KY............-..K...S..
human eEF-2K   450  GDESASRPRKCGFVDLNSLRQRHDSFRSSVGTYSMNSSRQTRDTEKDEFW        494
C.elegans eEF-2K 437 -DLDDEPPREHG--HSNGNR-RHESDEDSLGS-SGRVCVETWNLNPSRL         486
mouse eEF-2K   449  GDESASRPRKCGFVDLNSLRQRHDSFRSSVGTYSMNSSRQTRDTEKDEFW        493

....A.........EK...........................I.
human eEF-2K   495  KVLRKQSVPANILSLQLQQMAANLENDEDVPQVTGHQFSVLGQIHDLSR         532
C.elegans eEF-2K 487 HLPRPSAVALEVQRLNALDLGRKIGK                                536
mouse eEF-2K   494  SVLGKVHLAMVR                                              531
```

Figure 2B

```
human eEF-2K    533 .........YHELGRFVEVDSEHKEMLEGSENDARVPIKYDKQSAIFHLDIARKCGILE 565
C.elegans eEF-2K 537 ..G......YHEGGRFCEKDEE------------------WDRESAIFHLEHAADLGELE 586
mouse eEF-2K    532 ---------------------------------------------------------- 564 human eEF-2K    566 AVLTSAHIVLGLPHELLKEVTVDDLFPNGFGEQENGIRADKGQKPCDLEE 596
C.elegans eEF-2K 587 AIVGLGLMYSQLPHHILADVSLKE---TEENKTK--------------- 636
mouse eEF-2K    565 ---------------------------------------------------------- 595 human eEF-2K    597 ...Q....S.Q.....L........FCSDLMEIAAEMGDKGAMLYMAHAYETGQHLGPNRTDYKKSIDWYQRVV 645
C.elegans eEF-2K 637 GFDYLLKAAEAGDRHSMIVARAFDTGLNILSPDRCQDWSEALHWYNTAL 686
mouse eEF-2K    596 ---------------------------------------------------------- 644 human eEF-2K    646 ------M........M..R.MM...F..Y..E.D..GFQEEELDSDCKTTESSFAPLTRHEILAKAEMYKEGGYGLNQDFERA 689
C.elegans eEF-2K 687 ----ETTDCDEG-GEYDGIQDEPQYALLAREAEMLLTGGFGIDKNPQRS 736
mouse eEF-2K    645 ---------------------------------------------------------- 688 human eEF-2K    690 ...........Q......YGLFNEAAEAAMEAAMNGKLANKYYEKAEMC----GE 725
C.elegans eEF-2K 737 GDLYTQAAEAAMEAAMKGRLANQYYEKAEFAWAQMEE 768
mouse eEF-2K    689 --------------------------------------- 724
```

Figure 2C

```
H. EF-2K       124 WLDDEVLIKMASQPFGRGAMRECFRTKKLSNFLHAQ----------------------QWKGASNYAKRYIEPVD-----
C.e. EF-2K     110 WTEDIVDVRLHPDSFARGAMRECYRLKKCSKHGTSQ----------------------DW--SSNYVAKRYICQVD-----
MHCK A         572 WIRLSMKLKVERKPFAEGALREAYHTVSLGVGTDENVPLGTTTKLFPPIEMISPISKNEAMTQLKNGTKFVLKLYKKEAE--
MHCK B         132 WTCATLVKVEPVPFAEGAFRKAYHTLDLSKSGA------------------------------SGRFVSKIGKK------
MhkC            48 WTHSIVCVSIEKTPFAKGSCRTAHKLKDWS------------------------------QPDQQLVGKFSTNKK-----
Heart K        189 GDHLRGQISTEELHFGEGVHRKAFRSKVMQGLM----------------------PVFOPGHACVLKVHNAVAHGTRNNDEL
Melanoma K      58 QLGLCAKIEFLSKEEMGGGLRRAVKVLCTWSEH----------------------DILKSGHLYIIKSFLPEVINTWSSIYR
Ch 4 K        1027 AQETIVYLGDYLITVKKKGRQRNAFWVHHLHQEEIL---------------------------GRYVGKDYKEQ--------
Consensus          ********o*o****F**g*oR*Ao****o*******************************o*F*o*********
                                          I                                                          II H. EF-2K       178 ----RVVYF EDVRLQMEAKLWGEKNR-----HKPPKQVDIMQMCIELKDR-----PGKPLP-HLEHYIEGKYIKYNSNSGFVRDNI--
C.e. EF-2K     162 ----RRVLF DDVRLQMDAKLWAEENR-----YNPPKKIDIVQMCVIRMIDV----KGSPLY-HLEHFIEGKYIKYNSNSGFVSNAA--
MHCK A         653 QQASRELYF EDVRKMQMVCRDMGNKPNQ----KFPKKIEFLMSWVVELIDRSPSSNGQPFLCSIEPLLVGEFVKKNNSNYGAVLTN--
MHCK B         177 -PTPRPSYF EDVRKMQMIAKKWADKYNS----FKPPKKIEFLQSCVLRFVDRTSSD---LICGAEPYVESQYRKYNNSGFVSNDE--
MhkC            89 --TTRDSYF TDVLMQTFCAKWAERKFNE---AKPPKPITFLPSYVVELIDHPPFY--PV-CGGEPFIEGDYKKHNNSGYVSSDA---
Heart K        249 VQRNYKLAAQECYVQNTARYYAKIYAA-----EAQPLEGFGEVPEIIPIFLIHRPENNIPY-ATVBEELIGEFVRYSIRDGKEINFLRRDSE
Melanoma K     118 EDTVLHLCLREIQQQRAAQKLTFAPNQ----MKP-KSIPYSP-RFLEVFLLYCHSAGQ-WFA-VBECMTGEFRRYNNNNGDEIIPTNTL--
Ch 4 K        1073 -KGLMHHFTDVEROMTAQHYVTEFNKRLYEQNIPTOIFYIPSTILLILEDKTI--KGC-I--SVEPYILGEFVKLSNNTKVVKTEYK---
Consensus          *******oOF*DV*oQ*A*oN*******PPK*Io*oEoQ***oEoo*G*o*KOH*N*g*v********
                                          III                                             IV                       V H. EF-2K       252 -RLTPQAFSHFTEERSGHQLIVDIQGVGD-----LYTDPQIHTET-----GTDEFGDSNLGVRGMALFFY-SH-ACHRICESMGLAPF
C.e. EF-2K     235 -RSTPQAFSHFTEFRSGHQMKAVVDIQGVGD----LYTDPQINTVV-----GTDYGDKSNLGTRGMALFFH-SH-RCRNDICETMELSNF
MHCK A         734 -RNTPQSFBHFTYEHSNHQLLIDIQGVGD-----LYTDPQIHTPD----GKGFGLGNLGKAGINKFIT-TH-KCNAVCALLDL-DV
MHCK B         254 -RNTPQSFSHFSYELSNHELLIVPIQGVND-----HYTOPQIHTVD----GVGFGIGNLGQKGFEKPLD-TH-KCNAICQYINLQSI
MhkC           165 AGQKCCTFQMWVYQKTSGCLIVTDMQGVGM----FYTDPQIHTKS----GEGFGEGNLGETGFHKFLQ-TH-KCNPVCDFLKIKPI
Heart K        335 ATEYGLAYGHPSVEFSNHRDVVDLQGWTGNGKGLLYLTUPQIHSVD----KLTDVGIATLAR--GYKGF-KGNCSMTFIDQFRA-LH-OGRKYCKMLGLKSL
Melanoma K     199                                                               NLTDPSVIKAEEKRSCDMVFGPANLGEDAIKNFRA-KH-HCNSCCRKKJKLPDL
Ch 4 K        1153                                                               QKVF-TUNFGKRGIFYFFNNGHVECMEICHRLSLTRP
Consensus          ********FSHF*YE*S**oOVoDCoQGv**ooTDPQIHT*******FG*GNLG**Go*FoHCN*oCH*L**o
                                          VI                                   VII                     VIII
```

Figure 4

```
   1 cgggcgcggg cgcgtccctc tggccagtca cccggcggag ctggtcgcac aattatgaaa
  61 gactcgactt ctgctgctag cgctggagct gagttagttc tgagaaggtt tcccggggct
 121 gtccttgttc ggtggcccgt gccaccgcct ccggagacgc tttccgatag gtggctgcag
 181 gccgcggagg tggaggagga gccgctgccc ttccggagtc cgccccgtga ggagaatgtc
 241 ccagaaatcc tggatagaga gcactttgac caagagggag tgtgtatata ttataccaag
 301 ctccaaagac cctcacagat gtcttccagg atgtcagatt tgtcagcaac ttgtcagatg
 361 tttctgtggt cgtttggtca agcaacatgc atgctttact gcaagtcttg ccatgaaata
 421 ctcagatgtg agattgggtg aacactttaa ccaggcaata gaagaatggt ctgtggaaaa
 481 gcacacggag cagagcccaa cagatgctta tggagtcatc aatttcaag ggggttctca
 541 ttcctacaga gctaagtatg tgagactatc atatgatacc aaacctgaaa tcattctgca
 601 acttctgctt aaagaatggc aaatggagtt acccaaactt gttatttctg tacatggagg
 661 catgcagaag tttgaacttc atccaagaat caagcagttg cttggaaagg gtcttattaa
 721 agctgcagtt acaaccggag cttggatttt aactggagga gtcaatacag gtgtggcaaa
 781 acatgttggt gatgccctca agaacatgc ttccagatca tctcgaaaaa tttgcactat
 841 tggaatagct ccatgggag tgatagaaaa cagaaatgat cttgttggga gagatgtggt
 901 tgctccttat caaacccctat tgaatccctt gagcaaattg aatgttctga ataatctaca
 961 ctccatttc atcttggtgg atgatggcac tgttggaaag tatgggcag aagtcagact
1021 gagaagagaa cttgaaaaaa ccattaatca gcaaagaatt catgctagaa ttgggcaagg
1081 agttcctgtg gtggctttga tatttgaagg cgggccaaat gtcatcctta cagtactgga
1141 gtaccttcag gaaagccccc cagttccagt tgttgtgtgt gaagggacag gcagagctgc
1201 agatttacta gcctatatcc acaaacagac agaggaagga ggaaatcttc ctgatgcagc
1261 agagcctgat attatatcaa ctatcaagaa aacatttaac tttggccaga gtgaagcagt
1321 tcatttattt caaacaatga tggagtgtat gaaaaaaaaa gagcttatca ctgtttttca
1381 cattggatca gaggatcatc aagatataga tgtggccata ctcactgcac tgctgaaagg
1441 tactaatgca tctgcatttg accagcttat ccttacactg gcatgggaca gagttgatat
1501 tgccaaaaat catgtatttg tttatggaca acagtggctg gttggatcct ggaacaggc
1561 tatgcttgat gctcttgtaa tggacagagt ttcatttgta aacttctta ttgaaaacgg
1621 agtaagcatg cataaattcc ttaccattcc cagactggaa gaactttata acactaaaca
1681 aggtccaacc aatccaatgt tgttccatct cattcgggat gtcaagcagg gtaatctccc
1741 cccggggtac aagatcactt taattgatat aggacttgtg attgagtatc tcatgggagg
1801 aacctacaga tgcacataca cacgaaaacg ttttcgattg atatataata gtcttggtgg
1861 aaataaccgg aggtcaggtc gaaatacctc cagcagcacc cctcagttgc gaaagagtca
1921 tgaaactttt ggcaatagag ctgataaaaa ggaaaaaatg agacacaatc atttcattaa
1981 aacagcccaa ccctacagac caaagatgga tgcatctatg gaagaaggaa agaagaaaag
2041 aaccaaagat gaaattgtag atatagatga tccagagacc aagcgctttc cttatcctct
2101 taatgaatta ttaatttggg cttgccttat gaagaggcag gtcatggccc gcttttatg
2161 gcagcatggt gaagaatcaa tggctaaagc attagttgcc tgtaaaatct atcgttcaat
2221 ggcttatgag gcaaagcaga gtgacctggt agatgatact tcagaggaac tgaagcagta
2281 ttccaatgat tttggccaac tggcagttga attactggaa cagtccttca gacaggatga
2341 aacgatggct atgaaattac tcacttatga actcaaaaac tggagtaatt caacctgcct
2401 caagttagca gtttcttcaa gacttagacc ttttgtagct cacacttgta cagatgtt
2461 gttatctgat atgtggatgg gacggctgaa tatgagaaaa aattcctggt ataaggtcat
2521 attaagcatt ttagttccac ctgccatatt aatgctagag tataaaacca aggctgaaat
2581 gtcccatatc ccacaatctc aagatgctca tcaaatgacg atggaggata gtgaaaacaa
2641 ttttcacaac ataacagaag agatacccat ggaagtattt aagaagtaa agatttgga
2701 cagcagtgat ggaagaatg aaatggagat acatattaaa tcaaaaaagc ttccaatcac
2761 acgaaaattt tatgcctttt atcatgcacc aattgtaaag ttctggttta acacattggc
2821 atatttagga tttctgatgc tttatacatt tgtagttctt gtaaaaatgg aacagttacc
2881 ttcagttcaa gaatggattg ttatcgctta tattttacc tatgctattg aaaaagtccg
```

Figure 5A

```
2941 tgaggtcttc atgtctgaag ctgggaaaat cagccagaag attaaagtat ggtttagtga
3001 ctacttcaat gtcagtgaca caattgccat catttctttc tttgttggat ttggactaag
3061 atttggagca aaatggaact atattaatgc atatgataat catgttttg tggctggaag
3121 attaatttac tgtcttaata taatattttg gtatgtgcgt ttgctagact ttctagccgt
3181 aaatcaacag gcaggacctt atgtaatgat gattggaaaa atggtggcca atatgttcta
3241 cattgtagtg ataatggctc ttgtattgct tagttttggt gttcccagaa aagcaatact
3301 ttatccacat gaagaaccat cttggtctct tgctaaagat atagttttc atccatactg
3361 gatgatttt ggtgaagttt atgcatatga aattgatgtg tgtgcaaatg actccactct
3421 cccgacaatc tgtggtcctg gaacttggtt gactccattt cttcaagcag tctacctctt
3481 tgtacagtat atcattatgg ttaatctcct tatcgcattt ttcaataatg tatatttaca
3541 agtgaaggca atttccaata ttgtatgaa gtatcagcgg tatcatttta ttatggctta
3601 tcatgaaaaa ccagtcctgc ctcctcctct tatcatcctc agccatatag tttcactgtt
3661 ttgctgtgta tgcaaaagaa gaaagaaaga taagacttcc gatgggccaa aactttctt
3721 aacagaagaa gatcaaaaga aactccatga ttttgaagag cagtgtgttg agatgtactt
3781 tgatgagaaa gatgacaaat tcaattctgg gagtgaagag agaatccggg tcacttttga
3841 aagagtggag cagatgagca ttcagattaa agaagttgga gatcgtgtca actacataaa
3901 aagatcatta cagtctttag attctcaaat tggtcatctg caagatctct cagccctaac
3961 agtagataca ttgaaaacac ttacagccca gaaagcttca gaagctagta aagtgcacaa
4021 tgagatcaca cgagaattga gtatttccaa acacttggct cagaatctta ttgatgatgt
4081 tcctgtaaga cctttgtgga agaaacctag tgctgtaaac acactgagtt cctctcttcc
4141 tcaaggtgat cgggaaagta ataatccttt tctttgtaat attttatga aagatgaaaa
4201 agacccccaa tataatctgt ttggacaaga tttgcccgtg atacccagaa gaaaagaatt
4261 caacattcca gaggctggtt cctcctgtgg tgccttattc ccaagtgctg tttctccccc
4321 agaattacga cagagacgac atggggtaga aatgttaaaa atatttaata aaaatcaaaa
4381 attaggcagt tcacctaata gttcaccaca tatgtcctcc ccaccaacca aattttctgt
4441 gagtacccca tcccagccaa gttgcaaaag ccacttggaa tccacaacca aagatcaaga
4501 acccattttc tataaagctg cagaagggga taacatagaa tttggagcat ttgtgggaca
4561 cagagatagt atggacttac agaggtttaa agaaacatca aacaaaataa gagaactgtt
4621 atctaatgat actcctgaaa acactctgaa acatgtgggt gctgctggat atagtgaatg
4681 ttgtaagact tctacttctc ttcactcagt gcaagcagaa agctgtagta gaagagcgtc
4741 gacggaagac tctccagaag tcgattctaa agcagctttg ttaccggatt ggttacgaga
4801 tagaccatca aacagagaaa tgccatctga aggaggaaca ttaaatggtc ttgcttctcc
4861 atttaagccc gttttggata caaattacta ttattcagct gtggaaagaa ataacctgat
4921 gaggttgtca cagagtattc ccttcgttcc tgtacctcca cgaggcgagc ctgtcacagt
4981 gtaccgtctg gaggagagtt ctcccagtat actgaataac agcatgtctt catggtctca
5041 gctaggcctc tgtgccaaaa ttgagttttt aagtaaagag gaaatgggag gtggtttacg
5101 aagagcagtc aaagtgctgt gtacctggtc agagcacgat atcctgaagt cagggcatct
5161 ctatatcatt aagtcatttc ttcctgaggt gataaacaca tggtcaagca tttataaaga
5221 agatacggtt ctacatctct gtctcagaga aatacaacaa cagagagcag cacaaaagct
5281 cacatttgcc tttaatcaga tgaaacccaa atccatacca tattctccaa ggttccttga
5341 agttttcctg ttgtactgcc attcagcagg gcagtggttt gctgtagaag agtgcatgac
5401 tggtgaattt agaaaataca acaacaataa tggtgatgaa atcattccta caaatactct
5461 agaagagatc atgctagcct ttagccactg gacctatgaa tataccagag gggagttact
5521 ggtacttgac ttacaaggag tgggagaaaa cttgactgac ccatctgtaa taaaagctga
5581 agaaaaaaga tcctgtgaca tggttttgg ccctgccaat ctaggagaag atgcaataaa
5641 aaacttcaga gccaaacatc actgtaattc ttgctgtcga aagcttaaac ttccagattt
5701 gaagaggaat gactacacgc ctgataaaat tatatttcct caggatgagt catcagattt
5761 gaatcttcaa tctggaaatt ccaccaaaga atcagaagca acaaattctg ttcgtctgat
5821 gttatagtgc tgagtcattg gttttgcct acacttcaca aaagtgtaac tgtcagtttt
```

Figure 5B

```
5881 cctttcgggg gaattgatga tataggaaga tgtgtgcaaa atgagcttgc tggccccaca
5941 catagtctag aggtaatgtt ctcattgaaa aacgcctgga ggctgcagat gacagctgga
6001 aagtgctagc tggcagagag tcagtgctct cggctggtga agggcgggaa ccttgctgct
6061 gagagtggtg gttctctcac ctggtgcagg accattaacc aaagtcaagt cttcagattt
6121 gattggctgc tcagtcacag ccattcagct aaggaaacta aattgcgcag cttttttaaat
6181 ggctgaagtc ttcctcagtt tgtgctctat gataatgatg ttagctctca actaggtgtt
6241 tgtggccacg ggagaactac tccttacaat tttgcttcac aggcatgtta caaagcctgc
6301 actgaaaacc gtttgtcttc cctctctccc tccctctttt ccctgtagta ttgaggatca
6361 aacccagggc ctcatgaaga ccattttcta agagacattt tatttaagaa tcaactatag
6421 agtctatgtt tatggataca gccagttttt gttaaacaaa acctgaattg tgcaaaaggg
6481 ttttttaaca tttatcaatg ttaagtaaaa gaaagccatg ataaataaga attaactcac
6541 tgttcaatgg gtgtttcctg tgaggaaggt tacagttgta acagcctgca gttgcataca
6601 tctccaaaga tttacagact tagtgtatca aatcagagtg tcatgtgagc tctcacattg
6661 aaaattctat aggaatgtgt caatgtgaat tctatttctg gtacttaaga aatcagttgt
6721 tggattatcc ttatacagta tagggagatc acaatacaac tttatgccaa taaaatctaa
6781 cttaattgcc cagatatttt tgcatattta gcaacaagaa aagcttatca tttgactcaa
6841 gtttatgct ttctcttct tttcatttcc taggtactaa ttttaattt tatttggaag
6901 gagcagtgta aagcttactt gtattcaata gtgtatctca tagatacaga caaggccgca
6961 gagataagct gttaaatagt gtttaatgtt gatgtggaga gaaaggtgta ttacttaaaa
7021 atactatacc atatacgttt tgtatatcat taaatcttta aagaaatta aatttattct
7081 tgtttacaaa
```

Figure 5C

```
MSQKSWIESTLTKRECVYIIPSSKDPHRCLPGCQICQQLVRCFGRLVKQHACFTASLAM
KYSDVRLGEHFNQAIEEWSVEKHTEQSPTDAYGVINFQGGSHSYRAKYVRLSYDTKPEII
LQLLLKEWQMELPKLVISVHGGMQKFELHPRIKQLLGKGLIKAAVTTGAWILTGGVNTGV
AKHVGDALKEHASRSSRKICTIGIAPWGVIENRNDLVGRDVVAPYQTLLNPLSKLNVLNN
LHSHFILVDDGTVGKYGAEVRLRRELEKTINQQRIHARIGQGVPVVALIFEGGPNVILTV
LEYLQESPPVPVVVCEGTGRAADLLAYIHKQTEEGGNLPDAAEPDIISTIKKTFNFGQSE
AVHLFQTMMECMKKKELITVFHIGSEDHQDIDVAILTALLKGTNASAFDQLILTLAWDRV
DIAKNHVFVYGQQWLVGSLEQAMLDALVMDRVSFVKLLIENGVSMHKFLTIPRLEELYNT
KQGPTNPMLFHLIRDVKQGNLPPGYKITLIDIGLVIEYLMGGTYRCTYTRKRFRLIYNSL
GGNNRRSGRNTSSSTPQLRKSHETFGNRADKKEKMRHNHFIKTAQPYRPKMDASMEEGKK
KRTKDEIVDIDDPETKRFPYPLNELLIWACLMKRQVMARFLWQHGEESMAKALVACKIYR
SMAYEAKQSDLVDDTSEELKQYSNDFGQLAVELLEQSFRQDETMAMKLLTYELKNWSNST
CLKLAVSSRLRPFVAHTCTQMLLSDMWMGRLNMRKNSWYKVILSILVPPAILMLEYKTKA
EMSHIPQSQDAHQMTMEDSENNFHNITEEIPMEVFKEVKILDSSDGKNEMEIHIKSKKLP
ITRKFYAFYHAPIVKFWFNTLAYLGFLMLYTFVVLVKMEQLPSVQEWIVIAYIFTYAIEK
VREVFMSEAGKISQKIKVWFSDYFNVSDTIAIISFFVGFGLRFGAKWNYINAYDNHVFVA
GRLIYCLNIIFWYVRLLDFLAVNQQAGPYVMMIGKMVANMFYIVVIMALVLLSFGVPRKA
ILYPHEEPSWSLAKDIVFHPYWMIFGEVYAYEIDVCANDSTLPTICGPGTWLTPFLQAVY
LFVQYIIMVNLLIAFFNNVYLQVKAISNIVWKYQRYHFIMAYHEKPVLPPPLIILSHIVS
LFCCVCKRRKKDKTSDGPKLFLTEEDQKKLHDFEEQCVEMYFDEKDDKFNSGSEERIRVT
FERVEQMSIQIKEVGDRVNYIKRSLQSLDSQIGHLQDLSALTVDTLKTLTAQKASEASKV
HNEITRELSISKHLAQNLIDDVPVRPLWKKPSAVNTLSSSLPQGDRESNNPFLCNIFMKD
```

Figure 6A

```
EKDPQYNLFGQDLPVIPQRKEFNIPEAGSSCGALFPSAVSPPELRQRRHGVEMLKIFNKN

QKLGSSPNSSPHMSSPPTKFSVSTPSQPSCKSHLESTTKDQEPIFYKAAEGDNIEFGAFV

GHRDSMDLQRFKETSNKIRELLSNDTPENTLKHVGAAGYSECCKTSTSLHSVQAESCSRR

ASTEDSPEVDSKAALLPDWLRDRPSNREMPSEGGTLNGLASPFKPVLDTNYYYSAVERNN

LMRLSQSIPFVPVPPRGEPVTVYRLEESSPSILNNSMSSWSQLGLCAKIEFLSKEEMGGG

LRRAVKVLCTWSEHDILKSGHLYIIKSFLPEVINTWSSIYKEDTVLHLCLREIQQQRAAQ

KLTFAFNQMKPKSIPYSPRFLEVFLLYCHSAGQWFAVEECMTGEFRKYNNNNGDEIIPTN

TLEEIMLAFSHWTYEYTRGELLVLDLQGVGENLTDPSVIKAEEKRSCDMVFGPANLGEDA

IKNFRAKHHCNSCCRKLKLPDLKRNDYTPDKIIFPQDESSDLNLQSGNSTKESEATNSVR

LML
```

Figure 6B

```
cgggcgcgggcgcgctccctgtggccagtcacccggaggagttggtcgcacaattatgaaagactcggcttctgctgctagcgccggagctgagttagttctgagaaggtttc
cctgggcgttccttgtccggcggcctctgctgccgcctccggagacgcttcccgatagatggctacaggccgcggaggaggaggaggtggagttgctgccettccggagtc
cgccccgtgaggagaatgtcccagaaatcctggatagaaagcactttgaccaagagggaatgtgtatatattataccaagttccaaggaccctcacagatgccttccaggatgt
caaatttgtcagcaactcgtcaggtgtttttgtggtcgctggtcaagcaacatgcttgttttactgcaagtcttgccatgaaatactcagatgtgaaattgggtgaccattttaatcag
gcaatagaagaatggtctgtggaaaagcatacagaacagagcccaacggatgcttatggagtcataaattttcaaggggggttctcattcctacagagctaagtatgtgaggcta
tcatatgacaccaaacctgaagtcattctgcaacttctgcttaaagaatggcaaatggagttacccaaacttgttatctctgtacatgggggcatgcagaaatttgagcttcaccca
cgaatcaagcagttgcttggaaaaggtcttattaaagctgcagttacaactggagcctggattttaactggaggagtaaacacaggtgtggcaaaacatgttggagatgccctc
aaagaacatgcttccagatcatctcgaaagatttgcactatcggaatagctccatggggagtgattgaaaacagaaatgatcttgttgggagagatgtggttgctccttatcaaac
cttattgaaccccctgagcaaattgaatgttttgaataatctgcattcccatttcatattggtggatgatggcactgttggaaagtatggggcggaagtcagactgagaagagaact
tgaaaaactattaatcagcaaagaattcatgctaggattggccagggtgtccctgtggtggcacttatattgagggtgggccaaatgttatcctcacagttcttgaataccttca
ggaaagccccctgttccagtagtgtgtgtgaaggaacaggcagagctgcagatctgctagcgtatattcataaacaaacagaagaaggagggaatcttcctgatgcagca
gagcccgatattatttccactatcaaaaaaacatttaactttggccagaatgaagcacttcatttatttcaaacactgatggagtgcatgaaaagaaaggagcttatcactgttttcc
atatattgggtcagatgaacatcaagatatagatgtagcaatacttactgcactgctaaaaggtactaatgcatctgcatttgaccagcttatccttacattggcatgggatagagttga
cattgccaaaaatcatgtattttgtttatggacagcagtggctggttggatcctggaacaagctatgcttgatgctcttgtaatggatagagttgcatttgtaaaacttcttattgaaaa
tggagtaagcatgcataaattccttaccattccgagactggaagaacttacaacactaaacaaggtccaactaatccaatgctgtttcatcttgttcgagacgtcaaacagggaa
atcttcctccaggatataagatcactctgattgatataggacttgttattgaatatctcatgggaggaacctacagatgcacctatactaggaaacgttttcgattaatatataatagtc
ttggtggaaataatcggaggtctggccgaaatacctccagcagcactcctcagttgcgaaagagtcatgaatctttggcaataggcagataaaaaggaaaaa
atgaggcataaccattcattaagacagcacagccctaccgaccaaagattgatacagttatggaagaaggaaagaagaaaagaaccaaagatgaaattgtagacattgatg
aatggattgttattgcttatattttacttatgccattgagaaagtccgtgagatctttatgtctgaagctgggaaagtaaaccagaagattaaagtatggtttagtgattacttcaaacat
cagtgatacaattgccataatttctttcttcattggatttggactaagatttggagcaaaatggaactttgcaaatgcatatgataatcatgtttttgtggctggaagattaattactgtc
ttaacataatattttggtatgtgcgtttgctagatttttctagctgtaaatcaacaggcaggaccttatgtaatgatgattggaaaaatggtggccaatatgttctacattgtagtgattat
ggctcttgtattacttagttttggtgttcccagaaaggcaatactttatcctcatgaagcaccatcttggactcttgctaaagatataagttttttcacccatactggatgatttttggtgaa
gtttatgcatacgaaattgatgtgtgtgcaaatgattctgttatccctcaaatctgtggtcctgggacgtggttgactccatttcttcaagcagtctacctctttgtacagtatatcattat
ggttaatcttcttattgcatttttcaacaatgtgtatttacaagtgaaggcaatttccaatattgtatggaagtaccagcgttatcatttattatggcttatcatgagaaaccagttctgcc
tcctccacttatcattcttagccatatagttttctctgttttgctgcatatgtaagagaagaaagaaagataagacttccgatggaccaaaacttttcttaacagaagaagatcaaaag
aaacttcatgattttgaagagcagtgtgttgaaatgtatttcaatgaaaaagatgacaaatttcattctgggagtgaagagagaattcgtgtcacttttgaaagagtggaacagatg
tgcattcagattaaagaagttggagatcgtgtcaactacataaaaagatcatttacaatcattagattctcaaattggccatttgcaagatcttcagccctgacggtagatacattaa
aaacactcactgcccagaaagcgtcggaagctagcaaagttcataatgaaatcacacgagaacttgagcatttccaaacacttggctcaaaaccttattgatgatggtcctgtaa
gacctctgtatggaaaaagcatggtgttgtaaatacacttagctcctctctcctcaaggtgatcttgaaagtaataatcctttcattgtaatatttttaatgaaagatgacaaagatc
cccagtgtaatatatttggtcaagacttacctgcagtacccccagagaaaagaattttaattttccagaggctggttcctcttctggtgccttattccaagtgctgtttcccctccagaa
ctgcgacagagactacatggggtagaactctttaaaaatatttaataaaaatcaaaaattaggcagttcatctactagcataccacatctgtcatccccaccaaccaaatttttgtta
gtacaccatctcagccaagttgcaaaagccacttggaaactggaaccaaagatcaagaaactgtttgctctaaagctacagaaggagataatacagaatttggagcatttgtag
gacacagagatagcatggattacagaggtttaaagaaacatcaaacaagataaaaatactatccaataacaatacttctgaaaacactttgaaacgagtgagttctcttgctgga
tttactgactgtcacagaacttccattcctgttcattcaaaacaagaaaaaatcagtagaaggccatctaccgaagacactcatgaagtagatgaaagcagctttaataccggtt
tggttacaagatagaccatcaaacagagaaatgccatctgaagaaggaaacattaaatgtgtcacttctccatttaagccagctgtggatacaaattactattattcagctgtggaa
agaaatnacttgatgaggttatcacagagcattccatttacacctgtgcctccaagaggggagcctgtcacagtgtatcgtttggaagagagttcacccaacatactaaataaca
gcatgtcttcttggtcacaactaggcctctgtgccaaaatagagtttttaagcaaagaggagatgggaggaggtttacgaagagctgtcaaagtacagtgtacctggtcagaac
atgatatcctcaaatcagggcatctttatattatcaaatcttttcttccagaggtggttaatacatggtcaagtatttacaaagaagatacagttctgcatctctgtctgagagaaatc
aacaacagagagcagcacaaaagcttacgtttgccttaatcaaatgaaacccaaatccatacentattctccaaggttccttgaagttttcctgctgtattgccattcagcaggac
agtggtttgctgtggaagaatgtatgactggagaatttagaaaataccaactaataatggaagagatattattccaactaatactctggaagagatcatgctagcctttagccact
ggacttacgaatatacaagaggggagttactggtacttgatttgcaaggtgttggtgaaaatttgactgacccatctgtgataaaagcagaagaaaagagatctctgtgatatggtt
tttggcccagcaaatctaggagaagatgcaattaaaaacttcagagcaaaacatcactgtaattcttgctgtagaaagcttaaacttccagatcgtaagaggaatgattatacgcc
tgataaaattatatttcctcaggatgagccttcagatttgaatcttcagcctggaaattccaccaaagaatcagaatcaactaattctgttcgtctgatgttataatattaatattactga
atcattggttttgcctgcacctcacagaaatgttactgtgtcactttcctcgggggaggaaattgtttggtaatatagaaaggtgtatgcaagttgaatttgctgactccagcacagtt
aaaaggtcaatattctttttgacctgattaatcagtcagaaagtccctataggatagagctggcagctgagaaattttaaaggtaattgataattagtatttataactttttaaagggctc
tttgtatagcagaggatctcatttgactttgttttgatgagggtgatgctctctcttatgtggtacaataccattaaccaaaggtaggtgtccatgcagattttattggcagctgttttatt
gccattcaactagggaaatgaagaaatcacgcagcctttggttaaatggcagtcaaaattttcctcagtgtatttagtgtgttcagtgatgatatcactggttcccaactagatgctt
gttggccacgggaagggaaatgacttgttctaattctaggttcacagaggtatgagaagcctgaactgaagaccattttcaagaggacggtatttatgaatcagggttaggctc
catatttaaagatagagccagttttttttttttaaatagaacccaaattgtgtaaaaatgttaattgggttttttaaacattgttttatcaagtcactgttaagtagaagaaagccatggtaa
actgatacataacctaaattataaaagcagaaaacctaactcactcgtcaagggaagttacctttgaggaaagttaaagtacttttttccctatctgtatctatagcaacaacccaga
acttacaaaacttctccaaagatttttattgattgttatatcaaatcagaatgtaaacatgaactcttgcatatatttaaaattgtgttggaacatttgaacatgaatgctgtttgtggtactta
agaaattaattcagttggattatcattatgtgatactggcagattgcagtgcaacctatgccaataaaatgtaatttaacagcccagatattgttgaatattcaacaataacaagaa
aagcttttcatctaagtttatgctttaattttttttctttttttttcttttctttgttccttggtactaattttaattttatttgggaggggagcagtataagcttatttgtatttagtagtgtatctc
catagatacagacaaggccaagagatgataagctgtttaaatagtgtttaatattgattgggggtggggagaaagaaaaagtgtattacttaaagatactatatacgttttgtatatca
ttaaatcttttaaaagaaatgaaataaatttattgtttacagataaaaaaa
```

Figure 7A

MSQKSWIESTLTKRECVYIIPSSKDPHRCLPGCQICQQLVRCFCGRLVKQHACFTA
SLAMKYSDVKLGDHFNQAIEEWSVEKHTEQSPTDAYGVINFQGGSHSYRAKYVRL
SYDTKPEVILQLLLKEWQMELPKLVISVHGGMQKFELHPRIKQLLGKGLIKAAVT
TGAWILTGGVNTGVAKHVGDALKEHASRSSRKICTIGIAPWGVIENRNDLVGRDVV
APYQTLLNPLSKLNVLNNLHSHFILVDDGTVGKYGAEVRLRRELEKTINQQRIHAR
IGQGVPVVALIFEGGPNVILTVLEYLQESPPVPVVVCEGTGRAADLLAYIHKQTEEG
GNLPDAAEPDIISTIKKTFNFGQNEALHLFQTLMECMKRKELITVFHIGSDEHQDID
VAILTALLKGTNASAFDQLILTLAWDRVDIAKNHVFVYGQQWLVGSLEQAMLDAL
VMDRVAFVKLLIENGVSMHKFLTIPRLEELYNTKQGPTNPMLFHLVRDVKQGNLP
PGYKITLIDIGLVIEYLMGGTYRCTYTRKRFRLIYNSLGGNNRRSGRNTSSSTPQLR
KSHESFGNRADKKEKMRHNHFIKTAQPYRPKIDTVMEEGKKKRTKDEIVDIDDPE
TKRFPYPLNELLIWACLMKRQVMARFLWQHGEESMAKALVACKIYRSMAYEAKQ
SDLVDDTSEELKQYSNDFGQLAVELLEQSFRQDETMAMKLLTYELKNWSNSTCLK
LAVAAKHRDFIAHTCSQMLLTDMWMGRLRMRKNPGLKVILSILVPPAILLLEYKT
KAEMSHIPQSQDAHQMTMDDSENNFQNITEEIPMEVFKEVRILDSNEGKNEMEIQM
KSKKLPITRKFYAFYHAPIVKFWFNTLAYLGFLMLYTFVVLVQMEQLPSVQEWIVI
AYIFTYAIEKVREIFMSEAGKVNQKIKVWFSDYFNISDTIAIISFFIGFGLRFGAKWNF
ANAYDNHVFVAGRLIYCLNIIFWYVRLLDFLAVNQQAGPYVMMIGKMVANMFYIV
VIMALVLLSFGVPRKAILYPHEAPSWTLAKDIVFHPYWMIFGEVYAYEIDVCANDS
VIPQICGPGTWLTPFLQAVYLFVQYIIMVNLLIAFFNNVYLQVKAISNIVWKYQRYH
FIMAYHEKPVLPPPLIILSHIVSLFCCICKRRKKDKTSDGPKLFLTEEDQKKLHDFEE
QCVEMYFNEKDDKFHSGSEERIRVTFERVEQMCIQIKEVGDRVNYIKRSLQSLDSQI
GHLQDLSALTVDTLKTLTAQKASEASKVHNEITRELSISKHLAQNLIDDGPVRPSV
WKKHGVVNTLSSSLPQGDLESNNPFHCNILMKDDKDPQCNIFGQDLPAVPQRKEF
NFPEAGSSSGALFPSAVSPPELRQRLHGVELLKIFNKNQKLGSSSTSIPHLSSPPTKFF
VSTPSQPSCKSHLETGTKDQETVCSKATEGDNTEFGAFVGHRDSMDLQRFKETSN
KIKILSNNNTSENTLKRVSSLAGFTDCHRTSIPVHSKQEKISRRPSTEDTHEVDSKAA
LIPVWLQDRPSNREMPSEEGTLNGLTSPFKPAMDTNYYYSAVERNNLMRLSQSIPF
TPVPPRGEPVTVYRLEESSPNILNNSMSSWSQLGLCAKIEFLSKEEMGGGLRRAVK
VQCTWSEHDILKSGHLYIIKSFLPEVVNTWSSIYKEDTVLHLCLREIQQQRAAQKLT
FAFNQMKPKSIPYSPRFLEVFLLYCHSAGQWFAVEECMTGEF
RKYNNNNGDEIIPTNTLEEIMLAFSHWTYEYTRGELLVLDLQGVGENLTDPSVIKA
EEKRSCDMVFGPANLGEDAIKNFRAKHHCNSCCRKLKLPDLKRNDYTPDKIIFPQD
EPSDLNLQPGNSTKESESTNSVRLML

ESAEPPLTQSDKRETSHTTAAATGRSSHADARECAISTQAEQEAKTLQTSDSVSKEGNTNCKGEGMQVN
TLFETSQVPDWSDPPQVQVQETVRETISCSQMPAFSEPAGEESPFTGTTISFSNLGGVHKENASLAQHSEV
KPCTCGPQQEEKQDRDGNIPDNFREDLKYEQSISEANDEIMSPGVFSRHLPKDARADFREPVAVSVASPEP
TDTALTLENVCDEPRDREAVCAMECFEASDQGTCFDTIDSLVGTPVDNYSPQEICSVDTELAEGQNKVSD
LCSSNDKTLEVFFQTQVSETSVSTCKSSKDGNSVMSPLFISTFTLNISHTASEGATGENLAKVEKSTYPLAS
TVHAGQEQPSPSNSGGLDETQLLSSENNPLVQFKEGGDKSPSPSAADTTATPASYSSIVSFPWEKPTLTAN
NECFQATRETVTIATEVHPAKYLAVSIPEDKHAGGTEERFPRASHEKVSQFPSQVQVDHILSGATIKSTKEL
LCRAPSVPGVPHHVLQLPEGEGFCSNSPLQVDNLSGDKSQTVDRADFRSYEENFQERGSETKQGVQQSL
SQQQGSLSAPDFQQSLPTTSAAQFERNLVPTAPSPASSREGAGQRSGWGTRVSVVAETAGEEDSQALSNVPS
LSDILLEESKEYRPGNWEAGNKLKIITLEASASEIWPPRQLTNSESKASDGGLIIPDKVWAVPDSLKADAVV
PELAPSEIAALAHSPEDAESALADSRESHKGEEPTISVHWRSLSSRGFSQPRLLESSVDPVDEKELSVTDSLS
AASETGGKENVNNVSQDQEEKQLKMDHTAFFKKFLTCPKILESSVDPIDEISVIEYTRAGKPEPSETTPQGA
REGGQSNDGNMGHEAEIQSAILQVPCLQGTILSENRISRSQEGSMKQEAEQIQPEEAKTAIWQVLQPSEGG
ERIPSGCSIGQIQESSDGSLGEAEQSKKDKAELISPTSPLSSCLPIMTHSSLGVDTHNSTGQIHDVPENDIVEP
RKRQYVFPVSQKRGTIENERGKPLPSSPDLTRFPCTSSPEGNVTDFLJISHKMEEPKIEVLQIGETKPPSSSSSS
AKTLAFISGERELEKAPKJLQDPCQKGTLGCAKKSREREKSLEARAGKSPGILTAVTGSEEVKRKPEAPGS
GHLAEGVKKKILSRVAALRLKLEEKENIRKNSAFLKKMPKLETSLSHTEEKQDPKKPSCKREGRAPVLLK
KIQAEMFPEHSGNVKLSCQFAEIHEDSTICWTKDSKSIAQVQRSAGDNSTVSFAIVQASPKDQGLYCCIK
NSYGKVTAEFNLTAEVLKQLSSRQDTKGCEEIEFSQLIFKEDFLHDSYFGGRLRGQIATEELHFGEGVHRK
AFRSTVMHGLMPVFKPGHACVLKVHNAIAYGTRNNDELIQRNYKLAAQECYVQNTARYYAKIYAAEAQ
PLEGFGEVPEIIPIFLIHRPENNIPYATVEEELIGEFVKYSIRDGKEINFLRRESEAGQKCCTFQHWVYQKTSG
CLLVTDMQGVGMKLTDVGIATLAKGYKGFKGNCSMTFIDQFKALHQCNKYCKMLGLKSLQNNNQKQK
QPSIGKSKVQTNSMTVKKAGPETPGEKKT

Figure 8B

| | |
|---:|:---|
| 1 | atgtcccaga aatcctggat taaaggagta tttgacaaga gagaatgtag cacaatcata |
| 61 | cccagctcaa aaaatcctca cagatgtact ccagtatgcc aagtctgcca gaatttaatc |
| 121 | aggtgttact gtggccgact gattggagac catgctggga tagattattc ctggaccatc |
| 181 | tcagctgcca agggtaaaga aagtgaacaa tggtctgttg aaaagcacac aacgaaaagc |
| 241 | ccaacagata cttttggcac gattaatttc caagatggag agcacaccca tcatgccaag |
| 301 | tatattagaa cttcttatga tacaaaactg gatcatctgt tacatttaat gttgaaagag |
| 361 | tggaaaatgg aactgcccaa gcttgtgatc tcagtccatg ggggcatcca gaactttact |
| 421 | atgccctcta aatttaaaga gattttcagc caaggtttgg ttaaagctgc agagacaaca |
| 481 | ggagcgtgga taataactga aggcatcaat acagtgtcca agcatgttgg ggatgccttg |
| 541 | aaatcccatt cctctcattc cttgagaaaa atctggacag ttggaatccc tccttggggt |
| 601 | gtcattgaga accagagaga ccttattgga aaagatgtgg tgtgcctgta ccagactctg |
| 661 | gataaccccc tcagcaagct cacaacactc aacagcatgc actcgcactt catcctgtct |
| 721 | gatgatggga ccgtgggcaa gtatggaaat gaaatgaagc tcagaaggaa cctggagaag |
| 781 | tacctctctc tgcagaaaat acactgccgc tcaagacaag gcgtgccggt cgtggggctg |
| 841 | gtggtggaag gcggtcccaa cgtcatcctg tcagtgtggg agactgtcaa ggacaaggac |
| 901 | ccagtggtgg tgtgtgaggg cacaggtagg gcggctgacc tcctggcctt cacacacaaa |
| 961 | cacctggcag atgaagggat gctgcgacct caggtgaaag aggagatcat ctgcatgatt |
| 1021 | cagaacactt tcaactttag tcttaaacag tccaagcacc ttttccaaat tctaatggag |
| 1081 | tgtatggttc acagggattg tattaccata tttgatgctg actctgaaga gcagcaagac |
| 1141 | ctggacttag caatcctaac agctttgctg aagggcacaa atttatcagc gtcagagcaa |
| 1201 | ttaaatctgg caatgcttg ggacagggtg gacattgcca agaaacatat cctaatttat |
| 1261 | gaacaacact ggaagcctga tgccctggaa caagcaatgt cagatgcttt agtgatggat |
| 1321 | cgggtggatt ttgtgaagct cttaatagaa tatggagtga acctccatcg cttcttacc |
| 1381 | atccctcgac tggaagagct ctacaataca aaacaaggac ctactaatac actcttgcat |
| 1441 | catctcgtcc aagatgtgaa acagcatacc cttctttcg gctaccgaat aaccttgatt |
| 1501 | gacattggat tagtagtaga atacctcatt ggtagagcat atcgcagcaa ctacactaga |
| 1561 | aaacatttca gagccctcta caacaacctc tacagaaaat acaagcacca gagacactcc |
| 1621 | tcaggaaata gaaatgagtc tgcagaaagt acgctgcact cccagttcat tagaactgca |
| 1681 | cagccataca aattcaagga aaagtctata gtccttcata aatcaaggaa gaagtcaaaa |
| 1741 | gaacaaaatg tatcagatga ccctgagtct actggctttc tttaccctta caatgacctg |
| 1801 | ctggtttggg ctgtgctgat gaaaaggcag aagatggcta tgttcttctg gcagcatgga |
| 1861 | gaggaggcca cggttaaagc cgtgattgcg tgtatcctct accgggcaat ggcccatgaa |
| 1921 | gctaaggaga gtcacatggt ggatgatgcc tcagaagagt tgaagaatta ctcaaaacag |
| 1981 | tttggccagc tggctctgga cttgttggag aaggcattca gcagaatga gcgcatggcc |
| 2041 | atgacgctgt tgacgtatga actcaggaac tggagcaatt cgacctgcct taaactggcc |
| 2101 | gtgtcgggag gattacgacc ctttgtttca catacttgta cccagatgct actgacagac |
| 2161 | atgtggatgg ggaggctgaa aatgaggaaa aactcttggt taaagattat tataagcatt |
| 2221 | atttaccac ccaccatttt gacactgaa tttaaaagca aagctgagat gtcacatgtt |
| 2281 | ccccagtccc aggacttcca atttatgtgg tattacagtg accagaacgc cagcagttcc |
| 2341 | aaagaaagtg cttctgtgaa agagtatgat ttggaaaggg gccatgatga gaactggat |
| 2401 | gaaaatcagc attttggttt ggaagtgggg caccaacacc ttccgtggac caggaaagtc |
| 2461 | tatgagttct acagtgctcc aattgtcaag ttttggtttt atacgatggc gtatttggca |
| 2521 | ttcctcatgc tgttcactta caccgtgttg gtggagatgc agccccagcc cagcgtgcag |
| 2581 | gagtggcttg ttagcattta catcttcacc aatgctattg aggtggtcag ggaggtgagt |
| 2641 | atttcagaac ctgggaagtt tacccaaaag gtgaaggtat ggattagtga gtactggaac |
| 2701 | ttaacagaaa ctgtggccat tggcctgttt tcagctggct tgtcctcg atggggtgac |
| 2761 | cctcctttc acacagcggg aagactgatc tactgcatag acatcatatt ctggttctca |
| 2821 | cggctcctgg acttctttgc tgtgaatcaa catgcaggtc catatgtgac catgattgca |
| 2881 | aaaatgacag caaacatgtt ctattgtgtg atcatcatgg ccatagtcct gctgagcttt |
| 2941 | ggagtggcac gcaaggccat cctttcgcca aaagagccac catcttggag tctagctcga |
| 3001 | gatattgtat ttgagccata ctggatgata tacggagaag tctatgctgg agaaatagat |
| 3061 | gtttgttcaa gccagccatc ctgcctcctc ggttcttttc ttactccatt cttgcaagct |
| 3121 | gtctacctct tcgtgcaata tatcatcatg gtgaacctgt tgattgcttt cttcaacaac |
| 3181 | gtttacttag atatggaatc catttcaaat aacctgtgga atacaaccg ctatcgctac |

Figure 9A 3241 atcatgacct accacgagaa gccctggctg cccccacctc tcatcctgct gagccacgtg
3301 ggccttctcc tccgccgcct gtgctgtcat cgagctcctc acgaccaaga agagggtgac
3361 gttggattaa aactctacct cagtaaggag gatctgaaaa aacttcatga tttgaggag
3421 cagtgcgtgg aaaatactt ccatgagaag atggaagatg tgaattgtag ttgtgaggaa
3481 cgaatccgag tgcatcaga aagggttaca gagatgtact tccagctgaa agaaatgaat
3541 gaaaaggtgt cttttataaa ggactcctta ctgtctttgg acagccaggt gggacacctg
3601 caggatctct ctgccctgac tgtggatacc ctgaaagtcc tttctgctgt tgacactttg
3661 caagaggatg aggctctcct ggccaagaga aagcattcta cttgcaaaaa acttccccac
3721 agctggagca atgtcatctg tgcagaggtt ctaggcagca tggagatcgc tggagagaag
3781 aaataccagt attatagcat gccctcttct ttgctgagga gcctggctgg aggccggcat
3841 cccccaagag tgcagagggg ggcacttctt gagattacaa acagtaaaag agaggctaca
3901 aatgtaagaa atgaccagga aaggcaagaa acacaaagta gtatagtggt ttctggggtg
3961 tctcctaaca ggcaagcaca ctcaaagtat ggccagtttc ttctggtccc ctctaatcta
4021 aagcgagttc cttttcagc agaaactgtc ttgcctctgt ccagaccctc tgtgccagat
4081 gtgctggcaa ctgaacagga catccagact gaggttcttg ttcatctgac tgggcagacc
4141 ccagttgtct ctgactgggc atcagtggat gaacccaagg aaaagcacga gcctattgct
4201 cacttactgg atggacaaga caaggcagag caagtgctac ccactttgag ttgcacacct
4261 gaacccatga caatgagctc ccctctttcc caagccaaga tcatgcaaac tggaggtgga
4321 tatgtaaact gggcattttc agaaggtgat gaaactggtg tgtttagcat caagaaaaag
4381 tggcaaacct gcttgccctc cacttgtgac agtgattcct ctcggagtga acagcaccag
4441 aagcaggccc aggacagctc cctatctgat aactcaacaa gatcggccca gagtagtgaa
4501 tgctcagagg tgggaccatg gcttcagcca aacacatcct tttggatcaa tcctctccgc
4561 agatacaggc ccttcgctag gagtcatagt tttagattcc ataaggagga gaaattgatg
4621 aagatctgta agattaaaaa tctttcaggc tcttcagaaa tagggcaggg agcatgggtc
4681 aaagcgaaaa tgctaaccaa agacaggaga ctgtcaaaga aaagaagaa tactcaagga
4741 ctccaggtgc caatcataac agtcaatgcc tgctctcaga gtgaccagtt gaatccagag
4801 ccaggagaaa acagcatctc tgaagaggag tacagcaaga actggttcac agtgtccaaa
4861 tttagtcaca caggtgtaga accttacata catcagaaaa tgaaaactaa agaaattgga
4921 caatgtgcta tacaaatcag tgattaccta aagcagtctc aagaggatct cagcaaaaac
4981 tctttgtgga attccaggag caccaacctc aataggaact ccctgctgaa aagttcaatt
5041 ggagttcaca agatctcagc ctccttaaaa agccctcaag agcctcacca tcattattca
5101 gccattgaaa ggaataattt aatgaggctt tctcagacca taccattac accagtccaa
5161 ctgtttgcag gagaagaaat aactgtctac aggttggagg agagttccc tttaaacctt
5221 gataaaagca tgtcctcttg gtctcagcgt gggagagcgg caatgatcca ggtattgtcc
5281 cgagaggaga tggatggggg cctccgtaaa gctatgagag tcgtcagcac ttggtctgag
5341 gatgacattc tcaagccggg acaagttttc attgtcaagt cctttcttcc tgaggttgtg
5401 cggacatggc ataaaatctt ccaggagagc actgtgcttc atctttgcct cagggaaatt
5461 caacaacaaa gagctgctca aaaattgatc tatacccttca accaagtgaa accacaaacc
5521 ataccctaca caccaaggtt cctgaagtt ttcttaatct actgccattc agccaaccag
5581 tggttgacca ttgagaagta tatgacaggg gagttccgga agtataacaa caacaatggt
5641 gatgaaatca cccccaccaa caccctggag gagctgatgt tggcttctc tcactggacc
5701 tatgagtaca ctcggggaga gctgctggtt ttagattgc aaggtgttgg agaaaatttg
5761 acagatccat ctgttatata acctgaagtc aaacaatcaa gaggaatggt gtttggaccg
5821 gccaatttgg gggaagatgc aattagaaac ttcattgcaa aacatcattg taactcctgc
5881 tgccggaagc tcaaactccc ggatttaaaa agaaatgact attcccctga aaggataaat
5941 tccaccttg gacttgagat aaaaatagaa tcagctgagg agcctccagc aagggagacg
6001 ggtagaaatt cccagaaga tgatatgcaa ctataaaaag ggaggagcaa gaagatccca
6061 gtgcttgccc tgcctgccag gaactctgtg ataacataga ttgatcaacg tgatgttgat
6121 tacatcagcg tctccttggg acacgccttc tgagcctcac atctccttct gttcaaaggc
6181 ctcattggta tatgatcaat gggttctcct agacactgac ctctgtccag ggcactttgc
6241 agctccatcc tcaagttcca cacgaagatg cttggatgag tcagctggga atattgttct
6301 tgtgtacctc attgctttag ctggtcactt ggaacttgg agcagaatcc tgcacattaa
6361 aggatggggt tggggggat acatttattt tattttctca ctatgtatgc agactggacc
6421 ccctactact atttgtcacc tcacccacag attgtattta tgtctatata tatgttcata

Figure 9A

```
6481  aaaagttatg tgatttcctc ctctgtcttt tccacaacat aggactttga atagcaatga
6541  taggaaaaac aatggaacaa gggtgggttt gcacagattg gagcacattc ctgcacaaac
6601  taccaagtat actggtgaaa tctcgatggg tttcagatat tgtcagtgaa tcatatgatg
6661  cctggatatt tcaggtttct gtaaaagaaa gggaaaccta aaacaaatac ccttccatat
6721  ataatatata tggaatatgt atattatata tatttttata tataatat atatggaata
6781  tatatattat atatataaaa tacatatgga atatatatat tttatatata tatatatatt
6841  tttatttttg agatggagtt tcactctttt tacccaggct ggagtgcaat gatgcgatct
6901  cactgcaacc tctgcctccc gggcttgagc gattcttgtg tctcagtctt ccgggtagct
6961  gggactacag gtgtgcacca ctatgcctgg ctaattttgt attttagta gagatggggt
7021  ttcaccatgt tggccaggct ggtctcaaac tcctgacctc agatgatcca cctgccttgg
7081  cttcccaaag tgctgggatt acaggcgtga gccactgcgc ctggcctttt tttttttt
7141  tttaaacgag aacaagaata tgaagaactg gaaatcatta agaaagggt tccttcctt
7201  aaagctcagg ggtactatta gttaggagtt gactaactca acctgtaaaa caccactcct
7261  ccttccaaag ttgtatatat aatattgcag gttaaattac tttatgtcag gtcctatgaa
7321  gaaagatacg gtttcagact gaaaacatgt ttcacaggtg tttgcttcct tccagagcag
7381  agttccctat tcccctggca taaagaatgt atatatattt tgaaatatgg ctgagaacat
7441  gtcattggtt tgtgaggcct aaggtgaagc actcctggca gccacactgt gtagtgtatt
7501  tgagggatca gtcatccctc ttgtatgctg ggcctggttg ccctacctcg aacaagcacc
7561  agcttttcac acaaggagag atgtggggct gggagtcctc tccccatcct attgcatctc
7621  ctttcttatt ataagctgtt ccagttcaca ggcagcaaac ctcctgggtt tgaaaaattc
7681  caacttattt ttatctttaa tcctgacatt agctgacttg ctagtgagct tgctttaaaa
7741  atctacactc ttgcattctt aggcatacag gggaaatgtt gaaaaggaag gtggaaaacc
7801  aagaatttag tttgccaatg attgcctctg attcttgtaa gtttgagttc cacaagggct
7861  aatttattcc cctttactt gggttttggg gtggtggaaa gcgggaaatt tgggtgattt
7921  gttgattggc aatgaggata aaatgttaat acttttttgg ggacttaaca actttatcct
7981  attctacaag tcagtaaagg aacaattggt actcacctca gtgctgcact caactatgga
8041  aagaggcaga gtttgcttgc ccaattgcca aactaaagac atcagttcat tggtcaaata
8101  tttgttacct ggaatggaac ttgaaagcaa atacatttgg atttcaaatt tcaaaaaa
```

Figure 9A

MSQKSWIKGVFDKRECSTIPSSKNPHRCTPVCQVCQNLIRCYCGRLIGDHAGIDYS
WTISAAKGKESEQWSVEKHTTKSPTDTFGTINFQDGEHTHHAKYIRTSYDTKLDHL
LHLMLKEWKMELPKLVISVHGGIQNFTMPSKFKEIFSQGLVKAAETTGAWIITEGI
NTVSKHVGDALKSHSSHSLRKIWTVGIPPWGVIENQRDLIGKDVVCLYQTLDNPLS
KLTTLNSMHSHFILSDDGTVGKYGNEMKLRRNLEKYLSLQKIHCRSRQGVPVVGL
VVEGGPNVILSVWETVKDKDPVVVCEGTGRAADLLAFTHKHLADEGMLRPQVKE
EIICMIQNTFNFSLKQSKHLFQILMECMVHRDCITIFDADSEEQQDLDLAILTALLK
GTNLSASEQLNLAMAWDRVDIAKKHILIYEQHWKPDALEQAMSDALVMDRVDFV
KLLIEYGVNLHRFLTIPRLEELYNTKQGPTNTLLHHLVQDVKQHTLLSGYRITLIDI
GLVVEYLIGRAYRSNYTRKHFRALYNNLYRKYKHQRHSSGNRNESAESTLHSQFIR
TAQPYKFKEKSIVLHKSRKKSKEQNVSDDPESTGFLYPYNDLLVWAVLMKRQKMA
MFFWQHGEEATVKAVIACILYRAMAHEAKESHMVDDASEELKNYSKQFGQLALD
LLEKAFKQNERMAMTLLTYELRNWSNSTCLKLAVSGGLRPFVSHTCTQMLLTDM
WMGRLKMRKNSWLKIISIILPPTILTLEFKSKAEMSHVPQSQDFQFMWYYSDQNA
SSSKESASVKEYDLERGHDEKLDENQHFGLESGHQHLPWTRKVYEFYSAPIVKFW
FYTMAYLAFLMLFTYTVLVEMQPQPSVQEWLVSIYIFTNAIEVVREVSISEPGKFTQ
KVKVWISEYWNLTETVAIGLFSAGFVLRWGDPPFHTAGRLIYCIDIIFWFSRLLDFF
AVNQHAGPYVTMIAKMTANMFYIVIIMAIVLLSFGVARKAILSPKEPPSWSLARDIV
FEPYWMIYGEVYAGEIDVCSSQPSCPPGSFLTPFLQAVYLFVQYIIMVNLLIAFFNNV
YLDMESISNNLWKYNRYRYIMTYHEKPWLPPPLILLSHVGLLLRRLCCHRAPHDQ
EEGDVGLKLYLSKEDLKKLHDFEEQCVEKYFHEKMEDVNCSCEERIRVTSERVTE
MYFQLKEMNEKVSFIKDSLLSLDSQVGHLQDLSALTVDTLKVLSAVDTLQEDEALL
AKRKHSTCKKLPHSWSNVICAEVLGSMEIAGEKKYQYYSMPSSLLRSLAGGRHPP
RVQRGALLEITNSKREATNVRNDQERQETQSSIVVSGVSPNRQAHSKYGQFLLVPS
NLKRVPFSAETVLPLSRPSVPDVLATEQDIQTEVLVHLTGQTPVVSDWASVDEPKE
KHEPIAHLLDGQDKAEQVLPTLSCTPEPMTMSSPLSQAKIMQTGGGYVNWAFSEG
DETGVFSIKKKWQTCLPSTCDSDSSRSEQHQKQAQDSSLSDNSTRSAQSSECSEVGP
WLQPNTSFWINPLRRYRPFARSHSFRFHKEEKLMKICKIKNLSGSSEIGQGAWVKA
KMLTKDRRLSKKKKNTQGLQVPIITVNACSQSDQLNPEPGENSISEEEYSKNWFTV
SKFSHTGVEPYIHQKMKTKEIGQCAIQISDYLKQSQEDLSKNSLWNSRSTNLNRNSL
LKSSIGVDKISASLKSPQEPHHHYSAIERNNLMRLSQTIPFTPVQLFAGEEITVYRLE
ESSPLNLDKSMSSWSQRGRAAMIQVLSREEMDGGLRKAMRVVSTWSEDDILKPGQ
VFIVKSFLPEVVRTWHKIFQESTVLHLCLREIQQQRAAQKLIYTFNQVKPQTIPYTP
RFLEVFLIYCHSANQWLTIEKYMTGEFRKYNNNNGDEITPTNTLEELMLAFSHWTY
EYTRGELLVLDLQGVGENLTDPSVIKPEVKQSRGMVFGPANLGEDAIRNFIAKHHC
NSCCRKLKLPDLKRNDYSPERINSTFGLEIKIESAEEPPARETGRNSPEDDMQL

MEVAWLVYVLGQQPLARQGEGQSRLVPGRGLVLWLPGLPKSSPSWPAVDLAPLAPARPRGPLICHTGHEQAGREPG
PGSSTKGPVLHDQDTRCAFLPRPPGPLQTRRVCRHQGRQGSGLGAGPGAGTWAPAPPGVSKPRCPGRARPGEGQQQ
VTTARPPAINRGARQPRAGAAAAGRGPGAGAWRTGEAAASAGPAVGEGGAMGSRRAPTRGWGAGGRSGAGGDGE
DDGPVWIPSPASRSYLLSVRPETSLSSNRLSHPSSGRSTFCSIIAQLTEETQPLFETTLKSRSVSEDSDVRFTCIVTGYPEP
FVTWYKIDDTELDRYCGLPKYEITHQGNRHTLQLYRCREEDAAIYQASAQNSKGIVSCSGVLEVGTMTEYKIHQRWF
AKLKRKAAAKLREIEQSWKHEKAVPGEVDTLRKLSPDRFQRKRRLSGAQAPGPSVPTREPEGGTLAAWQEGETETA
QHSGLGLINSFASGEVTTNGEAAPENGEDGEHGLLTYICDAMELGPQRALKEESGAKKKKDEESKQGLRKPELEKA
AQSRRSSENCIPSSDEPDSCGTQGPVGVEQVQTQPRGRAARGPGSSGTDSTRKPASAVGTPDKAQKAPGPGPGQEVYF
SLKDMYLFNTQAVRPLGEEGPQTLSVRAPGESPKGKAPLRARSEGVPGAPGQPTHSLTPQPTRPFNRKRFAPPKPKG
EATTDSKPISSI.SQAPECGAQSI.GKAPPQASVQVPTPARRRHGTRDSTLQGQAGHRTPGEVLECQTTTAPTMSASSSS
DVASIGVSTSGSQGHEPMDMETQEDGRTSANQRTGSKKNVQADGKIQVDGRTRGDGTQTAQRTRADRKTQVDAGT
QESKRPQSDRSAQKGMMTQGRAETQLETTQAGEKIQEDRKAQADKGTQEDRRMQGEKGMQGEKGTQSEGSAPTA
MEGQSEQEVATSLGPPSRTPKLPPTAGPRAPLNIECFVQTPEGSCFPKKPGCLPRSEEAVVTASRNHEQTVLGPLSGNL
MLPAQPPHEGSVEQVGGERCRGPQSSGPVEAKQEDSPFQCPKEERPGGVPCMDQGGCPLAGLSQEVPTMPSLPGTG
LTASPKAGPCSTPTSQHGSTATFLPSEDQVLMSSAPTLHLGLGTPTQSHPPETMATSSEGACAQVPDVEGRTPGPRSC
DPGLIDSLKNYLLLLKLSSTETSGAGGESQVGAATGGLVPSATLTPTVEVAGLSPRTSRRILERVENNHLVQSAQTLL
LSPCTSRRLTGLLDREVQAGRQALAAARGSWGPGPSSLTVPAIVDEEDPGLASEGASFGEGEVSLEGPGLLGASQES
SMAGRLGEAGGQAAPGQGPSAESIAQEPSQEEKFPGEALTGLPAATPEELALGARRKRFLPKVRAAGDGEATTPEER
ESPTVSPRGPRKSLVPGSPGTPGRERRSPTQGRKASMLEVPRAEEELAAGDLGPSPKAGGLDTEVALDEGKQETLAKP
RKAKDLLKAPQVIRKIRVEQFPDASGSLKLWGQFFNILSDSVLTWAKDQRPVGEVGRSAGDEGPAALAIVQASPVDC
GVYRCTIHNEHGSASTDFCLSPEVLSGFISREEGEVGEEIEMTPMVFAKGLADSGCWGDKLFGRLVSEELRGGGYGC
GLRKASQAKVTYGLEPIFESGRTCIHKVSSLLVFGPSSETSLVGRNYDVTIQGCKIQNMSREYCKIFAAEARAAPGFGEV
PEIIPLYLIYRPANNIPYATLEEDLGKPLESYCSREWGCAEAPTASGSSEAMQKCQTFQHWLYQWTNGSFLVTDLAGV
DWKMTIDVQIATKLRGYQGLKESCFPALLDRFASSHQCNAYCELLGLTPLKGPEAAHPQAKAKGSKSPSAGRKGSQL
SPQPQKKGLPSPQGTRKSAPSSKATPQASEPVTTQLLGQPPTQEEGSKAQGMR

MNNQKVVAVLLQECKQVLDQLLLEAPDVSEEDKSEDQRCRALLPSELRTLIQEAKEMKWPFVPEK
WQYKQAVGPEDKTNLKDVIGAGLQQLLASLRASILARDCAAAAIVFLVDRFLYGLDVSGKLLQVA
KGLHKLQPATPIAPQVVIRQARISVNSGKLLKAFYILSSLISNNGATGTWLYRNESDKVLVQSVCIQI
RGQILQKLGMWYEAAELIWASIVGYLALPQPDKKGLSTSLGILADIFVSMSKNDYEKFKNNPQINLS
LLKEFDHHLLSAAEACKLAAAFSAYTPLFVLTAVNIRGTCLLSYSSNDCPPELKNLHLCEAKEAFEI
GLLTKRDDEPVTGKQELHSFVKAAFGLTTVHRRLHGETGTVHAASQLCKEAMGKLYNFSTSSRSQ
DREALSQEVMSVIAQVKEHLQVQSFSNVDDRSYVPESFECRLDKLILHGQGDFQKILDTYSQHHTSV
CEVFESDCGNNKNEQKDAKTGVCITALKTEIKNIDTVSTTQEKPHCQRDTGISSSLMGKNVQREIRR
GGRRNWTHSDAFRVSLDQDVETETEPSDYSNGEGAVFNKSLSGSQTSSAWSNLSGFSSSASWEEVNY
HVDDRSARKEPGKEHLVDTQCSTALSEELENDREGRAMHSLHSQLHDLSLQEPNNDNLEPSQNOPQ
QQMPLTPFSPHNTPGIFLAPGAGLLEGAPEGIQEVRNMGPRNTSAHSRPSYRSASWSSDSGRPKNMG
THPSVQKEEAFEIVEFPETNCDVKIDRQGKEQGEEISERGAGPTFKASPSWVDPEGETAESTEDAPLD
FHRVLHNSLGNISMLPCSSFTPNWPVQNPDSRKSGGPVAEQGIDPDASTVDEEGQLLDSMDVPCTNG
HGSHRLCILRQPPGQRAETPNSSVSGNILFPVLSEDCTTEEGNQPGNMLNCSQNSSSSVWLKSP
AFSSGSSEGDSPWSYLNSSGSSWVSLPGKMRKEILEARTLQPDDFEKLLAGVRHDWLFQRLENTGV
FKPSQLHRAHSALLLKYSKKSELWTAQETIVYLGDYLTVKKKGRQRNAFWVHIILHQEEILGRYVG
KDYKEQKGLWHHFTDVERQMTAQHYVTEFNKRLYEQNIPTQIFYIPSTILLILEDKTIKGCISVEPYI
LGEFVKLSNNTKVVKTEYKATEYGLAYGHFSYEFSNHRDVVVDLQGWVTGNGKGLIYLTDPQIIHSV
DQKVFTTNFGKRGIFYFFNNQHVECNEICHRLSLTRPSMEKP

SEQUENCE LISTING

<160> NUMBER OF SEQ ID NOS: 45

<210> SEQ ID NO 1
<211> LENGTH: 238
<212> TYPE: PRT
<213> ORGANISM: Homo sapiens

<400> SEQUENCE: 1

Gly Glu Trp Leu Asp Asp Glu Val Leu Ile Lys Met Ala Ser Gln Pro
1               5                   10                  15

Phe Gly Arg Gly Ala Met Arg Glu Cys Phe Arg Thr Lys Lys Leu Ser
            20                  25                  30

Asn Phe Leu His Ala Gln Gln Trp Lys Gly Ala Ser Asn Tyr Val Ala
        35                  40                  45

Lys Arg Tyr Ile Glu Pro Val Asn Arg Asp Val Tyr Phe Glu Asp Val
    50                  55                  60

Arg Leu Gln Met Glu Ala Lys Leu Trp Gly Asp Tyr Asn Arg His
65                  70                  75                  80

Lys Pro Pro Lys Gln Val Asp Ile Met Gln Met Cys Ile Ile Glu Leu
                85                  90                  95

Lys Asp Arg Pro Gly Lys Pro Leu Phe His Leu Asp His Tyr Ile Asp
            100                 105                 110

Gly Lys Tyr Ile Lys Tyr Asn Ser Asn Ser Gly Phe Val Arg Asp Asp
        115                 120                 125

Asn Ile Arg Leu Thr Pro Gln Ala Phe Ser His Phe Thr Phe Glu Arg
    130                 135                 140

Ser Gly His Gln Leu Ile Val Val Asp Ile Gln Gly Val Gly Asp Leu
145                 150                 155                 160

Tyr Thr Asp Pro Gln Ile His Thr Glu Thr Gly Thr Asp Phe Gly Asn
                165                 170                 175

Gly Asn Leu Gly Val Arg Gly Met Ala Leu Phe Phe Tyr Ser His Ala
            180                 185                 190

Cys Asn Arg Ile Cys Glu Ser Met Gly Leu Ala Pro Phe Asp Leu Ser
        195                 200                 205

Pro Arg Glu Arg Asp Ala Val Asn Gln Asn Thr Lys Leu Leu Gln Ser
    210                 215                 220

Ala Lys Thr Ile Leu Arg Gly Thr Asp Asp Lys Cys Gly Ser
225                 230                 235

<210> SEQ ID NO 2
<211> LENGTH: 233
<212> TYPE: PRT
<213> ORGANISM: C. elegans

<400> SEQUENCE: 2

Leu Gln Trp Thr Glu Asp Ile Val Asp Val Arg Leu His Pro Asp Ser
1               5                   10                  15

Phe Ala Arg Gly Ala Met Arg Glu Cys Tyr Arg Leu Lys Lys Cys Ser
            20                  25                  30

Lys His Gly Thr Ser Gln Asp Trp Ser Ser Asn Tyr Val Ala Lys Arg
        35                  40                  45

Tyr Ile Cys Gln Val Asp Arg Arg Val Leu Phe Asp Val Arg Leu
    50                  55                  60

Gln Met Asp Ala Lys Leu Trp Ala Glu Glu Tyr Asn Arg Tyr Asn Pro
65                  70                  75                  80

```
Pro Lys Lys Ile Asp Ile Val Gln Met Cys Val Ile Glu Met Ile Asp
                85                  90                  95
Val Lys Gly Ser Pro Leu Tyr His Leu Glu His Phe Ile Glu Gly Lys
            100                 105                 110
Tyr Ile Lys Tyr Asn Ser Asn Ser Gly Phe Val Ser Asn Ala Ala Arg
        115                 120                 125
Leu Thr Pro Gln Ala Phe Ser His Phe Thr Phe Glu Arg Ser Gly His
    130                 135                 140
Gln Met Met Val Val Asp Ile Gln Gly Val Gly Asp Leu Tyr Thr Asp
145                 150                 155                 160
Pro Gln Ile His Thr Val Val Gly Thr Asp Tyr Gly Asp Gly Asn Leu
                165                 170                 175
Gly Ile Arg Gly Met Ala Leu Phe His Ser His Arg Cys Asn Asp
            180                 185                 190
Ile Cys Glu Thr Met Asp Leu Ser Asn Phe Glu Leu Ser Pro Pro Glu
        195                 200                 205
Ile Glu Ala Thr Glu Val Ala Met Glu Val Ala Ala Lys Gln Lys Lys
    210                 215                 220
Ser Cys Ile Val Pro Pro Thr Val Phe
225                 230

<210> SEQ ID NO 3
<211> LENGTH: 259
<212> TYPE: PRT
<213> ORGANISM: Dictyostelium discoideum

<400> SEQUENCE: 3

Asn Lys Trp Ile Arg Leu Ser Met Lys Leu Lys Val Glu Arg Lys Pro
1               5                   10                  15
Phe Ala Glu Gly Ala Leu Arg Glu Ala Tyr His Thr Val Ser Leu Gly
            20                  25                  30
Val Gly Thr Asp Glu Asn Tyr Asp Pro Leu Gly Thr Thr Lys Leu
        35                  40                  45
Phe Pro Pro Ile Glu Met Ile Ser Pro Ile Ser Lys Asn Asn Gly Ala
    50                  55                  60
Met Thr Gln Leu Lys Asn Gly Thr Lys Phe Val Leu Lys Leu Tyr Lys
65                  70                  75                  80
Lys Glu Ala Glu Gln Gln Ala Ser Arg Glu Leu Tyr Phe Glu Asp Val
                85                  90                  95
Lys Met Gln Met Val Cys Arg Asp Trp Gly Asn Lys Phe Asn Gln Lys
            100                 105                 110
Lys Pro Pro Lys Lys Ile Glu Phe Leu Met Ser Trp Val Val Glu Leu
        115                 120                 125
Ile Asp Arg Ser Pro Ser Ser Asn Gly Gln Pro Ile Leu Cys Ser Ile
    130                 135                 140
Glu Pro Leu Leu Val Gly Glu Phe Lys Lys Asn Asn Ser Asn Tyr Gly
145                 150                 155                 160
Ala Val Leu Thr Asn Arg Ser Thr Pro Gln Ala Phe Ser His Phe Thr
                165                 170                 175
Tyr Gly Leu Ser Asn Lys Gln Met Ile Val Asp Ile Gln Gly Val
            180                 185                 190
Asp Asp Leu Tyr Thr Asp Pro Gln Ile His Thr Pro Asp Gly Lys Gly
        195                 200                 205
Phe Gly Leu Gly Asn Leu Gly Lys Ala Gly Ile Asn Lys Phe Ile Thr
```

```
                210                 215                 220
Thr His Lys Cys Asn Ala Val Cys Ala Leu Leu Asp Leu Asp Val Lys
225                 230                 235                 240

Leu Gly Gly Val Leu Ser Gly Asn Asn Lys Lys Gln Leu Gln Gln Gly
                245                 250                 255

Thr Met Val

<210> SEQ ID NO 4
<211> LENGTH: 212
<212> TYPE: PRT
<213> ORGANISM: Dictyostelium discoideum

<400> SEQUENCE: 4

Ala Gln Trp Thr Cys Thr Ala Thr Leu Val Lys Val Glu Pro Val Pro
1               5                   10                  15

Phe Ala Glu Gly Ala Phe Arg Lys Ala Tyr His Thr Leu Asp Leu Ser
                20                  25                  30

Lys Ser Gly Ala Ser Gly Arg Tyr Val Ser Lys Ile Gly Lys Lys Pro
            35                  40                  45

Thr Pro Arg Pro Ser Tyr Phe Glu Asp Val Lys Met Gln Met Ile Ala
        50                  55                  60

Lys Lys Trp Ala Asp Lys Tyr Asn Ser Phe Lys Pro Pro Lys Lys Ile
65                  70                  75                  80

Glu Phe Leu Gln Ser Cys Val Leu Glu Phe Val Asp Arg Thr Ser Ser
                85                  90                  95

Asp Leu Ile Cys Gly Ala Glu Pro Tyr Val Glu Gly Gln Tyr Arg Lys
                100                 105                 110

Tyr Asn Asn Ser Gly Phe Val Ser Asn Asp Glu Arg Asn Thr Pro
            115                 120                 125

Gln Ser Phe Ser His Phe Thr Tyr Glu His Ser Asn His Gln Leu Leu
130                 135                 140

Ile Ile Asp Ile Gln Gly Val Gly Asp His Tyr Thr Asp Pro Gln Ile
145                 150                 155                 160

His Thr Tyr Asp Gly Val Gly Phe Gly Ile Gly Asn Leu Gly Gln Lys
                165                 170                 175

Gly Phe Glu Lys Phe Leu Asp Thr His Lys Cys Asn Ala Ile Cys Gln
            180                 185                 190

Tyr Leu Asn Leu Gln Ser Ile Asn Pro Lys Ser Glu Lys Ser Asp Cys
        195                 200                 205

Gly Thr Val Pro
    210

<210> SEQ ID NO 5
<211> LENGTH: 2178
<212> TYPE: DNA
<213> ORGANISM: Homo sapiens

<400> SEQUENCE: 5
atggcagacg aagacctcat cttccgcctg gaaggtgttg atggcggcca gtcccccga      60 gctggccatg atggtgattc tgatggggac agcgacgatg aggaaggtta cttcatctgc    120
cccatcacgg atgacccaag ctcgaaccag aatgtcaatt ccaaggttaa taagtactac    180
agcaacctaa caaaaagtga gcggtatagc tccagcgggt ccccggcaaa ctccttccac    240
ttcaaggaag cctggaagca cgcaatccag aaggccaagc acatgccgga cccctgggct    300
gagttccacc tggaagatat tgccaccgaa cgtgctactc gacacaggta caacgccgtc    360
```

-continued

```
accggggaat ggctggatga tgaagttctg atcaagatgg catctcagcc cttcggccga      420
ggagcaatga gggagtgctt ccggacgaag aagctctcca acttcttgca tgcccagcag      480
tggaagggcg cctccaacta cgtggcgaag cgctacatcg agcccgtaga ccgggatgtg      540
tactttgagg acgtgcgtct acagatggag gccaagctct gggggagga gtataatcgg      600
cacaagcccc ccaagcaggt ggacatcatg cagatgtgca tcatcgagct gaaggacaga      660
ccgggcaagc ccctcttcca cctggagcac tacatcgagg gcaagtacat caagtacaac      720
tccaactctg gctttgtccg tgatgacaac atccgactga cgccgcaggc cttcagccac      780
ttcacttttg agcgttccgg ccatcagctg atagtggtgg acatccaggg agttggggat      840
ctctacactg acccacagat ccacacggag acgggcactg actttggaga cggcaaccta      900
ggtgtccgcg ggatggcgct cttcttctac tctcatgcct gcaaccggat ttgcgagagc      960
atgggccttg ctccctttga cctctcgccc cgggagaggg atgcagtgaa tcagaacacc     1020
aagctgctgc aatcagccaa gaccatcttg agaggaacag aggaaaaatg tgggagcccc     1080
cgagtaagga ccctctctgg gagccggcca cccctgctcc gtccccttc agagaactct      1140
ggagacgaga acatgagcga cgtgaccttc gactctctcc cttcttcccc atcttcggcc     1200
acaccacaca gccagaagct agaccacctc cattggccag tgttcagtga cctcgataac     1260
atggcatcca gagaccatga tcatctagac aaccaccggg agtctgagaa tagtggggac     1320
agcggatacc ccagtgagaa gcggggtgag ctggatgacc ctgagccccg agaacatggc     1380
cactcataca gtaatcggaa gtacgagtct gacgaagaca gcctgggcag ctctggacgg     1440
gtatgtgtag agaagtggaa tctcctcaac tcctcccgcc tccacctgcc gagggcttcg     1500
gccgtggccc tggaagtgca aaggcttaat gctctgacc tcgaaaagaa atcgggaag      1560
tccattttgg ggaaggtcca tctggccatg gtgcgctacc acgagggtgg gcgcttctgc     1620
gagaagggcg aggagtggga ccaggagtcg gctgtcttcc acctggagca cgcagccaac     1680
ctgggcgagc tggaggccat cgtgggcctg ggactcatgt actcgcagtt gcctcatcac     1740
atcctagccg atgtctctct gaaggagaca gaagagaaca aaaccaaagg atttgattac     1800
ttactaaagg ccgctgaagc tggcgacagg cagtccatga tcctagtggc gcgagctttt     1860
gactctggcc agaacctcag cccggacagg tgccaagact ggctagaggc cctgcactgg     1920
tacaacactg ccctggagat gacggactgt gatgagggcg gtgagtacga cggaatgcag     1980
gacgagcccc ggtacatgat gctggccagg gaggcagaga tgctgttcac aggaggctac     2040
gggctggaga aggacccgca gagatcaggg gacttgtata cccaggcagc agaggcagcg     2100
atggaagcca tgaagggccg actggccaac cagtactacc aaaaggctga gaggcctggg     2160
gcccagatgg aggaataa                                                    2178
```

<210> SEQ ID NO 6
<211> LENGTH: 724
<212> TYPE: PRT
<213> ORGANISM: Homo sapiens

<400> SEQUENCE: 6

```
Met Ala Asp Glu Asp Leu Ile Phe Arg Leu Glu Gly Val Asp Gly Gly
1               5                   10                  15

Gln Ser Pro Arg Ala Gly His Asp Gly Asp Ser Asp Gly Asp Ser Asp
                20                  25                  30

Asp Glu Glu Gly Tyr Phe Ile Cys Pro Ile Thr Asp Asp Pro Ser Ser
            35                  40                  45
```

```
Asn Gln Asn Val Asn Ser Lys Val Asn Lys Tyr Tyr Ser Asn Leu Thr
     50                  55                  60

Lys Ser Glu Arg Tyr Ser Ser Gly Ser Pro Ala Asn Ser Phe His
 65                  70                  75                  80

Phe Lys Glu Ala Asn Lys His Ala Ile Gln Lys Ala Lys His Met Pro
                 85                  90                  95

Asp Pro Trp Ala Glu Phe His Leu Glu Asp Ile Ala Thr Glu Arg Ala
                100                 105                 110

Thr Arg His Arg Tyr Asn Ala Val Thr Gly Glu Trp Leu Asp Asp Glu
            115                 120                 125

Val Leu Ile Lys Met Ala Ser Gln Pro Phe Gly Arg Gly Ala Met Arg
    130                 135                 140

Glu Cys Phe Arg Thr Lys Lys Leu Ser Asn Phe Leu His Ala Gln Gln
145                 150                 155                 160

Trp Lys Gly Ala Ser Asn Tyr Val Ala Lys Arg Tyr Ile Glu Pro Val
                165                 170                 175

Asp Arg Asp Val Tyr Phe Glu Asp Val Arg Leu Gln Met Glu Ala Lys
            180                 185                 190

Leu Trp Gly Glu Glu Tyr Asn Arg His Lys Pro Lys Gln Val Asp
    195                 200                 205

Ile Met Gln Met Cys Ile Ile Glu Leu Lys Asp Arg Pro Gly Lys Pro
    210                 215                 220

Leu Phe His Leu Glu His Tyr Ile Glu Gly Lys Tyr Ile Lys Tyr Asn
225                 230                 235                 240

Ser Asn Ser Gly Phe Val Arg Asp Asp Asn Ile Arg Leu Thr Pro Gln
                245                 250                 255

Ala Phe Ser His Phe Thr Phe Glu Arg Ser Gly His Gln Leu Ile Val
            260                 265                 270

Val Asp Ile Gln Gly Val Gly Asp Leu Tyr Thr Asp Pro Gln Ile His
    275                 280                 285

Thr Glu Thr Gly Thr Asp Phe Gly Asp Gly Asn Leu Gly Val Arg Gly
    290                 295                 300

Met Ala Leu Phe Phe Tyr Ser His Ala Cys Asn Arg Ile Cys Glu Ser
305                 310                 315                 320

Met Gly Leu Ala Pro Phe Asp Leu Ser Pro Arg Glu Arg Asp Ala Val
                325                 330                 335

Asn Gln Asn Thr Lys Leu Leu Gln Ser Ala Lys Thr Ile Leu Arg Gly
            340                 345                 350

Thr Glu Glu Lys Cys Gly Ser Pro Arg Val Arg Thr Leu Ser Gly Ser
            355                 360                 365

Arg Pro Pro Leu Leu Arg Pro Leu Ser Glu Asn Ser Gly Asp Gly Asn
    370                 375                 380

Met Ser Asp Val Thr Pro Asp Ser Leu Pro Ser Ser Pro Ser Ser Ala
385                 390                 395                 400

Thr Pro His Ser Gln Lys Leu Asp His Leu His Trp Pro Val Phe Ser
            405                 410                 415

Asp Leu Asp Asn Met Ala Ser Arg Asp His Asp His Leu Asp Asn His
                420                 425                 430

Arg Glu Ser Glu Asn Ser Gly Asp Ser Gly Tyr Pro Ser Glu Lys Arg
            435                 440                 445

Gly Glu Leu Asp Asp Pro Glu Pro Arg Glu His Gly His Ser Tyr Ser
    450                 455                 460
```

```
Asn Arg Lys Tyr Gly Ser Asp Glu Asp Ser Leu Gly Ser Ser Gly Arg
465                 470                 475                 480

Val Cys Val Glu Lys Trp Asn Leu Leu Asn Ser Ser Arg Leu His Leu
                485                 490                 495

Pro Arg Ala Ser Ala Val Ala Leu Glu Val Gln Arg Leu Asn Ala Leu
            500                 505                 510

Asp Leu Glu Lys Lys Ile Gly Lys Ser Ile Leu Gly Asp Val His Leu
        515                 520                 525

Ala Met Val Arg Tyr His Glu Gly Gly Arg Phe Cys Glu Lys Gly Glu
    530                 535                 540

Glu Trp Asp Gln Glu Ser Ala Val Phe His Leu Glu His Ala Ala Asn
545                 550                 555                 560

Leu Gly Glu Leu Glu Ala Ile Val Gly Leu Gly Leu Met Tyr Ser Gln
                565                 570                 575

Leu Pro His His Ile Leu Ala Asp Val Ser Leu Lys Glu Thr Glu Glu
            580                 585                 590

Asn Lys Thr Lys Gly Phe Asp Tyr Leu Leu Lys Ala Ala Glu Ala Gly
        595                 600                 605

Asp Arg Gln Ser Met Ile Leu Val Ala Arg Ala Phe Asp Ser Gly Gln
    610                 615                 620

Asn Leu Ser Pro Asp Arg Cys Gln Asp Trp Leu Glu Ala Leu His Trp
625                 630                 635                 640

Tyr Asn Thr Ala Leu Glu Met Thr Asp Cys Asp Glu Gly Gly Glu Tyr
                645                 650                 655

Asp Gly Met Gln Asp Glu Arg Tyr Met Met Leu Ala Arg Glu Ala Glu
            660                 665                 670

Met Leu Phe Thr Gly Gly Tyr Gly Leu Glu Lys Asp Pro Gln Arg Ser
        675                 680                 685

Gly Asp Leu Tyr Thr Gln Ala Ala Glu Ala Ala Met Glu Ala Met Lys
    690                 695                 700

Gly Arg Leu Ala Asn Gln Tyr Tyr Gln Lys Ala Glu Glu Ala Trp Ala
705                 710                 715                 720

Gln Met Glu Glu

<210> SEQ ID NO 7
<211> LENGTH: 2175
<212> TYPE: DNA
<213> ORGANISM: Mus musculus

<400> SEQUENCE: 7
atggcagacg aagacctcat cttctgcctg gaaggtgttg acggtggcag gtgctcccga      60
gctggccaca atgcggactc tgacacagac agtgacgatg atgagggcta tttcatctgc     120
cccatcactg atgaccacat gtccaatcag aatgtcagct ccaaagtcca gagctactat     180
agcaacctaa caaaaacaga gtgcggctcc acagggtcac cagccagctc cttccacttc     240
aaggaagcct ggaagcatgc gatcgagaaa gccaagcaca tgcctgaccc ctgggctgaa     300
ttccatctcg aggacatcgc cacagaacat gctactcggc acaggtacaa cgctgtcacc     360
ggggaatggc tgaaagacga ggttctgatc aagatggcgt ctcagccctt cggccgtgga     420
gcaatgaggg agtgcttcag gacgaagaaa ctctccaact tcttgcacgc ccagcaatgg     480
aagggggcct ccaactacgt ggccaagcgc tacatcgagc cggtggacag gagcgtgtac     540
tttgaggatg tgcagctcca gatggaggcg aagctctggg gggaggatta caatcggcac     600 aagccccccca agcaggtgga tatcatgcag atgtgcatca ttgagctaaa ggacagacca     660
```

```
ggccagcccc tcttccactt ggagcactac attgagggca agtacatcaa gtacaattcc    720
aactcaggct ttgtccgtga tgacaacatc cgactaaccc cacaggcctt cagccatttc    780
acatttgagc gttctggtca tcagctgatt gtagtggaca tccagggtgt gggtgacctt    840
tataccgacc cacagatcca cactgagaaa ggcactgact ttggagatgg taaccttggt    900
gtccggggaa tggctctctt cttctactct catgcctgca accggatttg tcagagcatg    960
ggccttacgc cctttgacct ctccccacgg gaacaggatg cggtgaatca gagcaccagg   1020
ctattgcaat cagccaagac catcttgagg gggacagagg agaagtgtgg gagtccccgc   1080
ataaggacac tctctagcag ccggcccccct tgctccttc gcctgtcaga gaactccggg   1140
gatgagaaca tgagtgacgt gacctttgac tctctgcctt cctccccgtc ttcagctaca   1200
ccacacagcc agaaactgga ccacctccat tggccagtgt ttggtgacct cgataacatg   1260
ggccctagag accatgaccg tatggacaat caccgggact ctgagaatag tggggacagt   1320
gggtatccaa gcgagaagcg aagtgacctg gatgatcctg agccccgaga cacggccac    1380 tccaacggca accgaaggca tgaatctgac gaggatagcc tgggcagctc tggacgggtc   1440
tgtgtggaga cgtggaacct gctcaatccc tcccgcctgc acctgccgag ccctcggcc    1500 gtggccctag aagtgcagag gctaaatgcc ctggaccttg aaggaaaat cgggaagtct   1560 gttttgggga aagtccattt ggccatggtg cgataccacg agggcgggcg cttctgcgag   1620
aaggatgagg agtgggatcg agagtcagcc atcttccatc tggagcatgc agctgacctg   1680
ggagaactgg aggccatcgt gggcctaggc ctcatgtact ctcagctgcc ccaccacatc   1740
ctggctgatg tctctctgaa ggagacagag gagaacaaga caaaaggctt tgattactta   1800
ctgaaggcgc agaagctgg tgacaggcat tccatgattt tagtggcccg agcttttgac   1860
actggcctga acctcagccc agacaggtgt caagactggt cggaagcctt gcactggtac   1920
aacacagccc tggagacaac agactgcgat gaaggcgggg agtacgatgg gatacaggac   1980
gagccccagt acgcactgct ggccagggag gcggagatgc tgctcaccgg gggatttgga   2040
ctggacaaga accccaaag atcaggagat ttgtacaccc aggcagctga ggcagcaatg   2100
gaagccatga agggccggct agccaaccag tactacgaga aggcggaaga ggcctgggcc   2160
cagatggagg aataa                                                    2175
```

<210> SEQ ID NO 8
<211> LENGTH: 725
<212> TYPE: PRT
<213> ORGANISM: Mus musculus

<400> SEQUENCE: 8

```
Met Ala Asp Glu Asp Leu Ile Phe Cys Leu Glu Gly Val Asp Gly
1               5                   10                  15

Arg Cys Ser Arg Ala Gly His Asn Ala Asp Ser Asp Thr Asp Ser Asp
            20                  25                  30

Asp Asp Glu Gly Tyr Phe Ile Cys Pro Ile Thr Asp Asp His Met Ser
        35                  40                  45

Asn Gln Asn Val Ser Ser Lys Val Gln Ser Tyr Tyr Ser Asn Leu Thr
    50                  55                  60

Lys Thr Glu Leu Cys Gly Ser Thr Gly Ser Pro Ala Ser Ser Phe His
65                  70                  75                  80

Phe Lys Glu Ala Trp Lys His Ala Ile Glu Lys Ala Lys His Met Pro
                85                  90                  95
```

-continued

```
Asp Pro Trp Ala Glu Phe His Leu Glu Asp Ile Ala Thr Glu His Ala
            100                 105                 110

Thr Arg His Arg Tyr Asn Ala Val Thr Gly Glu Trp Leu Lys Asp Glu
        115                 120                 125

Val Leu Ile Lys Met Ala Ser Gln Pro Phe Gly Arg Gly Ala Met Arg
    130                 135                 140

Glu Cys Phe Arg Thr Lys Lys Leu Ser Asn Phe Leu His Ala Gln Gln
145                 150                 155                 160

Trp Lys Gly Ala Ser Asn Tyr Val Ala Lys Arg Tyr Ile Glu Pro Val
                165                 170                 175

Asp Arg Ser Val Tyr Phe Glu Asp Val Gln Leu Gln Met Glu Ala Lys
            180                 185                 190

Leu Trp Gly Glu Asp Tyr Asn Arg His Lys Pro Pro Lys Gln Val Asp
        195                 200                 205

Ile Met Gln Met Cys Ile Ile Glu Leu Lys Asp Arg Pro Gly Gln Pro
    210                 215                 220

Leu Phe His Leu Glu His Tyr Ile Glu Gly Lys Tyr Ile Lys Tyr Asn
225                 230                 235                 240

Ser Asn Ser Gly Phe Val Arg Asp Asn Ile Arg Leu Thr Pro Gln
                245                 250                 255

Ala Phe Ser His Phe Thr Phe Glu Arg Ser Gly His Gln Leu Ile Val
            260                 265                 270

Val Asp Ile Gln Gly Val Gly Asp Leu Tyr Thr Asp Pro Gln Ile His
    275                 280                 285

Thr Glu Lys Gly Thr Asp Phe Gly Asp Gly Asn Leu Gly Val Arg Gly
    290                 295                 300

Met Ala Leu Phe Phe Tyr Ser His Ala Cys Asn Arg Ile Cys Gln Ser
305                 310                 315                 320

Met Gly Leu Thr Pro Phe Asp Leu Ser Pro Arg Glu Gln Asp Ala Val
                325                 330                 335

Asn Gln Ser Thr Arg Leu Leu Gln Ser Ala Lys Thr Ile Leu Arg Gly
            340                 345                 350

Thr Glu Glu Lys Cys Gly Ser Pro Arg Ile Arg Thr Leu Ser Ser Ser
        355                 360                 365

Arg Pro Pro Leu Leu Arg Leu Ser Glu Asn Ser Gly Asp Glu Asn
    370                 375                 380

Met Ser Asp Val Thr Phe Asp Ser Leu Pro Ser Ser Pro Ser Ser Ala
385                 390                 395                 400

Thr Pro His Ser Gln Lys Leu Asp His Leu His Trp Pro Val Phe Gly
                405                 410                 415

Asp Leu Asp Asn Met Gly Pro Arg Asp His Asp Arg Met Asp Asn His
            420                 425                 430

Arg Asp Ser Glu Asn Ser Gly Asp Ser Gly Tyr Pro Ser Glu Lys Arg
        435                 440                 445

Ser Asp Leu Asp Asp Pro Glu Pro Arg Glu His Gly His Ser Asn Gly
    450                 455                 460

Asn Arg Arg His Glu Ser Asp Glu Asp Ser Leu Gly Ser Ser Gly Arg
465                 470                 475                 480

Val Cys Val Glu Thr Trp Asn Leu Leu Asn Pro Ser Arg Leu His Leu
                485                 490                 495

Pro Arg Pro Ser Ala Val Ala Leu Glu Val Gln Arg Leu Asn Ala Leu
            500                 505                 510

Asp Leu Gly Arg Lys Ile Gly Lys Ser Val Leu Gly Lys Val His Leu
```

```
                    515              520              525
Ala Met Val Arg Tyr His Glu Gly Gly Arg Phe Cys Glu Lys Asp Glu
        530              535              540

Glu Trp Asp Arg Glu Ser Ala Ile Phe His Leu Glu His Ala Ala Asp
545             550              555              560

Leu Gly Glu Leu Glu Ala Ile Val Gly Leu Gly Leu Met Tyr Ser Gln
                565              570              575

Leu Pro His His Ile Leu Ala Asp Val Ser Leu Lys Glu Thr Glu Glu
            580              585              590

Asn Lys Thr Lys Gly Phe Asp Tyr Leu Leu Lys Ala Ala Glu Ala Gly
        595              600              605

Asp Arg His Ser Met Ile Leu Val Ala Arg Ala Phe Asp Thr Gly Leu
    610              615              620

Asn Leu Ser Pro Asp Arg Cys Gln Asp Trp Ser Glu Ala Leu His Trp
625             630              635              640

Tyr Asn Thr Ala Leu Glu Thr Thr Asp Cys Thr Glu Gly Gly Glu Tyr
                645              650              655

Asp Gly Ile Gln Asp Glu Pro Gln Tyr Ala Leu Leu Ala Arg Glu Ala
            660              665              670

Glu Met Leu Leu Thr Gly Gly Phe Gly Leu Asp Lys Asn Pro Gln Arg
        675              680              685

Ser Gly Asp Leu Tyr Thr Gln Ala Ala Glu Ala Ala Met Glu Ala Met
    690              695              700

Lys Gly Arg Leu Ala Asn Gln Tyr Tyr Gly Lys Ala Glu Glu Ala Trp
705             710              715              720

Ala Gln Met Glu Glu
            725

<210> SEQ ID NO 9
<211> LENGTH: 3465
<212> TYPE: DNA
<213> ORGANISM: Dictyostelium discoideum

<400> SEQUENCE: 9
atgtttaata taaaaaagag aaaagagagt ataacaggta taccaccaat aaatgttaat       60
agtccacaat cagttccatt gagtggaaca ttgcaatcac cattgattac accaaattca      120
ccaaattttg tttcacgtca atgtccattc aaaaagtttg gatgtagtag ttttttagtt      180
tcaaaggcag agtttgataa tcacttaaag gatgacgcac aatttcattt acaattggca      240
gtggagaaat ttgatcatca atttgattta cacacacaat tgatggcaca ttttactgag      300
caaatggagg atcaattaga gaaaacaatg aaggtcgtac gtaatcatac agatagttta      360
ggcggtaatg ttcaaaccaa attggatgaa ggcattgaaa aatgtatggc ttttgctaaa      420
aaggttgaac aacaacaaca acaattggcc aaaagattaa tcactcaaca aattcaagag      480
aagaaatcaa cctcttcacc tttagttaaa ggtggtatta gtggtggtgg tggtagtggt      540
ggcgatgatt cttttgatgg cgcaaatata tcatcaatgt caactagtaa acaagaatta      600
caacaagaat tacaatcatt atcaattaaa atgaaaaaag aattgacaga attatccgat      660
gaactatcac aaaaattaga acgttcaaca ggtaatatag atattaaaat aaagagaatc      720
gaaggtgaag ttaatgaaaa gattgataaa cgtcaattgg tctctacgat cgatgattca      780
attggaaaga aaacagattc catcggttat acattggaga gttcaatcat taaaaaggtt      840
gaagagaaag agaaaaagaa atccgaacaa atcaacttct ctttgattca aagattgaa       900
```

```
tccttaaaag ataagattaa aatcattgaa actcaacaat tggatacttc atcagaggtt      960
agaaaattga aattagaaag tacaagtagt ggaaatttaa tggcaggtct taatggtacc     1020
tctggtagac cttcatcatc ttctcacttt attccatcct ctgtttctgc cgctgctaac     1080
aatatcaaca agaatgaaat catggaagag gttaaaaagg tagaagagaa acttcaaaag     1140
aaaattcgtg aagagattga taatacaaaa gctgaactct caaaggttga acgttccgtt     1200
aaagataatc gtagtgaaat tgaaggtttg gaaaaagatt gtaagaatca attcgataaa     1260
caagacaata agatcaaaca agttgaggat gatttgaaaa agagtgattc attactttg      1320
ttaatgcaaa ataacctcaa gaaatataat gaatttgttg atagagaacg tgatcgtgaa     1380
agtgaacgtt tgaaacttca agattctatc aaacgtttag aacaaaatca aagaaaaatc     1440
gaagctgaaa ttcaagaagg taatgaacaa gttgaacgtg ttttacgtga ggaagcttca     1500
atctcaccaa ttagttcagt tccaaaatca ccaatcacaa ccaaacgttc atcgattatt     1560
ttaaattcac caccaatgac ttcacaacaa tcatcaccaa agattcaaga tcttctctca     1620
agtagtggta gtagtagtgt tagtggtata aatatttcct ctgaaaccgg tgaaatgggt     1680
attctttggg aatttgatcc aatcattaac aaatggatta gattatcaat gaagctaaag     1740
gtagaaagaa aaccatttgc agagggtgct cttagagagg cttatcatac cgtttcattg     1800
ggtgttggaa ccgatgaaaa ttatccatta ggtacaacca ccaaattatt cccaccaatt     1860
gaaatgattt caccaatttc aaagaataat gaggcaatga ctcaattgaa gaatggtaca     1920
aaatttgttt tgaaactcta caaaaaggaa gctgaacaac aagctagcag agaattatac     1980
tttgaagatg ttaaaatgca aatggtctgt agagattggg gtaataaatt caatcaaaag     2040
aaaccaccaa agaaaattga attccttatg tcttgggttg tagagttaat cgatagatct     2100
ccttcttcca atggtcaacc aatactttgt tccattgaac cattattggt tggtgaattc     2160
aaaaagaata attcaaatta tggtgcagtt ttaaccaatc gttcaactcc acaagcattc     2220
tctcatttca cctatgaact ctcaaataaa caaatgatcg ttgtcgatat tcaaggtgtt     2280
gatgatcttt acactgatcc tcaaattcat acacccgatg gtaaaggatt tggtcttggt     2340
aatcttggta aagcaggtat caataaattc atcaccactc acaaatgtaa tgctgtttgt     2400
gctctttag atttagatgt taaattgggt ggtgtactat ctggaaataa taagaaacaa      2460
cttcaacaag gtactatggt tatgccagat attctcccag aacttatgcc atctgataac     2520
accattaaag tgggtgcaaa acaacttcca aaagctgaat tctcaaagaa agatctcaaa     2580
tgtgttagca ccattcaaag ttttccgtgaa cgtgttaact cgatcgcatt ctttgataat      2640
caaaagttat tatgcgctgg ttatggtgat ggtacctata gagttttcga tgtcaatgac     2700
aattggaaat gtttatacac tgtcaatggt catagaaaat caattgaaag tatcgcttgt     2760
aatagtaatt acattttcac ttcatcacct gataacacca tcaaagttca tatcattcgt     2820
agtggtaaca ccaaatgtat agagacattg gttggtcaca ctggtgaagt taattgtgtc     2880
gtggccaatg aaaaatatct tttcagttgt agttatgata aaactatcaa ggtttgggat     2940
ttgtcaacct ttaagaaat taatcatttt gagggtgttc atacaaagta cattaaaaca      3000
ttggctttga gtggacgtta tcttttttagt ggtggtaacg atcaaatcat ttacgtttgg     3060
gatactgaaa cacttagtat gcttttcaat atgcaaggtc atgaagattg ggtactctct     3120
cttcattgta ccgctagtta tcttttctca acctcaaaag ataatgtcat caagatttgg     3180
gatctctcaa atttcagttg tatcgatact ctaaaaggtc attggaattc tgtctcaagt     3240
tgtgtcgtaa aagatcgtta tctatacagt ggttctgaag ataattcaat caaagtttgg     3300
```

```
gatctcgata cacttgaatg tgtttacacc attccaaaat ctcattcttt gggtgtaaaa    3360
tgtttaatgg ttttcaataa tcaaatcatt tctgctgctt tcgatggttc aattaaagtt    3420
tgggaatggc aatcgaaata atctttgtaa attttttgtta aaaaa                   3465
```

<210> SEQ ID NO 10
<211> LENGTH: 1146
<212> TYPE: PRT
<213> ORGANISM: Dictyostelium discoideum

<400> SEQUENCE: 10

```
Met Phe Asn Ile Lys Lys Arg Lys Glu Ser Ile Thr Gly Ile Pro Pro
1               5                   10                  15

Ile Asn Val Asn Ser Pro Gln Ser Val Pro Leu Ser Gly Thr Leu Gln
            20                  25                  30

Ser Pro Leu Ile Thr Pro Asn Ser Pro Asn Phe Val Ser Arg Gln Cys
        35                  40                  45

Pro Phe Lys Lys Phe Gly Cys Ser Ser Phe Leu Val Ser Lys Ala Glu
    50                  55                  60

Phe Asp Asn His Leu Lys Asp Asp Ala Gln Phe His Leu Gln Leu Ala
65                  70                  75                  80

Val Glu Lys Phe Asp His Gln Phe Asp Leu His Thr Gln Leu Met Ala
                85                  90                  95

His Phe Thr Glu Gln Met Glu Asp Gln Leu Glu Lys Thr Met Lys Val
            100                 105                 110

Val Arg Asn His Thr Asp Ser Leu Gly Gly Asn Val Gln Thr Lys Leu
        115                 120                 125

Asp Glu Gly Ile Glu Lys Cys Met Ala Phe Ala Lys Lys Val Glu Gln
    130                 135                 140

Gln Gln Gln Gln Leu Ala Lys Arg Leu Ile Thr Gln Gln Ile Gln Glu
145                 150                 155                 160

Lys Lys Ser Thr Ser Ser Pro Leu Val Lys Gly Gly Ile Ser Gly Gly
                165                 170                 175

Gly Gly Ser Gly Gly Asp Asp Ser Phe Asp Gly Ala Asn Ile Ser Ser
            180                 185                 190

Met Ser Thr Ser Lys Gln Glu Leu Gln Gln Glu Leu Gln Ser Leu Ser
        195                 200                 205

Ile Lys Met Lys Lys Glu Leu Thr Glu Leu Ser Asp Glu Leu Ser Gln
    210                 215                 220

Lys Leu Glu Arg Ser Thr Gly Asn Ile Asp Ile Lys Ile Lys Arg Ile
225                 230                 235                 240

Glu Gly Glu Val Asn Glu Lys Ile Asp Lys Arg Gln Leu Val Ser Thr
                245                 250                 255

Ile Asp Asp Ser Ile Gly Lys Lys Thr Asp Ser Ile Gly Tyr Thr Leu
            260                 265                 270

Glu Ser Ser Ile Ile Lys Lys Val Glu Glu Lys Glu Lys Lys Lys Ser
        275                 280                 285

Glu Gln Asn Gln Leu Leu Phe Asp Ser Lys Ile Glu Ser Leu Lys Asp
    290                 295                 300

Lys Ile Lys Ile Ile Glu Thr Gln Gln Leu Asp Thr Ser Ser Glu Val
305                 310                 315                 320

Arg Lys Leu Lys Leu Glu Ser Thr Ser Ser Glu Asn Leu Met Ala Gly
                325                 330                 335

Leu Asn Gly Thr Ser Gly Arg Pro Ser Ser Ser Ser His Phe Ile Pro
```

-continued

```
                340                 345                 350
Ser Ser Val Ser Ala Ala Asn Asn Ile Asn Lys Asn Glu Ile Met
            355                 360                 365
Glu Glu Val Lys Lys Val Glu Glu Lys Leu Gln Lys Lys Ile Arg Glu
        370                 375                 380
Glu Ile Asp Asn Thr Lys Ala Glu Leu Ser Lys Val Glu Arg Ser Val
385                 390                 395                 400
Lys Asp Asn Arg Ser Glu Leu Glu Gly Leu Glu Lys Asp Cys Lys Asn
                405                 410                 415
Gln Phe Asp Lys Gln Asp Asn Lys Ile Lys Gln Val Glu Asp Asp Leu
            420                 425                 430
Lys Lys Ser Asp Ser Leu Leu Leu Leu Met Gln Asn Asn Leu Lys Lys
        435                 440                 445
Tyr Asn Glu Phe Val Asp Arg Glu Arg Asp Arg Glu Ser Glu Arg Leu
    450                 455                 460
Lys Leu Gln Asp Ser Ile Lys Arg Leu Glu Gln Asn Gln Lys Lys Ile
465                 470                 475                 480
Glu Ala Glu Ile Gln Glu Gly Asn Glu Gln Val Glu Arg Val Leu Arg
                485                 490                 495
Glu Glu Ala Ser Ile Ser Pro Ile Ser Ser Val Pro Lys Ser Pro Ile
            500                 505                 510
Thr Thr Lys Arg Ser Ser Ile Ile Leu Asn Ser Pro Met Thr Ser
        515                 520                 525
Gln Gln Ser Ser Pro Lys Ile Gln Asp Leu Leu Ser Ser Ser Gly Ser
    530                 535                 540
Ser Ser Val Ser Gly Ile Asn Ile Ser Ser Glu Thr Gly Glu Met Gly
545                 550                 555                 560
Ile Leu Trp Glu Phe Asp Pro Ile Ile Asn Lys Trp Ile Arg Leu Ser
                565                 570                 575
Met Lys Leu Lys Val Glu Arg Lys Pro Phe Ala Glu Gly Ala Leu Arg
            580                 585                 590
Glu Ala Tyr His Thr Val Ser Leu Gly Val Gly Thr Asp Glu Asn Tyr
        595                 600                 605
Pro Leu Gly Thr Thr Thr Lys Leu Phe Pro Pro Ile Glu Met Ile Ser
    610                 615                 620
Pro Ile Ser Lys Asn Asn Glu Ala Met Thr Gln Leu Lys Asn Gly Thr
625                 630                 635                 640
Lys Phe Val Leu Lys Leu Tyr Lys Lys Glu Ala Glu Gln Gln Ala Ser
                645                 650                 655
Arg Glu Leu Tyr Phe Glu Asp Val Lys Met Gln Met Val Cys Arg Asp
            660                 665                 670
Trp Gly Asn Lys Phe Asn Gln Lys Lys Pro Pro Lys Lys Ile Glu Phe
        675                 680                 685
Leu Met Ser Trp Val Val Glu Leu Ile Asp Arg Ser Pro Ser Ser Asn
    690                 695                 700
Gly Gln Pro Ile Leu Cys Ser Ile Glu Pro Leu Leu Val Gly Glu Phe
705                 710                 715                 720
Lys Lys Asn Asn Ser Asn Tyr Gly Ala Val Leu Thr Asn Arg Ser Thr
                725                 730                 735
Pro Gln Ala Phe Ser His Phe Thr Tyr Glu Leu Ser Asn Lys Gln Met
            740                 745                 750
Ile Val Val Asp Ile Gln Gly Val Asp Asp Leu Tyr Thr Asp Pro Gln
        755                 760                 765
```

```
Ile His Thr Pro Asp Gly Lys Gly Phe Gly Leu Gly Asn Leu Gly Lys
770                 775                 780

Ala Gly Ile Asn Lys Phe Ile Thr Thr His Lys Cys Asn Ala Val Cys
785                 790                 795                 800

Ala Leu Leu Asp Leu Asp Val Lys Leu Gly Gly Val Leu Ser Gly Asn
            805                 810                 815

Asn Lys Lys Gln Leu Gln Gln Gly Thr Met Val Met Pro Asp Ile Leu
            820                 825                 830

Pro Glu Leu Met Pro Ser Asp Asn Thr Ile Lys Val Gly Ala Lys Gln
            835                 840                 845

Leu Pro Lys Ala Glu Phe Ser Lys Lys Asp Leu Lys Cys Val Ser Thr
850                 855                 860

Ile Gln Ser Phe Arg Glu Arg Val Asn Ser Ile Ala Phe Phe Asp Asn
865                 870                 875                 880

Gln Lys Leu Leu Cys Ala Gly Tyr Gly Asp Gly Thr Tyr Arg Val Phe
                885                 890                 895

Asp Val Asn Asp Asn Trp Lys Cys Leu Tyr Thr Val Asn Gly His Arg
            900                 905                 910

Lys Ser Ile Glu Ser Ile Ala Cys Asn Ser Asn Tyr Ile Phe Thr Ser
            915                 920                 925

Ser Pro Asp Asn Thr Ile Lys Val His Ile Ile Arg Ser Gly Asn Thr
930                 935                 940

Lys Cys Ile Glu Thr Leu Val Gly His Thr Gly Glu Val Asn Cys Val
945                 950                 955                 960

Val Ala Asn Glu Lys Tyr Leu Phe Ser Cys Ser Tyr Asp Lys Thr Ile
                965                 970                 975

Lys Val Trp Asp Leu Ser Thr Phe Lys Glu Ile Lys Ser Phe Glu Gly
            980                 985                 990

Val His Thr Lys Tyr Ile Lys Thr Leu Ala Leu Ser Gly Arg Tyr Leu
            995                 1000                1005

Phe Ser Gly Gly Asn Asp Gln Ile Ile Tyr Val Trp Asp Thr Glu
1010                1015                1020

Thr Leu Ser Met Leu Phe Asn Met Gln Gly His Glu Asp Trp Val
1025                1030                1035

Leu Ser Leu His Cys Thr Ala Ser Tyr Leu Phe Ser Thr Ser Lys
1040                1045                1050

Asp Asn Val Ile Lys Ile Trp Asp Leu Ser Asn Phe Ser Cys Ile
1055                1060                1065

Asp Thr Leu Lys Gly His Trp Asn Ser Val Ser Ser Cys Val Val
1070                1075                1080

Lys Asp Arg Tyr Leu Tyr Ser Gly Ser Glu Asp Asn Ser Ile Lys
1085                1090                1095

Val Trp Asp Leu Asp Thr Leu Glu Cys Val Tyr Thr Ile Pro Lys
1100                1105                1110

Ser His Ser Leu Gly Val Lys Cys Leu Met Val Phe Asn Asn Gln
1115                1120                1125

Ile Ile Ser Ala Ala Phe Asp Gly Ser Ile Lys Val Trp Glu Trp
1130                1135                1140

Gln Ser Lys
1145

<210> SEQ ID NO 11
<211> LENGTH: 2237
```

<212> TYPE: DNA
<213> ORGANISM: Dictyostelium discoideum

<400> SEQUENCE: 11

| | | | | | |
|---|---|---|---|---|---|
| ataagaagat | agaagatgat | atttaaagtt | tggttttcat | atgaagatga | ggaagtggaa | 60 |
| ctatcagaat | taacaaatga | tacaacagtg | tcagcaatta | gaaagatctt | acatgaaggt | 120 |
| aaaatattta | gatttccata | tggtacatct | caaacagact | tgcaaattgg | aaagatgtta | 180 |
| ccatctggta | gtggtggagg | tgcaactgca | gacagcaaat | ttgagaagtt | taaagcacgt | 240 |
| aatacattag | cagatattca | atataaagtt | ggtgatacat | tatatgttag | agttaaaaaa | 300 |
| agtaaaccaa | caaatgattc | attattacca | acattaaata | tagcattttt | agatggatca | 360 |
| gaacgtgcaa | ttaaatggga | atatgaccca | tatactacaa | ctgctcaatg | gacctgtaca | 420 |
| gcaacattag | tcaaagttga | accagtacca | tttgctgaag | gtgcatttag | gaaagcttat | 480 |
| catacattgg | atttaagtaa | atctggtgca | agtggaagat | atgtatcaaa | gattggtaaa | 540 |
| aaaccaacac | caagaccatc | atattttgaa | gatgtaaaga | tgcaaatgat | agcaaagaaa | 600 |
| tgggcagata | aatataattc | atttaaacct | ccaaaaaaga | ttgaattttt | acaatcatgc | 660 |
| gttttagagt | ttgtagatag | aacatcatca | gatttaattt | gtggagcaga | accatatgta | 720 |
| gaaggacaat | atagaaagta | taataataat | agtggattcg | ttagtaatga | tgaaagaaat | 780 |
| acaccacaat | cattctctca | tttcacatat | gaacattcaa | atcatcaatt | attgattata | 840 |
| gatattcaag | tgttggtga | tcactataca | gacccacaaa | ttcataccta | tgatggtgtt | 900 |
| ggttttggta | ttggtaattt | gggtcaaaaa | ggttttgaaa | agttttttaga | tactcataaa | 960 |
| tgtaatgcaa | tttgccaata | tttaaattta | caatcaatta | atccaaaatc | tgaaaaaagt | 1020 |
| gattgtggta | ctgtaccaag | accagattta | attttccctg | atacatctga | aagagataat | 1080 |
| aataataata | ataataataa | taataataat | aataataata | ataataataa | taatagtaat | 1140 |
| aataataata | ataacaatag | tagtatttca | aaatcattag | ttgaaatttc | aagtggtagt | 1200 |
| aaagaaagaa | atgatagaga | ttcgccaagt | agacaattat | ttgtttcaaa | tgatggtaat | 1260 |
| acattaaata | caaataaaga | gagatcaaaa | tcaaaatcaa | tagatttaga | aaaaccagaa | 1320 |
| attttaataa | ataataagaa | aaaagagagt | ataaatttgg | aaacgataaa | attaattgaa | 1380 |
| actattaaag | gatatcatgt | tacaagtcat | ttatgtattt | tgtgataattt | attatttaca | 1440 |
| ggatgttcag | ataattcaat | tagagtgtat | gattataaga | gtcaaaatat | ggaatgtgtt | 1500 |
| caaaccttga | aaggtcatga | aggtccagtt | gaatcaattt | gttataatga | tcaatatttg | 1560 |
| tttagtggtt | catcagatca | ttcaattaaa | gtttgggatt | taaagaaatt | aagatgtatt | 1620 |
| tttactttgg | agggtcatga | taaacctgtc | catacggttc | tattgaatga | taaatatttg | 1680 |
| tttagtggtt | cctctgacaa | aactatcaaa | gtttgggatt | tgaaaacttt | ggaatgtaaa | 1740 |
| tatacccttg | aaagtcatgc | cagagccgtc | aaaacacttt | gtatatctgg | tcaatattta | 1800 |
| tttagtggtt | caaatgataa | aactatcaag | gtttgggatt | tgaaaacttt | tcgttgtaac | 1860 |
| tacactctaa | aaggtcatac | taatgggtc | accactatct | gtatattagg | taccaatctc | 1920 |
| tacagtggct | cctatgataa | aactataaga | gtttggaatt | taaagagttt | agaatgttcc | 1980 |
| gctactttaa | gaggccatga | tagatgggtt | gaacatatgg | taatttgtga | taaattatta | 2040 |
| tttactgcta | gtgacgataa | tacaattaaa | atttgggatt | tagaaacatt | aagatgtaat | 2100 |
| acaactttgg | aaggacataa | tgcaaccgtt | caatgtttag | cagtttggga | agataaaaaa | 2160 |
| tgtgttatta | gttgtagtca | tgatcaaagt | attagagttt | ggggtggaa | ttaatttaaa | 2220 |

-continued ataaaaaaaa aaaacat 2237

<210> SEQ ID NO 12
<211> LENGTH: 732
<212> TYPE: PRT
<213> ORGANISM: Dictyostelium discoideum

<400> SEQUENCE: 12

Met Ile Phe Lys Val Trp Phe Ser Tyr Glu Asp Glu Val Glu Leu
1               5                   10                  15

Ser Glu Leu Thr Asn Asp Thr Thr Val Ser Ala Ile Arg Lys Ile Leu
            20                  25                  30

His Glu Gly Lys Ile Phe Arg Phe Pro Tyr Gly Thr Ser Gln Thr Asp
        35                  40                  45

Leu Gln Ile Gly Lys Met Leu Pro Ser Gly Ser Gly Gly Ala Thr
    50                  55                  60

Ala Asp Ser Lys Phe Glu Lys Phe Lys Ala Arg Asn Thr Leu Ala Asp
65                  70                  75                  80

Ile Gln Tyr Lys Val Gly Asp Thr Leu Tyr Val Arg Val Lys Lys Ser
                85                  90                  95

Lys Pro Thr Asn Asp Ser Leu Leu Pro Thr Leu Asn Ile Ala Phe Leu
            100                 105                 110

Asp Gly Ser Glu Arg Ala Ile Lys Trp Glu Tyr Asp Pro Tyr Thr Thr
        115                 120                 125

Thr Ala Gln Trp Thr Cys Thr Ala Thr Leu Val Lys Val Glu Pro Val
    130                 135                 140

Pro Phe Ala Glu Gln Ala Phe Arg Lys Ala Tyr His Thr Leu Asp Leu
145                 150                 155                 160

Ser Lys Ser Gly Ala Ser Gly Arg Tyr Val Ser Lys Ile Gly Lys Lys
                165                 170                 175

Pro Thr Pro Arg Pro Ser Tyr Phe Glu Asp Val Lys Met Gln Met Ile
            180                 185                 190

Ala Lys Lys Trp Ala Asp Lys Tyr Asn Ser Phe Lys Pro Pro Lys Lys
        195                 200                 205

Ile Glu Phe Leu Gln Ser Cys Val Leu Glu Phe Val Asp Arg Thr Ser
    210                 215                 220

Ser Asp Leu Ile Cys Gly Ala Glu Pro Tyr Val Glu Gly Gln Tyr Arg
225                 230                 235                 240

Lys Tyr Asn Asn Asn Ser Gly Phe Val Ser Asn Asp Glu Arg Asn Thr
                245                 250                 255

Pro Gln Ser Phe Ser His Phe Thr Tyr Glu His Ser Asn His Gln Leu
            260                 265                 270

Leu Ile Ile Asp Ile Gln Gly Val Gly Asp His Tyr Thr Asp Pro Gln
        275                 280                 285

Ile His Thr Tyr Asp Gly Val Gly Phe Gly Ile Gly Asn Leu Gly Gln
    290                 295                 300

Lys Gly Phe Glu Lys Phe Leu Asp Thr His Lys Cys Asn Ala Ile Cys
305                 310                 315                 320

Gln Tyr Leu Asn Leu Gln Ser Ile Asn Pro Lys Ser Glu Lys Ser Asp
                325                 330                 335

Cys Gly Thr Val Pro Arg Pro Asp Leu Ile Phe Pro Asp Thr Ser Glu
            340                 345                 350

Arg Asp Asn Asn Asn Asn Asn Asn Asn Asn Asn Asn Asn Asn
        355                 360                 365

```
Asn Asn Asn Asn Asn Ser Asn Asn Asn Asn Asn Asn Ser Ser Ile
            370                 375                 380

Ser Lys Ser Leu Val Glu Ile Ser Ser Gly Ser Lys Glu Arg Asn Asp
385                 390                 395                 400

Arg Asp Ser Pro Ser Arg Gln Leu Phe Val Ser Asn Asp Gly Asn Thr
                405                 410                 415

Leu Asn Thr Asn Lys Glu Arg Ser Lys Ser Lys Ser Ile Asp Leu Glu
            420                 425                 430

Lys Pro Glu Ile Leu Ile Asn Asn Lys Lys Glu Ser Ile Asn Leu
        435                 440                 445

Glu Thr Ile Lys Leu Ile Glu Thr Ile Lys Gly Tyr His Val Thr Ser
    450                 455                 460

His Leu Cys Ile Cys Asp Asn Leu Leu Phe Thr Gly Cys Ser Asp Asn
465                 470                 475                 480

Ser Ile Arg Val Tyr Asp Tyr Lys Ser Gln Asn Met Glu Cys Val Gln
                485                 490                 495

Thr Leu Lys Gly His Glu Gly Pro Val Glu Ser Ile Cys Tyr Asn Asp
            500                 505                 510

Gln Tyr Leu Phe Ser Gly Ser Ser Asp His Ser Ile Lys Val Trp Asp
        515                 520                 525

Leu Lys Lys Leu Arg Cys Ile Phe Thr Leu Glu Gly His Asp Lys Pro
530                 535                 540

Val Thr His Val Leu Leu Asn Asp Lys Tyr Leu Phe Ser Gly Ser Ser
545                 550                 555                 560

Asp Lys Thr Ile Lys Val Trp Asp Leu Lys Thr Leu Glu Cys Lys Tyr
                565                 570                 575

Thr Leu Glu Ser His Ala Arg Ala Val Lys Thr Leu Cys Ile Ser Gly
            580                 585                 590

Gln Tyr Leu Phe Ser Gly Ser Asn Asp Lys Ile Thr Lys Val Trp Asp
        595                 600                 605

Leu Lys Thr Phe Arg Cys Asn Tyr Thr Leu Lys Gly His Thr Lys Trp
610                 615                 620

Val Thr Thr Ile Cys Ile Leu Gly Thr Asn Leu Tyr Ser Gly Ser Tyr
625                 630                 635                 640

Asp Lys Thr Ile Arg Val Trp Asn Leu Lys Ser Leu Glu Cys Ser Ala
                645                 650                 655

Thr Leu Arg Gly His Asp Arg Trp Val Glu His Met Val Ile Cys Asp
            660                 665                 670

Lys Leu Leu Phe Thr Ala Ser Asp Asp Asn Thr Ile Lys Ile Trp Asp
        675                 680                 685

Leu Glu Thr Leu Arg Cys Asn Thr Thr Leu Glu Gly His Asn Ala Thr
690                 695                 700

Val Gln Cys Leu Ala Val Trp Glu Asp Lys Lys Cys Val Ile Ser Cys
705                 710                 715                 720

Ser His Asp Gln Ser Ile Arg Val Trp Gly Trp Asn
                725                 730
```

<210> SEQ ID NO 13
<211> LENGTH: 2307
<212> TYPE: DNA
<213> ORGANISM: C. elegans

<400> SEQUENCE: 13
atgacgatcg acacaacaaa tgagagcgac aatagtccaa ctaactcacc aggattggag    60

```
gcctcggctc ggacattctc gctcaatgcg tcaaaaatgg ttcggataac cgacgactac     120
gcagatgaag tgttcattga acagaatgat gtcgttatcg agaagcctcg tatggatcct     180
ctccacgtta gaaaacttat ggagacatgg cgcaaggctg ctcgccgagc aagaacaaac     240
tatatagatc catgggatga gttcaacatc cacgagtatc cagtacaacg agctaaacga     300
tataggtatt ctgcaatcag aaagcaatgg acagaggata tagtcgatgt gagacttcat     360
ccggacagtt ttgcacgtgg agccatgcga gaatgctacc gactcaaaaa gtgctccaag     420
cacggaacaa gtcaagattg gagcagcaac tatgtcgcaa aaagatacat ttgtcaagtc     480
gatcgtagag ttcttttcga tgatgtcaga cttcagatgg atgccaaatt atgggctgaa     540
gaatataatc ggtataatcc accgaagaaa attgatattg ttcaaatgtg tgtcattgag     600
atgattgatg taaaaggttc tccactctat catttggagc atttcatcga gggaaaatat     660
ataaaataca attcaaactc aggatttgta tcaaatgcag ctcgtcttac accacaagca     720
ttttctcact tcaccttcga acgttctggt catcaaatga tggttgtcga tattcaagga     780
gttggtgatc tttacacaga tcctcagatt catacagttg tgggaactga ttatggagat     840
ggaaacctcg gaactcgtgg aatggctctt ttcttccatt cacacagatg taacgatatt     900
tgtgagacaa tggatctatc aaatttcgaa cttttcgccac ctgaaatcga ggctaccgaa     960
gttgcgatgg aagtagctgc aaagcagaaa aagtcatgca tagttcctcc aactgtgttc    1020
gaagcaagaa gaaatcgaat tcaagtgaaa tgtgtacatg tcgagcatgg tatttcgatg    1080
gatcaattga gaaaaggaa gacgttgaat caatcgtcaa ccgatttgtc agcaaagagt    1140
cacaacgaag actgtgtatg tcctgagtgt attccagttg ttgagcaact ctgtgagcct    1200
tgctccgaaa tgaagagga cgaagaagaa gactatccaa gaagtgaaaa agtggaaat     1260
agtcagaaaa gtcgacgtag tagaatgagc atttcaacga gatcttctgg cgatgaatca    1320
gcatctcgtc ctagaaaatg cggatttgta gatttaaact cacttcgtca gagacatgat    1380
agcttcagaa gttctgttgg gacatattct atgaatagtt ctagacaaac cagagacact    1440
gaaaaggatg aattctggaa ggttcttcga aaacaatcag ttccagcaaa cattctatca    1500
cttcaacttc aacaaatggc tgctaacctg gaaaatgatg aagacgtacc acaagtcacc    1560
gggcatcagt tctctgtcct cggtcagatt catattgatc tctcacgata tcatgagctc    1620
gggcggttcg tagaagttga ttcagaacat aaggaaatgc ttgagggaag tgaaaatgac    1680
gctcgtgtac caatcaaata cgacaagcag tctgcaattt tccatttgga tatcgctcgg    1740
aagtgtggaa tccttgaggc tgtgctaaca tcggctcata ttgttctcgg attaccacat    1800
gaattgttga agaagtcac cgttgatgat ctgtttccta atgggttttgg agaacaggaa    1860
aatggaattc gagctgataa aggacaaaaa ccttgtgacc tagaagagtt cggctccgat    1920
ctgatggaaa ttgctgcaga gatgggtgat aagggtgcaa tgctgtacat ggcacacgct    1980
tatgaaactg gtcagcatct cggaccgaat cgaagaacgg attataagaa atcgattgat    2040
tggtatcaac gcgtcgttgg attccaagaa gaagaagaac ttgactctga ttgtggaaaa    2100
acgacattct cctcatttgc tccactgact cgtcacgaga ttctagccaa atggctgaa     2160
atgtacaaag agggaggtta tggcctgaat caagacttcg aacgagcata tggtctattc    2220
aatgaagctg ctgaagcagc aatggaagca atgaatggaa agctcgcaaa taaatactat    2280
gaaaaagcgg aaatgtgtgg agaatga                                         2307
```

<210> SEQ ID NO 14
<211> LENGTH: 767

```
<212> TYPE: PRT
<213> ORGANISM: C. elegans

<400> SEQUENCE: 14
```

| | | | | | | | | | | | | | | |
|---|---|---|---|---|---|---|---|---|---|---|---|---|---|---|
| Met | Thr | Ile | Asp | Thr | Asn | Glu | Ser | Asp | Asn | Ser | Pro | Thr | Asn | Ser |
| 1 | | | | 5 | | | | | 10 | | | | | 15 |
| Pro | Gly | Leu | Glu | Ala | Ser | Ala | Arg | Thr | Phe | Ser | Leu | Asn | Ala | Ser | Lys |
| | | | 20 | | | | | 25 | | | | | 30 | | |
| Met | Val | Arg | Ile | Thr | Asp | Asp | Tyr | Ala | Asp | Glu | Val | Phe | Ile | Glu | Gln |
| | | 35 | | | | | 40 | | | | | 45 | | | |
| Asn | Asp | Val | Val | Ile | Glu | Lys | Pro | Arg | Met | Asp | Pro | Leu | His | Val | Arg |
| 50 | | | | | 55 | | | | | 60 | | | | | |
| Lys | Leu | Met | Glu | Thr | Trp | Arg | Lys | Ala | Ala | Arg | Arg | Ala | Arg | Thr | Asn |
| 65 | | | | | 70 | | | | | 75 | | | | | 80 |
| Tyr | Ile | Asp | Pro | Trp | Lys | Glu | Phe | Asn | Ile | His | Glu | Tyr | Pro | Val | Gln |
| | | | | 85 | | | | | 90 | | | | | 95 | |
| Arg | Ala | Lys | Arg | Tyr | Arg | Tyr | Ser | Ala | Ile | Arg | Lys | Gln | Trp | Thr | Glu |
| | | | 100 | | | | | 105 | | | | | 110 | | |
| Asp | Ile | Val | Asp | Val | Arg | Leu | His | Pro | Asp | Ser | Phe | Ala | Arg | Gly | Ala |
| | | 115 | | | | | 120 | | | | | 125 | | | |
| Met | Arg | Glu | Cys | Tyr | Arg | Leu | Lys | Lys | Cys | Ser | Lys | His | Gly | Thr | Ser |
| | 130 | | | | | 135 | | | | | 140 | | | | |
| Gln | Asp | Trp | Ser | Ser | Asn | Tyr | Val | Ala | Lys | Arg | Tyr | Ile | Cys | Gln | Val |
| 145 | | | | | 150 | | | | | 155 | | | | | 160 |
| Asp | Arg | Arg | Val | Leu | Phe | Asp | Asp | Val | Arg | Leu | Gln | Met | Asp | Ala | Lys |
| | | | | 165 | | | | | 170 | | | | | 175 | |
| Leu | Trp | Ala | Glu | Glu | Tyr | Asn | Arg | Tyr | Asn | Pro | Pro | Lys | Lys | Ile | Asp |
| | | | 180 | | | | | 185 | | | | | 190 | | |
| Ile | Val | Gln | Met | Cys | Val | Ile | Glu | Met | Ile | Asp | Val | Lys | Gly | Ser | Pro |
| | | | | 195 | | | | | 200 | | | | | 205 | |
| Leu | Tyr | His | Leu | Glu | His | Phe | Ile | Glu | Gly | Lys | Tyr | Ile | Lys | Tyr | Asn |
| | 210 | | | | | 215 | | | | | 220 | | | | |
| Ser | Asn | Ser | Gly | Phe | Val | Ser | Asn | Ala | Ala | Arg | Leu | Thr | Pro | Gly | Ala |
| 225 | | | | | 230 | | | | | 235 | | | | | 240 |
| Phe | Ser | His | Phe | Thr | Phe | Glu | Arg | Ser | Gly | His | Gln | Met | Met | Val | Val |
| | | | | 245 | | | | | 250 | | | | | 255 | |
| Asp | Ile | Gln | Gly | Val | Gly | Asp | Leu | Tyr | Thr | Asp | Pro | Gln | Ile | His | Thr |
| | | | 260 | | | | | 265 | | | | | 270 | | |
| Val | Val | Gly | Thr | Asp | Tyr | Gly | Asp | Gly | Asn | Leu | Gly | Thr | Arg | Gly | Met |
| | | | | 275 | | | | | 280 | | | | | 285 | |
| Ala | Leu | Phe | Phe | His | Ser | His | Arg | Cys | Asn | Asp | Ile | Cys | Glu | Thr | Met |
| | 290 | | | | | 295 | | | | | 300 | | | | |
| Asp | Leu | Ser | Asn | Phe | Glu | Leu | Ser | Pro | Pro | Glu | Ile | Glu | Ala | Thr | Glu |
| 305 | | | | | 310 | | | | | 315 | | | | | 320 |
| Val | Ala | Met | Glu | Val | Ala | Ala | Lys | Gln | Lys | Lys | Ser | Cys | Ile | Val | Pro |
| | | | | 325 | | | | | 330 | | | | | 335 | |
| Pro | Thr | Val | Phe | Glu | Ala | Arg | Arg | Asn | Arg | Ile | Ser | Ser | Glu | Cys | Val |
| | | | 340 | | | | | 345 | | | | | 350 | | |
| His | Val | Glu | His | Gly | Ile | Ser | Met | Asp | Gln | Leu | Arg | Lys | Arg | Lys | Thr |
| | | | | 355 | | | | | 360 | | | | | 365 | |
| Leu | Asn | Gln | Ser | Ser | Thr | Asp | Leu | Ser | Ala | Lys | Ser | His | Asn | Glu | Asp |
| | 370 | | | | | 375 | | | | | 380 | | | | |
| Cys | Val | Cys | Pro | Glu | Cys | Ile | Pro | Val | Val | Glu | Gln | Leu | Cys | Glu | Pro |
| 385 | | | | | 390 | | | | | 395 | | | | | 400 |

```
Cys Ser Glu Asp Glu Glu Asp Glu Glu Asp Tyr Pro Arg Ser Glu
                405                 410                 415
Lys Ser Gly Asn Ser Gln Lys Ser Arg Arg Ser Arg Met Ser Ile Ser
            420                 425                 430
Thr Arg Ser Ser Gly Asp Glu Ser Ala Ser Arg Pro Arg Lys Cys Gly
        435                 440                 445
Phe Val Asp Leu Asn Ser Leu Arg Gln Arg His Asp Ser Phe Arg Ser
    450                 455                 460
Ser Val Gly Thr Tyr Ser Met Asn Ser Ser Arg Gln Thr Arg Asp Thr
465                 470                 475                 480
Glu Lys Asp Glu Phe Trp Lys Val Leu Arg Lys Gln Ser Val Pro Ala
                485                 490                 495
Asn Ile Leu Ser Leu Gln Leu Gln Gln Met Ala Ala Asn Leu Glu Asn
            500                 505                 510
Asp Glu Asp Val Pro Gln Val Thr Gly His Gln Phe Ser Val Leu Gly
        515                 520                 525
Gln Ile His Ile Asp Leu Ser Arg Tyr His Glu Leu Gly Arg Phe Val
    530                 535                 540
Glu Val Asp Ser Glu His Lys Glu Met Leu Glu Gly Ser Glu Asn Asp
545                 550                 555                 560
Ala Arg Val Pro Ile Lys Tyr Asp Lys Gln Ser Ala Ile Phe His Leu
                565                 570                 575
Asp Ile Ala Arg Lys Cys Gly Ile Leu Glu Ala Val Leu Thr Ser Ala
            580                 585                 590
His Ile Val Leu Gly Leu Pro His Glu Leu Leu Lys Glu Val Thr Val
        595                 600                 605
Asp Asp Leu Phe Pro Asn Gly Phe Gly Glu Gln Glu Asn Gly Ile Arg
    610                 615                 620
Ala Asp Lys Gly Gln Lys Pro Cys Asp Leu Glu Glu Phe Gly Ser Asp
625                 630                 635                 640
Leu Met Glu Ile Ala Ala Glu Met Gly Asp Lys Gly Ala Met Leu Tyr
                645                 650                 655
Met Ala His Ala Tyr Glu Thr Gly Gln His Leu Gly Pro Asn Arg Arg
            660                 665                 670
Thr Asp Tyr Lys Lys Ser Ile Asp Trp Tyr Gln Arg Val Val Gly Phe
        675                 680                 685
Gln Glu Glu Glu Leu Asp Ser Asp Cys Gly Lys Thr Thr Phe Ser Ser
    690                 695                 700
Phe Ala Pro Leu Thr Arg His Glu Ile Leu Ala Lys Met Ala Glu Met
705                 710                 715                 720
Tyr Lys Glu Gly Gly Tyr Gly Leu Asn Gln Asp Phe Glu Arg Ala Tyr
                725                 730                 735
Gly Leu Phe Asn Glu Ala Ala Glu Ala Met Glu Ala Met Asn Gly
            740                 745                 750
Lys Leu Ala Asn Lys Tyr Tyr Glu Lys Ala Glu Met Cys Gly Glu
        755                 760                 765

<210> SEQ ID NO 15
<211> LENGTH: 13
<212> TYPE: PRT
<213> ORGANISM: rabbit

<400> SEQUENCE: 15

Leu Thr Pro Gln Ala Phe Ser His Phe Thr Phe Glu Arg
```

-continued

```
<210> SEQ ID NO 16
<211> LENGTH: 10
<212> TYPE: PRT
<213> ORGANISM: rabbit
<220> FEATURE:
<221> NAME/KEY: MISC_FEATURE
<222> LOCATION: (4)..(4)
<223> OTHER INFORMATION: X can be any amino acid

<400> SEQUENCE: 16

Leu Ala Asn Xaa Tyr Tyr Glu Lys Ala Glu
1               5                   10

<210> SEQ ID NO 17
<211> LENGTH: 29
<212> TYPE: DNA
<213> ORGANISM: Unknown
<220> FEATURE:
<223> OTHER INFORMATION: primer
<221> NAME/KEY: misc_feature
<222> LOCATION: (3)..(3)
<223> OTHER INFORMATION: n can be G or A
<221> NAME/KEY: misc_feature
<222> LOCATION: (6)..(6)
<223> OTHER INFORMATION: n can be C, G, T or A
<221> NAME/KEY: misc_feature
<222> LOCATION: (9)..(9)
<223> OTHER INFORMATION: n can be C or T
<221> NAME/KEY: misc_feature
<222> LOCATION: (10)..(10)
<223> OTHER INFORMATION: n can be T or A
<221> NAME/KEY: misc_feature
<222> LOCATION: (11)..(11)
<223> OTHER INFORMATION: n can be C or G
<221> NAME/KEY: misc_feature
<222> LOCATION: (12)..(12)
<223> OTHER INFORMATION: n can be T or C
<221> NAME/KEY: misc_feature
<222> LOCATION: (15)..(15)
<223> OTHER INFORMATION: n can be C or T
<221> NAME/KEY: misc_feature
<222> LOCATION: (18)..(18)
<223> OTHER INFORMATION: n can be C or T
<221> NAME/KEY: misc_feature
<222> LOCATION: (21)..(21)
<223> OTHER INFORMATION: n can be C, G, T or A
<221> NAME/KEY: misc_feature
<222> LOCATION: (24)..(24)
<223> OTHER INFORMATION: n can be C or T
<221> NAME/KEY: misc_feature
<222> LOCATION: (27)..(27)
<223> OTHER INFORMATION: n can be G or A
<221> NAME/KEY: misc_feature
<222> LOCATION: (28)..(28)
<223> OTHER INFORMATION: n can be C or A

<400> SEQUENCE: 17
cangcnttnn nncanttnac nttnganng                                    29

<210> SEQ ID NO 18
<211> LENGTH: 26
<212> TYPE: DNA
<213> ORGANISM: Unknown
<220> FEATURE:
<223> OTHER INFORMATION: primer
<221> NAME/KEY: misc_feature
<222> LOCATION: (3)..(3)
<223> OTHER INFORMATION: n can be C, G, T or A
<221> NAME/KEY: misc_feature
<222> LOCATION: (6)..(6)
<223> OTHER INFORMATION: n can be C or T
<221> NAME/KEY: misc_feature
```

```
<222> LOCATION: (9)..(9)
<223> OTHER INFORMATION: n can be C or T
<221> NAME/KEY: misc_feature
<222> LOCATION: (12)..(12)
<223> OTHER INFORMATION: n can be G or A
<221> NAME/KEY: misc_feature
<222> LOCATION: (15)..(15)
<223> OTHER INFORMATION: n can be G or A
<221> NAME/KEY: misc_feature
<222> LOCATION: (18)..(18)
<223> OTHER INFORMATION: n can be C or T
<221> NAME/KEY: misc_feature
<222> LOCATION: (21)..(21)
<223> OTHER INFORMATION: n can be G or A
<221> NAME/KEY: misc_feature
<222> LOCATION: (24)..(24)
<223> OTHER INFORMATION: n can be C, G, A or T

<400> SEQUENCE: 18
tcngcnttnt cntantantt nttngc                                            26

<210> SEQ ID NO 19
<211> LENGTH: 27
<212> TYPE: DNA
<213> ORGANISM: Unknown
<220> FEATURE:
<223> OTHER INFORMATION: primer

<400> SEQUENCE: 19
tacaatcagc tgatgaccag aacgctc                                           27

<210> SEQ ID NO 20
<211> LENGTH: 25
<212> TYPE: DNA
<213> ORGANISM: Unknown
<220> FEATURE:
<223> OTHER INFORMATION: primer

<400> SEQUENCE: 20
ggatttggac tggacaagaa ccccc                                             25

<210> SEQ ID NO 21
<211> LENGTH: 6
<212> TYPE: PRT
<213> ORGANISM: Artificial sequence
<220> FEATURE:
<223> OTHER INFORMATION: consensus sequence
<221> NAME/KEY: MISC_FEATURE
<222> LOCATION: (2)..(2)
<223> OTHER INFORMATION: X can be any amino acid
<221> NAME/KEY: MISC_FEATURE
<222> LOCATION: (4)..(4)
<223> OTHER INFORMATION: X can be any amino acid
<221> NAME/KEY: MISC_FEATURE
<222> LOCATION: (5)..(5)
<223> OTHER INFORMATION: X can be any amino acid

<400> SEQUENCE: 21

Gly Xaa Gly Xaa Xaa Gly
1               5

<210> SEQ ID NO 22
<211> LENGTH: 5
<212> TYPE: PRT
<213> ORGANISM: Unknown
<220> FEATURE:
<223> OTHER INFORMATION: consensus sequence
<221> NAME/KEY: MISC_FEATURE
<222> LOCATION: (2)..(2)
<223> OTHER INFORMATION: X can be any amino acid
<221> NAME/KEY: MISC_FEATURE
```

```
<222> LOCATION: (3)..(3)
<223> OTHER INFORMATION: X can be any amino acid
<221> NAME/KEY: MISC_FEATURE
<222> LOCATION: (4)..(4)
<223> OTHER INFORMATION: X can be any amino acid

<400> SEQUENCE: 22

Asp Xaa Xaa Xaa Asn
1               5

<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23
tgaccaggta cacagcactt tgactgctct                                        30

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
gttagtacac catctcagcc aagttgcaaa                                        30

<210> SEQ ID NO 25
<211> LENGTH: 40
<212> TYPE: DNA
<213> ORGANISM: Artificial Sequence
<220> FEATURE:
<223> OTHER INFORMATION: primer

<400> SEQUENCE: 25
ttataacatc agacgaacag aattagttga ttctgattct                             40

<210> SEQ ID NO 26
<211> LENGTH: 6405
<212> TYPE: DNA
<213> ORGANISM: Homo sapiens

<400> SEQUENCE: 26
cgggcgcggg cgcgtccctg tggccagtca cccggaggag ttggtcgcac aattatgaaa       60
gactcggctt ctgctgctag cgccggagct gagttagttc tgagaaggtt tccctgggcg      120
ttccttgtcc ggcggcctct gctgccgcct ccggagacgc ttcccgatag atggctacag      180
gccgcggagg aggaggaggt ggagttgctg cccttccgga gtccgccccg tgaggagaat      240
gtcccagaaa tcctggatag aaagcacttt gaccaagagg gaatgtgtat atattatacc      300
aagttccaag accctcaca gatgccttcc aggatgtcaa atttgtcagc aactcgtcag      360 gtgttttgt ggtcgcttgg tcaagcaaca tgcttgtttt actgcaagtc ttgccatgaa      420
atactcagat gtgaaattgg gtgaccattt taatcaggca atagaagaat ggtctgtgga      480
aaagcataca gaacagagcc aacggatgc ttatggagtc ataaatttc aaggggttc         540 tcattcctac agagctaagt atgtgaggct atcatatgac accaaacctg aagtcattct      600
gcaacttctg cttaaagaat ggcaaatgga gttaccaaa cttgttatct ctgtacatgg       660
gggcatgcag aaatttgagc ttcacccacg aatcaagcag ttgcttggaa aagtcttat       720
```

-continued

```
taaagctgca gttacaactg gagcctggat tttaactgga ggagtaaaca caggtgtggc    780
aaaacatgtt ggagatgccc tcaaagaaca tgcttccaga tcatctcgaa agatttgcac    840
tatcggaata gctccatggg gagtgattga aaacagaaat gatcttgttg ggagagatgt    900
ggttgctcct tatcaaacct tattgaaccc cctgagcaaa ttgaatgttt tgaataatct    960
gcattcccat ttcatattgg tggatgatgg cactgttgga aagtatgggg cggaagtcag   1020
actgagaaga gaacttgaaa aaactattaa tcagcaaaga attcatgcta ggattggcca   1080
gggtgtccct gtggtggcac ttatatttga gggtgggcca aatgttatcc tcacagttct   1140
tgaataccct caggaaagcc ccctgttcc agtagttgtg tgtgaaggaa caggcagagc    1200
tgcagatctg ctagcgtata ttcataaaca aacagaagaa ggagggaatc ttcctgatgc   1260
agcagagccc gatattattt ccactatcaa aaaacatttt aactttggcc agaatgaagc   1320
acttcattta tttcaaacac tgatggagtg catgaaaaga aaggagctta tcactgtttt   1380
ccatattggg tcagatgaac atcaagatat agatgtagca atacttactg cactgctaaa   1440
aggtactaat gcatctgcat ttgaccagct tatccttaca ttggcatggg atagagttga   1500
cattgccaaa aatcatgtat ttgtttatgg acagcagtgg ctggttggat ccttggaaca   1560
agctatgctt gatgctcttg taatggatag agttgcattt gtaaaacttc ttattgaaaa   1620
tggagtaagc atgcataaat tccttaccat tccgagactg gaagaacttt acaacactaa   1680
acaaggtcca actaatccaa tgctgtttca tcttgttcga gacgtcaaac agggaaatct   1740
tcctccagga tataagatca ctctgattga tataggactt gttattgaat atctcatggg   1800
aggaacctac agatgcacct atactaggaa acgttttcga ttaatatata atagtcttgg   1860
tggaaataat cggaggtctg gccgaaatac ctccagcagc actcctcagt tgcgaaagag   1920
tcatgaatct tttggcaata gggcagataa aaaggaaaaa atgaggcata accatttcat   1980
taagacagca cagccctacc gaccaaagat tgatacagtt atggaagaag gaaagaagaa   2040
aagaaccaaa gatgaaattg tagacattga tgaatggatt gttattgctt atattttac    2100
ttatgccatt gagaaagtcc gtgagatctt tatgtctgaa gctgggaaag taaaccagaa   2160
gattaaagta tggtttagtg attacttcaa catcagtgat acaattgcca taatttcttt   2220
cttcattgga tttggactaa gatttggagc aaaatggaac tttgcaaatg catatgataa   2280
tcatgttttt gtggctggaa gattaattta ctgtcttaac ataatatttt ggtatgtgcg   2340
tttgctagat tttctagctg taaatcaaca ggcaggacct tatgtaatga tgattggaaa   2400
aatggtggcc aatatgttct acattgtagt gattatggct cttgtattac ttagttttgg   2460
tgttcccaga aagcaatac tttatcctca tgaagcacca tcttggactc ttgctaaaga    2520
tatagttttt cacccatact ggatgatttt tggtgaagtt tatgcatacg aaattgatgt   2580
gtgtgcaaat gattctgtta tccctcaaat ctgtggtcct gggacgtggt tgactccatt   2640
tcttcaagca gtctacctct ttgtacagta tatcattatg gttaatcttc ttattgcatt   2700
tttcaacaat gtgtatttac aagtgaaggc aatttccaat attgtatgga agtaccagcg   2760
ttatcatttt attatggctt atcatgagaa accagttctg cctcctccac ttatcattct   2820
tagccatata gtttctctgt tttgctgcat atgtaagaga agaaagaaag ataagacttc   2880
cgatggacca aaacttttct taacagaaga agatcaaaag aaacttcatg attttgaaga   2940
gcagtgtgtt gaaatgtatt tcaatgaaaa agatgacaaa tttcattctg ggagtgaaga   3000
gagaattcgt gtcactttg aaagagtgga acagatgtgc attcagatta agaagttggg    3060
agatcgtgtc aactacataa aaagatcatt acaatcatta gattctcaaa ttggccattt   3120
```

-continued

```
gcaagatctt tcagccctga cggtagatac attaaaaaca ctcactgccc agaaagcgtc  3180
ggaagctagc aaagttcata atgaaatcac acgagaactg agcatttcca aacacttggc  3240
tcaaaacctt attgatgatg gtcctgtaag accttctgta tggaaaaagc atggtgttgt  3300
aaatacactt agctcctctc ttcctcaagg tgatcttgaa agtaataatc cttttcattg  3360
taatatttta atgaaagatg acaaagatcc ccagtgtaat atatttggtc aagacttacc  3420
tgcagtaccc cagagaaaag aatttaattt tccagaggct ggttcctctt ctggtgcctt  3480
attcccaagt gctgtttccc ctccagaact gcgacagaga ctacatgggg tagaactctt  3540
aaaaatattt aataaaaatc aaaaattagg cagttcatct actagcatac cacatctgtc  3600
atccccacca accaaatttt ttgttagtac accatctcag ccaagttgca aaagccactt  3660
ggaaactgga accaaagatc aagaaactgt tgctctaaa gctacagaag gagataatac  3720
agaatttgga gcatttgtag gacacagaga tagcatggat ttacagaggt ttaaagaaac  3780
atcaaacaag ataaaaatac tatccaataa caatacttct gaaaacactt tgaaacgagt  3840
gagttctctt gctggattta ctgactgtca cagaacttcc attcctgttc attcaaaaca  3900
agaaaaaatc agtagaaggc catctaccga agacactcat gaagtagatt ccaaagcagc  3960
tttaataccg gtttggttac aagatagacc atcaaacaga gaaatgccat ctgaagaagg  4020
aacattaaat ggtctcactt ctccatttaa gccagctatg gatacaaatt actattattc  4080
agctgtggaa agaaataact tgatgaggtt atcacagagc attccattta cacctgtgcc  4140
tccaagaggg gagcctgtca cagtgtatcg tttggaagag agttcaccca acatactaaa  4200
taacagcatg tcttcttggt cacaactagg cctctgtgcc aaaatagagt ttttaagcaa  4260
agaggagatg ggaggaggtt tacgaagagc tgtcaaagta cagtgtacct ggtcagaaca  4320
tgatatcctc aaatcagggc atctttatat tatcaaatct tttcttccag aggtggttaa  4380
tacatggtca agtatttaca aagaagatac agttctgcat ctctgtctga gagaaattca  4440
acaacagaga gcagcacaaa agcttacgtt tgcctttaat caaatgaaac ccaaatccat  4500
accatattct ccaaggttcc ttgaagtttt cctgctgtat tgccattcag caggacagtg  4560
gtttgctgtg gaagaatgta tgactggaga atttagaaaa tacaacaata ataatggaga  4620
tgagattatt ccaactaata ctctggaaga gatcatgcta gcctttagcc actggactta  4680
cgaatataca agaggggagt tactggtact tgatttgcaa ggtgttggtg aaaatttgac  4740
tgacccatct gtgataaaag cagaagaaaa gagatcctgt gatatggttt ttggcccagc  4800
aaatctagga gaagatgcaa ttaaaaactt cagagcaaaa catcactgta attcttgctg  4860
tagaaagctt aaacttccag atcgtaagag gaatgattat acgcctgata aaattatatt  4920
tcctcaggat gagccttcag atttgaatct tcagcctgga aattccacca agaatcaga  4980
atcaactaat tctgttcgtc tgatgttata atattaatat tactgaatca ttggttttgc  5040
ctgcacctca cagaaatgtt actgtgtcac ttttccctcg ggaggaaatt gtttggtaat  5100
atagaaaggt gtatgcaagt tgaatttgct gactccagca cagttaaaag gtcaatattc  5160
ttttgacctg attaatcagt cagaaagtcc ctataggata gagctggcag ctgagaaatt  5220
ttaaaggtaa ttgataatta gtattttataa ctttttaaag ggctctttgt atagcagagg  5280
atctcatttg actttgtttt gatgagggtg atgctctctc ttatgtggta caataccatt  5340
aaccaaaggt aggtgtccat gcagatttta ttggcagctg ttttattgcc attcaactag  5400
ggaaatgaag aaatcacgca gccttttggt taaatggcag tcaaaatttt cctcagtgta  5460
```

```
tttagtgtgt tcagtgatga tatcactggt tcccaactag atgcttgttg gccacgggaa    5520
gggaaatgac ttgttctaat tctaggttca cagaggtatg agaagcctga actgaagacc    5580
attttcaaga gggacggtat ttatgaatca gggttaggct ccatatttaa agatagagcc    5640
agtttttttt tttaaataga acccaaattg tgtaaaaatg ttaattgggt tttttaaaca    5700
ttgttttatc aagtcactgt taagtagaag aaagccatgg taaactgata cataacctaa    5760
attataaaag cagaaaccta actcactcgt caagggaagt tacctttga ggaaagttaa     5820 agtactttt tccctatctg tatctatagc aacaacccag aacttacaaa cttctccaaa     5880
gattttattg attgttatat caaatcagaa tgtaaacatg aactcttgca tatatttaaa    5940
attgtgttgg aacatttgaa catgaatgct gtttgtggta cttaagaaat taattcagtt    6000
ggattatcat tatgtgatac tggcagattg cagtgcaacc ttatgccaat aaaatgtaat    6060
ttaacagccc cagatattgt tgaatattca acaataacaa gaaaagcttt tcatctaagt    6120
tttatgcttt aattttttt cttttttttt cttttctttt tgtttccttg gtactaattt     6180
taatttttat ttggaaggga gcagtataaa gcttatttgt atttagtagt gtatctccat    6240
agatacagac aaggcaagag atgataagct gtttaaatag tgtttaatat tgattggggg    6300
tggggagaaa gaaaaagtgt attacttaaa gatactatat acgttttgta tatcattaaa    6360
tctttaaaag aaatgaaata aatttattgt ttacagataa aaaaa                    6405
```

<210> SEQ ID NO 27
<211> LENGTH: 1864
<212> TYPE: PRT
<213> ORGANISM: Homo sapiens

<400> SEQUENCE: 27

```
Met Ser Gln Lys Ser Trp Ile Glu Ser Thr Leu Thr Lys Arg Glu Cys
1               5                   10                  15

Val Tyr Ile Ile Pro Ser Ser Lys Asp Pro His Arg Cys Leu Pro Gly
            20                  25                  30

Cys Gln Ile Cys Gln Gln Leu Val Arg Cys Phe Cys Gly Arg Leu Val
        35                  40                  45

Lys Gln His Ala Cys Phe Thr Ala Ser Leu Ala Met Lys Tyr Ser Asp
    50                  55                  60

Val Lys Leu Gly Asp His Phe Asn Gln Ala Ile Glu Glu Trp Ser Val
65                  70                  75                  80

Glu Lys His Thr Glu Gln Ser Pro Thr Asp Ala Tyr Gly Val Ile Asn
                85                  90                  95

Phe Gln Gly Gly Ser His Ser Tyr Arg Ala Lys Tyr Val Arg Leu Ser
            100                 105                 110

Tyr Asp Thr Lys Pro Glu Val Ile Leu Gln Leu Leu Leu Lys Glu Trp
        115                 120                 125

Gln Met Glu Leu Pro Lys Leu Val Ile Ser Val His Gly Gly Met Gln
    130                 135                 140

Lys Phe Glu Leu His Pro Arg Ile Lys Gln Leu Leu Gly Lys Gly Leu
145                 150                 155                 160

Ile Lys Ala Ala Val Thr Thr Gly Ala Trp Ile Leu Thr Gly Gly Val
                165                 170                 175

Asn Thr Gly Val Ala Lys His Val Gly Asp Ala Leu Lys Glu His Ala
            180                 185                 190

Ser Arg Ser Ser Arg Lys Ile Cys Thr Ile Gly Ile Ala Pro Trp Gly
        195                 200                 205
```

```
Val Ile Glu Asn Arg Asn Asp Leu Val Gly Arg Asp Val Val Ala Pro
    210                 215                 220
Tyr Gln Thr Leu Leu Asn Pro Leu Ser Lys Leu Asn Val Leu Asn Asn
225                 230                 235                 240
Leu His Ser His Phe Ile Leu Val Asp Asp Gly Thr Val Gly Lys Tyr
                245                 250                 255
Gly Ala Glu Val Arg Leu Arg Arg Glu Leu Glu Lys Thr Ile Asn Gln
            260                 265                 270
Gln Arg Ile His Ala Arg Ile Gly Gln Gly Val Pro Val Ala Leu
        275                 280                 285
Ile Phe Glu Gly Gly Pro Asn Val Ile Leu Thr Val Leu Glu Tyr Leu
    290                 295                 300
Gln Glu Ser Pro Pro Val Pro Val Val Cys Glu Gly Thr Gly Arg
305                 310                 315                 320
Ala Ala Asp Leu Leu Ala Tyr Ile His Lys Gln Thr Glu Glu Gly Gly
                325                 330                 335
Asn Leu Pro Asp Ala Ala Glu Pro Asp Ile Ile Ser Thr Ile Lys Lys
            340                 345                 350
Thr Phe Asn Phe Gly Gln Asn Glu Ala Leu His Leu Phe Gln Thr Leu
        355                 360                 365
Met Glu Cys Met Lys Arg Lys Glu Leu Ile Thr Val Phe His Ile Gly
370                 375                 380
Ser Asp Glu His Gln Asp Ile Asp Val Ala Ile Leu Thr Ala Leu Leu
385                 390                 395                 400
Lys Gly Thr Asn Ala Ser Ala Phe Asp Gln Leu Ile Leu Thr Leu Ala
                405                 410                 415
Trp Asp Arg Val Asp Ile Ala Lys Asn His Val Phe Val Tyr Gly Gln
            420                 425                 430
Gln Trp Leu Val Gly Ser Leu Glu Gln Ala Met Leu Asp Ala Leu Val
        435                 440                 445
Met Asp Arg Val Ala Phe Val Lys Leu Leu Ile Glu Asn Gly Val Ser
450                 455                 460
Met His Lys Phe Leu Thr Ile Pro Arg Leu Glu Glu Leu Tyr Asn Thr
465                 470                 475                 480
Lys Gln Gly Pro Thr Asn Pro Met Leu Phe His Leu Val Arg Asp Val
                485                 490                 495
Lys Gln Gly Asn Leu Pro Pro Gly Tyr Lys Ile Thr Leu Ile Asp Ile
            500                 505                 510
Gly Leu Val Ile Glu Tyr Leu Met Gly Gly Thr Tyr Arg Cys Thr Tyr
        515                 520                 525
Thr Arg Lys Arg Phe Arg Leu Ile Tyr Asn Ser Leu Gly Gly Asn Asn
530                 535                 540
Arg Arg Ser Gly Arg Asn Thr Ser Ser Thr Pro Gln Leu Arg Lys
545                 550                 555                 560
Ser His Glu Ser Phe Gly Asn Arg Ala Asp Lys Lys Glu Lys Met Arg
                565                 570                 575
His Asn His Phe Ile Lys Thr Ala Gln Pro Tyr Arg Pro Lys Ile Asp
            580                 585                 590
Thr Val Met Glu Glu Gly Lys Lys Arg Thr Lys Asp Glu Ile Val
        595                 600                 605
Asp Ile Asp Asp Pro Glu Thr Lys Arg Phe Pro Tyr Pro Leu Asn Glu
610                 615                 620
Leu Leu Ile Trp Ala Cys Leu Met Lys Arg Gln Val Met Ala Arg Phe
```

-continued

```
            625                 630                 635                 640
Leu Trp Gln His Gly Glu Glu Ser Met Ala Lys Ala Leu Val Ala Cys
                645                 650                 655
Lys Ile Tyr Arg Ser Met Ala Tyr Glu Ala Lys Gln Ser Asp Leu Val
                660                 665                 670
Asp Asp Thr Ser Glu Glu Leu Lys Gln Tyr Ser Asn Asp Phe Gly Gln
                675                 680                 685
Leu Ala Val Glu Leu Leu Glu Gln Ser Phe Arg Gln Asp Glu Thr Met
                690                 695                 700
Ala Met Lys Leu Leu Thr Tyr Glu Leu Lys Asn Trp Ser Asn Ser Thr
705                 710                 715                 720
Cys Leu Lys Leu Ala Val Ala Lys His Arg Asp Phe Ile Ala His
                725                 730                 735
Thr Cys Ser Gln Met Leu Leu Thr Asp Met Trp Met Gly Arg Leu Arg
                740                 745                 750
Met Arg Lys Asn Pro Gly Leu Lys Val Ile Leu Ser Ile Leu Val Pro
                755                 760                 765
Pro Ala Ile Leu Leu Leu Glu Tyr Lys Thr Lys Ala Glu Met Ser His
                770                 775                 780
Ile Pro Gln Ser Gln Asp Ala His Gln Met Thr Met Asp Asp Ser Glu
785                 790                 795                 800
Asn Asn Phe Gln Asn Ile Thr Glu Glu Ile Pro Met Glu Val Phe Lys
                805                 810                 815
Glu Val Arg Ile Leu Asp Ser Asn Glu Gly Lys Asn Glu Met Glu Ile
                820                 825                 830
Gln Met Lys Ser Lys Lys Leu Pro Ile Thr Arg Lys Phe Tyr Ala Phe
                835                 840                 845
Tyr His Ala Pro Ile Val Lys Phe Trp Phe Asn Thr Leu Ala Tyr Leu
                850                 855                 860
Gly Phe Leu Met Leu Tyr Thr Phe Val Val Leu Val Gln Met Glu Gln
865                 870                 875                 880
Leu Pro Ser Val Gln Glu Trp Ile Val Ile Ala Tyr Ile Phe Thr Tyr
                885                 890                 895
Ala Ile Glu Lys Val Arg Glu Ile Phe Met Ser Glu Ala Gly Lys Val
                900                 905                 910
Asn Gln Lys Ile Lys Val Trp Phe Ser Asp Tyr Phe Asn Ile Ser Asp
                915                 920                 925
Thr Ile Ala Ile Ile Ser Phe Phe Ile Gly Phe Gly Leu Arg Phe Gly
                930                 935                 940
Ala Lys Trp Asn Phe Ala Asn Ala Tyr Asp Asn His Val Phe Val Ala
945                 950                 955                 960
Gly Arg Leu Ile Tyr Cys Leu Asn Ile Ile Phe Trp Tyr Val Arg Leu
                965                 970                 975
Leu Asp Phe Leu Ala Val Asn Gln Gln Ala Gly Pro Tyr Val Met Met
                980                 985                 990
Ile Gly Lys Met Val Ala Asn Met Phe Tyr Ile Val Val Ile Met Ala
                995                 1000                1005
Leu Val Leu Leu Ser Phe Gly Val Pro Arg Lys Ala Ile Leu Tyr
                1010                1015                1020
Pro His Glu Ala Pro Ser Trp Thr Leu Ala Lys Asp Ile Val Phe
                1025                1030                1035
His Pro Tyr Trp Met Ile Phe Gly Glu Val Tyr Ala Tyr Glu Ile
                1040                1045                1050
```

-continued

```
Asp Val Cys Ala Asn Asp Ser Val Ile Pro Gln Ile Cys Gly Pro
1055                1060                1065

Gly Thr Trp Leu Thr Pro Phe Leu Gln Ala Val Tyr Leu Phe Val
1070                1075                1080

Gln Tyr Ile Ile Met Val Asn Leu Leu Ile Ala Phe Phe Asn Asn
1085                1090                1095

Val Tyr Leu Gln Val Lys Ala Ile Ser Asn Ile Val Trp Lys Tyr
1100                1105                1110

Gln Arg Tyr His Phe Ile Met Ala Tyr His Glu Lys Pro Val Leu
1115                1120                1125

Pro Pro Pro Leu Ile Ile Leu Ser His Ile Val Ser Leu Phe Cys
1130                1135                1140

Cys Ile Cys Lys Arg Arg Lys Asp Lys Thr Ser Asp Gly Pro
1145                1150                1155

Lys Leu Phe Leu Thr Glu Glu Asp Gln Lys Lys Leu His Asp Phe
1160                1165                1170

Glu Glu Gln Cys Val Glu Met Tyr Phe Asn Glu Lys Asp Asp Lys
1175                1180                1185

Phe His Ser Gly Ser Glu Glu Arg Ile Arg Val Thr Phe Glu Arg
1190                1195                1200

Val Glu Gln Met Cys Ile Gln Ile Lys Glu Val Gly Asp Arg Val
1205                1210                1215

Asn Tyr Ile Lys Arg Ser Leu Gln Ser Leu Asp Ser Gln Ile Gly
1220                1225                1230

His Leu Gln Asp Leu Ser Ala Leu Thr Val Asp Thr Leu Lys Thr
1235                1240                1245

Leu Thr Ala Gln Lys Ala Ser Glu Ala Ser Lys Val His Asn Glu
1250                1255                1260

Ile Thr Arg Glu Leu Ser Ile Ser Lys His Leu Ala Gln Asn Leu
1265                1270                1275

Ile Asp Asp Gly Pro Val Arg Pro Ser Val Trp Lys Lys His Gly
1280                1285                1290

Val Val Asn Thr Leu Ser Ser Ser Leu Pro Gln Gly Asp Leu Glu
1295                1300                1305

Ser Asn Asn Pro Phe His Cys Asn Ile Leu Met Lys Asp Asp Lys
1310                1315                1320

Asp Pro Gln Cys Asn Ile Phe Gly Gln Asp Leu Pro Ala Val Pro
1325                1330                1335

Gln Arg Lys Glu Phe Asn Phe Pro Glu Ala Gly Ser Ser Ser Gly
1340                1345                1350

Ala Leu Phe Pro Ser Ala Val Ser Pro Pro Glu Leu Arg Gln Arg
1355                1360                1365

Leu His Gly Val Glu Leu Leu Lys Ile Phe Asn Lys Asn Gln Lys
1370                1375                1380

Leu Gly Ser Ser Ser Thr Ser Ile Pro His Leu Ser Ser Pro Pro
1385                1390                1395

Thr Lys Phe Phe Val Ser Thr Pro Ser Gln Pro Ser Cys Lys Ser
1400                1405                1410

His Leu Glu Thr Gly Thr Lys Asp Gln Glu Thr Val Cys Ser Lys
1415                1420                1425

Ala Thr Glu Gly Asp Asn Thr Glu Phe Gly Ala Phe Val Gly His
1430                1435                1440
```

-continued

```
Arg Asp Ser Met Asp Leu Gln Arg Phe Lys Glu Thr Ser Asn Lys
1445                1450                1455
Ile Lys Ile Leu Ser Asn Asn Asn Thr Ser Glu Asn Thr Leu Lys
1460                1465                1470
Arg Val Ser Ser Leu Ala Gly Phe Thr Asp Cys His Arg Thr Ser
1475                1480                1485
Ile Pro Val His Ser Lys Gln Glu Lys Ile Ser Arg Arg Pro Ser
1490                1495                1500
Thr Glu Asp Thr His Glu Val Asp Ser Lys Ala Ala Leu Ile Pro
1505                1510                1515
Val Trp Leu Gln Asp Arg Pro Ser Asn Arg Glu Met Pro Ser Glu
1520                1525                1530
Glu Gly Thr Leu Asn Gly Leu Thr Ser Pro Phe Lys Pro Ala Met
1535                1540                1545
Asp Thr Asn Tyr Tyr Ser Ala Val Glu Arg Asn Asn Leu Met
1550                1555                1560
Arg Leu Ser Gln Ser Ile Pro Phe Thr Pro Val Pro Pro Arg Gly
1565                1570                1575
Glu Pro Val Thr Val Tyr Arg Leu Glu Glu Ser Ser Pro Asn Ile
1580                1585                1590
Leu Asn Asn Ser Met Ser Ser Trp Ser Gln Leu Gly Leu Cys Ala
1595                1600                1605
Lys Ile Glu Phe Leu Ser Lys Glu Glu Met Gly Gly Gly Leu Arg
1610                1615                1620
Arg Ala Val Lys Val Gln Cys Thr Trp Ser Glu His Asp Ile Leu
1625                1630                1635
Lys Ser Gly His Leu Tyr Ile Ile Lys Ser Phe Leu Pro Glu Val
1640                1645                1650
Val Asn Thr Trp Ser Ser Ile Tyr Lys Glu Asp Thr Val Leu His
1655                1660                1665
Leu Cys Leu Arg Glu Ile Gln Gln Gln Arg Ala Ala Gln Lys Leu
1670                1675                1680
Thr Phe Ala Phe Asn Gln Met Lys Pro Lys Ser Ile Pro Tyr Ser
1685                1690                1695
Pro Arg Phe Leu Glu Val Phe Leu Leu Tyr Cys His Ser Ala Gly
1700                1705                1710
Gln Trp Phe Ala Val Glu Glu Cys Met Thr Gly Glu Phe Arg Lys
1715                1720                1725
Tyr Asn Asn Asn Gly Asp Glu Ile Ile Pro Thr Asn Thr Leu
1730                1735                1740
Glu Glu Ile Met Leu Ala Phe Ser His Trp Thr Tyr Glu Tyr Thr
1745                1750                1755
Arg Gly Glu Leu Leu Val Leu Asp Leu Gln Gly Val Gly Glu Asn
1760                1765                1770
Leu Thr Asp Pro Ser Val Ile Lys Ala Glu Lys Arg Ser Cys
1775                1780                1785
Asp Met Val Phe Gly Pro Ala Asn Leu Gly Glu Asp Ala Ile Lys
1790                1795                1800
Asn Phe Arg Ala Lys His His Cys Asn Ser Cys Cys Arg Lys Leu
1805                1810                1815
Lys Leu Pro Asp Leu Lys Arg Asn Asp Tyr Thr Pro Asp Lys Ile
1820                1825                1830
Ile Phe Pro Gln Asp Glu Pro Ser Asp Leu Asn Leu Gln Pro Gly
```

1835                1840               1845

Asn Ser Thr Lys Glu Ser Glu Ser Thr Asn Ser Val Arg Leu Met
     1850                1855                1860

Leu

<210> SEQ ID NO 28
<211> LENGTH: 7090
<212> TYPE: DNA
<213> ORGANISM: Mus musculus

<400> SEQUENCE: 28

| | | | | | |
|---|---|---|---|---|---|
| cgggcgcggg | cgcgtccctc | tggccagtca | cccggcggag | ctggtcgcac | aattatgaaa | 60 |
| gactcgactt | ctgctgctag | cgctggagct | gagttagttc | tgagaaggtt | tcccggggct | 120 |
| gtccttgttc | ggtggcccgt | gccaccgcct | ccggagacgc | tttccgatag | gtggctgcag | 180 |
| gccgcgagg | tggaggagga | gccgctgccc | ttccggagtc | cgccccgtga | ggagaatgtc | 240 |
| ccagaaatcc | tggatagaga | gcactttgac | caagagggag | tgtgtatata | ttataccaag | 300 |
| ctccaaagac | cctcacagat | gtcttccagg | atgtcagatt | tgtcagcaac | ttgtcagatg | 360 |
| tttctgtggt | cgtttggtca | gcaacatgc | atgctttact | gcaagtcttg | ccatgaaata | 420 |
| ctcagatgtg | agattgggtg | aacactttaa | ccaggcaata | aagaatggt | ctgtggaaaa | 480 |
| gcacacggag | cagagcccaa | cagatgctta | tggagtcatc | aattttcaag | ggggttctca | 540 |
| ttcctacaga | gctaagtatg | tgagactatc | atatgatacc | aaacctgaaa | tcattctgca | 600 |
| acttctgctt | aaagaatggc | aaatggagtt | acccaaactt | gttatttctg | tacatggagg | 660 |
| catgcagaag | tttgaacttc | atccaagaat | caagcagttg | cttggaaagg | gtcttattaa | 720 |
| agctgcagtt | acaaccggag | cttggatttt | aactggagga | gtcaatacag | gtgtggcaaa | 780 |
| acatgttggt | gatgccctca | agaacatgc | ttccagatca | tctcgaaaaa | tttgcactat | 840 |
| tggaatagct | ccatggggag | tgatagaaaa | cagaaatgat | cttgttggga | gagatgtggt | 900 |
| tgctccttat | caaacccctat | tgaatcccctt | gagcaaattg | aatgttctga | ataatctaca | 960 |
| ctcccatttc | atcttggtgg | atgatggcac | tgttggaaag | tatggggcag | aagtcagact | 1020 |
| gagaagagaa | cttgaaaaaa | ccattaatca | gcaaagaatt | catgctagaa | ttgggcaagg | 1080 |
| agttcctgtg | gtggctttga | tatttgaagg | cgggccaaat | gtcatcctta | cagtactgga | 1140 |
| gtaccttcag | gaaagcccccc | cagttccagt | tgttgtgtgt | gaagggacag | gcagagctgc | 1200 |
| agatttacta | gcctatatcc | acaaacagac | agaggaagga | ggaaatcttc | ctgatgcagc | 1260 |
| agagcctgat | attatatcaa | ctatcaagaa | acatttaac | tttggccaga | gtgaagcagt | 1320 |
| tcatttattt | caaacaatga | tggagtgtat | gaaaaaaaaa | gagcttatca | ctgttttttca | 1380 |
| cattggatca | gaggatcatc | aagatataga | tgtggccata | ctcactgcac | tgctgaaagg | 1440 |
| tactaatgca | tctgcatttg | accagcttat | ccttacactg | gcatgggaca | gagttgatat | 1500 |
| tgccaaaaat | catgtatttg | tttatggaca | acagtggctg | gttggatcct | ggaacaggc | 1560 |
| tatgcttgat | gctcttgtaa | tggacagagt | ttcatttgta | aaacttctta | ttgaaaacgg | 1620 |
| agtaagcatg | cataaattcc | ttaccattcc | cagactggaa | gaactttata | cactaaaca | 1680 |
| aggtccaacc | aatccaatgt | tgttccatct | cattcgggat | gtcaagcagg | gtaatctccc | 1740 |
| cccgggtac | aagatcactt | taattgatat | aggacttgtg | attgagtatc | tcatgggagg | 1800 |
| aacctacaga | tgcacataca | cacgaaaacg | ttttcgattg | atatataata | gtcttggtgg | 1860 |
| aaataaccgg | aggtcaggtc | gaaataccctc | cagcagcacc | cctcagttgc | gaaagagtca | 1920 |

```
tgaaactttt ggcaatagag ctgataaaaa ggaaaaaatg agacacaatc atttcattaa   1980
aacagcccaa ccctacagac caaagatgga tgcatctatg aagaaggaa agaagaaaag    2040 aaccaaagat gaaattgtag atatagatga tccagagacc aagcgctttc cttatcctct   2100
taatgaatta ttaatttggg cttgccttat gaagaggcag gtcatggccc gcttttatg    2160 gcagcatggt gaagaatcaa tggctaaagc attagttgcc tgtaaaatct atcgttcaat   2220
ggcttatgag gcaaagcaga gtgacctggt agatgatact tcagaggaac tgaagcagta   2280
ttccaatgat tttggccaac tggcagttga attactggaa cagtccttca gacaggatga   2340
aacgatggct atgaaattac tcacttatga actcaaaaac tggagtaatt caacctgcct   2400
caagttagca gtttcttcaa gacttagacc ttttgtagct cacacttgta cacagatgtt   2460
gttatctgat atgtggatgg gacggctgaa tatgagaaaa aattcctggt ataaggtcat   2520
attaagcatt ttagttccac ctgccatatt aatgctagag tataaaacca aggctgaaat   2580
gtcccatatc ccacaatctc aagatgctca tcaaatgacg atggaggata gtgaaaacaa   2640
ttttcacaac ataacagaag agatacccat ggaagtattt aagaagtaa agattttgga    2700 cagcagtgat ggaaagaatg aaatggagat acatattaaa tcaaaaaagc ttccaatcac   2760
acgaaaattt tatgcctttt atcatgcacc aattgtaaag ttctggttta acacattggc   2820
atatttagga tttctgatgc tttatacatt tgtagttctt gtaaaaatgg aacagttacc   2880
ttcagttcaa gaatggattg ttatcgctta tatttttacc tatgctattg aaaaagtccg   2940
tgaggtcttc atgtctgaag ctgggaaaat cagccagaag attaaagtat ggtttagtga   3000
ctacttcaat gtcagtgaca caattgccat catttctttc tttgttggat ttggactaag   3060
atttggagca aaatggaact atattaatgc atatgataat catgtttttg tggctggaag   3120
attaatttac tgtcttaata taatattttg gtatgtgcgt ttgctagact tctagccgt    3180 aaatcaacag gcaggacctt atgtaatgat gattggaaaa atggtggcca atatgttcta   3240
cattgtagtg ataatggctc ttgtattgct tagttttggt gttcccagaa aagcaatact   3300
ttatccacat gaagaaccat cttggtctct tgctaaagat atagttttc atccatactg    3360 gatgattttt ggtgaagttt atgcatatga aattgatgtg tgtgcaaatg actccactct   3420
cccgacaatc tgtggtcctg gaacttggtt gactccattt cttcaagcag tctacctctt   3480
tgtacagtat atcattatgg ttaatctcct tatcgcattt ttcaataatg tatatttaca   3540
agtgaaggca atttccaata ttgtatgaa gtatcagcgg tatcatttta ttatggctta    3600
tcatgaaaaa ccagtcctgc ctcctcctct tatcatcctc agccatatag tttcactgtt   3660
ttgctgtgta tgcaaaagaa gaaagaaaga taagacttcc gatgggccaa aacttttctt   3720
aacagaagaa gatcaaaaga aactccatga ttttgaagag cagtgtgttg agatgtactt   3780
tgatgagaaa gatgacaaat tcaattctgg gagtgaagag agaatccggg tcacttttga   3840
aagagtggag cagatgagca ttcagattaa agaagttgga gatcgtgtca actacataaa   3900
aagatcatta cagtctttag attctcaaat tggtcatctg caagatctct cagccctaac   3960
agtagataca ttgaaaacac ttacagccca gaaagcttca gaagctagta agtgcacaa    4020 tgagatcaca cgagaattga gtatttccaa acttggct cagaatctta ttgatgatgt     4080
tcctgtaaga ccttttgtgga agaaaccctag tgctgtaaac acactgagtt cctctcttcc  4140
tcaaggtgat cgggaagta ataatccttt tctttgtaat atttttatga agatgaaaa     4200 agacccccaa tataatctgt ttggacaaga tttgcccgtg atacccaga gaaaagaatt    4260 caacattcca gaggctggtt cctcctgtgg tgccttattc ccaagtgctg tttctccccc   4320
```

```
agaattacga cagagacgac atgggtaga aatgttaaaa atatttaata aaaatcaaaa    4380
attaggcagt tcacctaata gttcaccaca tatgtcctcc ccaccaacca aattttctgt    4440
gagtacccca tcccagccaa gttgcaaaag ccacttggaa tccacaacca agatcaaga    4500 acccattttc tataaagctg cagaagggga taacatagaa tttggagcat tgtgggaca    4560 cagagatagt atggacttac agaggtttaa agaaacatca aacaaaataa gagaactgtt    4620
atctaatgat actcctgaaa acactctgaa acatgtgggt gctgctggat atagtgaatg    4680
ttgtaagact tctacttctc ttcactcagt gcaagcagaa agctgtagta gaagagcgtc    4740
gacggaagac tctccagaag tcgattctaa agcagctttg ttaccggatt ggttacgaga    4800
tagaccatca aacagagaaa tgccatctga aggaggaaca ttaaatggtc ttgcttctcc    4860
atttaagccc gttttggata caaattacta ttattcagct gtggaaagaa ataacctgat    4920
gaggttgtca cagagtattc ccttcgttcc tgtacctcca cgaggcgagc ctgtcacagt    4980
gtaccgtctg gaggagagtt ctcccagtat actgaataac agcatgtctt catggtctca    5040
gctaggcctc tgtgccaaaa ttgagttttt aagtaaagag gaaatgggag gtggtttacg    5100
aagagcagtc aaagtgctgt gtacctggtc agagcacgat atcctgaagt cagggcatct    5160
ctatatcatt aagtcatttc ttcctgaggt gataaacaca tggtcaagca tttataaaga    5220
agatacggtt ctacatctct gtctcagaga aatacaacaa cagagagcag cacaaaagct    5280
cacatttgcc tttaatcaga tgaaacccaa atccatacca tattctccaa ggttccttga    5340
agttttcctg ttgtactgcc attcagcagg gcagtggttt gctgtagaag agtgcatgac    5400
tggtgaattt agaaaataca acaacaataa tggtgatgaa atcattccta caaatactct    5460
agaagagatc atgctagcct ttagccactg gacctatgaa tataccagag gggagttact    5520
ggtacttgac ttacaaggag tgggagaaaa cttgactgac ccatctgtaa taaaagctga    5580 agaaaaaga tcctgtgaca tggttttttgg ccctgccaat ctaggagaag atgcaataaa    5640
aaacttcaga gccaaacatc actgtaattc ttgctgtcga agcttaaac ttccagattt    5700 gaagaggaat gactacacgc ctgataaaat tatatttcct caggatgagt catcagattt    5760
gaatcttcaa tctggaaatt ccaccaaaga atcagaagca acaaattctg ttcgtctgat    5820
gttatagtgc tgagtcattg gttttttgcct acacttcaca aaagtgtaac tgtcagtttt    5880
cctttcgggg gaattgatga tataggaaga tgtgtgcaaa atgagcttgc tggccccaca    5940
catagtctag aggtaatgtt ctcattgaaa acgcctggga ggctgcagat gacagctgga    6000
aagtgctagc tggcagagag tcagtgctct cggctggtga agggcgggaa ccttgctgct    6060
gagagtggtg gttctctcac ctggtgcagg accattaacc aaagtcaagt cttcagattt    6120
gattggctgc tcagtcacag ccattcagct aaggaaacta aattgcgcag cttttttaaat    6180 ggctgaagtc ttcctcagtt tgtgctctat gataatgatg ttagctctca actaggtgtt    6240
tgtggccacg ggagaactac tccttacaat tttgcttcac aggcatgtta caaagcctgc    6300
actgaaaacc gtttgtcttc cctctctccc tccctctttt ccctgtagta ttgaggatca    6360
aacccagggc ctcatgaaga ccatttctcta agagacattt tatttaagaa tcaactatag    6420
agtctatgtt tatggataca gccagttttt gttaaacaaa acctgaattg tgcaaagggg    6480
ttttttaaca tttatcaatg ttaagtaaaa gaaagccatg ataaataaga attaactcac    6540
tgttcaatgg gtgtttcctg tgaggaaggt tacagttgta acagcctgca gttgcataca    6600
tctccaaaga tttacagact tagtgtatca aatcagagtg tcatgtgagc tctcacattg    6660
```

-continued

```
aaaattctat aggaatgtgt caatgtgaat tctatttctg gtacttaaga aatcagttgt   6720
tggattatcc ttatacagta tagggagatc acaatacaac tttatgccaa taaaatctaa   6780
cttaattgcc cagatatttt tgcatattta gcaacaagaa aagcttatca tttgactcaa   6840
gttttatgct ttctctttct tttcatttcc taggtactaa ttttaatttt tatttggaag   6900
gagcagtgta aagcttactt gtattcaata gtgtatctca tagatacaga caaggccgca   6960
gagataagct gttaaatagt gtttaatgtt gatgtggaga gaaaggtgta ttacttaaaa   7020
atactatacc atatacgttt tgtatatcat taaatcttta aaagaaatta aatttattct   7080
tgtttacaaa                                                           7090
```

<210> SEQ ID NO 29
<211> LENGTH: 1863
<212> TYPE: PRT
<213> ORGANISM: Mus musculus

<400> SEQUENCE: 29

```
Met Ser Gln Lys Ser Trp Ile Glu Ser Thr Leu Thr Lys Arg Glu Cys
  1               5                  10                  15

Val Tyr Ile Ile Pro Ser Ser Lys Asp Pro His Arg Cys Leu Pro Gly
             20                  25                  30

Cys Gln Ile Cys Gln Gln Leu Val Arg Cys Phe Cys Gly Arg Leu Val
         35                  40                  45

Lys Gln His Ala Cys Phe Thr Ala Ser Leu Ala Met Lys Tyr Ser Asp
     50                  55                  60

Val Arg Leu Gly Glu His Phe Asn Gln Ala Ile Glu Glu Trp Ser Val
 65                  70                  75                  80

Glu Lys His Thr Glu Gln Ser Pro Thr Asp Ala Tyr Gly Val Ile Asn
                 85                  90                  95

Phe Gln Gly Gly Ser His Ser Tyr Arg Ala Lys Tyr Val Arg Leu Ser
            100                 105                 110

Tyr Asp Thr Lys Pro Glu Ile Ile Leu Gln Leu Leu Leu Lys Glu Trp
        115                 120                 125

Gln Met Glu Leu Pro Lys Leu Val Ile Ser Val His Gly Gly Met Gln
    130                 135                 140

Lys Phe Glu Leu His Pro Arg Ile Lys Gln Leu Leu Gly Lys Gly Leu
145                 150                 155                 160

Ile Lys Ala Ala Val Thr Thr Gly Ala Trp Ile Leu Thr Gly Gly Val
                165                 170                 175

Asn Thr Gly Val Ala Lys His Val Gly Asp Ala Leu Lys Glu His Ala
            180                 185                 190

Ser Arg Ser Ser Arg Lys Ile Cys Thr Ile Gly Ile Ala Pro Trp Gly
        195                 200                 205

Val Ile Glu Asn Arg Asn Asp Leu Val Gly Arg Asp Val Val Ala Pro
    210                 215                 220

Tyr Gln Thr Leu Leu Asn Pro Leu Ser Lys Leu Asn Val Leu Asn Asn
225                 230                 235                 240

Leu His Ser His Phe Ile Leu Val Asp Asp Gly Thr Val Gly Lys Tyr
                245                 250                 255

Gly Ala Glu Val Arg Leu Arg Arg Glu Leu Glu Lys Thr Ile Asn Gln
            260                 265                 270

Gln Arg Ile His Ala Arg Ile Gly Gln Gly Val Pro Val Val Ala Leu
        275                 280                 285

Ile Phe Glu Gly Gly Pro Asn Val Ile Leu Thr Val Leu Glu Tyr Leu
```

-continued

```
            290                 295                 300
Gln Glu Ser Pro Pro Val Pro Val Val Cys Glu Gly Thr Gly Arg
305                 310                 315                 320

Ala Ala Asp Leu Leu Ala Tyr Ile His Lys Gln Thr Glu Gly Gly
                325                 330                 335

Asn Leu Pro Asp Ala Ala Glu Pro Asp Ile Ile Ser Thr Ile Lys Lys
                340                 345                 350

Thr Phe Asn Phe Gly Gln Ser Glu Ala Val His Leu Phe Gln Thr Met
            355                 360                 365

Met Glu Cys Met Lys Lys Glu Leu Ile Thr Val Phe His Ile Gly
370                 375                 380

Ser Glu Asp His Gln Asp Ile Asp Val Ala Ile Leu Thr Ala Leu Leu
385                 390                 395                 400

Lys Gly Thr Asn Ala Ser Ala Phe Asp Gln Leu Ile Leu Thr Leu Ala
                405                 410                 415

Trp Asp Arg Val Asp Ile Ala Lys Asn His Val Phe Val Tyr Gly Gln
                420                 425                 430

Gln Trp Leu Val Gly Ser Leu Glu Gln Ala Met Leu Asp Ala Leu Val
            435                 440                 445

Met Asp Arg Val Ser Phe Val Lys Leu Leu Ile Glu Asn Gly Val Ser
450                 455                 460

Met His Lys Phe Leu Thr Ile Pro Arg Leu Glu Glu Leu Tyr Asn Thr
465                 470                 475                 480

Lys Gln Gly Pro Thr Asn Pro Met Leu Phe His Leu Ile Arg Asp Val
                485                 490                 495

Lys Gln Gly Asn Leu Pro Pro Gly Tyr Lys Ile Thr Leu Ile Asp Ile
                500                 505                 510

Gly Leu Val Ile Glu Tyr Leu Met Gly Gly Thr Tyr Arg Cys Thr Tyr
            515                 520                 525

Thr Arg Lys Arg Phe Arg Leu Ile Tyr Asn Ser Leu Gly Gly Asn Asn
530                 535                 540

Arg Arg Ser Gly Arg Asn Thr Ser Ser Ser Thr Pro Gln Leu Arg Lys
545                 550                 555                 560

Ser His Glu Thr Phe Gly Asn Arg Ala Asp Lys Lys Glu Lys Met Arg
                565                 570                 575

His Asn His Phe Ile Lys Thr Ala Gln Pro Tyr Arg Pro Lys Met Asp
                580                 585                 590

Ala Ser Met Glu Glu Gly Lys Lys Lys Arg Thr Lys Asp Glu Ile Val
            595                 600                 605

Asp Ile Asp Asp Pro Glu Thr Lys Arg Phe Pro Tyr Pro Leu Asn Glu
610                 615                 620

Leu Leu Ile Trp Ala Cys Leu Met Lys Arg Gln Val Met Ala Arg Phe
625                 630                 635                 640

Leu Trp Gln His Gly Glu Glu Ser Met Ala Lys Ala Leu Val Ala Cys
                645                 650                 655

Lys Ile Tyr Arg Ser Met Ala Tyr Glu Ala Lys Gln Ser Asp Leu Val
                660                 665                 670

Asp Asp Thr Ser Glu Glu Leu Lys Gln Tyr Ser Asn Asp Phe Gly Gln
            675                 680                 685

Leu Ala Val Glu Leu Leu Glu Gln Ser Phe Arg Gln Asp Glu Thr Met
690                 695                 700

Ala Met Lys Leu Leu Thr Tyr Glu Leu Lys Asn Trp Ser Asn Ser Thr
705                 710                 715                 720
```

```
Cys Leu Lys Leu Ala Val Ser Ser Arg Leu Arg Pro Phe Val Ala His
            725                 730                 735

Thr Cys Thr Gln Met Leu Leu Ser Asp Met Trp Met Gly Arg Leu Asn
            740                 745                 750

Met Arg Lys Asn Ser Trp Tyr Lys Val Ile Leu Ser Ile Leu Val Pro
            755                 760                 765

Pro Ala Ile Leu Met Leu Glu Tyr Lys Thr Lys Ala Glu Met Ser His
            770                 775                 780

Ile Pro Gln Ser Gln Asp Ala His Gln Met Thr Met Glu Asp Ser Glu
785                 790                 795                 800

Asn Asn Phe His Asn Ile Thr Glu Glu Ile Pro Met Glu Val Phe Lys
            805                 810                 815

Glu Val Lys Ile Leu Asp Ser Ser Asp Gly Lys Asn Glu Met Glu Ile
            820                 825                 830

His Ile Lys Ser Lys Lys Leu Pro Ile Thr Arg Lys Phe Tyr Ala Phe
            835                 840                 845

Tyr His Ala Pro Ile Val Lys Phe Trp Phe Asn Thr Leu Ala Tyr Leu
    850                 855                 860

Gly Phe Leu Met Leu Tyr Thr Phe Val Val Leu Val Lys Met Glu Gln
865                 870                 875                 880

Leu Pro Ser Val Gln Glu Trp Ile Val Ile Ala Tyr Ile Phe Thr Tyr
            885                 890                 895

Ala Ile Glu Lys Val Arg Glu Val Phe Met Ser Glu Ala Gly Lys Ile
            900                 905                 910

Ser Gln Lys Ile Lys Val Trp Phe Ser Asp Tyr Phe Asn Val Ser Asp
            915                 920                 925

Thr Ile Ala Ile Ile Ser Phe Phe Val Gly Phe Gly Leu Arg Phe Gly
            930                 935                 940

Ala Lys Trp Asn Tyr Ile Asn Ala Tyr Asp Asn His Val Phe Val Ala
945                 950                 955                 960

Gly Arg Leu Ile Tyr Cys Leu Asn Ile Ile Phe Trp Tyr Val Arg Leu
            965                 970                 975

Leu Asp Phe Leu Ala Val Asn Gln Gln Ala Gly Pro Tyr Val Met Met
            980                 985                 990

Ile Gly Lys Met Val Ala Asn Met  Phe Tyr Ile Val Val  Ile Met Ala
            995                 1000                 1005

Leu Val Leu Leu Ser Phe Gly Val Pro Arg Lys Ala  Ile Leu Tyr
        1010                1015                1020

Pro His Glu Glu Pro Ser Trp Ser Leu Ala Lys Asp  Ile Val Phe
        1025                1030                1035

His Pro Tyr Trp Met Ile Phe Gly Glu Val Tyr Ala  Tyr Glu Ile
        1040                1045                1050

Asp Val Cys Ala Asn Asp Ser Thr Leu Pro Thr Ile  Cys Gly Pro
        1055                1060                1065

Gly Thr Trp Leu Thr Pro Phe Leu Gln Ala Val Tyr  Leu Phe Val
        1070                1075                1080

Gln Tyr Ile Ile Met Val Asn Leu Leu Ile Ala Phe  Phe Asn Asn
        1085                1090                1095

Val Tyr Leu Gln Val Lys Ala Ile Ser Asn Ile Val  Trp Lys Tyr
        1100                1105                1110

Gln Arg Tyr His Phe Ile Met Ala Tyr His Glu Lys  Pro Val Leu
        1115                1120                1125
```

-continued

```
Pro Pro Pro Leu Ile Ile Leu Ser His Ile Val Ser Leu Phe Cys
1130                1135                1140

Cys Val Cys Lys Arg Arg Lys Lys Asp Lys Thr Ser Asp Gly Pro
1145                1150                1155

Lys Leu Phe Leu Thr Glu Glu Asp Gln Lys Lys Leu His Asp Phe
1160                1165                1170

Glu Glu Gln Cys Val Glu Met Tyr Phe Asp Lys Asp Asp Lys
1175                1180                1185

Phe Asn Ser Gly Ser Glu Glu Arg Ile Arg Val Thr Phe Glu Arg
1190                1195                1200

Val Glu Gln Met Ser Ile Gln Ile Lys Glu Val Gly Asp Arg Val
1205                1210                1215

Asn Tyr Ile Lys Arg Ser Leu Gln Ser Leu Asp Ser Gln Ile Gly
1220                1225                1230

His Leu Gln Asp Leu Ser Ala Leu Thr Val Asp Thr Leu Lys Thr
1235                1240                1245

Leu Thr Ala Gln Lys Ala Ser Glu Ala Ser Lys Val His Asn Glu
1250                1255                1260

Ile Thr Arg Glu Leu Ser Ile Ser Lys His Leu Ala Gln Asn Leu
1265                1270                1275

Ile Asp Asp Val Pro Val Arg Pro Leu Trp Lys Lys Pro Ser Ala
1280                1285                1290

Val Asn Thr Leu Ser Ser Ser Leu Pro Gln Gly Asp Arg Glu Ser
1295                1300                1305

Asn Asn Pro Phe Leu Cys Asn Ile Phe Met Lys Asp Glu Lys Asp
1310                1315                1320

Pro Gln Tyr Asn Leu Phe Gly Gln Asp Leu Pro Val Ile Pro Gln
1325                1330                1335

Arg Lys Glu Phe Asn Ile Pro Glu Ala Gly Ser Ser Cys Gly Ala
1340                1345                1350

Leu Phe Pro Ser Ala Val Ser Pro Pro Glu Leu Arg Gln Arg Arg
1355                1360                1365

His Gly Val Glu Met Leu Lys Ile Phe Asn Lys Asn Gln Lys Leu
1370                1375                1380

Gly Ser Ser Pro Asn Ser Ser Pro His Met Ser Ser Pro Pro Thr
1385                1390                1395

Lys Phe Ser Val Ser Thr Pro Ser Gln Pro Ser Cys Lys Ser His
1400                1405                1410

Leu Glu Ser Thr Thr Lys Asp Gln Glu Pro Ile Phe Tyr Lys Ala
1415                1420                1425

Ala Glu Gly Asp Asn Ile Glu Phe Gly Ala Phe Val Gly His Arg
1430                1435                1440

Asp Ser Met Asp Leu Gln Arg Phe Lys Glu Thr Ser Asn Lys Ile
1445                1450                1455

Arg Glu Leu Leu Ser Asn Asp Thr Pro Glu Asn Thr Leu Lys His
1460                1465                1470

Val Gly Ala Ala Gly Tyr Ser Glu Cys Cys Lys Thr Ser Thr Ser
1475                1480                1485

Leu His Ser Val Gln Ala Glu Ser Cys Ser Arg Arg Ala Ser Thr
1490                1495                1500

Glu Asp Ser Pro Glu Val Asp Ser Lys Ala Ala Leu Leu Pro Asp
1505                1510                1515

Trp Leu Arg Asp Arg Pro Ser Asn Arg Glu Met Pro Ser Glu Gly
```

| | | | | | | | | | |
|---|---|---|---|---|---|---|---|---|---|
| | | 1520 | | | 1525 | | | 1530 | |
| Gly | Thr | Leu | Asn | Gly | Leu | Ala | Ser | Pro | Phe | Lys | Pro | Val | Leu | Asp |
| | | 1535 | | | 1540 | | | 1545 | |

Gly Thr Leu Asn Gly Leu Ala Ser Pro Phe Lys Pro Val Leu Asp
         1535              1540              1545

Thr Asn Tyr Tyr Tyr Ser Ala Val Glu Arg Asn Asn Leu Met Arg
         1550              1555              1560

Leu Ser Gln Ser Ile Pro Phe Val Pro Val Pro Pro Arg Gly Glu
         1565              1570              1575

Pro Val Thr Val Tyr Arg Leu Glu Glu Ser Ser Pro Ser Ile Leu
         1580              1585              1590

Asn Asn Ser Met Ser Ser Trp Ser Gln Leu Gly Leu Cys Ala Lys
         1595              1600              1605

Ile Glu Phe Leu Ser Lys Glu Glu Met Gly Gly Gly Leu Arg Arg
         1610              1615              1620

Ala Val Lys Val Leu Cys Thr Trp Ser Glu His Asp Ile Leu Lys
         1625              1630              1635

Ser Gly His Leu Tyr Ile Ile Lys Ser Phe Leu Pro Glu Val Ile
         1640              1645              1650

Asn Thr Trp Ser Ser Ile Tyr Lys Glu Asp Thr Val Leu His Leu
         1655              1660              1665

Cys Leu Arg Glu Ile Gln Gln Gln Arg Ala Ala Gln Lys Leu Thr
         1670              1675              1680

Phe Ala Phe Asn Gln Met Lys Pro Lys Ser Ile Pro Tyr Ser Pro
         1685              1690              1695

Arg Phe Leu Glu Val Phe Leu Leu Tyr Cys His Ser Ala Gly Gln
         1700              1705              1710

Trp Phe Ala Val Glu Glu Cys Met Thr Gly Glu Phe Arg Lys Tyr
         1715              1720              1725

Asn Asn Asn Asn Gly Asp Glu Ile Ile Pro Thr Asn Thr Leu Glu
         1730              1735              1740

Glu Ile Met Leu Ala Phe Ser His Trp Thr Tyr Glu Tyr Thr Arg
         1745              1750              1755

Gly Glu Leu Leu Val Leu Asp Leu Gln Gly Val Gly Glu Asn Leu
         1760              1765              1770

Thr Asp Pro Ser Val Ile Lys Ala Glu Glu Lys Arg Ser Cys Asp
         1775              1780              1785

Met Val Phe Gly Pro Ala Asn Leu Gly Glu Asp Ala Ile Lys Asn
         1790              1795              1800

Phe Arg Ala Lys His His Cys Asn Ser Cys Cys Arg Lys Leu Lys
         1805              1810              1815

Leu Pro Asp Leu Lys Arg Asn Asp Tyr Thr Pro Asp Lys Ile Ile
         1820              1825              1830

Phe Pro Gln Asp Glu Ser Ser Asp Leu Asn Leu Gln Ser Gly Asn
         1835              1840              1845

Ser Thr Lys Glu Ser Glu Ala Thr Asn Ser Val Arg Leu Met Leu
         1850              1855              1860

<210> SEQ ID NO 30
<211> LENGTH: 8158
<212> TYPE: DNA
<213> ORGANISM: Homo sapiens

<400> SEQUENCE: 30
atgtcccaga atcctggat taaaggagta tttgacaaga gagaatgtag cacaatcata    60
cccagctcaa aaatcctca cagatgtact ccagtatgcc aagtctgcca gaatttaatc   120

-continued

```
aggtgttact gtggccgact gattggagac catgctggga tagattattc ctggaccatc      180
tcagctgcca agggtaaaga aagtgaacaa tggtctgttg aaaagcacac aacgaaaagc      240
ccaacagata cttttggcac gattaatttc caagatggag agcacaccca tcatgccaag      300
tatattagaa cttcttatga tacaaaactg gatcatctgt tacatttaat gttgaaagag      360
tggaaaatgg aactgcccaa gcttgtgatc tcagtccatg ggggcatcca gaactttact      420
atgccctcta aatttaaaga gattttcagc caaggtttgg ttaaagctgc agagacaaca      480
ggagcgtgga taataactga aggcatcaat acagtgtcca agcatgttgg ggatgccttg      540
aaatcccatt cctctcattc cttgagaaaa atctggacag ttggaatccc tccttggggt      600
gtcattgaga accagagaga ccttattgga aagatgtgg tgtgcctgta ccagactctg       660
gataaccccc tcagcaagct cacaacactc aacagcatgc actcgcactt catcctgtct      720
gatgatggga ccgtgggcaa gtatggaaat gaaatgaagc tcagaaggaa cctggagaag      780
tacctctctc tgcagaaaat acactgccgc tcaagacaag gcgtgccggt cgtggggctg      840
gtggtggaag gcggtcccaa cgtcatcctg tcagtgtggg agactgtcaa ggacaaggac      900
ccagtggtgg tgtgtgaggg cacaggtagg gcggctgacc tcctggcctt cacacacaaa      960
cacctggcag atgaagggat gctgcgacct caggtgaaag aggagatcat ctgcatgatt     1020
cagaacactt tcaactttag tcttaaacag tccaagcacc ttttccaaat tctaatggag     1080
tgtatggttc acaggattg tattaccata tttgatgctg actctgaaga gcagcaagac      1140
ctggacttag caatcctaac agctttgctg aagggcacaa atttatcagc gtcagagcaa     1200
ttaaatctgg caatggcttg ggacagggtg gacattgcca agaaacatat cctaatttat     1260
gaacaacact ggaagcctga tgccctggaa caagcaatgt cagatgcttt agtgatggat     1320
cgggtggatt ttgtgaagct cttaatagaa tatggagtga acctccatcg ctttcttacc     1380
atccctcgac tggaagagct ctacaataca aacaaggac ctactaatac actcttgcat      1440
catctcgtcc aagatgtgaa acagcatacc cttctttcag gctaccgaat aaccttgatt     1500
gacattggat tagtagtaga atacctcatt ggtagagcat atcgcagcaa ctacactaga     1560
aaacatttca gagccctcta caacaacctc tacagaaaat acaagcacca gagacactcc     1620
tcaggaaata gaaatgagtc tgcagaaagt acgctgcact cccagttcat tagaactgca     1680
cagccataca aattcaagga aaagtctata gtccttcata aatcaaggaa gaagtcaaaa     1740
gaacaaaatg tatcagatga ccctgagtct actggctttc tttacccta caatgacctg      1800
ctggtttggg ctgtgctgat gaaaaggcag aagatggcta tgttcttctg gcagcatgga     1860
gaggaggcca cggttaaagc cgtgattgcg tgtatcctct accgggcaat ggcccatgaa     1920
gctaaggaga gtcacatggt ggatgatgcc tcagaagagt tgaagaatta ctcaaaacag     1980
tttggccagc tggctctgga cttgttggag aaggcattca gcagaatga gcgcatggcc      2040
atgacgctgt tgacgtatga actcaggaac tggagcaatt cgacctgcct taaactggcc     2100
gtgtcgggag gattacgacc ctttgtttca catacttgta cccagatgct actgacagac     2160
atgtggatgg ggaggctgaa aatgaggaaa aactcttggt taaagattat tataagcatt     2220
attttaccac ccaccatttt gacactgaa tttaaaagca aagctgagat gtcacatgtt      2280
ccccagtccc aggacttcca atttatgtgg tattacagtg accagaacgc cagcagttcc     2340
aaagaaagtg cttctgtgaa agagtatgat ttggaaaggg gccatgatga aaactggat       2400
gaaaatcagc attttggttt ggaaagtggg caccaacacc ttccgtgac caggaaagtc       2460
```

```
tatgagttct acagtgctcc aattgtcaag ttttggtttt atacgatggc gtatttggca    2520
ttcctcatgc tgttcactta caccgtgttg gtggagatgc agccccagcc cagcgtgcag    2580
gagtggcttg ttagcattta catcttcacc aatgctattg aggtggtcag ggaggtgagt    2640
atttcagaac ctgggaagtt tacccaaaag gtgaaggtat ggattagtga gtactggaac    2700
ttaacagaaa ctgtggccat tggcctgttt tcagctggct tcgtccttcg atggggtgac    2760
cctccttttc acacagcggg aagactgatc tactgcatag acatcatatt ctggttctca    2820
cggctcctgg acttctttgc tgtgaatcaa catgcaggtc catatgtgac catgattgca    2880
aaaatgacag caaacatgtt ctatattgtg atcatcatgg ccatagtcct gctgagcttt    2940
ggagtggcac gcaaggccat cctttcgcca aaagagccac catcttggag tctagctcga    3000
gatattgtat ttgagccata ctggatgata tacgagaag tctatgctgg agaaatagat     3060
gtttgttcaa gccagccatc ctgcctcct ggttcttttc ttactccatt cttgcaagct     3120
gtctacctct tcgtgcaata tatcatcatg gtgaacctgt tgattgcttt cttcaacaac    3180
gtttacttag atatggaatc catttcaaat aacctgtgga atacaaccg ctatcgctac     3240 atcatgacct accacgagaa gccctggctg ccccacctc tcatcctgct gagccacgtg     3300
ggccttctcc tccgccgcct gtgctgtcat cgagctcctc acgaccaaga gagggtgac     3360 gttggattaa aactctacct cagtaaggag gatctgaaaa aacttcatga ttttgaggag    3420
cagtgcgtgg aaaaatactt ccatgagaag atggaagatg tgaattgtag ttgtgaggaa    3480
cgaatccgag tgacatcaga aagggttaca gagatgtact tccagctgaa agaaatgaat    3540
gaaaaggtgt ctttttataaa ggactcctta ctgtctttgg acagccaggt gggacacctg    3600
caggatctct ctgccctgac tgtggatacc ctgaaagtcc tttctgctgt tgacactttg    3660
caagaggatg aggctctcct ggccaagaga aagcattcta cttgcaaaaa acttccccac    3720
agctggagca atgtcatctg tgcagaggtt ctaggcagca tggagatcgc tggagagaag    3780
aaataccagt attatagcat gccctcttct ttgctgagga gcctggctgg aggccggcat    3840
cccccaagag tgcagagggg ggcacttctt gagattacaa acagtaaaag agaggctaca    3900
aatgtaagaa atgaccagga aaggcaagaa acacaaagta gtatagtggt ttctggggtg    3960
tctcctaaca ggcaagcaca ctcaaagtat ggccagtttc ttctggtccc ctctaatcta    4020
aagcgagttc cttttcagc agaaactgtc ttgcctctgt ccagaccctc tgtgccagat     4080
gtgctggcaa ctgaacagga catccagact gaggttcttg ttcatctgac tgggcagacc    4140
ccagttgtct ctgactgggc atcagtggat gaacccaagg aaaagcacga gcctattgct    4200
cacttactgg atggacaaga caaggcagag caagtgctac ccactttgag ttgcacacct    4260
gaacccatga caatgagctc ccctctttcc caagccaaga tcatgcaaac tggaggtgga    4320
tatgtaaact gggcattttc agaaggtgat gaaactggtg tgtttagcat caagaaaaag    4380
tggcaaacct gcttgccctc cacttgtgac agtgattcct ctcggagtga acagcaccag    4440
aagcaggccc aggacagctc cctatctgat aactcaacaa gatcggccca gagtagtgaa    4500
tgctcagagg tgggaccatg gcttcagcca aacacatcct tttggatcaa tcctctccgc    4560
agatacaggc ccttcgctag gagtcatagt tttagattcc ataaggagga gaaattgatg    4620
aagatctgta agattaaaaa tctttcaggc tcttcagaaa tagggcaggg agcatgggtc    4680
aaagcgaaaa tgctaaccaa agacaggaga ctgtcaaaga aaagaagaa tactcaagga    4740 ctccaggtgc caatcataac agtcaatgcc tgctctcaga gtgaccagtt gaatccagag    4800
ccaggagaaa acagcatctc tgaagaggag tacagcaaga actggttcac agtgtccaaa    4860
```

-continued

```
tttagtcaca caggtgtaga accttacata catcagaaaa tgaaaactaa agaaattgga   4920
caatgtgcta tacaaatcag tgattaccta aagcagtctc aagaggatct cagcaaaaac   4980
tctttgtgga attccaggag caccaacctc aataggaact ccctgctgaa aagttcaatt   5040
ggagttgaca agatctcagc ctccttaaaa agccctcaag agcctcacca tcattattca   5100
gccattgaaa ggaataattt aatgaggctt tctcagacca taccatttac accagtccaa   5160
ctgtttgcag gagaagaaat aactgtctac aggttggagg agagttcccc tttaaacctt   5220
gataaaagca tgtcctcttg gtctcagcgt gggagagcgg caatgatcca ggtattgtcc   5280
cgagaggaga tggatggggg cctccgtaaa gctatgagag tcgtcagcac ttggtctgag   5340
gatgacattc tcaagccggg acaagttttc attgtcaagt cctttcttcc tgaggttgtg   5400
cggacatggc ataaaatctt ccaggagagc actgtgcttc atctttgcct cagggaaatt   5460
caacaacaaa gagctgctca aaaattgatc tataccttca accaagtgaa accacaaacc   5520 atacctaca caccaaggtt cctggaagtt ttcttaatct actgccattc agccaaccag   5580
tggttgacca ttgagaagta tatgacaggg gagttccgga agtataacaa caacaatggt   5640
gatgaaatca cccccaccaa caccctggag gagctgatgt tggctttctc tcactggacc   5700
tatgagtaca ctcggggaga gctgctggtt ttagatttgc aaggtgttgg agaaaatttg   5760
acagatccat ctgttataaa acctgaagtc aaacaatcaa gaggaatggt gtttggaccg   5820
gccaatttgg gggaagatgc aattagaaac ttcattgcaa acatcattg taactcctgc   5880 tgccggaagc tcaaactccc ggatttaaaa agaaatgact attcccctga aaggataaat   5940
tccacctttg gacttgagat aaaaatagaa tcagctgagg agcctccagc aagggagacg   6000
ggtagaaatt ccccagaaga tgatatgcaa ctataaaaag ggaggagcaa aagatccca   6060 gtgcttgccc tgcctgccag gaactctgtg ataacataga ttgatcaacg tgatgttgat   6120
tacatcagcg tctccttggg acacgccttc tgagcctcac atctccttct gttcaaaggc   6180
ctcattggta tatgatcaat gggttctcct agacactgac ctctgtccag gcactttgc   6240 agctccatcc tcaagttcca cacgaagatg cttggatgag tcagctggga atattgttct   6300
tgtgtacctc attgctttag ctggtcactt ggaactttgg agcagaatcc tgcacattaa   6360
aggatggggt tgggggggat acatttattt tattttctca ctatgtatgc agactggacc   6420
ccctactact atttgtcacc tcacccacag attgtattta tgtctatata tatgttcata   6480
aaaagttatg tgatttcctc ctctgtcttt tccacaacat aggactttga atagcaatga   6540
taggaaaaac aatggaacaa gggtgggttt gcacagattg gagcacattc ctgcacaaac   6600
taccaagtat actggtgaaa tctcgatggg tttcagatat tgtcagtgaa tcatatgatg   6660
cctggatatt tcaggtttct gtaaaagaaa gggaaaccta aaacaaatac ccttccatat   6720
ataatatata tggaatatgt atattatata tattttata tatataatat atatggaata   6780
tatatattat atatataaaa tacatatgga atatatatat tttatatata tatatatatt   6840 tttattttg agatggagtt tcactctttt tacccaggct ggagtgcaat gatgcgatct   6900
cactgcaacc tctgcctccc gggcttgagc gattcttgtg tctcagtctt ccgggtagct   6960
gggactacag gtgtgcacca ctatgcctgg ctaattttgt attttttagta gagatggggt   7020 ttcaccatgt tggccaggct ggtctcaaac tcctgacctc agatgatcca cctgccttgg   7080
cttcccaaag tgctgggatt acaggcgtga gccactgcgc ctggcctttt ttttttttt   7140 tttaaacgag aacaagaata tgaagaactg gaaatcatta agaaagggtt tcccttcctt   7200
```

-continued

| | |
|---|---|
| aaagctcagg ggtactatta gttaggagtt gactaactca acctgtaaaa caccactcct | 7260 |
| ccttccaaag ttgtatatat aatattgcag gttaaattac tttatgtcag gtcctatgaa | 7320 |
| gaaagatacg gtttcagact gaaaacatgt tcacaggtg tttgcttcct tccagagcag | 7380 |
| agttccctat tccctggca taaagaatgt atatatattt tgaaatatgg ctgagaacat | 7440 |
| gtcattggtt tgtgaggcct aaggtgaagc actcctggca gccacactgt gtagtgtatt | 7500 |
| tgagggatca gtcatccctc ttgtatgctg ggcctggttg ccctacctcg aacaagcacc | 7560 |
| agcttttcac acaaggagag atgtggggct gggagtcctc tccccatcct attgcatctc | 7620 |
| ctttcttatt ataagctgtt ccagttcaca ggcagcaaac ctcctgggtt tgaaaaattc | 7680 |
| caacttattt ttatctttaa tcctgacatt agctgacttg ctagtgagct tgctttaaaa | 7740 |
| atctacactc ttgcattctt aggcatacag gggaaatgtt gaaaggaag gtggaaaacc | 7800 |
| aagaatttag tttgccaatg attgcctctg attcttgtaa gtttgagttc cacaagggct | 7860 |
| aatttattcc ccttttactt gggttttggg gtggtggaaa gcgggaaatt tgggtgattt | 7920 |
| gttgattggc aatgaggata aaatgttaat acttttttgg ggacttaaca actttatcct | 7980 |
| attctacaag tcagtaaagg aacaattggt actcacctca gtgctgcact caactatgga | 8040 |
| aagaggcaga gtttgcttgc ccaattgcca aactaaagac atcagttcat tggtcaaata | 8100 |
| tttgttacct ggaatggaac ttgaaagcaa atacatttgg atttcaaatt tcaaaaaa | 8158 |

<210> SEQ ID NO 31
<211> LENGTH: 2011
<212> TYPE: PRT
<213> ORGANISM: Homo sapiens

<400> SEQUENCE: 31

```
Met Ser Gln Lys Ser Trp Ile Lys Gly Val Phe Asp Lys Arg Glu Cys
1               5                   10                  15

Ser Thr Ile Ile Pro Ser Ser Lys Asn Pro His Arg Cys Thr Pro Val
            20                  25                  30

Cys Gln Val Cys Gln Asn Leu Ile Arg Cys Tyr Cys Gly Arg Leu Ile
        35                  40                  45

Gly Asp His Ala Gly Ile Asp Tyr Ser Trp Thr Ile Ser Ala Ala Lys
    50                  55                  60

Gly Lys Glu Ser Glu Gln Trp Ser Val Glu Lys His Thr Thr Lys Ser
65                  70                  75                  80

Pro Thr Asp Thr Phe Gly Thr Ile Asn Phe Gln Asp Gly Glu His Thr
                85                  90                  95

His His Ala Lys Tyr Ile Arg Thr Ser Tyr Asp Thr Lys Leu Asp His
            100                 105                 110

Leu Leu His Leu Met Leu Lys Glu Trp Lys Met Glu Leu Pro Lys Leu
        115                 120                 125

Val Ile Ser Val His Gly Gly Ile Gln Asn Phe Thr Met Pro Ser Lys
    130                 135                 140

Phe Lys Glu Ile Phe Ser Gln Gly Leu Val Lys Ala Ala Glu Thr Thr
145                 150                 155                 160

Gly Ala Trp Ile Ile Thr Glu Gly Ile Asn Thr Val Ser Lys His Val
                165                 170                 175

Gly Asp Ala Leu Lys Ser His Ser Ser His Ser Leu Arg Lys Ile Trp
            180                 185                 190

Thr Val Gly Ile Pro Pro Trp Gly Val Ile Glu Asn Gln Arg Asp Leu
        195                 200                 205
```

```
Ile Gly Lys Asp Val Val Cys Leu Tyr Gln Thr Leu Asp Asn Pro Leu
210                 215                 220

Ser Lys Leu Thr Thr Leu Asn Ser Met His Ser His Phe Ile Leu Ser
225                 230                 235                 240

Asp Asp Gly Thr Val Gly Lys Tyr Gly Asn Glu Met Lys Leu Arg Arg
            245                 250                 255

Asn Leu Glu Lys Tyr Leu Ser Leu Gln Lys Ile His Cys Arg Ser Arg
            260                 265                 270

Gln Gly Val Pro Val Val Gly Leu Val Val Glu Gly Pro Asn Val
            275                 280                 285

Ile Leu Ser Val Trp Glu Thr Val Lys Asp Lys Asp Pro Val Val Val
    290                 295                 300

Cys Glu Gly Thr Gly Arg Ala Ala Asp Leu Leu Ala Phe Thr His Lys
305                 310                 315                 320

His Leu Ala Asp Glu Gly Met Leu Arg Pro Gln Val Lys Glu Ile
            325                 330                 335

Ile Cys Met Ile Gln Asn Thr Phe Asn Phe Ser Leu Lys Gln Ser Lys
                340                 345                 350

His Leu Phe Gln Ile Leu Met Glu Cys Met Val His Arg Asp Cys Ile
            355                 360                 365

Thr Ile Phe Asp Ala Asp Ser Glu Glu Gln Gln Asp Leu Asp Leu Ala
    370                 375                 380

Ile Leu Thr Ala Leu Leu Lys Gly Thr Asn Leu Ser Ala Ser Glu Gln
385                 390                 395                 400

Leu Asn Leu Ala Met Ala Trp Asp Arg Val Asp Ile Ala Lys Lys His
                405                 410                 415

Ile Leu Ile Tyr Glu Gln His Trp Lys Pro Asp Ala Leu Glu Gln Ala
            420                 425                 430

Met Ser Asp Ala Leu Val Met Asp Arg Val Asp Phe Val Lys Leu Leu
            435                 440                 445

Ile Glu Tyr Gly Val Asn Leu His Arg Phe Leu Thr Ile Pro Arg Leu
    450                 455                 460

Glu Glu Leu Tyr Asn Thr Lys Gln Gly Pro Thr Asn Thr Leu Leu His
465                 470                 475                 480

His Leu Val Gln Asp Val Lys Gln His Thr Leu Leu Ser Gly Tyr Arg
            485                 490                 495

Ile Thr Leu Ile Asp Ile Gly Leu Val Val Glu Tyr Leu Ile Gly Arg
            500                 505                 510

Ala Tyr Arg Ser Asn Tyr Thr Arg Lys His Phe Arg Ala Leu Tyr Asn
    515                 520                 525

Asn Leu Tyr Arg Lys Tyr Lys His Gln Arg His Ser Ser Gly Asn Arg
    530                 535                 540

Asn Glu Ser Ala Glu Ser Thr Leu His Ser Gln Phe Ile Arg Thr Ala
545                 550                 555                 560

Gln Pro Tyr Lys Phe Lys Glu Lys Ser Ile Val Leu His Lys Ser Arg
            565                 570                 575

Lys Lys Ser Lys Glu Gln Asn Val Ser Asp Asp Pro Glu Ser Thr Gly
            580                 585                 590

Phe Leu Tyr Pro Tyr Asn Asp Leu Leu Val Trp Ala Val Leu Met Lys
            595                 600                 605

Arg Gln Lys Met Ala Met Phe Phe Trp Gln His Gly Glu Glu Ala Thr
610                 615                 620

Val Lys Ala Val Ile Ala Cys Ile Leu Tyr Arg Ala Met Ala His Glu
```

-continued

```
            625                 630                 635                 640
Ala Lys Glu Ser His Met Val Asp Asp Ala Ser Glu Glu Leu Lys Asn
                    645                 650                 655
Tyr Ser Lys Gln Phe Gly Gln Leu Ala Leu Asp Leu Leu Glu Lys Ala
                660                 665                 670
Phe Lys Gln Asn Glu Arg Met Ala Met Thr Leu Leu Thr Tyr Glu Leu
            675                 680                 685
Arg Asn Trp Ser Asn Ser Thr Cys Leu Lys Leu Ala Val Ser Gly Gly
        690                 695                 700
Leu Arg Pro Phe Val Ser His Thr Cys Thr Gln Met Leu Leu Thr Asp
705                 710                 715                 720
Met Trp Met Gly Arg Leu Lys Met Arg Lys Asn Ser Trp Leu Lys Ile
                725                 730                 735
Ile Ser Ile Ile Leu Pro Pro Thr Ile Leu Thr Leu Glu Phe Lys
                740                 745                 750
Ser Lys Ala Glu Met Ser His Val Pro Gln Ser Gln Asp Phe Gln Phe
                755                 760                 765
Met Trp Tyr Tyr Ser Asp Gln Asn Ala Ser Ser Lys Glu Ser Ala
770                 775                 780
Ser Val Lys Glu Tyr Asp Leu Glu Arg Gly His Asp Glu Lys Leu Asp
785                 790                 795                 800
Glu Asn Gln His Phe Gly Leu Glu Ser Gly His Gln His Leu Pro Trp
                805                 810                 815
Thr Arg Lys Val Tyr Glu Phe Tyr Ser Ala Pro Ile Val Lys Phe Trp
                820                 825                 830
Phe Tyr Thr Met Ala Tyr Leu Ala Phe Leu Met Leu Phe Thr Tyr Thr
            835                 840                 845
Val Leu Val Glu Met Gln Pro Gln Pro Ser Val Gln Glu Trp Leu Val
        850                 855                 860
Ser Ile Tyr Ile Phe Thr Asn Ala Ile Glu Val Val Arg Glu Val Ser
865                 870                 875                 880
Ile Ser Glu Pro Gly Lys Phe Thr Gln Lys Val Lys Val Trp Ile Ser
                885                 890                 895
Glu Tyr Trp Asn Leu Thr Glu Thr Val Ala Ile Gly Leu Phe Ser Ala
                900                 905                 910
Gly Phe Val Leu Arg Trp Gly Asp Pro Pro Phe His Thr Ala Gly Arg
            915                 920                 925
Leu Ile Tyr Cys Ile Asp Ile Ile Phe Trp Phe Ser Arg Leu Leu Asp
        930                 935                 940
Phe Phe Ala Val Asn Gln His Ala Gly Pro Tyr Val Thr Met Ile Ala
945                 950                 955                 960
Lys Met Thr Ala Asn Met Phe Tyr Ile Val Ile Met Ala Ile Val
                965                 970                 975
Leu Leu Ser Phe Gly Val Ala Arg Lys Ala Ile Leu Ser Pro Lys Glu
            980                 985                 990
Pro Pro Ser Trp Ser Leu Ala Arg Asp Ile Val Phe Glu Pro Tyr Trp
        995                 1000                1005
Met Ile Tyr Gly Glu Val Tyr Ala Gly Glu Ile Asp Val Cys Ser
        1010                1015                1020
Ser Gln Pro Ser Cys Pro Pro Gly Ser Phe Leu Thr Pro Phe Leu
        1025                1030                1035
Gln Ala Val Tyr Leu Phe Val Gln Tyr Ile Ile Met Val Asn Leu
        1040                1045                1050
```

```
Leu Ile Ala Phe Phe Asn Asn Val Tyr Leu Asp Met Glu Ser Ile
1055                1060                1065

Ser Asn Asn Leu Trp Lys Tyr Asn Arg Tyr Arg Tyr Ile Met Thr
1070                1075                1080

Tyr His Glu Lys Pro Trp Leu Pro Pro Pro Leu Ile Leu Leu Ser
1085                1090                1095

His Val Gly Leu Leu Leu Arg Arg Leu Cys Cys His Arg Ala Pro
1100                1105                1110

His Asp Gln Glu Glu Gly Asp Val Gly Leu Lys Leu Tyr Leu Ser
1115                1120                1125

Lys Glu Asp Leu Lys Lys Leu His Asp Phe Glu Glu Gln Cys Val
1130                1135                1140

Glu Lys Tyr Phe His Glu Lys Met Glu Asp Val Asn Cys Ser Cys
1145                1150                1155

Glu Glu Arg Ile Arg Val Thr Ser Glu Arg Val Thr Glu Met Tyr
1160                1165                1170

Phe Gln Leu Lys Glu Met Asn Glu Lys Val Ser Phe Ile Lys Asp
1175                1180                1185

Ser Leu Leu Ser Leu Asp Ser Gln Val Gly His Leu Gln Asp Leu
1190                1195                1200

Ser Ala Leu Thr Val Asp Thr Leu Lys Val Leu Ser Ala Val Asp
1205                1210                1215

Thr Leu Gln Glu Asp Glu Ala Leu Leu Ala Lys Arg Lys His Ser
1220                1225                1230

Thr Cys Lys Lys Leu Pro His Ser Trp Ser Asn Val Ile Cys Ala
1235                1240                1245

Glu Val Leu Gly Ser Met Glu Ile Ala Gly Glu Lys Lys Tyr Gln
1250                1255                1260

Tyr Tyr Ser Met Pro Ser Ser Leu Leu Arg Ser Leu Ala Gly Gly
1265                1270                1275

Arg His Pro Pro Arg Val Gln Arg Gly Ala Leu Leu Glu Ile Thr
1280                1285                1290

Asn Ser Lys Arg Glu Ala Thr Asn Val Arg Asn Asp Gln Glu Arg
1295                1300                1305

Gln Glu Thr Gln Ser Ser Ile Val Val Ser Gly Val Ser Pro Asn
1310                1315                1320

Arg Gln Ala His Ser Lys Tyr Gly Gln Phe Leu Leu Val Pro Ser
1325                1330                1335

Asn Leu Lys Arg Val Pro Phe Ser Ala Glu Thr Val Leu Pro Leu
1340                1345                1350

Ser Arg Pro Ser Val Pro Asp Val Leu Ala Thr Glu Gln Asp Ile
1355                1360                1365

Gln Thr Glu Val Leu Val His Leu Thr Gly Gln Thr Pro Val Val
1370                1375                1380

Ser Asp Trp Ala Ser Val Asp Glu Pro Lys Glu Lys His Glu Pro
1385                1390                1395

Ile Ala His Leu Leu Asp Gly Gln Asp Lys Ala Glu Gln Val Leu
1400                1405                1410

Pro Thr Leu Ser Cys Thr Pro Glu Pro Met Thr Met Ser Ser Pro
1415                1420                1425

Leu Ser Gln Ala Lys Ile Met Gln Thr Gly Gly Gly Tyr Val Asn
1430                1435                1440
```

-continued

```
Trp Ala Phe Ser Glu Gly Asp Glu Thr Gly Val Phe Ser Ile Lys
1445                1450                1455

Lys Lys Trp Gln Thr Cys Leu Pro Ser Thr Cys Asp Ser Asp Ser
    1460                1465                1470

Ser Arg Ser Glu Gln His Gln Lys Gln Ala Gln Asp Ser Ser Leu
    1475                1480                1485

Ser Asp Asn Ser Thr Arg Ser Ala Gln Ser Ser Glu Cys Ser Glu
    1490                1495                1500

Val Gly Pro Trp Leu Gln Pro Asn Thr Ser Phe Trp Ile Asn Pro
    1505                1510                1515

Leu Arg Arg Tyr Arg Pro Phe Ala Arg Ser His Ser Phe Arg Phe
    1520                1525                1530

His Lys Glu Glu Lys Leu Met Lys Ile Cys Lys Ile Lys Asn Leu
    1535                1540                1545

Ser Gly Ser Ser Glu Ile Gly Gln Gly Ala Trp Val Lys Ala Lys
    1550                1555                1560

Met Leu Thr Lys Asp Arg Arg Leu Ser Lys Lys Lys Asn Thr
    1565                1570                1575

Gln Gly Leu Gln Val Pro Ile Ile Thr Val Asn Ala Cys Ser Gln
    1580                1585                1590

Ser Asp Gln Leu Asn Pro Glu Pro Gly Glu Asn Ser Ile Ser Glu
    1595                1600                1605

Glu Glu Tyr Ser Lys Asn Trp Phe Thr Val Ser Lys Phe Ser His
    1610                1615                1620

Thr Gly Val Glu Pro Tyr Ile His Gln Lys Met Lys Thr Lys Glu
    1625                1630                1635

Ile Gly Gln Cys Ala Ile Gln Ile Ser Asp Tyr Leu Lys Gln Ser
    1640                1645                1650

Gln Glu Asp Leu Ser Lys Asn Ser Leu Trp Asn Ser Arg Ser Thr
    1655                1660                1665

Asn Leu Asn Arg Asn Ser Leu Leu Lys Ser Ser Ile Gly Val Asp
    1670                1675                1680

Lys Ile Ser Ala Ser Leu Lys Ser Pro Gln Glu Pro His His His
    1685                1690                1695

Tyr Ser Ala Ile Glu Arg Asn Asn Leu Met Arg Leu Ser Gln Thr
    1700                1705                1710

Ile Pro Phe Thr Pro Val Gln Leu Phe Ala Gly Glu Glu Ile Thr
    1715                1720                1725

Val Tyr Arg Leu Glu Glu Ser Ser Pro Leu Asn Leu Asp Lys Ser
    1730                1735                1740

Met Ser Ser Trp Ser Gln Arg Gly Arg Ala Ala Met Ile Gln Val
    1745                1750                1755

Leu Ser Arg Glu Glu Met Asp Gly Gly Leu Arg Lys Ala Met Arg
    1760                1765                1770

Val Val Ser Thr Trp Ser Glu Asp Asp Ile Leu Lys Pro Gly Gln
    1775                1780                1785

Val Phe Ile Val Lys Ser Phe Leu Pro Glu Val Val Arg Thr Trp
    1790                1795                1800

His Lys Ile Phe Gln Glu Ser Thr Val Leu His Leu Cys Leu Arg
    1805                1810                1815

Glu Ile Gln Gln Gln Arg Ala Ala Gln Lys Leu Ile Tyr Thr Phe
    1820                1825                1830

Asn Gln Val Lys Pro Gln Thr Ile Pro Tyr Thr Pro Arg Phe Leu
```

| | | | | | | | | | | |
|---|---|---|---|---|---|---|---|---|---|---|
| | | | 1835 | | | | 1840 | | | 1845 |
| Glu | Val | Phe | Leu | Ile | Tyr | Cys | His | Ser | Ala | Asn | Gln | Trp | Leu | Thr |
| 1850 | | | | | 1855 | | | | | 1860 |
| Ile | Glu | Lys | Tyr | Met | Thr | Gly | Glu | Phe | Arg | Lys | Tyr | Asn | Asn | Asn |
| 1865 | | | | | 1870 | | | | | 1875 |
| Asn | Gly | Asp | Glu | Ile | Thr | Pro | Thr | Asn | Thr | Leu | Glu | Glu | Leu | Met |
| 1880 | | | | | 1885 | | | | | 1890 |
| Leu | Ala | Phe | Ser | His | Trp | Thr | Tyr | Glu | Tyr | Thr | Arg | Gly | Glu | Leu |
| 1895 | | | | | 1900 | | | | | 1905 |
| Leu | Val | Leu | Asp | Leu | Gln | Gly | Val | Gly | Glu | Asn | Leu | Thr | Asp | Pro |
| 1910 | | | | | 1915 | | | | | 1920 |
| Ser | Val | Ile | Lys | Pro | Glu | Val | Lys | Gln | Ser | Arg | Gly | Met | Val | Phe |
| 1925 | | | | | 1930 | | | | | 1935 |
| Gly | Pro | Ala | Asn | Leu | Gly | Glu | Asp | Ala | Ile | Arg | Asn | Phe | Ile | Ala |
| 1940 | | | | | 1945 | | | | | 1950 |
| Lys | His | His | Cys | Asn | Ser | Cys | Cys | Arg | Lys | Leu | Lys | Leu | Pro | Asp |
| 1955 | | | | | 1960 | | | | | 1965 |
| Leu | Lys | Arg | Asn | Asp | Tyr | Ser | Pro | Glu | Arg | Ile | Asn | Ser | Thr | Phe |
| 1970 | | | | | 1975 | | | | | 1980 |
| Gly | Leu | Glu | Ile | Lys | Ile | Glu | Ser | Ala | Glu | Glu | Pro | Pro | Ala | Arg |
| 1985 | | | | | 1990 | | | | | 1995 |
| Glu | Thr | Gly | Arg | Asn | Ser | Pro | Glu | Asp | Asp | Met | Gln | Leu |
| 2000 | | | | | 2005 | | | | | 2010 |

<210> SEQ ID NO 32
<211> LENGTH: 1655
<212> TYPE: DNA
<213> ORGANISM: Mus musculus

<400> SEQUENCE: 32

| | |
|---|---|
| aaagtgccca gttggatgca gagccaggag aaactaacac caccgaagag ttcagcaaga | 60 |
| aatggctctc tgtatccaac ttcggccaga tgggtttaga gccttacata taccagaaaa | 120 |
| tgaaaatgaa ggaaatcaag cgacatacta cacaagccag tgaccaccta aggcagccac | 180 |
| aagagaaccg agataaaacc cccatatgga attccgggag caccagcctc agcaggagtt | 240 |
| ttctaacaag aagtccaaat gaagttcaca agatctcaac ctccttaaaa agccctcaag | 300 |
| agcctcacca ccattattca gccattgaaa ggaataattt aatgagactg tctcagacca | 360 |
| taccgtttac accaatccag ctgttcacag gagaggaagt gaccatctac aagcttgaag | 420 |
| aaagttctcc tctgaccctg gataagagca tgtcctcttg gtcgcagcat ggcagagctg | 480 |
| ccatgattca ggtgctgtca caagaggaaa tggatggggg tctccgcaaa gccatgcgag | 540 |
| ttatcagcac ctggtctgag gatgatgttc tcaagcctgg gcaggttttc attgtgaagt | 600 |
| cttttctccc cgaggttgtg cagacgtggt ataaaatctt ccaggagagc actgtgcttc | 660 |
| atctttgcct tagggaaatt caacagcaaa gagctgccca aaaactcatc tatacctta | 720 |
| accaagtaaa accacaaacc attccctata caccaaggtt tctcgaggtt tccttggtct | 780 |
| actgccattc agccaaccaa tggttaacca ttgagaagta catgacaggg gagttccgga | 840 |
| aatacaataa caacaatggt gatgaaatag ctcccaccaa taccctggaa gaactgatgt | 900 |
| tggctttctc tcactggacc tatgaatata cccggggaga gctgctggtt ttagatttgc | 960 |
| aaggtgttgg agaaaatttg acagatccga accggaaga caaacaatca gagggatgg | 1020 |
| tgtttggacc ggccaattta ggggaagatg caattagaag cttcattgca aaacatcgct | 1080 |

-continued

```
gcaactcctg ctgtgggaag ctcagactgc cggatttaaa aaggaatgat tactcccttt    1140
caagaacaca ctgcaacttg ggatttgggc aaaccattga accaactgag gagcttccag    1200
aaagagacaa aaatagaagt tccctggaag atcacacacg cctttaaaaa gatgatgaag    1260
gaagacggtg gtcctttagc tccttctgcc atgacttcta tagtgatgga catagactgg    1320
catgatcctg actatgtcag aatctccatc accatgactt tacaatgtgg acctccctgg    1380
aagtgccctg tgagcctcat ctccccctgc actagagggc acagtgcata atggaggggt    1440
tctcctgggt attgacttct aaaaagaatg tgtggcatgc gtttctcatc tcgccggttc    1500
tgcatgaaga tgctagatcg agtcagttgg gaattctttc ctcctatacc tcattgcttc    1560
agctggccac ttggagtaga attctgtgca ctaacgaact agggaattaa ttaatttatt    1620
ttctccctgc gtttggaaaa aaaaaaaaaa aaaaa                               1655
```

<210> SEQ ID NO 33
<211> LENGTH: 414
<212> TYPE: PRT
<213> ORGANISM: Mus musculus

<400> SEQUENCE: 33

```
Ser Ala Gln Leu Asp Ala Glu Pro Gly Glu Thr Asn Thr Thr Glu Glu
1               5                   10                  15

Phe Ser Lys Lys Trp Leu Ser Val Ser Asn Phe Gly Gln Met Gly Leu
            20                  25                  30

Glu Pro Tyr Ile Tyr Gln Lys Asn Lys Met Lys Glu Ile Lys Arg His
        35                  40                  45

Thr Thr Gln Ala Ser Asp His Leu Arg Gln Pro Gln Glu Asn Arg Asp
    50                  55                  60

Lys Thr Pro Ile Trp Asn Ser Gly Ser Thr Ser Leu Ser Arg Ser Phe
65                  70                  75                  80

Leu Thr Arg Ser Pro Asn Glu Val His Lys Ile Ser Thr Ser Leu Lys
                85                  90                  95

Ser Pro Gln Glu Pro His His His Tyr Ser Ala Ile Glu Arg Asn Asn
            100                 105                 110

Leu Met Arg Leu Ser Gln Thr Ile Pro Phe Thr Pro Ile Gln Leu Phe
        115                 120                 125

Thr Gly Glu Glu Val Thr Ile Tyr Lys Leu Glu Ser Ser Pro Leu
    130                 135                 140

Thr Leu Asp Lys Ser Met Ser Ser Trp Ser Gln His Gly Arg Ala Ala
145                 150                 155                 160

Met Ile Gln Val Leu Ser Gln Glu Met Asp Gly Gly Leu Arg Lys
                165                 170                 175

Ala Met Arg Val Ile Ser Thr Trp Ser Glu Asp Val Leu Lys Pro
            180                 185                 190

Gly Gln Val Phe Ile Val Lys Ser Phe Leu Pro Glu Val Val Gln Thr
        195                 200                 205

Trp Tyr Lys Ile Phe Gln Glu Ser Thr Val Leu His Leu Cys Leu Arg
    210                 215                 220

Glu Ile Gln Gln Gln Arg Ala Ala Gln Lys Leu Ile Tyr Thr Phe Asn
225                 230                 235                 240

Gln Val Lys Pro Gln Thr Ile Pro Tyr Thr Pro Arg Phe Leu Glu Val
                245                 250                 255

Ser Leu Val Tyr Cys His Ser Ala Asn Gln Trp Leu Thr Ile Glu Lys
            260                 265                 270
```

```
Tyr Met Thr Gly Glu Phe Arg Lys Tyr Asn Asn Asn Gly Asp Glu
        275                 280                 285
Ile Ala Pro Thr Asn Thr Leu Glu Glu Leu Met Leu Ala Phe Ser His
        290                 295                 300
Trp Thr Tyr Glu Tyr Thr Arg Gly Glu Leu Leu Val Leu Asp Leu Gln
305                 310                 315                 320
Gly Val Gly Glu Asn Leu Thr Asp Pro Lys Pro Glu Asp Lys Gln Ser
                325                 330                 335
Arg Gly Met Val Phe Gly Pro Ala Asn Leu Gly Glu Asp Ala Ile Arg
            340                 345                 350
Ser Phe Ile Ala Lys His Arg Cys Asn Ser Cys Cys Gly Lys Leu Arg
        355                 360                 365
Leu Pro Asp Leu Lys Arg Asn Asp Tyr Ser Leu Ser Arg Thr His Cys
        370                 375                 380
Asn Leu Gly Phe Gly Gln Thr Ile Glu Pro Thr Glu Glu Leu Pro Glu
385                 390                 395                 400
Arg Asp Lys Asn Arg Ser Ser Leu Glu Asp His Thr Arg Leu
                405                 410

<210> SEQ ID NO 34
<211> LENGTH: 5375
<212> TYPE: DNA
<213> ORGANISM: Homo sapiens

<400> SEQUENCE: 34
gaatctgctg agcccccact aacccagagt gataaaagag agacttctca caccacagca      60
gcagcgactg gtcggagttc ccatgctgat gcaagagaat gtgctatttc aacccaggca     120
gagcaagaag caaaaaccct tcaaacttca acagactcag tctccaaaga aggcaacaca     180
aattgcaagg gagaaggcat gcaagttaat actctatttg aaacaagcca ggttccagac     240
tggagtgatc ctcctcaggt acaagttcag gaaacagtca gagagacaat ctcttgcagc     300
cagatgccag cttttctcaga gcctgctggg gaggagtccc cattcactgg gaccacaaca     360
atttccttct caaacttagg aggggtccac aaggaaaatg catcattagc tcaacactcg     420
gaggtcaaac cctgtacctg tggtccacag caggaagaaa acaagacag atggcaac        480 atacctgaca atttcaggga agacctaaaa tatgagcaga gcatctcaga agccaatgat     540
gagactatgt ccccaggtgt gttctcaagg catctcccca aggatgctcg tgctgacttc     600
agggagcctg tggctgtctc tgttgcttcc cctgaaccca cagatactgc cctcaccctg     660
gaaaatgtgt gtgatgagcc aagggacaga gaagcagtgt gtgcaatgga gtgttttgag     720
gctagtgacc aaggaacatg ttttgatacc atagattctc ttgttgggac accagttgat     780
aactattcgc tcaagaaaat tgctctgta gatacggaac tggcagaagg tcaaaacaaa     840
gtatctgatt tatgttcttc taatgacaag acactggaag tcttttttca gacacaagtg     900
tctgagactt cagtgtctac gtgcaaaagc agcaaggacg gcaactcagt catgtcccct     960
ctttttatca gtactttcac cttgaacatt tcacacacag ctagtgaagg tgccacagga    1020
gaaaatctag ccaaggtgga gaaatccacc tacccactgg cctccacagt acatgctggc    1080
caggagcagc caagcccag caactcagga gggcttgatg aaacacagct cctttcttct    1140
gagaacaatc ctttagtgca atttaaagaa ggaggtgaca agagcccag tcctagtgcc    1200 gcagacacca cagccacacc agccagttat agtcaattg tgagttttcc ttgggagaag    1260
ccaacaacat taactgctaa taatgagtgc tttcaagcga ccagagagac tgttaccatt    1320
```

```
gccaccgaag tccacccagc caaatacctt gctgtgtcaa ttcctgagga caagcatgca    1380
ggtggcactg aggagaggtt ccctcgtgca tcccatgaaa aggtttccca atttccttcc    1440
caagtgcagg tggatcatat tttaagtggt gctaccatca aatctacaaa agagctactt    1500
tgcagggcac ccagtgtgcc aggagtccca caccatgtcc tgcagctccc agagggagag    1560
ggtttctgca gtaattcccc tcttcaggtt gataacctgt ctggagataa gagccagact    1620
gtggacagag cagactttag gagctatgaa gagaatttcc aagaaagagg aagtgaaaca    1680
aagcaggggg tccagcagca gagcctgtcc cagcagggtt ctctttctgc acctgatttc    1740
caacaaagtt tgcctacgac atctgctgca aagaggaaa gaaacttggt gcccacggcc    1800
ccctcaccag caagctctag ggaaggagca gggcagcgct caggttgggg gacgagggtc    1860
tccgtggtgg ctgaaactgc tggggaagaa gacagtcagg ctctgagcaa cgttccatct    1920
ctctctgata tccttttgga agagtctaaa gaatatagac ctggaaattg ggaggcaggc    1980
aacaagctga agattataac tctagaggct tccgcttctg aaatctggcc accacgacaa    2040
ctgacaaatt ctgagagcaa ggcatcagac ggtggtctca taattcctga caaggtctgg    2100
gctgtacctg atagtctaaa ggcagatgct gttgtgcctg aattggcccc ctctgaaata    2160
gcagcattgg ctcacagtcc agaggatgct gagtcagccc ttgctgatag cagagaaagc    2220
cataaaggcg aagagcccac catcagtgta cactggagaa gtctttcttc ccggggtttc    2280
agccaaccga gactcctgga gtcatccgtg gaccctgtag atgaaaagga gttatctgtc    2340
acagattcac tgtcagcggc ttctgaaact ggagggaagg aaaatgttaa caatgtgagt    2400
caagaccagg aggaaaaaca actcaagatg gatcacactg ccttctttaa aaagtttctg    2460
acctgcccta aaatcctaga gtcctctgta gatcccattg atgagataag tgtgatagag    2520
tacaccaggg ctggaaaacc agagccctct gaaaccacac cacagggcgc cagagaagga    2580
ggtcaatcaa atgacggaaa catgggccac gaagcggaaa tccagtcggc cattttgcaa    2640
gttccatgtc tccagggaac cattctgagt gaaaatagaa tcagcagaag ccaagaaggc    2700
agtatgaagc aggaggcaga acaaattcaa cctgaggagg caaaaactgc catttggcaa    2760
gtcctgcaac ccagcgaagg cggtgaaaga attccaagtg gatgtagcat aggccaaata    2820
caagaaagca gtgatgggag cttaggggag gctgagcaaa gcaaaaagga caaagcagaa    2880
ttgatttccc ccacttcacc tctttctagt tgtcttccaa taatgactca ctcttctctt    2940
ggggttgaca cgcacaactc cacaggccaa attcatgacg tccctgaaaa tgacatagtt    3000
gagcccagaa agcgtcagta tgtgtttcct gtttcacaga aaaggggaac tattgagaat    3060
gagcgtggga aacctttgcc ctcttctcct gatcttacca ggttcccttg tacttcatct    3120
cctgaaggaa atgtcacaga cttttgata agccacaaaa tggaggaacc taaaatagag    3180
gtgcttcaaa ttggggaaac caaaccccca agctcatcta gctcctcagc gaagaccttg    3240
gcatttattt caggagaacg tgagttagag aaagccccta gttactgca ggatccatgt    3300
caaaagggca ccctgggctg tgcgaaaaag tccagggaga gagaagtc cctggaagcc    3360
cgagcaggca atcgccagg accctcaca gcagtgacgg ggtcagagga ggtcaagagg    3420
aagccagaag ccccaggcag tggacattta gctgagggag taagaagaa aattttgtcc    3480
agggtggcag cactgaggct gaaactgaa gaaaaggaaa atatcagaaa gaactcagcc    3540
tttcttaaaa agatgcccaa actcgaaaca tcattatcac acacagaaga gaaacaagac    3600
ccaaaaaagc catcttgcaa aagagaagga agagctccag tattactgaa aaaaatccaa    3660
gctgagatgt tccctgaaca ctctggaaat gtaaaattaa gctgccaatt tgcagaaatt    3720
```

-continued

```
catgaagatt ctactatctg ctggacaaaa gattcaaagt ccatagccca agtgcagaga    3780
agtgcagggg acaactccac tgtttccttt gccatcgtgc aagccagtcc gaaggaccag    3840
ggactctatt actgctgcat caagaacagc tacggaaaag tgactgctga atttaacctc    3900
acagctgaag ttctcaaaca gctgtcaagt cgccaggata ctaaaggatg tgaagagatt    3960
gaattcagcc aactcatctt caaagaagac ttcctccatg acagctactt gggggccgc    4020 ctgcgtggtc agatcgccac ggaggagctg cactttggag aaggggttca ccgcaaagcc    4080
ttccgcagca cagtgatgca cggcctcatg cctgtcttca acctggcca tgcctgtgtg    4140 cttaaggtgc acaatgccat tgcctatggg accagaaata atgatgagct catccaaagg    4200
aactacaaac tcgctgccca ggaatgctat gttcaaaata ctgccaggta ttatgccaag    4260
atctacgctg ctgaagcaca gcctctggaa ggctttggag aagtacctga gatcattcct    4320 attttttctta tccatcggcc tgagaacaat atcccgtatg ctacagtgga ggaggagctg    4380
attggagaat ttgtgaagta ttccatcagg gatgggaaag aaataaactt cttgagaaga    4440
gaatcagaag ctggtcagaa atgttgcacc ttccagcact gggtgtacca gaaaacaagt    4500
ggctgcctcc tggtgacgga catgcaaggt gtaggaatga agctaactga cgttggcata    4560
gcaacgctgg ctaaagggta caagggattt aaaggcaact gttccatgac cttcattgat    4620
cagtttaaag cactacacca gtgtaacaag tattgcaaaa tgctgggact gaaatccctt    4680
caaaacaaca accagaaaca gaagcagccg agcattggga aaagcaaagt tcaaacaaac    4740
tctatgacag taagaaggc agggcctgag accccaggcg aaaagaaaac ctaacgtccc    4800 tgggtaaccct aatggccact ggctagcagc acacaatctc gccagggaaa atctgaggcc    4860
acacaggaga gaatatacag cctgcagaga gtgcgtggca atccttaccc ccagccgact    4920
gtgcgccaag atgcttctaa acccatcacc tgctgtcttc actcaaatga tttcagaaca    4980
ggatttgcga ccaggtttat ggggagattg aatcaacgat tggtctcaaa gacaggccat    5040
tctttatata cacgtttagc attttttacca acctcacatc atgtgtatat ttgtgtatt    5100 gcacatggtt gtgctgtcga ggacctggtg ctgagaagag tctgttcaca gccaaaattc    5160
ttcccactgt cattcctaac ctgggatttc tagacacatc ctgctgtgat gtaaacagaa    5220
atcacgaatt cgctcactgg atcaagttgt tccactggtg tctaatacgc tattgttgcc    5280
ggaggtgggt tctgtgacgt gaagccattt cccatcattc aacagccagt tacaattttc    5340
tgtttaatta aattcatatt taaacaaaaa aaaaa                              5375
```

<210> SEQ ID NO 35
<211> LENGTH: 1597
<212> TYPE: PRT
<213> ORGANISM: Homo sapiens

<400> SEQUENCE: 35

```
Glu Ser Ala Glu Pro Pro Leu Thr Gln Ser Asp Lys Arg Glu Thr Ser
1               5                   10                  15

His Thr Thr Ala Ala Thr Gly Arg Ser Ser His Ala Asp Ala Arg
            20                  25                  30

Glu Cys Ala Ile Ser Thr Gln Ala Glu Gln Glu Ala Lys Thr Leu Gln
        35                  40                  45

Thr Ser Thr Asp Ser Val Ser Lys Glu Gly Asn Thr Asn Cys Lys Gly
    50                  55                  60

Glu Gly Met Gln Val Asn Thr Leu Phe Glu Thr Ser Gln Val Pro Asp
65                  70                  75                  80
```

-continued

```
Trp Ser Asp Pro Pro Gln Val Gln Val Gln Glu Thr Val Arg Glu Thr
                85                  90                  95
Ile Ser Cys Ser Gln Met Pro Ala Phe Ser Glu Pro Ala Gly Glu Glu
            100                 105                 110
Ser Pro Phe Thr Gly Thr Thr Ile Ser Phe Ser Asn Leu Gly Gly
        115                 120                 125
Val His Lys Glu Asn Ala Ser Leu Ala Gln His Ser Glu Val Lys Pro
    130                 135                 140
Cys Thr Cys Gly Pro Gln Gln Glu Lys Gln Asp Arg Asp Gly Asn
145                 150                 155                 160
Ile Pro Asp Asn Phe Arg Glu Asp Leu Lys Tyr Glu Gln Ser Ile Ser
                165                 170                 175
Glu Ala Asn Asp Glu Thr Met Ser Pro Gly Val Phe Ser Arg His Leu
            180                 185                 190
Pro Lys Asp Ala Arg Ala Asp Phe Arg Glu Pro Val Ala Val Ser Val
        195                 200                 205
Ala Ser Pro Glu Pro Thr Asp Thr Ala Leu Thr Leu Glu Asn Val Cys
    210                 215                 220
Asp Glu Pro Arg Asp Arg Glu Ala Val Cys Ala Met Glu Cys Phe Glu
225                 230                 235                 240
Ala Ser Asp Gln Gly Thr Cys Phe Asp Thr Ile Asp Ser Leu Val Gly
                245                 250                 255
Thr Pro Val Asp Asn Tyr Ser Pro Gln Glu Ile Cys Ser Val Asp Thr
            260                 265                 270
Glu Leu Ala Glu Gly Gln Asn Lys Val Ser Asp Leu Cys Ser Ser Asn
        275                 280                 285
Asp Lys Thr Leu Glu Val Phe Phe Gln Thr Gln Val Ser Glu Thr Ser
    290                 295                 300
Val Ser Thr Cys Lys Ser Ser Lys Asp Gly Asn Ser Val Met Ser Pro
305                 310                 315                 320
Leu Phe Ile Ser Thr Phe Thr Leu Asn Ile Ser His Thr Ala Ser Glu
                325                 330                 335
Gly Ala Thr Gly Glu Asn Leu Ala Lys Val Glu Lys Ser Thr Tyr Pro
            340                 345                 350
Leu Ala Ser Thr Val His Ala Gly Gln Glu Gln Pro Ser Pro Ser Asn
        355                 360                 365
Ser Gly Gly Leu Asp Glu Thr Gln Leu Leu Ser Ser Glu Asn Asn Pro
    370                 375                 380
Leu Val Gln Phe Lys Glu Gly Gly Asp Lys Ser Pro Ser Pro Ser Ala
385                 390                 395                 400
Ala Asp Thr Thr Ala Thr Pro Ala Ser Tyr Ser Ser Ile Val Ser Phe
                405                 410                 415
Pro Trp Glu Lys Pro Thr Thr Leu Thr Ala Asn Asn Glu Cys Phe Gln
            420                 425                 430
Ala Thr Arg Glu Thr Val Thr Ile Ala Thr Glu Val His Pro Ala Lys
        435                 440                 445
Tyr Leu Ala Val Ser Ile Pro Glu Asp Lys His Ala Gly Gly Thr Glu
    450                 455                 460
Glu Arg Phe Pro Arg Ala Ser His Glu Lys Val Ser Gln Phe Pro Ser
465                 470                 475                 480
Gln Val Gln Val Asp His Ile Leu Ser Gly Ala Thr Ile Lys Ser Thr
                485                 490                 495
```

```
Lys Glu Leu Leu Cys Arg Ala Pro Ser Val Pro Gly Val Pro His His
            500                 505                 510

Val Leu Gln Leu Pro Glu Gly Glu Gly Phe Cys Ser Asn Ser Pro Leu
            515                 520                 525

Gln Val Asp Asn Leu Ser Gly Asp Lys Ser Gln Thr Val Asp Arg Ala
            530                 535                 540

Asp Phe Arg Ser Tyr Glu Glu Asn Phe Gln Glu Arg Gly Ser Glu Thr
545                 550                 555                 560

Lys Gln Gly Val Gln Gln Ser Leu Ser Gln Gln Gly Ser Leu Ser
            565                 570                 575

Ala Pro Asp Phe Gln Gln Ser Leu Pro Thr Thr Ser Ala Ala Gln Glu
            580                 585                 590

Glu Arg Asn Leu Val Pro Thr Ala Pro Ser Pro Ala Ser Ser Arg Glu
            595                 600                 605

Gly Ala Gly Gln Arg Ser Gly Trp Gly Thr Arg Val Ser Val Val Ala
            610                 615                 620

Glu Thr Ala Gly Glu Glu Asp Ser Gln Ala Leu Ser Asn Val Pro Ser
625                 630                 635                 640

Leu Ser Asp Ile Leu Leu Glu Ser Lys Glu Tyr Arg Pro Gly Asn
            645                 650                 655

Trp Glu Ala Gly Asn Lys Leu Lys Ile Ile Thr Leu Glu Ala Ser Ala
            660                 665                 670

Ser Glu Ile Trp Pro Pro Arg Gln Leu Thr Asn Ser Glu Ser Lys Ala
            675                 680                 685

Ser Asp Gly Gly Leu Ile Ile Pro Asp Lys Val Trp Ala Val Pro Asp
            690                 695                 700

Ser Leu Lys Ala Asp Ala Val Pro Glu Leu Ala Pro Ser Glu Ile
705                 710                 715                 720

Ala Ala Leu Ala His Ser Pro Glu Asp Ala Glu Ser Ala Leu Ala Asp
            725                 730                 735

Ser Arg Glu Ser His Lys Gly Glu Glu Pro Thr Ile Ser Val His Trp
            740                 745                 750

Arg Ser Leu Ser Ser Arg Gly Phe Ser Gln Pro Arg Leu Leu Glu Ser
            755                 760                 765

Ser Val Asp Pro Val Asp Glu Lys Glu Leu Ser Val Thr Asp Ser Leu
            770                 775                 780

Ser Ala Ala Ser Glu Thr Gly Lys Glu Asn Val Asn Asn Val Ser
785                 790                 795                 800

Gln Asp Gln Glu Glu Lys Gln Leu Lys Met Asp His Thr Ala Phe Phe
            805                 810                 815

Lys Lys Phe Leu Thr Cys Pro Lys Ile Leu Glu Ser Ser Val Asp Pro
            820                 825                 830

Ile Asp Glu Ile Ser Val Ile Glu Tyr Thr Arg Ala Gly Lys Pro Glu
            835                 840                 845

Pro Ser Glu Thr Thr Pro Gln Gly Ala Arg Glu Gly Gly Gln Ser Asn
            850                 855                 860

Asp Gly Asn Met Gly His Glu Ala Glu Ile Gln Ser Ala Ile Leu Gln
865                 870                 875                 880

Val Pro Cys Leu Gln Gly Thr Ile Leu Ser Glu Asn Arg Ile Ser Arg
            885                 890                 895

Ser Gln Glu Gly Ser Met Lys Gln Glu Ala Glu Gln Ile Gln Pro Glu
            900                 905                 910

Glu Ala Lys Thr Ala Ile Trp Gln Val Leu Gln Pro Ser Glu Gly Gly
```

```
                    915                 920                 925
Glu  Arg  Ile  Pro  Ser  Gly  Cys  Ser  Ile  Gly  Gln  Ile  Gln  Glu  Ser  Ser
               930                 935                 940

Asp  Gly  Ser  Leu  Gly  Glu  Ala  Glu  Gln  Ser  Lys  Lys  Asp  Lys  Ala  Glu
945                 950                 955                 960

Leu  Ile  Ser  Pro  Thr  Ser  Pro  Leu  Ser  Ser  Cys  Leu  Pro  Ile  Met  Thr
                965                 970                 975

His  Ser  Ser  Leu  Gly  Val  Asp  Thr  His  Asn  Ser  Thr  Gly  Gln  Ile  His
               980                 985                 990

Asp  Val  Pro  Glu  Asn  Asp  Ile  Val  Glu  Pro  Arg  Lys  Arg  Gln  Tyr  Val
              995                 1000                1005

Phe  Pro  Val  Ser  Gln  Lys  Arg  Gly  Thr  Ile  Glu  Asn  Glu  Arg  Gly
     1010                1015                1020

Lys  Pro  Leu  Pro  Ser  Ser  Pro  Asp  Leu  Thr  Arg  Phe  Pro  Cys  Thr
     1025                1030                1035

Ser  Ser  Pro  Glu  Gly  Asn  Val  Thr  Asp  Phe  Leu  Ile  Ser  His  Lys
     1040                1045                1050

Met  Glu  Glu  Pro  Lys  Ile  Glu  Val  Leu  Gln  Ile  Gly  Glu  Thr  Lys
     1055                1060                1065

Pro  Pro  Ser  Ser  Ser  Ser  Ser  Ala  Lys  Thr  Leu  Ala  Phe  Ile
     1070                1075                1080

Ser  Gly  Glu  Arg  Glu  Leu  Glu  Lys  Ala  Pro  Lys  Leu  Leu  Gln  Asp
     1085                1090                1095

Pro  Cys  Gln  Lys  Gly  Thr  Leu  Gly  Cys  Ala  Lys  Lys  Ser  Arg  Glu
     1100                1105                1110

Arg  Glu  Lys  Ser  Leu  Glu  Ala  Arg  Ala  Gly  Lys  Ser  Pro  Gly  Thr
     1115                1120                1125

Leu  Thr  Ala  Val  Thr  Gly  Ser  Glu  Glu  Val  Lys  Arg  Lys  Pro  Glu
     1130                1135                1140

Ala  Pro  Gly  Ser  Gly  His  Leu  Ala  Glu  Gly  Val  Lys  Lys  Lys  Ile
     1145                1150                1155

Leu  Ser  Arg  Val  Ala  Ala  Leu  Arg  Leu  Lys  Leu  Glu  Glu  Lys  Glu
     1160                1165                1170

Asn  Ile  Arg  Lys  Asn  Ser  Ala  Phe  Leu  Lys  Lys  Met  Pro  Lys  Leu
     1175                1180                1185

Glu  Thr  Ser  Leu  Ser  His  Thr  Glu  Glu  Lys  Gln  Asp  Pro  Lys  Lys
     1190                1195                1200

Pro  Ser  Cys  Lys  Arg  Glu  Gly  Arg  Ala  Pro  Val  Leu  Leu  Lys  Lys
     1205                1210                1215

Ile  Gln  Ala  Glu  Met  Phe  Pro  Glu  His  Ser  Gly  Asn  Val  Lys  Leu
     1220                1225                1230

Ser  Cys  Gln  Phe  Ala  Glu  Ile  His  Glu  Asp  Ser  Thr  Ile  Cys  Trp
     1235                1240                1245

Thr  Lys  Asp  Ser  Lys  Ser  Ile  Ala  Gln  Val  Gln  Arg  Ser  Ala  Gly
     1250                1255                1260

Asp  Asn  Ser  Thr  Val  Ser  Phe  Ala  Ile  Val  Gln  Ala  Ser  Pro  Lys
     1265                1270                1275

Asp  Gln  Gly  Leu  Tyr  Tyr  Cys  Cys  Ile  Lys  Asn  Ser  Tyr  Gly  Lys
     1280                1285                1290

Val  Thr  Ala  Glu  Phe  Asn  Leu  Thr  Ala  Glu  Val  Leu  Lys  Gln  Leu
     1295                1300                1305

Ser  Ser  Arg  Gln  Asp  Thr  Lys  Gly  Cys  Glu  Glu  Ile  Glu  Phe  Ser
     1310                1315                1320
```

-continued

```
Gln Leu Ile Phe Lys Glu Asp Phe Leu His Asp Ser Tyr Phe Gly
    1325                1330                1335
Gly Arg Leu Arg Gly Gln Ile Ala Thr Glu Glu Leu His Phe Gly
    1340                1345                1350
Glu Gly Val His Arg Lys Ala Phe Arg Ser Thr Val Met His Gly
    1355                1360                1365
Leu Met Pro Val Phe Lys Pro Gly His Ala Cys Val Leu Lys Val
    1370                1375                1380
His Asn Ala Ile Ala Tyr Gly Thr Arg Asn Asn Asp Glu Leu Ile
    1385                1390                1395
Gln Arg Asn Tyr Lys Leu Ala Ala Gln Glu Cys Tyr Val Gln Asn
    1400                1405                1410
Thr Ala Arg Tyr Tyr Ala Lys Ile Tyr Ala Ala Glu Ala Gln Pro
    1415                1420                1425
Leu Glu Gly Phe Gly Glu Val Pro Glu Ile Ile Pro Ile Phe Leu
    1430                1435                1440
Ile His Arg Pro Glu Asn Asn Ile Pro Tyr Ala Thr Val Glu Glu
    1445                1450                1455
Glu Leu Ile Gly Glu Phe Val Lys Tyr Ser Ile Arg Asp Gly Lys
    1460                1465                1470
Glu Ile Asn Phe Leu Arg Arg Glu Ser Glu Ala Gly Gln Lys Cys
    1475                1480                1485
Cys Thr Phe Gln His Trp Val Tyr Gln Lys Thr Ser Gly Cys Leu
    1490                1495                1500
Leu Val Thr Asp Met Gln Gly Val Gly Met Lys Leu Thr Asp Val
    1505                1510                1515
Gly Ile Ala Thr Leu Ala Lys Gly Tyr Lys Gly Phe Lys Gly Asn
    1520                1525                1530
Cys Ser Met Thr Phe Ile Asp Gln Phe Lys Ala Leu His Gln Cys
    1535                1540                1545
Asn Lys Tyr Cys Lys Met Leu Gly Leu Lys Ser Leu Gln Asn Asn
    1550                1555                1560
Asn Gln Lys Gln Lys Gln Pro Ser Ile Gly Lys Ser Lys Val Gln
    1565                1570                1575
Thr Asn Ser Met Thr Val Lys Lys Ala Gly Pro Glu Thr Pro Gly
    1580                1585                1590
Glu Lys Lys Thr
    1595

<210> SEQ ID NO 36
<211> LENGTH: 4846
<212> TYPE: DNA
<213> ORGANISM: Mus musculus

<400> SEQUENCE: 36
gcgtcgactc tgtctccaac ttgagtgaga tcaacaggga aaatctgtca ttggcccaat     60
acccaggact ggaaagctgt cctcaaagcc tccagcagga aggcagacca acagagaca    120 gagacttgcc tggtgctctc tgggcagaat cagcctgtga actgagtctc ctagaagaca    180
atgaggaaga agagtcgcag cctccagcct cagtggctct ccctcagggt gatggtgtcc    240
cctgcaggga gccagagggt ctctctgatt ctttccccca gcccactgct ccctccctcc    300
ccctggaaaa tgtgggcagt gggtcaaggg tcagagaagc tgcaggtggg gtgggtgtt    360 ttgaagccgg tgaccaagaa acatgttatg ctaccatgga tctccttgtt ggagcaccag    420
```

```
ttgataaata tttgcctcaa gaaatttgcc ccgaggactt ggagctgaca gaaggtcaaa    480
gcgaagtgtg tgatttatgt tctcctgaca agatactggc tgttctacag acacaaggtt    540
atgagcctcc acggtccaca gacaagcgca gccaggatgg caagtcagcc gagggccttc    600
tttttaacag taccttcacc tgggacacgg caaaggaggc cagtgaagat gctgtgggag    660
agacagcagc tgatgtggag aatcctccct ccaccttctc ttctacgcta ccctacagtg    720
aaagagggtt tggggagaca caaccccttt gttctgagac tatctccttt gtaaaggata    780
gtgaagggag ctacagaagt tccagtctca gcatcccagc tgccatagac acacttgcca    840
gctacagttc tgacagggag tgctcaaaag agcagtcagc cgaatcaact gctaatgtcg    900
actgtcatca ggtgaccagg gagatggagg catatcaac taatgccgct gaggtccacg     960
aaatcaaatg ccactccgtt tctgtccccc aggacaatga ctttgatgtt ggtgctgacc   1020
aggtctcgtg tgaggcacga gatgaagata attcccaatc tcttccagac gacgactcac   1080
agtcaggtcg ttcattaagt agctccacag gtgaagcaac cggggagact ctggtgccag   1140
cacccagcag tgcaggagat catgccact tctccatgcc cgagggacag ggtttgtgta    1200
gcagggctct tcagatggat aaccagcctg tgtgtcagag ccaggctatg gagggagccc   1260
acagcagagg ccttgaggag cacttccaag aaaagggaag tggaatgaag catggcatcc   1320
ggccacagag cacatcccac caggtttctc tttctgcaaa tgacttccaa gaaattttgc   1380
cctccatacc caccatgcaa caggagacca atgtggaacc cttggagcac tccctagcag   1440
attccaggga agaaattgag tgtagctcag acccgaggac cagtgacttg gtggtggctg   1500
agaagactgt gggagaagac agtcatttgg tagtcagtgt cccagctctc cctgacatcc   1560
tccttggaga gaaagatgac gttgggctag aagttgggc tgtgggcggc aaagtgaaga   1620
tcataactct agaagctccc gtctttgaaa tctggccacc agaactagtg aggcaccctg   1680
ggtacaagga ggcagaagct ggtctccacca tgcctggtag gagctgggct ctgtctgaca   1740
tcctcagagc aggtgccacc agatctgagc caggtgcctt gggaggagca gcatgggttc   1800
ccagccccca ggctgatgct ctcatggccc ttggagcgaa cagggacacc tggctaggtg   1860
ctgcaccaga cagacaagca aactgcaatt gtctgtcttc ccagtgtctg agtcaacccc   1920
gattcctgga gtcatctgta gaccctgttg aggacaagga gttagaggtc acggactctc   1980
catcagaggt ttccaaaact ggagagatgg aaatgcctga actctgaat gaggaacagg    2040 aggaaaccgt ggaccccatt gacgacaggg gtgagctgga gggtgtctgg cccgagaagc   2100
cagagccctc tgactccagc gtagaaggaa acgaattcat tgttggaaac acgtgtcaga   2160
gggtagacat ccaacctgct agcctacagc tcccacatcc ccaggacagc ggggaaatca   2220
ttccatatga acacacaacc aaccaaaatc gcgtagacgg agagagagca gaagccaaaa   2280
ccagtctgcc ggataaagcc aaagcggaag cagaagctgt tgtttggcag gcccaggggc   2340
ctggtgaaga gggacaagga attccaagtg tatgcagcat gagccaaaca caagatggtg   2400
gtgacagaag cctaggagaa gctgggcaaa ggggaacgga tgagaccgag gtcatttccc   2460
ccctgtctcc tctttctagc tgtctcacag gagtgacaca tacatgtgtc aaggctgaaa   2520
ccaacaactc cacaggccac atttatggcg gatctgagcc cagaacccgt caaagtgtaa   2580
ttcctatgaa gacagaaaag ggaactatcg agagcaagtg tgggaaccat gtgcgctctt   2640
cagatgatct cacaaacaca ccttgtactt catctcccaa aggaaatgtc acacgcttgt   2700
caataagcca tggcctggag gaactgaaat cagagaagct gcagattgcg gaaaccaaac   2760
```

-continued

```
ccctaaactc atctgactcc ccaacaatga ccttagctct catttcagga gaatgtgagt      2820
cagagaaaga ccccaaaagc ttgttacgta gggacccatg tccaaagggc tccaccctgg      2880
atagcgggaa gaagtccaga gaccaacagc agaagcctgt ggcagcccag gtcagcaagg      2940
cacctgggga ccaatcagca atggctgggt cagaggaggg caagaagaag caagaggctt      3000
cggggagtgg acacttgact gcagggataa agaagaaaat tctatccagg gtcgtagccc      3060
tgagactgag gctggaggaa aaggaaaatt cgaggaagaa ctccatcgtg aagaagacac      3120
ctaagtttga aaggtcctta tcccgcactg atgagaaaag agaccccaaa agggcccctt      3180
gcaaagctga agggaaagct ccagtattgc tgaagaggat ccaggccgag atggctcccg      3240
agcactccgg aaatataaag ttgagctgcc agttttcaga aatccatgaa gactctaccg      3300
tctgctggac aaaagattcc aagtcgatag cccaggccaa gaaaagcgca ggggacaact      3360
ccagtgtttc cttggccatc gtccaagctg gtcagaagga ccagggcctg tattactgct      3420
gcctcaagaa cagttatgga aaagtcactg ctgagtttaa cctcacagct gaagttctca      3480
aacagctttc aagtcacaca gaatatagag gatgtgaaga gattgaattc agccagctca      3540
tcttcaaaga gatgttttc aatgacagct acttcgggga ccacctacgt ggccagatct      3600
ccacggagga gcttcacttt ggcgaagggg tgcaccgcaa agctttccgg agcaaggtga      3660
tgcagggcct catgccggtc ttccagcccg gccacgcatg cgtactcaag gtgcacaatg      3720
ccgtcgccca tgggaccaga aacaatgacg aacttgtgca gaggaactac aaactggctg      3780
cccaggaatg ctacgtccag aatactgcca gatactacgc caagatctac gccgctgaag      3840
cacagcctct ggaaggcttc ggagaggtgc cggagatcat tcctattttc cttatccatc      3900
ggcccgagaa caatatccca tatgccacag tggaagaaga gctgattgga gaattcgtga      3960
agtattccat ccgggacggg aaggaaatca acttccttag acgagattca gaggctggcc      4020
agaaatgttg caccttccag cactgggtat accagaaaac aagtggctgt ctcctggtca      4080
cggacatgca gggtgtttcc atgaccttca ttgatcagtt cagagcgctg catcagtgta      4140
acaagtactg taaaatgctg gggctgaaat cccttcaaaa caacagccag aagcccagga      4200
agcccatcgt cgggaaaggc agggttccga caaacgccac gcaggtgaag acgcctgagt      4260
ctgagacgcc gcccgcagaa agaaaaaacct agcctccctc ctcccttcat caccagtgac      4320
caccaagcca gcatcgcgca ggcttgcgcg tggacatctg caagcacaca agggacacga      4380
gcctgcagcc tgcagccgag tgccagtcct ctcagctcct atcactggct gtctgctgaa      4440
atgacaatgg catggctctt ccagactagc cttgtagaga gacttagcag ttctgttgat      4500
gctctcaaag gcagcccact gtttgtgtac acagctagcc tttctacaca cacccctcccc      4560 tcccaccgca tcgtctatct atctgtgtgt cgcgcgtggt ttgttgacaa gagttcccc      4620 gctgccttgg cgactggcca ctgtcaaaat ccttcccacc tcgaccccct cacctcagga      4680
tgttcctgca gtcatgaatg tcaagttgtt gttatcagtg tcaccgacgc tattgttgct      4740
ggaggcggct tcccagatgc gagcccattt cccgccacta cccacgcagc ctggcacagt      4800
gttctgtttc attaaattca tatttaagca aaaaaaaaa aaaaaa                    4846
```

<210> SEQ ID NO 37
<211> LENGTH: 1475
<212> TYPE: PRT
<213> ORGANISM: Mus musculus

<400> SEQUENCE: 37

Val Ala Ser Val Ser Asn Leu Ser Glu Ile Asn Arg Glu Asn Leu Ser

-continued

```
1               5                  10                 15
Leu Ala Gln Tyr Pro Gly Leu Glu Ser Cys Pro Gln Ser Leu Gln Gln
                20                 25                 30

Glu Gly Arg Pro Asn Arg Asp Arg Asp Leu Pro Gly Ala Leu Trp Ala
                35                 40                 45

Glu Ser Ala Cys Glu Leu Ser Leu Leu Glu Asp Asn Glu Glu Glu Glu
 50                 55                 60

Ser Gln Pro Pro Ala Ser Val Ala Leu Pro Gln Gly Asp Gly Val Pro
 65                 70                 75                 80

Cys Arg Glu Pro Glu Gly Leu Ser Asp Ser Phe Pro Gln Pro Thr Ala
                85                 90                 95

Pro Ser Leu Pro Leu Glu Asn Val Gly Ser Gly Ser Arg Val Arg Glu
                100                105                110

Ala Ala Gly Gly Val Gly Cys Phe Glu Ala Gly Asp Gln Glu Thr Cys
                115                120                125

Tyr Ala Thr Met Asp Leu Leu Val Gly Ala Pro Val Asp Lys Tyr Leu
                130                135                140

Pro Gln Glu Ile Cys Pro Glu Asp Leu Glu Leu Thr Glu Gly Gln Ser
145                150                155                160

Glu Val Cys Asp Leu Cys Ser Pro Asp Lys Ile Leu Ala Val Leu Gln
                165                170                175

Thr Gln Gly Tyr Glu Pro Pro Arg Ser Thr Asp Lys Arg Ser Gln Asp
                180                185                190

Gly Lys Ser Ala Glu Gly Leu Leu Phe Asn Ser Thr Phe Thr Trp Asp
                195                200                205

Thr Ala Lys Glu Ala Ser Glu Asp Ala Val Gly Glu Thr Ala Ala Asp
                210                215                220

Val Glu Asn Pro Pro Ser Thr Phe Ser Ser Thr Leu Pro Tyr Ser Glu
225                230                235                240

Arg Gly Phe Gly Glu Thr Gln Pro Leu Cys Ser Glu Thr Ile Ser Phe
                245                250                255

Val Lys Asp Ser Glu Gly Ser Tyr Arg Ser Ser Ser Leu Ser Ile Pro
                260                265                270

Ala Ala Ile Asp Thr Leu Ala Ser Tyr Ser Ser Asp Arg Glu Cys Ser
                275                280                285

Lys Glu Gln Ser Ala Glu Ser Thr Ala Asn Val Asp Cys His Gln Val
                290                295                300

Thr Arg Glu Met Glu Gly Ile Ser Thr Asn Ala Ala Glu Val His Glu
305                310                315                320

Ile Lys Cys His Ser Val Ser Val Pro Gln Asp Asn Asp Phe Asp Val
                325                330                335

Gly Ala Asp Gln Val Ser Cys Glu Ala Arg Asp Glu Asp Asn Ser Gln
                340                345                350

Ser Leu Pro Asp Asp Ser Gln Ser Gly Arg Ser Leu Ser Ser Ser Ser
                355                360                365

Thr Gly Glu Ala Thr Gly Glu Thr Leu Val Pro Ala Pro Ser Ser Ala
                370                375                380

Gly Asp His Gly His Phe Ser Met Pro Glu Gly Gln Gly Leu Cys Ser
385                390                395                400

Arg Ala Leu Gln Met Asp Asn Gln Pro Val Cys Gln Ser Gln Ala Met
                405                410                415

Glu Gly Ala His Ser Arg Gly Leu Glu Glu His Phe Gln Glu Lys Gly
                420                425                430
```

-continued

```
Ser Gly Met Lys His Gly Ile Arg Pro Gln Ser Thr Ser His Gln Val
        435                 440                 445
Ser Leu Ser Ala Asn Asp Phe Gln Glu Ile Leu Pro Ser Ile Pro Thr
    450                 455                 460
Met Gln Gln Glu Thr Asn Val Glu Pro Leu Glu His Ser Leu Ala Asp
465                 470                 475                 480
Ser Arg Glu Glu Ile Glu Cys Ser Ser Asp Pro Arg Thr Ser Asp Leu
                485                 490                 495
Val Val Ala Glu Lys Thr Val Gly Glu Asp Ser His Leu Val Val Ser
            500                 505                 510
Val Pro Ala Leu Pro Asp Ile Leu Leu Gly Glu Lys Asp Asp Val Gly
        515                 520                 525
Leu Gly Ser Trp Ala Val Gly Lys Val Lys Ile Ile Thr Leu Glu
    530                 535                 540
Ala Pro Val Phe Glu Ile Trp Pro Pro Glu Leu Val Arg His Pro Gly
545                 550                 555                 560
Tyr Lys Glu Ala Glu Ala Gly Leu Thr Met Pro Gly Arg Ser Trp Ala
                565                 570                 575
Leu Ser Asp Ile Leu Arg Ala Gly Ala Thr Arg Ser Glu Pro Gly Ala
            580                 585                 590
Leu Gly Gly Ala Ala Trp Val Pro Ser Pro Gln Ala Asp Ala Leu Met
        595                 600                 605
Ala Leu Gly Ala Asn Arg Asp Thr Trp Leu Gly Ala Ala Pro Asp Arg
    610                 615                 620
Gln Ala Asn Cys Asn Cys Leu Ser Ser Gln Cys Leu Ser Gln Pro Arg
625                 630                 635                 640
Phe Leu Glu Ser Ser Val Asp Pro Val Glu Asp Lys Glu Leu Glu Val
                645                 650                 655
Thr Asp Ser Pro Ser Glu Val Ser Lys Thr Gly Glu Met Glu Met Pro
            660                 665                 670
Glu Thr Leu Asn Glu Glu Gln Glu Glu Thr Gln Gln Met Leu Arg His
        675                 680                 685
Pro Ala Val Val Asn Gln Ser Val Asn Phe Pro Arg Ile Leu Glu Ser
    690                 695                 700
Ser Val Asp Pro Ile Asp Asp Arg Gly Glu Leu Glu Gly Val Trp Pro
705                 710                 715                 720
Glu Lys Pro Glu Pro Ser Asp Ser Ser Val Glu Gly Asn Glu Pro Ile
                725                 730                 735
Val Gly Asn Thr Cys Gln Arg Val Asp Ile Gln Pro Ala Ser Leu Gln
            740                 745                 750
Leu Pro His Pro Gln Asp Ser Gly Glu Ile Ile Pro Tyr Glu His Thr
        755                 760                 765
Thr Asn Gln Asn Arg Val Asp Gly Glu Arg Ala Glu Ala Lys Thr Ser
    770                 775                 780
Leu Pro Asp Lys Ala Lys Ala Glu Ala Val Val Trp Gln Ala
785                 790                 795                 800
Gln Gly Pro Gly Glu Glu Gly Gln Gly Ile Pro Ser Val Cys Ser Met
                805                 810                 815
Ser Gln Thr Ser Asp Gly Asp Arg Ser Leu Gly Glu Ala Gly Gln
            820                 825                 830
Arg Gly Thr Asp Glu Thr Glu Val Ile Ser Pro Leu Ser Pro Leu Ser
        835                 840                 845
```

-continued

```
Ser Cys Leu Thr Gly Val Thr His Thr Cys Val Lys Ala Glu Thr Asn
    850                 855                 860

Asn Ser Thr Gly His Ile Tyr Gly Gly Ser Glu Pro Arg Thr Arg Gln
865                 870                 875                 880

Ser Val Ile Pro Met Lys Thr Glu Lys Gly Thr Ile Glu Ser Lys Cys
                885                 890                 895

Gly Asn His Val Arg Ser Ser Asp Asp Leu Thr Asn Thr Pro Cys Thr
            900                 905                 910

Ser Ser Pro Lys Gly Asn Val Thr Arg Leu Ser Ile Ser His Gly Leu
        915                 920                 925

Glu Glu Leu Lys Ser Glu Lys Leu Gln Ile Ala Glu Thr Lys Pro Leu
    930                 935                 940

Asn Ser Ser Asp Ser Pro Thr Met Thr Leu Ala Leu Ile Ser Gly Glu
945                 950                 955                 960

Cys Glu Ser Glu Lys Asp Pro Lys Ser Leu Leu Arg Arg Asp Pro Cys
                965                 970                 975

Pro Lys Gly Ser Thr Leu Asp Ser Gly Lys Lys Ser Arg Asp Gln Gln
            980                 985                 990

Gln Lys Pro Val Ala Ala Gln Val  Ser Lys Ala Pro Gly  Asp Gln Ser
        995                 1000                1005

Ala Met  Ala Gly Ser Glu Glu  Gly Lys Lys Lys  Gln Glu Ala Ser
    1010                1015                1020

Gly Ser  Gly His Leu Thr Ala  Gly Ile Lys Lys  Ile Leu Ser
    1025                1030                1035

Arg Val  Val Ala Leu Arg Leu  Arg Leu Glu Glu  Lys  Glu Asn Ser
    1040                1045                1050

Arg Lys  Asn Ser Ile Val Lys  Lys Thr Pro Lys  Phe  Glu Arg Ser
    1055                1060                1065

Leu Ser  Arg Thr Asp Glu Lys  Arg Asp Pro Lys  Arg  Ala Pro Cys
    1070                1075                1080

Lys Ala  Glu Gly Lys Ala Pro  Val Leu Leu Lys  Arg  Ile Gln Ala
    1085                1090                1095

Glu Met  Ala Pro Glu His Ser  Gly Asn Ile Lys  Leu  Ser Cys Gln
    1100                1105                1110

Phe Ser  Glu Ile His Glu Asp  Ser Thr Val Cys  Trp  Thr Lys Asp
    1115                1120                1125

Ser Lys  Ser Ile Ala Gln Ala  Lys Lys Ser Ala  Gly  Asp Asn Ser
    1130                1135                1140

Ser Val  Ser Leu Ala Ile Val  Gln Ala Gly Gln  Lys  Asp Gln Gly
    1145                1150                1155

Leu Tyr  Tyr Cys Cys Leu Lys  Asn Ser Tyr Gly  Lys  Val Thr Ala
    1160                1165                1170

Glu Phe  Asn Leu Thr Ala Glu  Val Leu Lys Lys  Gln  Leu Ser Ser
    1175                1180                1185

His Thr  Glu Tyr Arg Gly Cys  Glu Glu Ile Glu  Phe  Ser Gln Leu
    1190                1195                1200

Ile Phe  Lys Glu Asp Val Phe  Asn Asp Ser Tyr  Phe  Gly Asp His
    1205                1210                1215

Leu Arg  Gly Gln Ile Ser Thr  Glu Glu Leu His  Phe  Gly Glu Gly
    1220                1225                1230

Val His  Arg Lys Ala Phe Arg  Ser Lys Val Met  Gln  Gly Leu Met
    1235                1240                1245

Pro Val  Phe Gln Pro Gly His  Ala Cys Val Leu  Lys  Val His Asn
```

-continued

```
                    1250                1255                1260
Ala Val Ala His Gly Thr Arg Asn Asn Asp Glu Leu Val Gln Arg
    1265                1270                1275
Asn Tyr Lys Leu Ala Ala Gln Glu Cys Tyr Val Gln Asn Thr Ala
    1280                1285                1290
Arg Tyr Tyr Ala Lys Ile Tyr Ala Ala Glu Ala Gln Pro Leu Glu
    1295                1300                1305
Gly Phe Gly Glu Val Pro Glu Ile Ile Pro Ile Phe Leu Ile His
    1310                1315                1320
Arg Pro Glu Asn Asn Ile Pro Tyr Ala Thr Val Glu Glu Glu Leu
    1325                1330                1335
Ile Gly Glu Val Lys Tyr Ser Ile Arg Asp Gly Lys Glu Ile Asn
    1340                1345                1350
Phe Leu Arg Arg Asp Ser Glu Ala Gly Gln Lys Cys Cys Thr Phe
    1355                1360                1365
Gln His Trp Val Tyr Gln Lys Thr Ser Gly Cys Leu Leu Val Thr
    1370                1375                1380
Asp Met Gln Gly Val Gly Met Lys Leu Thr Asp Val Gly Ile Ala
    1385                1390                1395
Thr Leu Ala Arg Gly Tyr Lys Gly Phe Lys Gly Asn Cys Ser Met
    1400                1405                1410
Thr Phe Ile Asp Gln Phe Arg Ala Leu His Gln Cys Asn Lys Tyr
    1415                1420                1425
Cys Lys Met Leu Gly Leu Lys Ser Leu Gln Asn Asn Ser Gln Lys
    1430                1435                1440
Pro Arg Lys Pro Ile Val Gly Lys Gly Arg Val Pro Thr Asn Ala
    1445                1450                1455
Thr Gln Val Lys Thr Pro Glu Ser Glu Thr Pro Pro Ala Glu Arg
    1460                1465                1470
Lys Thr
    1475
```

<210> SEQ ID NO 38
<211> LENGTH: 7771
<212> TYPE: DNA
<213> ORGANISM: Homo sapiens

<400> SEQUENCE: 38

| | | | | |
|---|---|---|---|---|
| gtatcaggac | tcagcccatt | tccccctctg | gtgctgagaa | atggaggccg | aaggagtgat | 60 |
| ctagaagtgt | taattgagcc | cctaatctat | gctagttact | ggggtgttg | ggggagacag | 120 |
| gagagagatc | ccacggggtt | ccggcctccc | agggactcag | gtcactaatg | gaggtggctt | 180 |
| ggcttgtcta | tgtgctgggc | caacagccac | tggcgaggca | aggcgagggt | cagtcacggc | 240 |
| tggtgccagg | aagagggctg | gttctttggc | tccctggtct | cccgcggtct | agcccaagct | 300 |
| ggccagcggt | tgacctggct | cccctggccc | cggccaggcc | tcgtggaccc | ctcatatgcc | 360 |
| acacgggaca | tgagcaggcc | ggccgggagc | cgggtcccgg | gagctccacg | aaggggcctg | 420 |
| tcctccatga | ccaggacacc | cgctgcgcct | tcctcccgag | gcctcccggg | cctctccaga | 480 |
| cgcggcgcta | ctgcagacac | cagggccgcc | aaggagcgg | actcggagcc | ggccctgggg | 540 |
| cgggcacatg | ggccccggcg | ccccccggcg | tctccaagcc | gcgctgcccg | ggtcgggcca | 600 |
| ggccagggga | gggacagcag | caggtgacga | cggcccggcc | accggctata | aatagggggcg | 660 |
| cgcgtcagcc | gcgggcggga | gcggcggcgg | cgggcagggg | cccggggggcc | gggggcctgga | 720 |

-continued

| | |
|---|---|
| ggacaggcga ggcagcggcg agtgcggggc cggcggtcgg ggagggcggt gccatgggt | 780 |
| cgcggagggc ccccacccgg ggctggggcg cgggtgggcg gtcgggggcg gggggcgacg | 840 |
| gtgaggacga cggccccgtg tggatcccca gcccagccag ccggagctac ctgctcagcg | 900 |
| tgcggcccga gaccagctta tcaagcaacc ggttgtctca ccccagctct ggaaggagca | 960 |
| ccttctgctc catcattgct cagctcacag aggagaccca gccgctattt gagaccacgc | 1020 |
| tcaagtcccg gtctgtgtcc gaggacagcg acgtcaggtt cacctgcatc gtcacaggat | 1080 |
| acccagagcc agaggtgacc tggtacaagg atgatacgga gctggaccgc tactgtggct | 1140 |
| tgccaaaata tgagatcact catcaggca accgccacac actgcagctg tacaggtgtc | 1200 |
| gagaagaaga tgccgccatc taccaggcct ctgcccagaa cagcaagggc attgtgtcct | 1260 |
| gctcaggggt cctggaggtg gcaccatga ctgagtacaa gatccaccag cgctggttcg | 1320 |
| ccaagttgaa gcgcaaggct gcggcaaagc tgcgcgagat cgagcagagc tggaagcacg | 1380 |
| agaaggcggt gcctggggag gtcgacactc tgcgcaagct cagccccgac cgcttccagc | 1440 |
| gaaagcggcg attgagcggg gctcaagcgc cgggcccctc ggtccctacc agggagcctg | 1500 |
| agggtgggac cctggcggct tggcaggagg gagagactga gactgctcag cactcaggtt | 1560 |
| tgggcctgat caacagtttt gcttctggag aagtgaccac caacggggag gctgccccg | 1620 |
| agaatggaga ggacgagag catggcttgc tgacatacat ctgtgacgcc atggagctgg | 1680 |
| ggcctcagag agccctcaaa gaggagagtg gggccaagaa gaaaaagaaa gatgaggaat | 1740 |
| ccaagcaagg cctgcggaag ccagagttag agaaggcagc ccaaagccgc cgttcttcag | 1800 |
| aaaactgcat ccccagctca gacgagcctg actcctgtgg gactcagggg cccgtgggcg | 1860 |
| tggagcaggt tcagacccag cccagaggca gggctgcacg ggggcctggg tcctctggca | 1920 |
| cagatagtac caggaagcca gcctctgctg tgggcactcc agacaaggcc cagaaggccc | 1980 |
| ctggcccagg cccaggccag gaagtgtatt tctccttgaa ggacatgtac ctggagaaca | 2040 |
| cccaggcagt caggcctctt ggggaagagg accccagac cctgagtgtc cgggcgcctg | 2100 |
| gggagagtcc caaggggaag gcacccctca gggctagaag cgaggggggtg cctggcgctc | 2160 |
| ctggccagcc cacacactcc ttgaccccccc agccgactag gcctttcaac agaaagagat | 2220 |
| ttgcccctcc aaagcccaaa ggagaggcca ccactgacag caagcccatt tcttctctga | 2280 |
| gtcaagctcc agaatgcggg gcccagagct taggaaaggc cccacctcag gcctctgtgc | 2340 |
| aggtgccgac gccccctgcc cggcggagac atggcacccg ggacagcacg ttgcaggggc | 2400 |
| aagcaggcca caggactcca ggagaggtcc tggaatgcca gacaaccacg gctcctacca | 2460 |
| tgtcggccag cagcagctct gatgtagcct ccattggggt tagcacttcc ggaagtcaag | 2520 |
| gtatcattga acccatggat atggaaaccc aggaggatgg gagaacatct gctaaccaga | 2580 |
| gaactggaag caagaagaat gtgcaggcag atgggaagat acaagtggat ggaaggacca | 2640 |
| ggggagatgg aacacagaca gcccagagga cacgtgcaga taggaagacg caggtggatg | 2700 |
| ctgggacaca agaaagcaag aggccacagt cagacaggag tgcacagaag gcatgatga | 2760 |
| cacagggaag ggcagagaca cagctagaaa caacacaggc aggtgagaag atacaggaag | 2820 |
| acaggaaggc ccaggcagat aagggcacac aggaagacag aaggatgcag ggagagaagg | 2880 |
| ggatgcaggg agagaagggg acgcagtcag agggagcgc gcccacagcc atggaaggtc | 2940 |
| agtctgagca agaggtggca accagcctcg gcccaccatc cagaaccccc aaactcccac | 3000 |
| ctacagcggg tcctagagct cctctgaata ttgaatgttt tgtacagacc ccagaagggt | 3060 |
| cttgtttccc aaaaaaacct ggttgcctgc ccagatctga ggaggcagta gtaacagcct | 3120 |

```
ccaggaacca tgagcaaact gtgctgggtc ccctgtcagg gaacctcatg ctcccagcac    3180
agccgcccca tgagggggagt gtggagcagg tgggaggaga gagatgccga gggccacagt    3240
```

```
ccaggaacca tgagcaaact gtgctgggtc ccctgtcagg gaacctcatg ctcccagcac    3180
agccgcccca tgaggggagt gtggagcagg tgggaggaga gagatgccga gggccacagt    3240
catcaggccc agtcgaggcc aagcaggagg acagcccgtt ccagtgcccc aaggaggagc    3300
ggccaggggg agtgccgtgt atggatcagg gtggctgtcc tctagctggc ctgagccagg    3360
aggtacccac gatgccttct cttcctggaa ctgggctgac agctagccca aaggcgggc     3420
cgtgtagcac cccgacttct cagcacggga gcacagccac cttcctgccc tctgaggatc    3480
aggtcctgat gagttctgcc ccaacactgc acctggggct ggggacccc actcagagtc     3540
acccaccaga aaccatggcc accagcagtg agggggcctg cgcccaggta ccagatgtgg    3600
aggggcggac cccaggtccc cggagctgtg accctggcct catagattcc ctgaagaact    3660
acctgcttct gctgctgaag ctgtccagca cagagacaag tggagcaggg ggagagtccc    3720
aggtgggggc agccaccgga ggtctggtgc cctcagccac tctgacaccc actgtggaag    3780
tggctgggct tagtccccgg acatcgaggc gcatcctgga gcgtgtggag aacaaccacc    3840
tggtgcagag tgcacagacc ctgctgctga gcccctgtac ctcccgccgc ctcaccggcc    3900
tcctggaccg tgaggtgcag gctggccgcc aggcccttgc tgctgcccga ggctcctggg    3960
gtcctggtcc cagctccctc actgtccctg ccattgtggt agacgaggag gaccctgggc    4020
tggcctcaga aggagccagt gagggtgaag gagaggtttc ccttgagggg cctggcctcc    4080
tgggggcctc tcaggagagc agcatggctg tcgactggg ggaggcgggt gggcaggcag     4140
cccctggaca ggggccctca gcagagagca tagcccagga gccctcccaa gaggagaagt    4200
tcccagggga ggctctgaca ggcctcccgg cagctacacc tgaggaactg gctctagggg    4260
cccggaggaa gagatttctc cctaaggtca gagcagcagg agacggggag gcaaccacac    4320
ctgaagaaag ggagagcccc acggtttccc ccgggggcc caggaaaagc ctggtgcctg    4380
ggtcccagg gactccaggg cgggagagac gctcccctac gcagggcaga aaggcgagca    4440
tgctggaggt gcctcgggca gaggaggagc tggcggcagg agacctgggc cccagcccca    4500
aggccggcgg tctggacaca gaggtggccc tggatgaagg caagcaggag acactggcca    4560
agcccaggaa agccaaagac ctgctgaaag ccccacaggt gatccggaag attcgggtgg    4620
agcagtttcc tgatgcctcc ggtagcctga agctgtggtg ccagttttc aacattctta    4680
gtgactcagt cttgacatgg gccaaggatc agcgcccagt gggcgaggtg ggcaggagcg    4740
caggggatga ggggccggcg gccttggcca tcgtgcaggc ctcccccgta gactgcggtg    4800
tgtatcggtg caccatccac aatgagcacg gctcggcctc caccgacttc tgcctcagcc    4860
ctgaggtgtt gtcaggattc atctccagag aagaaggtga agttggagaa gagattgaga    4920
tgaccctat ggtgtttgct aagggtctgg ctgactctgg ctgctggggg gacaagctct    4980
ttgggcgact ggtaagcgag gagctccgag ggggtggata tgggtgtggc cttcggaagg    5040
cctcccaggc caaggtcatc tacgggctgg aacccatctt cgagtcgggc cgcacgtgca    5100
tcatcaaggt gtccagcctg cttgtgtttg ggcccagcag tgagacttct cttgtgggca    5160
gaaactacga cgtcaccatc cagggtgca agatccagaa catgagtcgg gagtactgca    5220
aaatcttcgc agcagaagcc cgggccgcgc ctggctttgg ggaggtgcct gagatcatcc    5280
cactgtatct gatctaccgg cctgcaaaca atatccata tgctaccctg gaggaagacc    5340
tgggcaagcc cctggagtct tactgttctc gggaatgggg ctgtgctgag gctccgacag    5400
catctggcag ctctgaggcc atgcagaaat gccagacctt ccaacactgg ctgtatcagt    5460
```

```
ggacaaatgg cagcttcctt gtcacagact tggcaggggt tgactggaag atgactgatg    5520
tgcagattgc taccaaactc cgaggatacc agggcctcaa ggaaagctgc ttccctgccc    5580
tgctggaccg gttcgcctcc tcccaccagt gcaatgccta ctgtgagctg ctggggctga    5640
cacctctcaa gggcccggag gcggcccacc cccaagccaa agccaaaggc tctaagagtc    5700
catctgctgg caggaaaggc tcccagctga gtcctcagcc ccagaagaaa ggcctcccta    5760
gtcctcaggg cacccggaag agtgctccaa gttccaaggc cacccctcag gcctcagagc    5820
cagtcaccac tcagttgttg gacagcctc ccacccaaga ggagggctcc aaggcccagg     5880
gcatgcggta gcctctgcag aggctggggg cctccaccca gcagcagacc aaccaggaag    5940
cagcttgaac tggatggaga cttttccaaat atggaactaa ctggagaagg tgcacgaagg   6000
agacaccact tggggacctc tctgagcagg ctctcgtgaa tcagctcgtc atcagatggc    6060
tttggtgcat ggcacatagc ccactggcct cttctggtgc cactgtcacc cagggctccc    6120
gggcctcaag cagtccccac ctccgagtgc ctggcaacct aggccctcct tgaagtttac    6180
actttgccac tgctggaggc tcccctgagt cctctgcatg agttctgcac cccaagccct    6240
tgccccagcc cagtccagca gcagatgtta caatctgagt gaggacatgc aggccaactt    6300
ttaccctcct gcatttgcct ggccctgatc tcgcctgtcc tcagggatcc agacttcctc    6360
tgctggtctg gcctggtgac tctcagggta tcttctcctt ccagctactt tcgctcactg    6420
atctcagctt atcctgcaac taaccatcct tgagcccaga tggggctcag ggcccttcca    6480
gagcctgtca tgtccttgtg cagtggcctt tgatgtgtgt tcacgctctt cccccttcac    6540
tcactcgcct gcttcccatg ctcccttgta ccccctcgcc acatccctgt cttggggccc    6600
agctgcagcc tgctgcctgc ccttcatggc tctgcacatg gccctttgct tgagggctcc    6660
ccactccctg cccaccaata cccaggtgag gaacagaccc tctggcctct caccccactt    6720
cagtgctctc ttccccaact tctctcgggc tctttgctca tgaggtgaga gctggtgtga    6780
gggttgtgtc agcagctgta gccagagaga ggtgttgact ctgagagacc ttgcactcca    6840
tactgaaagg aggtgggggtc acagtgaatt tcacatcccc tctcaaccag gagtggaggg    6900
ctaggtccct tccccatggg gagtacactt gggtgttcta ggagggatgc agtctatcca    6960
tgcacttggg tggaggggag tctctgtgcc tgggaattag acccctgct ccaaccatcg     7020 ctcttgatcc tggggcccca gctctgggtc ctcatgtatg ggctcccaag acccagcag    7080 cctggatcct tccagagcat ccctcctgga ggcctgggat ggggtaggtc tgcagctagc    7140
ctactccctt tggaatgcaa taaaggcagc attgtgtgcc ctgcttgccc tcatctggtg    7200
tggttggagg tctgtggagt caaggtcccc ctctcccagg caggctctct gagggcattc    7260
tgtagtccca ggcccactgg aaaaatgaat ctatattttg gttcctggac cgaagttcag    7320
tcgcagcctt ctgtgccac agaaagacag cttgtgctgc ttgcacaact gagctgctgg    7380
tgtgtacccc ttagcagggt gtctggggac ttacgccttt ggaattgctc ttcattcaga    7440
agaggaacac aaaggaagcc acccaggaag gaagcacaga gctgggggct ctggaaacgc    7500
cctgtgtctc tggctacagc aagaccagcc caggagccca ccagcacctg cctctcagct    7560
acttgctgac catttcctgc ttctcaagct gcagagaagc ttttcattcc cacccccacc    7620
cggaacctcc ccttgcctaa catttcccct ctatggtaac atctctgact tctctacctc    7680
ctctgtgctc aggtgactcc acatcttctg ccccagtgtg tccccacctc tcccagcctg    7740
tatacccaga ttactttggt gaactgaaaa a                                   7771
```

-continued

```
<210> SEQ ID NO 39
<211> LENGTH: 1907
<212> TYPE: PRT
<213> ORGANISM: Homo sapiens

<400> SEQUENCE: 39

Met Glu Val Ala Trp Leu Val Tyr Val Leu Gly Gln Gln Pro Leu Ala
1               5                   10                  15

Arg Gln Gly Glu Gly Gln Ser Arg Leu Val Pro Gly Arg Gly Leu Val
            20                  25                  30

Leu Trp Leu Pro Gly Leu Pro Arg Ser Ser Pro Ser Trp Pro Ala Val
        35                  40                  45

Asp Leu Ala Pro Leu Ala Pro Ala Arg Pro Arg Gly Pro Leu Ile Cys
    50                  55                  60

His Thr Gly His Glu Gln Ala Gly Arg Glu Pro Gly Pro Gly Ser Ser
65                  70                  75                  80

Thr Lys Gly Pro Val Leu His Asp Gln Asp Thr Arg Cys Ala Phe Leu
                85                  90                  95

Pro Arg Pro Pro Gly Pro Leu Gln Thr Arg Arg Tyr Cys Arg His Gln
            100                 105                 110

Gly Arg Gln Gly Ser Gly Leu Gly Ala Gly Pro Gly Ala Gly Thr Trp
        115                 120                 125

Ala Pro Ala Pro Gly Val Ser Lys Pro Arg Cys Pro Gly Arg Ala
    130                 135                 140

Arg Pro Gly Glu Gly Gln Gln Gln Val Thr Thr Ala Arg Pro Pro Ala
145                 150                 155                 160

Ile Asn Arg Gly Ala Arg Gln Pro Arg Ala Gly Ala Ala Ala Gly
                165                 170                 175

Arg Gly Pro Gly Ala Gly Ala Trp Arg Thr Gly Glu Ala Ala Ala Ser
            180                 185                 190

Ala Gly Pro Ala Val Gly Glu Gly Gly Ala Met Gly Ser Arg Arg Ala
        195                 200                 205

Pro Thr Arg Gly Trp Gly Ala Gly Gly Arg Ser Gly Ala Gly Gly Asp
    210                 215                 220

Gly Glu Asp Asp Gly Pro Val Trp Ile Pro Ser Pro Ala Ser Arg Ser
225                 230                 235                 240

Tyr Leu Leu Ser Val Arg Pro Glu Thr Ser Leu Ser Ser Asn Arg Leu
                245                 250                 255

Ser His Pro Ser Ser Gly Arg Ser Thr Phe Cys Ser Ile Ile Ala Gln
            260                 265                 270

Leu Thr Glu Glu Thr Gln Pro Leu Phe Glu Thr Thr Leu Lys Ser Arg
        275                 280                 285

Ser Val Ser Glu Asp Ser Asp Val Arg Phe Thr Cys Ile Val Thr Gly
    290                 295                 300

Tyr Pro Glu Pro Glu Val Thr Trp Tyr Lys Asp Asp Thr Glu Leu Asp
305                 310                 315                 320

Arg Tyr Cys Gly Leu Pro Lys Tyr Glu Ile Thr His Gln Gly Asn Arg
                325                 330                 335

His Thr Leu Gln Leu Tyr Arg Cys Arg Glu Glu Asp Ala Ala Ile Tyr
            340                 345                 350

Gln Ala Ser Ala Gln Asn Ser Lys Gly Ile Val Ser Cys Ser Gly Val
        355                 360                 365

Leu Glu Val Gly Thr Met Thr Glu Tyr Lys Ile His Gln Arg Trp Phe
    370                 375                 380
```

```
Ala Lys Leu Lys Arg Lys Ala Ala Lys Leu Arg Glu Ile Glu Gln
385                 390                 395                 400

Ser Trp Lys His Glu Lys Ala Val Pro Gly Glu Val Asp Thr Leu Arg
        405                 410                 415

Lys Leu Ser Pro Asp Arg Phe Gln Arg Lys Arg Leu Ser Gly Ala
        420                 425                 430

Gln Ala Pro Gly Pro Ser Val Pro Thr Arg Glu Pro Glu Gly Gly Thr
        435                 440                 445

Leu Ala Ala Trp Gln Glu Gly Glu Thr Glu Thr Ala Gln His Ser Gly
    450                 455                 460

Leu Gly Leu Ile Asn Ser Phe Ala Ser Gly Glu Val Thr Thr Asn Gly
465                 470                 475                 480

Glu Ala Ala Pro Glu Asn Gly Glu Asp Gly Glu His Gly Leu Leu Thr
                485                 490                 495

Tyr Ile Cys Asp Ala Met Glu Leu Gly Pro Gln Arg Ala Leu Lys Glu
            500                 505                 510

Glu Ser Gly Ala Lys Lys Lys Lys Asp Glu Glu Ser Lys Gln Gly
    515                 520                 525

Leu Arg Lys Pro Glu Leu Glu Lys Ala Ala Gln Ser Arg Arg Ser Ser
530                 535                 540

Glu Asn Cys Ile Pro Ser Ser Asp Glu Pro Asp Ser Cys Gly Thr Gln
545                 550                 555                 560

Gly Pro Val Gly Val Glu Gln Val Gln Thr Gln Pro Arg Gly Arg Ala
                565                 570                 575

Ala Arg Gly Pro Gly Ser Ser Gly Thr Asp Ser Thr Arg Lys Pro Ala
                580                 585                 590

Ser Ala Val Gly Thr Pro Asp Lys Ala Gln Lys Ala Pro Gly Pro Gly
            595                 600                 605

Pro Gly Gln Glu Val Tyr Phe Ser Leu Lys Asp Met Tyr Leu Glu Asn
        610                 615                 620

Thr Gln Ala Val Arg Pro Leu Gly Glu Glu Gly Pro Gln Thr Leu Ser
625                 630                 635                 640

Val Arg Ala Pro Gly Glu Ser Pro Lys Gly Lys Ala Pro Leu Arg Ala
                645                 650                 655

Arg Ser Glu Gly Val Pro Gly Ala Pro Gly Gln Pro Thr His Ser Leu
            660                 665                 670

Thr Pro Gln Pro Thr Arg Pro Phe Asn Arg Lys Arg Phe Ala Pro Pro
        675                 680                 685

Lys Pro Lys Gly Glu Ala Thr Thr Asp Ser Lys Pro Ile Ser Ser Leu
        690                 695                 700

Ser Gln Ala Pro Glu Cys Gly Ala Gln Ser Leu Gly Lys Ala Pro Pro
705                 710                 715                 720

Gln Ala Ser Val Gln Val Pro Thr Pro Ala Arg Arg His Gly
                725                 730                 735

Thr Arg Asp Ser Thr Leu Gln Gly Gln Ala Gly His Arg Thr Pro Gly
            740                 745                 750

Glu Val Leu Glu Cys Gln Thr Thr Thr Ala Pro Thr Met Ser Ala Ser
            755                 760                 765

Ser Ser Ser Asp Val Ala Ser Ile Gly Val Ser Thr Ser Gly Ser Gln
770                 775                 780

Gly Ile Ile Glu Pro Met Asp Met Glu Thr Gln Glu Asp Gly Arg Thr
785                 790                 795                 800

Ser Ala Asn Gln Arg Thr Gly Ser Lys Lys Asn Val Gln Ala Asp Gly
```

-continued

```
                805                 810                 815
Lys Ile Gln Val Asp Gly Arg Thr Arg Gly Asp Gly Thr Gln Thr Ala
                820                 825                 830
Gln Arg Thr Arg Ala Asp Arg Lys Thr Gln Val Asp Ala Gly Thr Gln
                835                 840                 845
Glu Ser Lys Arg Pro Gln Ser Asp Arg Ser Ala Gln Lys Gly Met Met
                850                 855                 860
Thr Gln Gly Arg Ala Glu Thr Gln Leu Glu Thr Thr Gln Ala Gly Glu
865                 870                 875                 880
Lys Ile Gln Glu Asp Arg Lys Ala Gln Ala Asp Lys Gly Thr Gln Glu
                885                 890                 895
Asp Arg Arg Met Gln Gly Glu Lys Gly Met Gln Gly Glu Lys Gly Thr
                900                 905                 910
Gln Ser Glu Gly Ser Ala Pro Thr Ala Met Glu Gly Gln Ser Glu Gln
                915                 920                 925
Glu Val Ala Thr Ser Leu Gly Pro Pro Ser Arg Thr Pro Lys Leu Pro
                930                 935                 940
Pro Thr Ala Gly Pro Arg Ala Pro Leu Asn Ile Glu Cys Phe Val Gln
945                 950                 955                 960
Thr Pro Glu Gly Ser Cys Phe Pro Lys Lys Pro Gly Cys Leu Pro Arg
                965                 970                 975
Ser Glu Glu Ala Val Val Thr Ala Ser Arg Asn His Glu Gln Thr Val
                980                 985                 990
Leu Gly Pro Leu Ser Gly Asn Leu  Met Leu Pro Ala Gln  Pro Pro His
                995                1000                1005
Glu Gly  Ser Val Glu Gln Val  Gly Gly Glu Arg Cys  Arg Gly Pro
               1010                1015                1020
Gln Ser  Ser Gly Pro Val Glu  Ala Lys Gln Glu Asp  Ser Pro Phe
               1025                1030                1035
Gln Cys  Pro Lys Glu Glu Arg  Pro Gly Gly Val Pro  Cys Met Asp
               1040                1045                1050
Gln Gly  Gly Cys Pro Leu Ala  Gly Leu Ser Gln Glu  Val Pro Thr
               1055                1060                1065
Met Pro  Ser Leu Pro Gly Thr  Gly Leu Thr Ala Ser  Pro Lys Ala
               1070                1075                1080
Gly Pro  Cys Ser Thr Pro Thr  Ser Gln His Gly Ser  Thr Ala Thr
               1085                1090                1095
Phe Leu  Pro Ser Glu Asp Gln  Val Leu Met Ser Ser  Ala Pro Thr
               1100                1105                1110
Leu His  Leu Gly Leu Gly Thr  Pro Thr Gln Ser His  Pro Pro Glu
               1115                1120                1125
Thr Met  Ala Thr Ser Ser Glu  Gly Ala Cys Ala Gln  Val Pro Asp
               1130                1135                1140
Val Glu  Gly Arg Thr Pro Gly  Pro Arg Ser Cys Asp  Pro Gly Leu
               1145                1150                1155
Ile Asp  Ser Leu Lys Asn Tyr  Leu Leu Leu Leu Leu  Lys Leu Ser
               1160                1165                1170
Ser Thr  Glu Thr Ser Gly Ala  Gly Gly Glu Ser Gln  Val Gly Ala
               1175                1180                1185
Ala Thr  Gly Gly Leu Val Pro  Ser Ala Thr Leu Thr  Pro Thr Val
               1190                1195                1200
Glu Val  Ala Gly Leu Ser Pro  Arg Thr Ser Arg Arg  Ile Leu Glu
               1205                1210                1215
```

-continued

```
Arg Val Glu Asn Asn His Leu Val Gln Ser Ala Gln Thr Leu Leu
    1220                1225                1230

Leu Ser Pro Cys Thr Ser Arg Arg Leu Thr Gly Leu Leu Asp Arg
    1235                1240                1245

Glu Val Gln Ala Gly Arg Gln Ala Leu Ala Ala Arg Gly Ser
    1250                1255                1260

Trp Gly Pro Gly Pro Ser Ser Leu Thr Val Pro Ala Ile Val Val
    1265                1270                1275

Asp Glu Glu Asp Pro Gly Leu Ala Ser Glu Gly Ala Ser Glu Gly
    1280                1285                1290

Glu Gly Glu Val Ser Leu Glu Gly Pro Gly Leu Leu Gly Ala Ser
    1295                1300                1305

Gln Glu Ser Ser Met Ala Gly Arg Leu Gly Glu Ala Gly Gly Gln
    1310                1315                1320

Ala Ala Pro Gly Gln Gly Pro Ser Ala Glu Ser Ile Ala Gln Glu
    1325                1330                1335

Pro Ser Gln Glu Glu Lys Phe Pro Gly Glu Ala Leu Thr Gly Leu
    1340                1345                1350

Pro Ala Ala Thr Pro Glu Glu Leu Ala Leu Gly Ala Arg Arg Lys
    1355                1360                1365

Arg Phe Leu Pro Lys Val Arg Ala Ala Gly Asp Gly Glu Ala Thr
    1370                1375                1380

Thr Pro Glu Glu Arg Glu Ser Pro Thr Val Ser Pro Arg Gly Pro
    1385                1390                1395

Arg Lys Ser Leu Val Pro Gly Ser Pro Gly Thr Pro Gly Arg Glu
    1400                1405                1410

Arg Arg Ser Pro Thr Gln Gly Arg Lys Ala Ser Met Leu Glu Val
    1415                1420                1425

Pro Arg Ala Glu Glu Leu Ala Ala Gly Asp Leu Gly Pro Ser
    1430                1435                1440

Pro Lys Ala Gly Gly Leu Asp Thr Glu Val Ala Leu Asp Glu Gly
    1445                1450                1455

Lys Gln Glu Thr Leu Ala Lys Pro Arg Lys Ala Lys Asp Leu Leu
    1460                1465                1470

Lys Ala Pro Gln Val Ile Arg Lys Ile Arg Val Glu Gln Phe Pro
    1475                1480                1485

Asp Ala Ser Gly Ser Leu Lys Leu Trp Cys Gln Phe Phe Asn Ile
    1490                1495                1500

Leu Ser Asp Ser Val Leu Thr Trp Ala Lys Asp Gln Arg Pro Val
    1505                1510                1515

Gly Glu Val Gly Arg Ser Ala Gly Asp Glu Gly Pro Ala Ala Leu
    1520                1525                1530

Ala Ile Val Gln Ala Ser Pro Val Asp Cys Gly Val Tyr Arg Cys
    1535                1540                1545

Thr Ile His Asn Glu His Gly Ser Ala Ser Thr Asp Phe Cys Leu
    1550                1555                1560

Ser Pro Glu Val Leu Ser Gly Phe Ile Ser Arg Glu Glu Gly Glu
    1565                1570                1575

Val Gly Glu Glu Ile Glu Met Thr Pro Met Val Phe Ala Lys Gly
    1580                1585                1590

Leu Ala Asp Ser Gly Cys Trp Gly Asp Lys Leu Phe Gly Arg Leu
    1595                1600                1605
```

```
Val Ser Glu Glu Leu Arg Gly Gly Gly Tyr Gly Cys Gly Leu Arg
1610                1615                1620

Lys Ala Ser Gln Ala Lys Val Ile Tyr Gly Leu Glu Pro Ile Phe
1625                1630                1635

Glu Ser Gly Arg Thr Cys Ile Ile Lys Val Ser Ser Leu Leu Val
1640                1645                1650

Phe Gly Pro Ser Ser Glu Thr Ser Leu Val Gly Arg Asn Tyr Asp
1655                1660                1665

Val Thr Ile Gln Gly Cys Lys Ile Gln Asn Met Ser Arg Glu Tyr
1670                1675                1680

Cys Lys Ile Phe Ala Ala Glu Ala Arg Ala Ala Pro Gly Phe Gly
1685                1690                1695

Glu Val Pro Glu Ile Ile Pro Leu Tyr Leu Ile Tyr Arg Pro Ala
1700                1705                1710

Asn Asn Ile Pro Tyr Ala Thr Leu Glu Glu Asp Leu Gly Lys Pro
1715                1720                1725

Leu Glu Ser Tyr Cys Ser Arg Glu Trp Gly Cys Ala Glu Ala Pro
1730                1735                1740

Thr Ala Ser Gly Ser Ser Glu Ala Met Gln Lys Cys Gln Thr Phe
1745                1750                1755

Gln His Trp Leu Tyr Gln Trp Thr Asn Gly Ser Phe Leu Val Thr
1760                1765                1770

Asp Leu Ala Gly Val Asp Trp Lys Met Thr Asp Val Gln Ile Ala
1775                1780                1785

Thr Lys Leu Arg Gly Tyr Gln Gly Leu Lys Glu Ser Cys Phe Pro
1790                1795                1800

Ala Leu Leu Asp Arg Phe Ala Ser Ser His Gln Cys Asn Ala Tyr
1805                1810                1815

Cys Glu Leu Leu Gly Leu Thr Pro Leu Lys Gly Pro Glu Ala Ala
1820                1825                1830

His Pro Gln Ala Lys Ala Lys Gly Ser Lys Ser Pro Ser Ala Gly
1835                1840                1845

Arg Lys Gly Ser Gln Leu Ser Pro Gln Pro Gln Lys Lys Gly Leu
1850                1855                1860

Pro Ser Pro Gln Gly Thr Arg Lys Ser Ala Pro Ser Ser Lys Ala
1865                1870                1875

Thr Pro Gln Ala Ser Glu Pro Val Thr Thr Gln Leu Leu Gly Gln
1880                1885                1890

Pro Pro Thr Gln Glu Glu Gly Ser Lys Ala Gln Gly Met Arg
1895                1900                1905

<210> SEQ ID NO 40
<211> LENGTH: 3726
<212> TYPE: DNA
<213> ORGANISM: Homo sapiens

<400> SEQUENCE: 40
atgaataatc aaaaagtggt agctgtgcta ctgcaagagt gcaagcaagt gctggatcag      60
ctcttgttgg aagcgccaga tgtgtcggaa gaggacaaga gcgaggacca gcgctgcaga     120
gctttactcc ccagcgagtt aaggaccctg atccaggagg caaggaaat  gaagtggccc     180 ttcgtgcctg aaaagtggca gtacaaacaa gccgtgggcc cagaggacaa aacaaacctg     240
aaggatgtga ttggcgccgg gttgcagcag ttactggcgt ccctgagggc ctccatcctc     300
gctcgggact gtgcggctgc ggcggctatt gtgttcttgg tggaccggtt cctgtatggg     360
```

```
ctcgacgtct ctggaaaact tctgcaggtc gccaaaggtc tccacaagtt gcagccagcc      420
acgccaattg ccccgcaggt ggttattcgc caagcccgaa tctccgtgaa ctcaggaaaa      480
cttttaaaag cagagtatat tctgagcagt ctaataagca acaatggagc aacgggtacc      540
tggctgtaca gaaatgaaag tgacaaggtc ctggtgcagt cggtctgtat acagatcaga      600
gggcagattc tgcaaaagct gggtatgtgg tacgaagcag cagagttaat atgggcctcc      660
attgtaggat atttggcact tcctcagccg ataaaaagg gcctctccac gtcgctaggt       720
atactggcag acatctttgt ttccatgagc aagaacgatt atgaaaagtt taaaaacaat      780
ccacaaatta atttgagcct gctgaaggag tttgaccacc atttgctgtc cgctgcagaa      840
gcctgcaagc tggcagctgc cttcagtgcc tatacgccgc tcttcgtgct cacagctgtg      900
aatatccgtg gcacgtgttt attgtcctac agtagttcaa atgactgtcc tccagaattg      960
aaaaacttac atctgtgtga agccaaagag gcctttgaga ttggcctcct caccaagaga     1020
gatgatgagc ctgttactgg aaaacaggag cttcacagct ttgtcaaagc tgctttcggt     1080
ctcaccacag tgcacagaag gctccatggg gagacaggga cggtccatgc agcaagtcag     1140
ctctgtaagg aagcaatggg gaagctgtac aatttcagca cttcctccag aagtcaggac     1200
agagaagctc tgtctcaaga agttatgtct gtgattgccc aggtgaagga acatttacaa     1260
gttcaaagct tctcaaatgt agatgacaga tcttatgttc ccgagagttt cgagtgcagg     1320
ttggataaac ttatcttgca tgggcaaggg gatttccaaa aaatccttga cacctattca     1380
cagcaccata cttcggtgtg tgaagtattt gaaagtgatt gtggaaacaa caaaaatgaa     1440
cagaaagatg caaaaacagg agtctgcatc actgctctaa aaacagaaat aaaaaacata     1500
gatactgtga gtactactca agaaaagcca cattgtcaaa gagacacagg aatatcttcc     1560
tccctaatgg gtaagaatgt tcagagggaa ctcagaaggg gaggaaggag aaactggacc     1620
cattctgatg catttcgagt ctccttggat caagatgtgg agactgagac tgagccatcg     1680
gactacagca atggtgaggg agctgttttc aacaagtctc tgagtggcag ccagacttcc     1740
agtgcttgga gcaacttatc agggtttagt tcctctgcaa gctgggagga agtgaattat     1800
cacgttgacg acaggtcagc cagaaaagag cctggcaaag aacatctggt ggacactcag     1860
tgttccactg ccttgtctga ggagctagag aatgacaggg aaggcagagc tatgcattca     1920
ttgcattcac agcttcatga tctctctctt caggaaccca acaatgacaa tttggagcct     1980
tctcaaaatc agccacagca acagatgccc ttgacaccct tctcgcctca taatacccca     2040
ggcattttct tggcccctgg tgcagggctt ctagaaggag ctccagaagg tatccaggaa     2100
gtcagaaata tgggacccag aaatacttct gctcactcca gaccctcata tcgttctgct     2160
tcttggtctt ctgattctgg taggcccaag aatatgggca cacatccttc agtccaaaaa     2220
gaagaagcct ttgaaataat tgttgagttt ccagaaacca actgcgatgt caaagacagg     2280 cagggaaag agcagggaga agaaattagt gaaagaggcg caggccctac atttaaagct     2340
agtccctcct gggttgaccc agaaggagaa acagcagaaa gcactgaaga tgcacccta     2400 gactttcaca gggtcctgca caattctctg ggaaacattt ccatgctgcc atgtagctcc     2460 ttcacccta attggcctgt tcaaaatcct gactccagaa aaagtggtgg cccagtcgca     2520
gagcagggca tcgaccctga tgcctccaca gtggatgagg aggggcaact gctcgacagc     2580
atggatgttc cctgcacaaa tgggcacggc tctcatagac tgtgcattct gagacagccg     2640
cctggtcaga gggcggagac ccccaattcc tctgtaagcg gtaacatcct cttccctgtc     2700
```

```
ctcagcgagg actgcactac cacagaggaa ggaaatcagc ctggaaacat gctaaactgc    2760
agccagaact ccagctcatc ctcagtgtgg tggctgaaat cacctgcatt ttccagtggt    2820
tcttctgagg gggacagccc ttggtcctat ctgaattcca gtgggagttc ttgggtttca    2880
ttgccgggaa agatgaggaa agagatcctt gaggctcgca ccttgcaacc tgatgacttt    2940
gaaaagctgt tggcaggagt gaggcatgat tggctgtttc agagactaga gaatacgggg    3000 gttttttaagc ccagtcaact ccaccgagca catagtgctc ttttgttaaa atattcaaaa    3060
aaatctgaac tgtggacggc ccaggaaact attgtctatt tgggggacta cttgactgtg    3120
aagaaaaaag gcagacaaag aaatgctttt tgggttcatc atcttcatca agaagaaatt    3180
ctggggaggt atgttgggaa agactataag gagcagaagg ggctctggca ccacttcact    3240
gatgtggagc gacagatgac cgcacagcac tatgtgacag aatttaacaa gagactctat    3300
gaacaaaaca ttcccaccca gatattctac atcccatcca caatactact gatttagag    3360 gacaagacaa taagggatg tatcagtgtg gagccttaca tactgggaga atttgtaaaa    3420
ttgtcaaata acacgaaagt ggtgaaaaca gaatacaaag ccacagaata tggcttggcc    3480
tatggccatt tttcttatga gttttctaat catagagatg ttgtggtcga tttacaaggt    3540
tgggtaaccg gtaatggaaa aggactcatc tacctcacag atccccagat tcactccgtt    3600
gatcagaaag ttttcactac caattttgga aagagaggaa ttttttactt ctttaataac    3660
cagcatgtgg aatgtaatga aatctgccat cgtctttctt tgactagacc ttcaatggag    3720
aaacca                                                                3726
```

<210> SEQ ID NO 41
<211> LENGTH: 1242
<212> TYPE: PRT
<213> ORGANISM: Homo sapiens

<400> SEQUENCE: 41

```
Met Asn Asn Gln Lys Val Val Ala Val Leu Gln Glu Cys Lys Gln
1               5                   10                  15

Val Leu Asp Gln Leu Leu Leu Glu Ala Pro Asp Val Ser Glu Glu Asp
            20                  25                  30

Lys Ser Glu Asp Gln Arg Cys Arg Ala Leu Leu Pro Ser Glu Leu Arg
        35                  40                  45

Thr Leu Ile Gln Glu Ala Lys Glu Met Lys Trp Pro Phe Val Pro Glu
    50                  55                  60

Lys Trp Gln Tyr Lys Gln Ala Val Gly Pro Glu Asp Lys Thr Asn Leu
65                  70                  75                  80

Lys Asp Val Ile Gly Ala Gly Leu Gln Gln Leu Leu Ala Ser Leu Arg
                85                  90                  95

Ala Ser Ile Leu Ala Arg Asp Cys Ala Ala Ala Ala Ile Val Phe
                    100                 105                 110

Leu Val Asp Arg Phe Leu Tyr Gly Leu Asp Val Ser Gly Lys Leu Leu
            115                 120                 125

Gln Val Ala Lys Gly Leu His Lys Leu Gln Pro Ala Thr Pro Ile Ala
        130                 135                 140

Pro Gln Val Val Ile Arg Gln Ala Arg Ile Ser Val Asn Ser Gly Lys
145                 150                 155                 160

Leu Leu Lys Ala Glu Tyr Ile Leu Ser Ser Leu Ile Ser Asn Asn Gly
                165                 170                 175

Ala Thr Gly Thr Trp Leu Tyr Arg Asn Glu Ser Asp Lys Val Leu Val
                    180                 185                 190
```

```
Gln Ser Val Cys Ile Gln Ile Arg Gly Gln Ile Leu Gln Lys Leu Gly
            195                 200                 205

Met Trp Tyr Glu Ala Ala Glu Leu Ile Trp Ala Ser Ile Val Gly Tyr
            210                 215                 220

Leu Ala Leu Pro Gln Pro Asp Lys Lys Gly Leu Ser Thr Ser Leu Gly
225                 230                 235                 240

Ile Leu Ala Asp Ile Phe Val Ser Met Ser Lys Asn Asp Tyr Glu Lys
            245                 250                 255

Phe Lys Asn Asn Pro Gln Ile Asn Leu Ser Leu Leu Lys Glu Phe Asp
            260                 265                 270

His His Leu Leu Ser Ala Ala Glu Ala Cys Lys Leu Ala Ala Ala Phe
            275                 280                 285

Ser Ala Tyr Thr Pro Leu Phe Val Leu Thr Ala Val Asn Ile Arg Gly
            290                 295                 300

Thr Cys Leu Leu Ser Tyr Ser Ser Ser Asn Asp Cys Pro Pro Glu Leu
305                 310                 315                 320

Lys Asn Leu His Leu Cys Glu Ala Lys Glu Ala Phe Glu Ile Gly Leu
            325                 330                 335

Leu Thr Lys Arg Asp Asp Glu Pro Val Thr Gly Lys Gln Glu Leu His
            340                 345                 350

Ser Phe Val Lys Ala Ala Phe Gly Leu Thr Thr Val His Arg Arg Leu
            355                 360                 365

His Gly Glu Thr Gly Thr Val His Ala Ala Ser Gln Leu Cys Lys Glu
            370                 375                 380

Ala Met Gly Lys Leu Tyr Asn Phe Ser Thr Ser Ser Arg Ser Gln Asp
385                 390                 395                 400

Arg Glu Ala Leu Ser Gln Glu Val Met Ser Val Ile Ala Gln Val Lys
            405                 410                 415

Glu His Leu Gln Val Gln Ser Phe Ser Asn Val Asp Asp Arg Ser Tyr
            420                 425                 430

Val Pro Glu Ser Phe Glu Cys Arg Leu Asp Lys Leu Ile Leu His Gly
            435                 440                 445

Gln Gly Asp Phe Gln Lys Ile Leu Asp Thr Tyr Ser Gln His His Thr
450                 455                 460

Ser Val Cys Glu Val Phe Glu Ser Asp Cys Gly Asn Asn Lys Asn Glu
465                 470                 475                 480

Gln Lys Asp Ala Lys Thr Gly Val Cys Ile Thr Ala Leu Lys Thr Glu
            485                 490                 495

Ile Lys Asn Ile Asp Thr Val Ser Thr Thr Gln Glu Lys Pro His Cys
            500                 505                 510

Gln Arg Asp Thr Gly Ile Ser Ser Ser Leu Met Gly Lys Asn Val Gln
            515                 520                 525

Arg Glu Leu Arg Arg Gly Gly Arg Arg Asn Trp Thr His Ser Asp Ala
            530                 535                 540

Phe Arg Val Ser Leu Asp Gln Asp Val Glu Thr Glu Thr Glu Pro Ser
545                 550                 555                 560

Asp Tyr Ser Asn Gly Glu Gly Ala Val Phe Asn Lys Ser Leu Ser Gly
            565                 570                 575

Ser Gln Thr Ser Ser Ala Trp Ser Asn Leu Ser Gly Phe Ser Ser Ser
            580                 585                 590

Ala Ser Trp Glu Glu Val Asn Tyr His Val Asp Asp Arg Ser Ala Arg
            595                 600                 605
```

-continued

Lys Glu Pro Gly Lys Glu His Leu Val Asp Thr Gln Cys Ser Thr Ala
610             615                 620

Leu Ser Glu Glu Leu Glu Asn Asp Arg Glu Gly Arg Ala Met His Ser
625             630                 635                 640

Leu His Ser Gln Leu His Asp Leu Ser Leu Gln Glu Pro Asn Asn Asp
            645                 650                 655

Asn Leu Glu Pro Ser Gln Asn Gln Pro Gln Gln Met Pro Leu Thr
            660                 665                 670

Pro Phe Ser Pro His Asn Thr Pro Gly Ile Phe Leu Ala Pro Gly Ala
            675                 680                 685

Gly Leu Leu Glu Gly Ala Pro Glu Gly Ile Gln Glu Val Arg Asn Met
690                 695                 700

Gly Pro Arg Asn Thr Ser Ala His Ser Arg Pro Ser Tyr Arg Ser Ala
705                 710                 715                 720

Ser Trp Ser Ser Asp Ser Gly Arg Pro Lys Asn Met Gly Thr His Pro
                725                 730                 735

Ser Val Gln Lys Glu Glu Ala Phe Glu Ile Ile Val Glu Phe Pro Glu
            740                 745                 750

Thr Asn Cys Asp Val Lys Asp Arg Gln Gly Lys Glu Gln Gly Glu Glu
            755                 760                 765

Ile Ser Glu Arg Gly Ala Gly Pro Thr Phe Lys Ala Ser Pro Ser Trp
770                 775                 780

Val Asp Pro Glu Gly Glu Thr Ala Glu Ser Thr Glu Asp Ala Pro Leu
785                 790                 795                 800

Asp Phe His Arg Val Leu His Asn Ser Leu Gly Asn Ile Ser Met Leu
                805                 810                 815

Pro Cys Ser Ser Phe Thr Pro Asn Trp Pro Val Gln Asn Pro Asp Ser
            820                 825                 830

Arg Lys Ser Gly Gly Pro Val Ala Glu Gln Gly Ile Asp Pro Asp Ala
            835                 840                 845

Ser Thr Val Asp Glu Glu Gly Gln Leu Leu Asp Ser Met Asp Val Pro
850                 855                 860

Cys Thr Asn Gly His Gly Ser His Arg Leu Cys Ile Leu Arg Gln Pro
865                 870                 875                 880

Pro Gly Gln Arg Ala Glu Thr Pro Asn Ser Ser Val Ser Gly Asn Ile
            885                 890                 895

Leu Phe Pro Val Leu Ser Glu Asp Cys Thr Thr Glu Glu Gly Asn
            900                 905                 910

Gln Pro Gly Asn Met Leu Asn Cys Ser Gln Asn Ser Ser Ser Ser Ser
            915                 920                 925

Val Trp Trp Leu Lys Ser Pro Ala Phe Ser Ser Gly Ser Ser Glu Gly
            930                 935                 940

Asp Ser Pro Trp Ser Tyr Leu Asn Ser Ser Gly Ser Ser Trp Val Ser
945                 950                 955                 960

Leu Pro Gly Lys Met Arg Lys Glu Ile Leu Glu Ala Arg Thr Leu Gln
                965                 970                 975

Pro Asp Asp Phe Glu Lys Leu Leu Ala Gly Val Arg His Asp Trp Leu
            980                 985                 990

Phe Gln Arg Leu Glu Asn Thr Gly Val Phe Lys Pro Ser Gln Leu His
            995                 1000                1005

Arg Ala His Ser Ala Leu Leu Leu Lys Tyr Ser Lys Lys Ser Glu
    1010            1015            1020

Leu Trp Thr Ala Gln Glu Thr Ile Val Tyr Leu Gly Asp Tyr Leu

```
                 1025                1030                1035

Thr Val Lys Lys Lys Gly Arg Gln Arg Asn Ala Phe Trp Val His
    1040                1045                1050

His Leu His Gln Glu Glu Ile Leu Gly Arg Tyr Val Gly Lys Asp
    1055                1060                1065

Tyr Lys Glu Gln Lys Gly Leu Trp His His Phe Thr Asp Val Glu
    1070                1075                1080

Arg Gln Met Thr Ala Gln His Tyr Val Thr Glu Phe Asn Lys Arg
    1085                1090                1095

Leu Tyr Glu Gln Asn Ile Pro Thr Gln Ile Phe Tyr Ile Pro Ser
    1100                1105                1110

Thr Ile Leu Leu Ile Leu Glu Asp Lys Thr Ile Lys Gly Cys Ile
    1115                1120                1125

Ser Val Glu Pro Tyr Ile Leu Gly Glu Phe Val Lys Leu Ser Asn
    1130                1135                1140

Asn Thr Lys Val Val Lys Thr Glu Tyr Lys Ala Thr Glu Tyr Gly
    1145                1150                1155

Leu Ala Tyr Gly His Phe Ser Tyr Glu Phe Ser Asn His Arg Asp
    1160                1165                1170

Val Val Val Asp Leu Gln Gly Trp Val Thr Gly Asn Gly Lys Gly
    1175                1180                1185

Leu Ile Tyr Leu Thr Asp Pro Gln Ile His Ser Val Asp Gln Lys
    1190                1195                1200

Val Phe Thr Thr Asn Phe Gly Lys Arg Gly Ile Phe Tyr Phe Phe
    1205                1210                1215

Asn Asn Gln His Val Glu Cys Asn Glu Ile Cys His Arg Leu Ser
    1220                1225                1230

Leu Thr Arg Pro Ser Met Glu Lys Pro
    1235                1240
```

<210> SEQ ID NO 42
<211> LENGTH: 30
<212> TYPE: DNA
<213> ORGANISM: Artificial Sequence
<220> FEATURE:
<223> OTHER INFORMATION: primer

<400> SEQUENCE: 42
ctgcgacaga gactacatgg ggtagaactc         30

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
tgagtgtctt cggtagatgg ccttctactg         30

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
atggagattg ctggagagaa g         21

```
<210> SEQ ID NO 45
<211> LENGTH: 21
<212> TYPE: DNA
<213> ORGANISM: Artificial Sequence
<220> FEATURE:
<223> OTHER INFORMATION: primer

<400> SEQUENCE: 45
attcactact ctgggccgat c                                            21
```

MAMMALIAN ALPHA-KINASE PROTEINS, NUCLEIC ACIDS AND DIAGNOSTIC AND THERAPEUTIC USES THEREOF

RELATED APPLICATIONS

The present application is a continuation-in-part of copending application Ser. No. 09/632,131 filed Aug. 3, 2000, of which the instant application claims the benefit of the filing date pursuant to 35 U.S.C. § 120, and which is incorporated herein by reference in its entirety. The present application claims priority pursuant to 35 U.S.C. § 119(e) to provisional application Ser. No. 60/188,957 filed Mar. 13, 2000, which is incorporated herein by reference in its entirety.

GOVERNMENTAL SUPPORT

The research leading to the present invention was supported, at least in part, by a grant from the National Institutes of Health, Grant No. CA81102 and Grant No. GM57300. Accordingly, the Government may have certain rights in the invention.

FIELD OF THE INVENTION

This invention relates generally to the identification of a new superfamily of eukaryotic protein alpha kinases, and particularly to members of a subfamily selected from the group of melanoma alpha kinase, kidney alpha kinase, heart alpha kinase, skeletal muscle alpha kinase and lymphocyte alpha kinase. The invention further relates to the use of the alpha kinases in assays to screen for specific modulators thereof. Isolated nucleic acids encoding the alpha kinases—melanoma alpha kinase, kidney alpha kinase, heart alpha kinase, skeletal muscle alpha kinase and lymphocyte alpha kinase—are provided herein.

BACKGROUND OF THE INVENTION

Protein phosphorylation plays a critical role in many cellular processes (Krebs (1994) *Trends Biochem. Sci.* 19:439; Hanks and Hunter, (1996) *FASEB J* 9:576–596; Hardie and Hanks, (1995) *The Protein Kinase Facts Book* (Academic, London)). There are two well-characterized superfamilies of protein kinases, with most of the protein kinases belonging to the serine/threonine/tyrosine kinase superfamily (Hanks and Hunter, (1996); Hardie and Hanks, (1995)). The characterization of several hundred members of this superfamily revealed that they all share a similar structural organization of their catalytic domains which consist of twelve conserved subdomains (Hanks and Hunter, (1996); Hardie and Hanks, (1995)). The other superfamily is referred to as the histidine kinase superfamily and is involved in the prokaryotic two-component signal transduction system, acting as sensor components (Stock et al., (1989) *Microbiol. Rev.* 53:450–490; Parkinson and Kofoid, (1992) *Annu. Rev. Genet.* 26:71–112; Swanson, et al., (1994) *Trends Biochem. Sci.* 19:485–490). Recently, eukaryotic members of this superfamily have also been described (Chang et al., (1993) *Science* 263:539–544; Ota and Varshavsky, (1993) *Science* 262:566–569; Maeda et al., (1994) *Nature* 369:242–245). Mitochondrial protein kinases have also recently been described that show structural homology to the histidine kinases, but phosphorylate their substrates on serine (Popov et al., (1992) *J. Biol. Chem.* 267:13127–13130; Popov et al., (1993) *J. Biol. Chem.* 268:26602–22606). Finally, several new protein kinases have been reported that show a lack of homology with either of the kinase superfamilies (Maru and Witte, (1991) *Cell* 67:459–468; Beeler et al., (1994) *Mol. Cell, Biol.* 14:982–988; Dikstein et al., (1996) *Cell* 84:781–790; Futey et al., (1995) *J. Biol. Chem.* 270:523–529; Eichenger et al., (1996) *EMBO J.* 15:5547–5556). However, these protein kinases are viewed as an exception to the general rule as they have yet to be fully characterized.

The cloning and sequencing of the extensively characterized eukaryotic elongation factor-2 kinase (eEF-2 kinase) from a variety of eukaryotic organisms has revealed the existence of a novel class of protein kinases (Ryazanov et al., (1997) *Proc. Natl. Acad. Sci., USA* 94:4884–4889). eEF-2 kinase, previously known as $Ca^{2+}$/calmodulin-dependent protein kinase III, is highly specific for phosphorylation of elongation factor-2 (eEF-2), an abundant cytoplasmic protein that catalyzes the movement of the ribosome along mRNA during translation in eukaryotic cells (reviewed in Ryazanov and Spirin, (1993) In *Translational Regulation of Gene Expression* (Plenum, New York) Vol. 2, pp. 433–455; Nairn and Palfrey, (1996) In *Translational Control* (CSHL Press, New York) pp. 295–318). All mammalian tissues, and various invertebrate organisms, exhibit eEF-2 kinase activity (Abdelmajid et al., (1993) *Int. J Dev. Biol.* 37:279–290). eEF-2 kinase catalyzes the phosphorylation of eEF-2 at two highly conserved threonine residues located within a GTP-binding domain (Ryazanov and Spirin, (1993) In *Translational Regulation of Gene Expression* (Plenum, New York) Vol. 2, pp. 433–455; Nairn and Palfrey, (1996) *In Translational Control* (CSHL Press, New York) pp. 295–318). When eEF-2 is phosphorylated, it becomes inactive with respect to protein synthesis (Ryazanov et al., (1988) *Nature* 334:170–173). Since eEF-2 phosphorylation is dependent on $Ca^{2+}$ and calmodulin, eEF-2 kinase plays a pivotal role in modulating the protein synthesis rate in response to changes in intracellular calcium concentration. Phosphorylation of eEF-2 has also been linked to the regulation of cell cycle progression. For example, transient phosphorylation of eEF-2 occurs during the mitogenic stimulation of quiescent cells (Palfrey et al., (1987) *J. Biol. Chem.* 262:9785–9792) and during mitosis (Celis et al., (1990) *Proc. Natl. Acad. Sci., USA* 87:4231–4235). In addition, changes in the level of eEF-2 kinase activity is associated with a host of cellular processes such as cellular differentiation (End et al., (1982) *J. Biol. Chem.* 257:9223–9225; Koizumi et al., (1989) *FEBS Lett.* 253:55–58; Brady et al., (1990) *J. Neurochem.* 54:1034–1039), oogenesis (Severinov et al., (1990) *New Biol.* 2: 887–893), and malignant transformation (Bagaglio et al., (1993) *Cancer Res.* 53:2260–2264).

The sequence of eEF-2 kinase appears to have no homology to either the $Ca^{2+}$/calmodulin-dependent protein kinases or to any members of the known protein kinase superfamilies (Ryazanov et al., (1997) *Proc. Natl. Acad. Sci., USA* 94:4884–4889). However, the recently described myosin heavy chain kinase A (MHCK A) from *Dictyostelium* (Futey et al., (1995) *J. Biol. Chem.* 270:523–529) shows a great deal of homology with eEF-2 kinase. These two kinases define a novel class of protein kinases that may represent a new superfamily.

Evidence for MHCK and eEF-2 kinase forming the core of a new superfamily is as follows. MHCK A from *Dictyostelium*, has a demonstrated role in the regulation of myosin assembly (Futey et al., (1995) *J. Biol. Chem.* 270:523–529; Côté et al., (1997) *J. Biol. Chem.* 272:6846–6849). eEF-2 kinase is a ubiquitous $Ca^{2+}$/calmodulin-dependant protein kinase involved in the regulation of protein synthesis by Ca$^{2+}$ (Redpath et al., (1996) *J. Biol. Chem* 271:17547–17554; Ryazanov et al., (1997) *Proc. Natl. Acad. Sci., USA* 94:4884–4889). Both MHCK A and eEF-2 kinase display no homology to any of the known protein kinases, but are strikingly similar to each other; amino acid sequences of their catalytic domains are 40% identical. Another protein kinase homologous to MHCK A and eEF-2 kinase has recently been identified in *Dictyostelium* (Clancy et al., (1997) *J. Biol. Chem.* 272:11812–11815), and an expressed sequence tag (EST) sequence, with a high degree of similarity to the catalytic domain common to both MHCK A and eEF-2 kinase, has been deposited in GenBank (clone FC-AN09/accession #C22986). An amino acid sequence alignment of the catalytic domains of these new protein kinases is shown in FIG. 1A. These kinases have a catalytic domain of approximately 200 amino acids which can be subdivided into seven conserved subdomains. Subdomains V, VI, and VII have a predicted β-sheet structure and are presumably involved in ATP-binding, while subdomains I through IV may be involved in substrate binding and catalysis. These new protein kinases have no homology to the members of the eukaryotic serine/threonine/tyrosine protein kinase superfamily with the exception of the GXGXXG (SEQ ID NO:21) motif in subdomain VI which is present in many ATP-binding proteins. Thus, MHCK A, eEF-2 kinase, and related protein kinases may represent a new superfamily. Evolutionary analysis of these new kinases (FIG. 1B) reveals that they can be subdivided into 2 families: the eEF-2 kinase family which includes eEF-2 kinases from different organisms, and the MHCK family which includes MHCK A, MHCK B and FC-AN09. These two families appear to have split more than a billion years ago.

An interesting question is why does nature employ these unusual kinases to phosphorylate eEF-2 and myosin heavy chains? Perhaps the answer is related to the secondary structure of the phosphorylation sites. As was originally reported by Small et al. (Small et al., (1977), *Biochim. Biophys. Res. Comm.* 79:341–346), phosphorylation sites are usually located at predicted β-turns. Subsequent studies, including X-ray crystallographic data, demonstrated that phosphoacceptor sites in substrates of conventional protein kinases are often located in turns or loops and usually have flexible extended conformation (Knighton et al., (1991) *Science* 253:414–420; Pinna and Ruzzene (1996) *Biochim. Biophys. Acta* 1314:191–225). In contrast to this, the existing evidence suggests that the peptides around phosphorylation sites for eEF-2 kinases and MHCK A have an α-helical conformation. The two major phosphorylation sites for MHCK A are located in a region which has a coiled-coil α-helical structure (Vaillancourt et al., (1988) *J. Biol. Chem.* 253:10082–10087). The major phosphorylation site in eEF-2, threonine 56, is located within a sequence which is homologous among all translational elongation factors. In the crystal structure of the prokaryotic elongation factor EF-Tu, this sequence has an α-helical conformation (Polekhina et al., (1996) *Structure* 4:1141–1151; Abel et al., (1996) *Structure* 4:1153–1159). These facts suggest that eEF-2 kinase and MHCK A differ from conventional protein kinases in that they phosphorylate amino acids located within α-helices. Thus, in addition to the two well-characterized superfamily of eukaryotic protein kinases, which phosphorylate amino acids located in loops and turns, there appears to be a third superfamily of α-helix-directed kinases.

The existence of several protein kinases which have very little or no homology to either the serine/threonine/tyrosine kinase superfamily or the histidine kinase superfamily, provides a new superfamily, the α-kinases. The isolation and analysis of additional members of this family of kinases will further our understanding of α-kinases and provide insight into the physiological roles of these kinases and their applications and uses.

The citation of references herein shall not be construed as an admission that such is prior art to the present invention.

SUMMARY OF THE INVENTION

In accordance with the present invention, a new superfamily of protein kinases, novel members thereof, and corresponding methods for assaying their phosphorylation activity are disclosed. The protein kinases of this new alpha-kinase superfamily have the following characteristics: 1) No significant sequence homology to protein kinases of either the serine/threonine/tyrosine kinase or histidine kinase super families; 2) moderate to high homology ($\geq$40%) to eEF-2 kinases from any organism; and, 3) the ability to phosphorylate an amino acid within an a-helical domain. In addition, a new subfamily of alpha-kinases is herein provided. In particular, a subfamily of alpha-kinases is provided in which an ion channel, particularly belonging to the TRP family of ion channels is covalently linked to a protein kinase. The placement of a kinase and channel on a single molecule is particularly interesting and suggests a self-regulated molecule, whereby the phosphorylation/autophosphorylation of these unique alpha kinases controls or contributes to the open or closed state of the channel.

The present invention provides an isolated nucleic acid encoding melanoma alpha kinase, or a fragment thereof having at least 15 nucleotides. In particular, the invention provides an isolated nucleic acid encoding human melanoma alpha kinase, wherein the nucleic acid is selected from the group consisting of:
 a. the DNA sequence of SEQ ID NO: 26;
 b. DNA sequences that hybridize to the sequence of subpart (a) under moderate stringency hybridization conditions;
 c. DNA sequences capable of encoding the amino acid sequence encoded by the DNA sequences of (a) or (b);
 d. degenerate variants thereof;
 e. alleles thereof; and
 f. hybridizable fragments thereof.

In particular, the invention provides an isolated nucleic acid encoding mouse melanoma alpha kinase, wherein the nucleic acid is selected from the group consisting of:
 a. the DNA sequence of SEQ ID NO: 28;
 b. DNA sequences that hybridize to the sequence of subpart (a) under moderate stringency hybridization conditions;
 c. DNA sequences capable of encoding the amino acid sequence encoded by the DNA sequences of (a) or (b);
 d. degenerate variants thereof;
 e. alleles thereof; and
 f. hybridizable fragments thereof.

In particular, the invention provides an isolated nucleic acid encoding mammalian melanoma alpha kinase, wherein the nucleic acid is selected from the group consisting of:
 a. the DNA sequence of SEQ ID NO: 28;
 b. the DNA sequence of SEQ ID NO: 26;
 c. DNA sequences that hybridize to the sequence of subparts (a) or (b) under standard hybridization conditions; and
 d. DNA sequences capable of encoding the amino acid sequence encoded by the DNA sequences of subparts (a), (b) or (c).

The present invention further provides an isolated nucleic acid encoding heart alpha kinase, or a fragment thereof having at least 15 nucleotides. In particular, the present invention provides an isolated nucleic acid encoding human heart alpha kinase, wherein the nucleic acid is selected from the group consisting of:
 a. nucleic acid comprising the DNA sequence of SEQ ID NO: 34;
 b. DNA sequences that hybridize to the sequence of subpart (a) under moderate stringency hybridization conditions;
 c. DNA sequences capable of encoding the amino acid sequence encoded by the DNA sequences of (a) or (b);
 d. degenerate variants thereof;
 e. alleles thereof; and
 f. hybridizable fragments thereof.

In particular, the present invention provides an isolated nucleic acid encoding mouse heart alpha kinase, wherein the nucleic acid is selected from the group consisting of:
 a. nucleic acid comprising the DNA sequence of SEQ ID NO: 36;
 b. DNA sequences that hybridize to the sequence of subpart (a) under moderate stringency hybridization conditions;
 c. DNA sequences capable of encoding the amino acid sequence encoded by the DNA sequences of (a) or (b);
 d. degenerate variants thereof;
 e. alleles thereof; and
 f. hybridizable fragments thereof.

In particular, the invention provides an isolated nucleic acid encoding mammalian heart alpha kinase, wherein the nucleic acid is selected from the group consisting of:
 a. the DNA sequence of SEQ ID NO: 34;
 b. the DNA sequence of SEQ ID NO: 36;
 c. DNA sequences that hybridize to the sequence of subparts (a) or (b) under standard hybridization conditions; and
 d. DNA sequences capable of encoding the amino acid sequence encoded by the DNA sequences of subparts (a), (b) or (c).

The present invention still further provides an isolated nucleic acid encoding kidney alpha kinase, or a fragment thereof having at least 15 nucleotides. In particular, the invention includes an isolated nucleic acid encoding human kidney alpha kinase, wherein the nucleic acid is selected from the group consisting of:
 a. the DNA sequence of SEQ ID NO: 30;
 b. DNA sequences that hybridize to the sequence of subpart (a) under moderate stringency hybridization conditions;
 c. DNA sequences capable of encoding the amino acid sequence encoded by the DNA sequences of (a) or (b);
 d. degenerate variants thereof;
 e. alleles thereof; and
 f. hybridizable fragments thereof.

In particular, the invention includes an isolated nucleic acid encoding mouse kidney alpha kinase, wherein the nucleic acid is selected from the group consisting of:
 a. the DNA sequence of SEQ ID NO: 32;
 b. DNA sequences that hybridize to the sequence of subpart (a) under moderate stringency hybridization conditions;
 c. DNA sequences capable of encoding the amino acid sequence encoded by the DNA sequences of (a) or (b);
 d. degenerate variants thereof;
 e. alleles thereof; and
 f. hybridizable fragments thereof.

In particular, the invention provides an isolated nucleic acid encoding mammalian kidney alpha kinase, wherein the nucleic acid is selected from the group consisting of
 a. the DNA sequence of SEQ ID NO: 30;
 b. the DNA sequence of SEQ ID NO: 32;
 c. DNA sequences that hybridize to the sequence of subparts (a) or (b) under standard hybridization conditions; and
 d. DNA sequences capable of encoding the amino acid sequence encoded by the DNA sequences of subparts (a), (b) or (c).

The present invention also provides an isolated nucleic acid encoding skeletal muscle alpha kinase, or a fragment thereof having at least 15 nucleotides. In particular, an isolated nucleic acid encoding skeletal muscle alpha kinase is provided, wherein the nucleic acid is selected from the group consisting of:
 a. nucleic acid comprising the DNA sequence of SEQ ID NO: 38;
 b. DNA sequences that hybridize to the sequence of subpart (a) under moderate stringency hybridization conditions;
 c. DNA sequences capable of encoding the amino acid sequence encoded by the DNA sequences of (a) or (b);
 d. degenerate variants thereof;
 e. alleles thereof; and
 f. hybridizable fragments thereof.

In particular, the invention provides an isolated nucleic acid encoding mammalian skeletal muscle alpha kinase, wherein the nucleic acid is selected from the group consisting of:
 a. the DNA sequence of SEQ ID NO: 38;
 b. DNA sequences that hybridize to the sequence of subpart (a) under standard hybridization conditions; and
 c. DNA sequences capable of encoding the amino acid sequence encoded by the DNA sequences of (a) or (b).

The present invention also includes an isolated nucleic acid encoding lymphocyte alpha kinase, or a fragment thereof having at least 15 nucleotides. In particular, the present invention provides an isolated nucleic acid encoding lymphocyte alpha kinase, wherein the nucleic acid is selected from the group consisting of:
 a. nucleic acid comprising the DNA sequence of SEQ ID NO: 40;
 b. DNA sequences that hybridize to the sequence of subpart (a) under moderate stringency hybridization conditions;
 c. DNA sequences capable of encoding the amino acid sequence encoded by the DNA sequences of (a) or (b);
 d. degenerate variants thereof;
 e. alleles thereof; and
 f. hybridizable fragments thereof.

In particular, the invention provides an isolated nucleic acid encoding mammalian lymphocyte alpha kinase, wherein the nucleic acid is selected from the group consisting of:
 a. the DNA sequence of SEQ ID NO: 40;
 b. DNA sequences that hybridize to the sequence of subpart (a) under standard hybridization conditions; and
 c. DNA sequences capable of encoding the amino acid sequence encoded by the DNA sequences of (a) or (b).

The invention provides an isolated nucleic acid encoding human melanoma alpha kinase, wherein the nucleic acid comprises the DNA sequence of SEQ ID NO: 26. The invention provides an isolated nucleic acid encoding mouse melanoma alpha kinase, wherein the nucleic acid comprises the DNA sequence of SEQ ID NO: 28.

The invention provides an isolated nucleic acid encoding human heart alpha kinase, wherein the nucleic acid comprises the DNA sequence of SEQ ID NO: 34. The invention provides an isolated nucleic acid encoding mouse heart alpha kinase, wherein the nucleic acid comprises the DNA sequence of SEQ ID NO: 36.

The invention provides an isolated nucleic acid encoding human kidney alpha kinase, wherein the nucleic acid comprises the DNA sequence of SEQ ID NO: 30. The invention provides an isolated nucleic acid encoding mouse kidney alpha kinase, wherein the nucleic acid comprises the DNA sequence of SEQ ID NO: 32.

The invention provides an isolated nucleic acid encoding human skeletal muscle alpha kinase, wherein the nucleic acid comprises the DNA sequence of SEQ ID NO: 38.

The invention provides an isolated nucleic acid encoding human lymphocyte alpha kinase, wherein the nucleic acid comprises the DNA sequence of SEQ ID NO: 40.

The present invention also relates to a recombinant DNA molecule or cloned gene, or a degenerate variant thereof, which encodes an alpha kinase selected from the group of melanoma kinase, heart kinase, kidney kinase, skeletal muscle kinase and lymphocyte kinase; preferably a nucleic acid molecule, in particular a recombinant DNA molecule or cloned gene, encoding the alpha kinase has a nucleotide sequence or is complementary to a DNA sequence as set forth in any of SEQ ID NOS: 26, 28, 30, 32, 34, 36, 38 and 40.

The murine and/or human DNA sequences of the alpha kinase genes of the present invention or portions thereof, may be prepared as probes to screen for complementary sequences and genomic clones in the same or alternate species. The present invention extends to probes so prepared that may be provided for screening cDNA and genomic libraries for the alpha kinase genes. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences set forth in any of SEQ ID NOS: 26, 28, 30, 32, 34, 36, 38 and 40. Correspondingly, the preparation of antisense RNA and ribozymes are included herein.

According to other preferred features of certain preferred embodiments of the present invention, a recombinant expression system is provided to produce biologically active animal or human alpha kinase selected from the group of melanoma kinase, heart kinase, kidney kinase, skeletal muscle kinase and lymphocyte kinase.

The present invention naturally contemplates several means for preparation of the alpha kinase of the present invention, including as illustrated herein known recombinant techniques, and the invention is accordingly intended to cover such synthetic preparations within its scope. The isolation of the cDNA and amino acid sequences disclosed herein facilitates the production of the alpha kinase of the present invention by such recombinant techniques, and accordingly, the invention extends to expression vectors prepared from the disclosed DNA sequences for expression in host systems by recombinant DNA techniques, and to the resulting transformed hosts.

In a further aspect, the invention provides a recombinant DNA expression vector comprising the nucleic acid encoding an alpha kinase protein selected from the group of melanoma alpha kinase, kidney alpha kinase, heart alpha kinase, skeletal muscle alpha kinase and lymphocyte alpha kinase, wherein the DNA encoding the alpha kinase is operatively associated with an expression control sequence. The invention also provides a transformed host cell transfected with said DNA vector.

The invention further includes a unicellular host transformed with a recombinant DNA molecule comprising a DNA sequence or degenerate variant thereof, which encodes an alpha kinase, or a fragment thereof, selected from the group consisting of:
 a. the DNA sequence of (SEQ ID NO: 26);
 b. the DNA sequence of (SEQ ID NO: 28);
 c. the DNA sequence of (SEQ ID NO: 30);
 d. the DNA sequence of (SEQ ID NO: 32);
 e. the DNA sequence of (SEQ ID NO: 34);
 d. the DNA sequence of (SEQ ID NO: 36);
 e. the DNA sequence of (SEQ ID NO: 38);
 h. the DNA sequence of (SEQ ID NO: 40);
 i. DNA sequences that hybridize to any of the foregoing DNA sequences under standard hybridization conditions; and
 j. DNA sequences that code on expression for an amino acid sequence encoded by any of the foregoing DNA sequences;
  wherein said DNA sequence is operatively linked to an expression control sequence.

Such a unicellular host is particularly selected from the group consisting of *E. coli, Pseudomonas, Bacillus, Streptomyces,* yeasts, CHO, R1.1, B-W, L-M, COS 1, COS 7, BSC1, BSC40, and BMT10 cells, plant cells, insect cells, mouse cells and human cells in tissue culture.

In a further aspect, the present invention includes an isolated protein characterized by the presence of at least two domains, one of the domains being an alpha-kinase catalytic domain and the other domain being an ion channel domain.

Thus, the present invention provides an isolated melanoma alpha kinase protein characterized by having an alpha-kinase catalytic domain and an ion channel domain. In particular, a melanoma alpha kinase protein is provided which comprises the amino acid sequence set out in SEQ ID NO: 27 and 29, and analogs, variants and fragments thereof. The invention provides a melanoma alpha kinase protein which comprises the amino acid sequence set out in SEQ ID NO: 27 or 29, and variants thereof wherein one or more amino acids is substituted with a conserved amino acid.

The invention further provides an isolated kidney alpha kinase protein characterized by having an alpha-kinase catalytic domain and an ion channel domain. In particular, the kidney alpha kinase protein comprises the amino acid sequence set out in SEQ ID NO: 31 and 33, and analogs, variants and fragments thereof. The invention provides a kidney alpha kinase protein which comprises the amino acid sequence set out in SEQ ID NO: 31 or 33, and variants thereof wherein one or more amino acids is substituted with a conserved amino acid.

The present invention further provides an isolated heart alpha kinase protein. In particular, the heart alpha kinase protein comprises the amino acid sequence set out in SEQ ID NO: 35 and 37, and analogs, variants and immunogenic fragments thereof. The invention provides a heart alpha kinase protein which comprises the amino acid sequence set out in SEQ ID NO: 35 or 37, and variants thereof wherein one or more amino acids is substituted with a conserved amino acid.

The present invention still further provides an isolated skeletal muscle alpha kinase protein. In particular, the skeletal muscle alpha kinase protein comprises the amino acid sequence set out in SEQ ID NO: 39, and analogs, variants and immunogenic fragments thereof. The invention provides a skeletal muscle alpha kinase protein which comprises the amino acid sequence set out in SEQ ID NO: 39, and variants thereof wherein one or more amino acids is substituted with a conserved amino acid.

The invention includes an isolated lymphocyte alpha kinase protein. In particular, the lymphocyte alpha kinase protein comprises the amino acid sequence set out in SEQ ID NO: 41, and analogs, variants and immunogenic fragments thereof. The invention provides a lymphocyte alpha kinase protein which comprises the amino acid sequence set out in SEQ ID NO: 41, and variants thereof wherein one or more amino acids is substituted with a conserved amino acid.

In a particular aspect, the present invention includes a pharmaceutical composition comprising one or more alpha kinase protein selected from the group of melanoma alpha kinase, kidney alpha kinase, heart alpha kinase, skeletal muscle alpha kinase and lymphocyte alpha kinase, and a pharmaceutically acceptable carrier.

In a further aspect, the invention provides a purified antibody to an alpha kinase protein selected from the group of melanoma alpha kinase, kidney alpha kinase, heart alpha kinase, skeletal muscle alpha kinase and lymphocyte alpha kinase.

A monoclonal antibody to an alpha kinase protein selected from the group of melanoma alpha kinase, kidney alpha kinase, heart alpha kinase, skeletal muscle alpha kinase and lymphocyte alpha kinase is still further provided. The invention includes an immortal cell line that produces a monoclonal antibody to an alpha kinase protein selected from the group of melanoma alpha kinase, kidney alpha kinase, heart alpha kinase, skeletal muscle alpha kinase and lymphocyte alpha kinase.

Any such contemplated antibody may be labeled with a detectable label. The label may be selected from the group consisting of an enzyme, a chemical which fluoresces, and a radioactive element.

The invention further includes an antibody to an alpha kinase protein selected from the group of melanoma alpha kinase, kidney alpha kinase, heart alpha kinase, skeletal muscle alpha kinase and lymphocyte alpha kinase, which recognizes the phosphorylated form of the alpha kinase or a phosphorylated fragment thereof.

The present invention likewise extends to antibodies against specifically phosphorylated alpha kinase targets, including naturally raised and recombinantly prepared antibodies. These antibodies and their labeled counterparts are included within the scope of the present invention for their particular ability in detecting alpha kinase activity via detection of the phosphorylated product by ELISA or any other immunoassay known to the skilled artisan.

In the instance where a radioactive label, such as the isotopes $^{3}H$, $^{14}C$, $^{32}P$, $^{33}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

The present invention provides a method for treating an animal in need of increased activity of melanoma alpha kinase which comprises administration of melanoma alpha kinase to the animal.

The present invention further provides a method for treating an animal in need of increased activity of melanoma alpha kinase which comprises administration of an antibody against melanoma alpha kinase to the animal.

The present invention also provides a method for treating an animal in need of increased activity of kidney alpha kinase which comprises administration of kidney alpha kinase to the animal.

The invention also includes a method for treating an animal in need of increased activity of kidney alpha kinase which comprises administration of an antibody against kidney alpha kinase to the animal.

The invention further provides a method for treating an animal in need of increased activity of heart alpha kinase which comprises administration of heart alpha kinase to the animal.

The present invention also contemplates a method for treating an animal in need of increased activity of heart alpha kinase which comprises administration of an antibody against heart alpha kinase to the animal.

In an additional aspect, the invention provides a method for treating an animal in need of increased activity of skeletal muscle alpha kinase which comprises administration of skeletal muscle alpha kinase to the animal.

A method for treating an animal in need of increased activity of skeletal muscle alpha kinase which comprises administration of an antibody against skeletal muscle alpha kinase to the animal is further provided.

The present invention includes method for treating an animal in need of increased activity of lymphocyte alpha kinase which comprises administration of lymphocyte alpha kinase to the animal.

The present invention further provides a method for treating an animal in need of increased activity of lymphocyte alpha kinase which comprises administration of an antibody against lymphocyte alpha kinase to the animal.

The therapeutic method provided herein could include the method for the treatment of various pathologies or other cellular dysfunctions and derangements by the administration of pharmaceutical compositions that may comprise effective inhibitors of alpha kinase activity, or other equally effective drugs developed for instance by a drug screening assay prepared and used in accordance with a further aspect of the present invention.

The invention includes an assay system for screening of potential drugs effective at attenuating alpha kinase activity of target mammalian cells by interrupting or potentiating the phosphorylation of alpha kinase selected from the group of melanoma kinase, heart kinase, kidney kinase, skeletal muscle kinase and lymphocyte kinase. In one instance, the test drug could be administered to a cellular sample along with ATP carrying a detectable label on its γ-phosphate that gets transferred to the kinase target, including the kinase itself, or a peptide substrate, by the particular alpha kinase. Quantification of the labeled kinase target or peptide substrate is diagnostic of the candidate drug's efficacy. A further embodiment would provide for the assay to be performed using a purely in vitro system comprised of the alpha kinase, ATP or labeled ATP, the kinase target or peptide substrate, appropriate buffer, and detection reagents and/or instrumentation to detect and quantify the extent of alpha kinase-directed phosphorylation activity.

The assay system could more importantly be adapted to identify drugs or other entities that are capable of binding to the alpha kinase and/or its cognate phosphorylation target, either in the cytoplasm or in the nucleus, thereby inhibiting or potentiating alpha kinase activity and its resultant phenotypic outcome. Such an assay would be useful in the development of drugs that would be specific against particular cellular activity, or that would potentiate such activity, in time or in level of activity. For example, such drugs might be used to treat various carcinomas or other hyperproliferative pathologies.

In an additional aspect, the present invention includes a method for detecting the presence or activity of an alpha kinase protein selected from the group of melanoma alpha kinase, kidney alpha kinase, heart alpha kinase, skeletal muscle alpha kinase and lymphocyte alpha kinase, wherein said alpha kinase is measured by:

A. contacting a biological sample from a mammal in which the presence or activity of said alpha kinase is suspected with a binding partner of said alpha kinase under conditions that allow binding of said alpha kinase to said binding partner to occur; and B. detecting whether binding has occurred between said alpha kinase from said sample and the binding partner;

wherein the detection of binding indicates that presence or activity of said alpha kinase in said sample.

The present invention further provides a method for detecting the presence of an alpha kinase protein selected from the group of melanoma alpha kinase, kidney alpha kinase, heart alpha kinase, skeletal muscle alpha kinase and lymphocyte alpha kinase, wherein the alpha kinase is measured by:

a. contacting a sample in which the presence or activity of an alpha kinase protein selected from the group of melanoma alpha kinase, kidney alpha kinase, heart alpha kinase, skeletal muscle alpha kinase and lymphocyte alpha kinase is suspected with an antibody to the said alpha kinase protein under conditions that allow binding of the alpha kinase protein to the binding partner to occur; and b. detecting whether binding has occurred between the alpha kinase protein from the sample and the antibody;

wherein the detection of binding indicates the presence or activity of the alpha kinase protein in the sample.

In a still further aspect, the invention provides a method of testing the ability of a drug or other entity to modulate the kinase activity of an alpha kinase protein selected from the group of melanoma alpha kinase, kidney alpha kinase, heart alpha kinase, skeletal muscle alpha kinase and lymphocyte alpha kinase which comprises:

A. culturing a colony of test cells containing the alpha kinase protein;

B. adding the drug or other entity under test; and

C. measuring the kinase activity of said alpha kinase protein in the test cells, wherein when the amount of kinase activity in the presence of the modulator is greater than in its absence, the modulator is identified as an agonist or activator of the alpha kinase protein, whereas when the amount of kinase activity in the presence of the modulator is less than in its absence, the modulator is identified as an antagonist or inhibitor of the alpha kinase protein.

Other objects and advantages will become apparent to those skilled in the art from a review of the ensuing description which proceeds with reference to the following illustrative drawings.

BRIEF DESCRIPTION OF THE DRAWINGS

FIG. 2 depicts a sequence alignment of *C. elegans*, mouse, human eEF-2 kinase, and the catalytic domain of *Dictyostelium discoideum* MHCK A. Identical amino acids are indicated by dark blue boxed regions and chemically conserved amino acids are indicated by light blue shaded regions. Amino acids in the human sequence that are identical to the mouse sequence are represented by dots. Amino acids underlined in black correspond to the six regions that match peptides obtained from the sequencing of purified rabbit reticulocyte eEF-2 kinase. The GXGXXG nucleotide-binding motif is underlined in red. The blue dashed line over residues 625–632 in *C. elegans* eEF-2 kinases designates the amino acids corresponding to exon 4, which is missing in Cefk-2.

FIG. 4 depicts a sequence alignment of *C. elegans*, mouse, human eEF-2 kinase, and the catalytic domain of *Dictyostelium discoideum* MHCK A, heart kinase, melanoma kinase and ch4 kinase. Identical amino acids are indicated by dark blue boxed regions and chemically conserved amino acids are indicated by light blue shaded regions.

FIGS. 5A through C depicts the nucleic acid sequence of mouse melanoma alpha-kinase (MK).

FIGS. 6A and B depicts the predicted amino acid sequence of mouse melanoma alpha-kinase (MK).

FIGS. 7A and B depicts the nucleic acid sequence (A) and predicted amino acid sequence (B) of human melanoma alpha-kinase (MK).

FIGS. 8A and B depicts the nucleic acid sequence (A) and predicted amino acid sequence (B) of human heart alpha-kinase (HK).

FIGS. 9A and B depicts the nucleic acid sequence (A) and predicted amino acid sequence (B) of human kidney alpha-kinase (KK).

FIGS. 10A and B depicts the nucleic acid sequence (A) and predicted amino acid sequence (B) of human skeletal muscle alpha-kinase (SK).

FIGS. 11A and B depicts the nucleic acid sequence (A) and predicted amino acid sequence (B) of human lymphocyte alpha-kinase (LK).

FIG. 12 shows the alignment of the catalytic domains of the cloned alpha-kinases.

Figure 16:
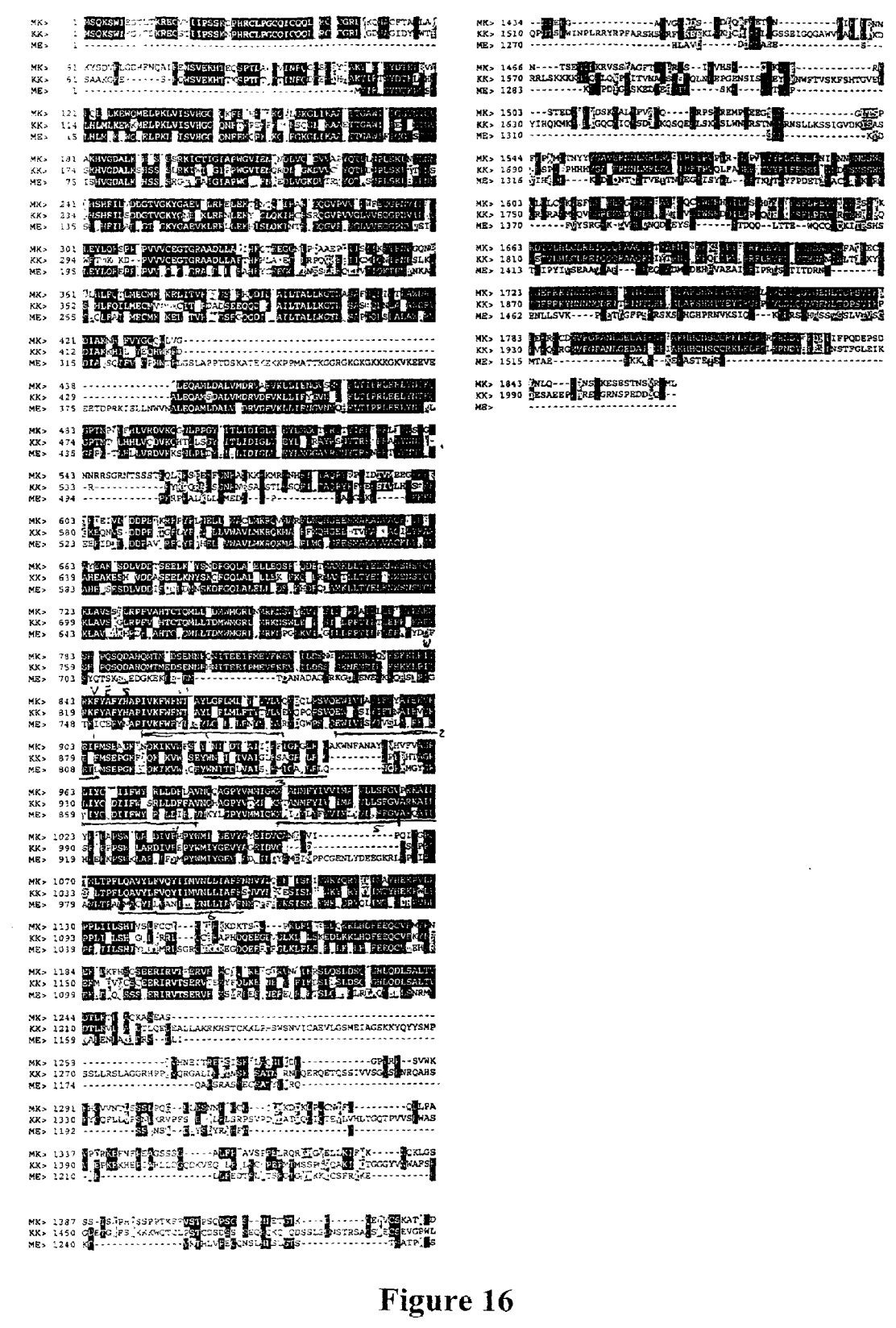

FIG. 16 shows a comparison of the ion channel portions of melanoma kinase (MK), kidney kinase (KK) and melastatin (ME).

FIG. 17 Sequence alignment of MK and KK with members of the LTRP channel subfamily. Roman numerals designate the six predicted transmembrane segments. Black boxes highlight identical amino acids. Gray boxes highlight conserved amino acids. The alignment was constructed using the ClustalW program and the shading was done using the Boxshade program.

DETAILED DESCRIPTION

Figure 1B:
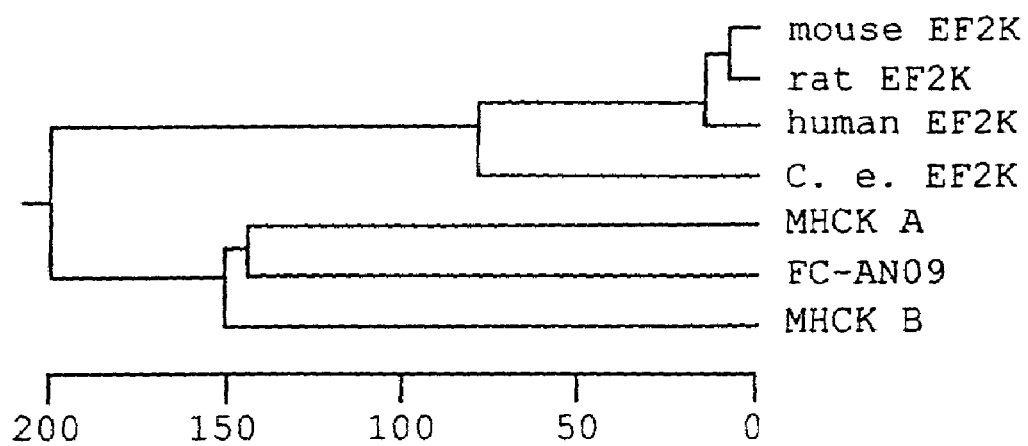
FIGS. 1A and B. A, Sequence alignment of the catalytic domains of human eEF-2 kinase, *C. elegans* eEF-2 kinase, MHCK A, MHCK B and clone FC-ANO9. Identical amino acids (bold) and conserved hydrophobic amino acids (°) are noted. B, Phylogenetic tree of sequences shown in (A), with the addition of mouse and rat eEF-2 kinases. Tree was obtained using the J. Hein method with PAM250 residue weight table. The following accession numbers were used for the sequences: U93846–U93850, 1495779, 1170675, 1903458, C22986.

Protein phosphorylation plays a pivotal role in a wide variety of cellular processes. Enzymes which assist in protein phosphorylation are referred to as "protein kinases." Two protein kinase superfamilies have been described. The vast majority of protein kinases belong to the serine/threonine/tyrosine kinase superfamily. Several hundred members of this superfamily have thus far been characterized and found to share similar structural organization of their catalytic domains consisting of 12 conserved subdomains. There is also the histidine kinase superfamily consisting primarily of sensor components of the prokaryotic two-component signal transduction systems. Eukaryotic members of this superfamily have been recently described. In addition, mitochondrial branched-chain-ketoacid dehydrogenase kinase and the mitochondrial pyruvate dehydrogenase kinase have been described which are structurally related to the histidine kinases, but phosphorylate their substrates on serine. The existence of several protein kinases have recently been reported which have very little or no homology to either superfamily. This new superfamily is termed alpha-kinase. The first two members eEF-2 kinase and MHCKA kinase differ from conventional protein kinases in that they phosphorylate amino acids located within α-helices. Thus, in addition to the two well-characterized superfamily of eukaryotic protein kinases, which phosphorylate amino acids located in loops and turns, there appears to be a third superfamily of α-helix-directed kinases.

Additional novel members of the alpha kinase superfamily have herein been cloned and sequenced. In particular, these new alpha kinases—melanoma alpha kinase, kidney alpha kinase, heart alpha kinase, skeletal muscle alpha kinase and lymphocyte kinase—represent new members of the alpha kinase superfamily. The alpha kinases of the present invention are related to eEF-2 kinase and MHCK A and join the alpha kinase superfamily. In addition, however, the novel alpha kinases of the present invention have new and unique characteristics.

In particular, the melanoma alpha kinase and kidney kinase of the present invention have a unique structure. These proteins have two domains, one domain is the alpha-kinase catalytic domain and the other is an ion channel. This is the first recognized example of an ion channel being covalently linked to a protein kinase. It is likely that these novel protein kinases can be regulated by ion flow through the membrane. Expression of the melanoma kinase was detected in all mouse tissues studied, including heart, skeletal muscle, brain, liver and lung. This kinase is the most abundant in the heart. In contrast, the kidney kinase is present almost exclusively in kidney tissue. The ion channel portion is very similar to (70% identical) to a previously identified protein called melastatin that is selectively downregulated in metastatic tumors, and therefore is believed to be a metastasis suppressor gene. Melanoma alpha-kinase, kidney alpha-kinase, as well as melastatin, belong to the TRP family of ion channels. All TRP proteins function as tetramers, and various TRP proteins can form tetramers in different combinations that result in ion channels with different properties. Considering the high degree of similarity between melanoma kinase, kidney kinase, and melastatin, it is likely that melanoma kinase and kidney kinase can form tetrameric complexes with melastatin.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994)]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "elongation factor-2 kinase", "eEF-2 kinase", "EF-2 kinase", "Cefk", and any variants not specifically listed, may be used herein interchangeably, and as used throughout the present application and claims refer to proteinaceous material including single or multiple proteins, and extends to those proteins having the amino acid sequence data described herein and presented in FIGS. 1 and 5 (SEQ ID NOS: 1, 2, 6, 8 and 14), and the profile of activities set forth herein and in the claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms elongation factor-2 kinase", "eEF-2 kinase", "EF-2 kinase", and "Cefk" are intended to include within their scope proteins specifically recited herein as well as all substantially homologous analogs and allelic variations. The terms "melanoma α kinase", "melanoma alpha kinase ", "melanoma kinase", "MK", and any variants not specifically listed, may be used herein interchangeably, and as used throughout the present application and claims refer to proteinaceous material including single or multiple proteins, and extends to those proteins having the amino acid sequence data described herein and presented in FIGS. 6 and 7 (SEQ ID NOS: 27 and 29), and the profile of activities set forth herein and in the claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "melanoma α kinase", "melanoma alpha kinase", "melanoma kinase" and "MK" are intended to include within their scope proteins specifically recited herein as well as all substantially homologous analogs and allelic variations.

The terms "heart α kinase", "heart alpha kinase", "heart kinase", "HK", and any variants not specifically listed, may be used herein interchangeably, and as used throughout the present application and claims refer to proteinaceous material including single or multiple proteins, and extends to those proteins having the amino acid sequence data described herein and presented in FIG. 8 (SEQ ID NOS: 35 and 37), and the profile of activities set forth herein and in the claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "heart α kinase", "heart alpha kinase ", "heart kinase", "HK" are intended to include within their scope proteins specifically recited herein as well as all substantially homologous analogs and allelic variations.

The terms "kidney α kinase", "kidney alpha kinase", "kidney kinase", "KK", and any variants not specifically listed, may be used herein interchangeably, and as used throughout the present application and claims refer to proteinaceous material including single or multiple proteins, and extends to those proteins having the amino acid sequence data described herein and presented in FIG. 9 (SEQ ID NOS: 31 and 33), and the profile of activities set forth herein and in the claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "kidney α kinase", "kidney alpha kinase", "kidney kinase", "KK" are intended to include within their scope proteins specifically recited herein as well as all substantially homologous analogs and allelic variations.

Figure 10A:
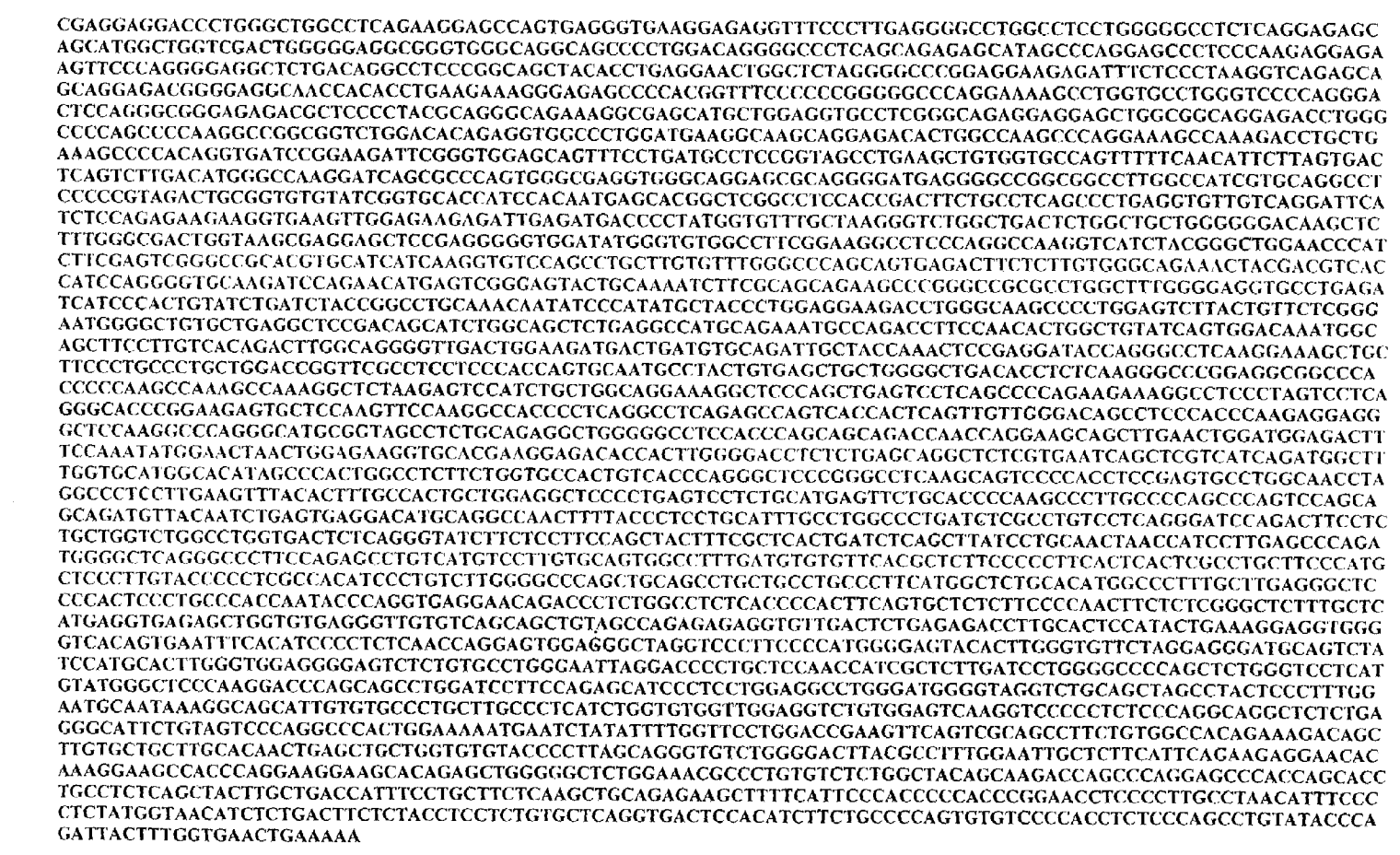

The terms "skeletal muscle α kinase", "skeletal muscle alpha kinase", "skeletal muscle kinase", "SK", and any variants not specifically listed, may be used herein interchangeably, and as used throughout the present application and claims refer to proteinaceous material including single or multiple proteins, and extends to those proteins having the amino acid sequence data described herein and presented in FIG. 10 (SEQ ID NO: 39), and the profile of activities set forth herein and in the claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "skeletal muscle α kinaes", "skeletal muscle alpha kinase", "skeletal muscle kinase", "SK" are intended to include within their scope proteins specifically recited herein as well as all substantially homologous analogs and allelic variations.

The terms "lymphocyte α kinase", "lymphocyte alpha kinase", "lymphocyte kinase", "LK", "Ch4" and any variants not specifically listed, may be used herein interchangeably, and as used throughout the present application and claims refer to proteinaceous material including single or multiple proteins, and extends to those proteins having the amino acid sequence data described herein and presented in FIG. 11 (SEQ ID NO: 41), and the profile of activities set forth herein and in the claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "lymphocyte α kinaes", "lymphocyte alpha kinase", "lymphocyte kinase", "LK", "Ch4" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired fractional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

TABLE OF CORRESPONDENCE

| SYMBOL | | |
| --- | --- | --- |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

Nucleic Acids

The present invention provides an isolated nucleic acid encoding melanoma alpha kinase, or a fragment thereof having at least 15 nucleotides. In particular, the invention provides an isolated nucleic acid encoding human melanoma alpha kinase, wherein the nucleic acid is selected from the group consisting of:
a. the DNA sequence of SEQ ID NO: 26;
b. DNA sequences that hybridize to the sequence of subpart (a) under moderate stringency hybridization conditions;
c. DNA sequences capable of encoding the amino acid sequence encoded by the DNA sequences of (a) or (b);
d. degenerate variants thereof;
e. alleles thereof; and
f. hybridizable fragments thereof.

In particular, the invention provides an isolated nucleic acid encoding mouse melanoma alpha kinase, wherein the nucleic acid is selected from the group consisting of:
a. the DNA sequence of SEQ ID NO: 28;
b. DNA sequences that hybridize to the sequence of subpart (a) under moderate stringency hybridization conditions;
c. DNA sequences capable of encoding the amino acid sequence encoded by the DNA sequences of (a) or (b);
d. degenerate variants thereof;
e. alleles thereof; and
f. hybridizable fragments thereof.

The present invention further provides an isolated nucleic acid encoding heart alpha kinase, or a fragment thereof having at least 15 nucleotides. In particular, the present invention provides an isolated nucleic acid encoding human heart alpha kinase, wherein the nucleic acid is selected from the group consisting of:
a. nucleic acid comprising the DNA sequence of SEQ ID NO: 34;
b. DNA sequences that hybridize to the sequence of subpart (a) under moderate stringency hybridization conditions;
c. DNA sequences capable of encoding the amino acid sequence encoded by the DNA sequences of (a) or (b);
d. degenerate variants thereof;
e. alleles thereof; and
f. hybridizable fragments thereof.

In particular, the present invention provides an isolated nucleic acid encoding mouse heart alpha kinase, wherein the nucleic acid is selected from the group consisting of:
a. nucleic acid comprising the DNA sequence of SEQ ID NO: 36;
b. DNA sequences that hybridize to the sequence of subpart (a) under moderate stringency hybridization conditions;
c. DNA sequences capable of encoding the amino acid sequence encoded by the DNA sequences of (a) or (b);
d. degenerate variants thereof;
e. alleles thereof; and
f. hybridizable fragments thereof.

The present invention still further provides an isolated nucleic acid encoding kidney alpha kinase, or a fragment thereof having at least 15 nucleotides. In particular, the invention includes an isolated nucleic acid encoding human kidney alpha kinase, wherein the nucleic acid is selected from the group consisting of:
a. the DNA sequence of SEQ ID NO: 30;
b. DNA sequences that hybridize to the sequence of subpart (a) under moderate stringency hybridization conditions;
c. DNA sequences capable of encoding the amino acid sequence encoded by the DNA sequences of (a) or (b);
d. degenerate variants thereof;
e. alleles thereof; and
f. hybridizable fragments thereof.

In particular, the invention includes an isolated nucleic acid encoding mouse kidney alpha kinase, wherein the nucleic acid is selected from the group consisting of:
a. the DNA sequence of SEQ ID NO: 32;
b. DNA sequences that hybridize to the sequence of subpart (a) under moderate stringency hybridization conditions;
c. DNA sequences capable of encoding the amino acid sequence encoded by the DNA sequences of (a) or (b);
d. degenerate variants thereof;
e. alleles thereof; and
f. hybridizable fragments thereof.

The present invention also provides an isolated nucleic acid encoding skeletal muscle alpha kinase, or a fragment thereof having at least 15 nucleotides. In particular, an isolated nucleic acid encoding skeletal muscle alpha kinase is provided, wherein the nucleic acid is selected from the group consisting of:
a. nucleic acid comprising the DNA sequence of SEQ ID NO: 38;
b. DNA sequences that hybridize to the sequence of subpart (a) under moderate stringency hybridization conditions;
c. DNA sequences capable of encoding the amino acid sequence encoded by the DNA sequences of (a) or (b);
d. degenerate variants thereof;
e. alleles thereof; and
f. hybridizable fragments thereof.

The present invention also includes an isolated nucleic acid encoding lymphocyte alpha kinase, or a fragment thereof having at least 15 nucleotides. In particular, the present invention provides an isolated nucleic acid encoding lymphocyte alpha kinase, wherein the nucleic acid is selected from the group consisting of:
a. nucleic acid comprising the DNA sequence of SEQ ID NO: 40;
b. DNA sequences that hybridize to the sequence of subpart (a) under moderate stringency hybridization conditions;
c. DNA sequences capable of encoding the amino acid sequence encoded by the DNA sequences of (a) or (b);
d. degenerate variants thereof;
e. alleles thereof, and
f. hybridizable fragments thereof.

The present invention also relates to a recombinant DNA molecule or cloned gene, or a degenerate variant thereof, which encodes an alpha kinase selected from the group of melanoma kinase, heart kinase, kidney kinase, skeletal muscle kinase and lymphocyte kinase; preferably a nucleic acid molecule, in particular a recombinant DNA molecule or cloned gene, encoding the alpha kinase has a nucleotide sequence or is complementary to a DNA sequence as set forth in any of SEQ ID NOS: 26, 28, 30, 32, 34, 36, 38 and 40.

The murine and/or human DNA sequences of the alpha kinase genes of the present invention or portions thereof, may be prepared as probes to screen for complementary sequences and genomic clones in the same or alternate species. The present invention extends to probes so prepared that may be provided for screening cDNA and genomic libraries for the alpha kinase genes. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences set forth in any of SEQ ID NOS: 26, 28, 30, 32, 34, 36, 38 and 40. Correspondingly, the preparation of antisense RNA and ribozymes are included herein.

According to other preferred features of certain preferred embodiments of the present invention, a recombinant expression system is provided to produce biologically active animal or human alpha kinase selected from the group of melanoma kinase, heart kinase, kidney kinase, skeletal muscle kinase and lymphocyte kinase.

The present invention naturally contemplates several means for preparation of the alpha kinase of the present invention, including as illustrated herein known recombinant techniques, and the invention is accordingly intended to cover such synthetic preparations within its scope. The isolation of the cDNA and amino acid sequences disclosed herein facilitates the production of the alpha kinase of the present invention by such recombinant techniques, and accordingly, the invention extends to expression vectors prepared from the disclosed DNA sequences for expression in host systems by recombinant DNA techniques, and to the resulting transformed hosts.

In a further aspect, the invention provides a recombinant DNA expression vector comprising the nucleic acid encoding an alpha kinase protein selected from the group of melanoma alpha kinase, kidney alpha kinase, heart alpha kinase, skeletal muscle alpha kinase and lymphocyte alpha kinase, wherein the DNA encoding the alpha kinase is operatively associated with an expression control sequence. The invention also provides a transformed host cell transfected with said DNA vector.

The invention further includes a unicellular host transformed with a recombinant DNA molecule comprising a DNA sequence or degenerate variant thereof, which encodes an alpha kinase, or a fragment thereof, selected from the group consisting of:
  a. the DNA sequence of (SEQ ID NO: 26);
  b. the DNA sequence of (SEQ ID NO: 28);
  c. the DNA sequence of (SEQ ID NO: 30);
  d. the DNA sequence of (SEQ ID NO: 32);
  e. the DNA sequence of (SEQ ID NO: 34);
  f. the DNA sequence of (SEQ ID NO: 36);
  g. the DNA sequence of (SEQ ID NO: 38);
  h. the DNA sequence of (SEQ ID NO: 40);
  i. DNA sequences that hybridize to any of the foregoing DNA sequences under standard hybridization conditions; and
  j. DNA sequences that code on expression for an amino acid sequence encoded by any of the foregoing DNA sequences;
wherein said DNA sequence is operatively linked to an expression control sequence.

Such a unicellular host is particularly selected from the group consisting of E. coli, Pseudomonas, Bacillus, Streptomyces, yeasts, CHO, R1.1, B-W, L-M, COS 1, COS 7, BSC1, BSC40, and BMT10 cells, plant cells, insect cells, mouse cells and human cells in tissue culture.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgamo sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA—RNA, DNA—DNA or RNA-DNA. Such standard hybridization conditions are easily determined by one skilled in the art according to well known formulae, wherein hybridization is typically 10–20° C. below the predicted or determined $T_m$ with washes of higher stringency, if desired.

In one aspect, the present invention relates to the identification of a new superfamily of protein kinases, denoted alpha kinases. Accordingly, it includes the DNA sequences coding for these family members. In addition, the invention also contemplates that each member of this new protein kinase superfamily has its own cognate phosphorylation target.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand.

Alternatively, non-complementary bases or longer sequences can be interspersed into the primer, provided that the primer sequence has sufficient complementarity with the sequence of the strand to hybridize therewith and thereby form the template for the synthesis of the extension product.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding alpha kinase, selected from the group of melanoma kinase, kidney kinase, heart kinase, skeletal muscle kinase and lymphocyte kinase, which code for a protein having the same amino acid sequence as any of SEQ ID NOS:, but which are degenerate to any of SEQ ID NOS:. By "degenerate to" is meant that a different three-letter codon is used to specify a particular amino acid. It is well known in the art that the following codons can be used interchangeably to code for each specific amino acid:

```
Phenylalanine (Phe or F)  UUU or UUC
Leucine (Leu or L)        UUA or UUG or CUU or CUC or CUA or CUG
Isoleucine (Ile or I)     AUU or AUC or AUA
Methionine (Met or M)     AUG
Valine (Val or V)         GUU or GUC of GUA or GUG
Serine (Ser or S)         UCU or UCC or UCA or UCG or AGU or AGC
Proline (Pro or P)        CCU or CCC or CCA or CCG
Threonine (Thr or T)      ACU or ACC or ACA or ACG
Alanine (Ala or A)        GCU or GCG or GCA or GCG
Tyrosine (Tyr or Y)       UAU or UAC
Histidine (His or H)      CAU or CAC
Glutamine (Gln or Q)      CAA or CAG
Asparagine (Asn or N)     AAU or AAC
Lysine (Lys or K)         AAA or AAG
Aspartic Acid (Asp or D)  GAU or GAC
Glutamic Acid (Glu or E)  GAA or GAG
Cysteine (Cys or C)       UGU or UGC
Arginine (Arg or R)       CGU or CGC or CGA or CGG or AGA or AGG
Glycine (Gly or G)        GGU or GGC or GGA or GGG
Tryptophan (Trp or W)     UGG
Termination codon         UAA (ochre) or UAG (amber) or UGA (opal)
```

It should be understood that the codons specified above are for RNA sequences. The corresponding codons for DNA have a T substituted for U.

Mutations can be made in any of SEQ ID NOS: such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids: (I) Amino acids with nonpolar R groups: Alanine, Valine, Leucine, Isoleucine, Proline, Phenylalanine, Tryptophan, Methionine; (II) Amino acids with uncharged polar R groups: Glycine, Serine, Threonine, Cysteine, Tyrosine, Asparagine, Glutamine; (III) Amino acids with charged polar R groups (negatively charged at pH 6.0): Aspartic acid, Glutamic acid; (IV) Basic amino acids (positively charged at pH 6.0): Lysine, Arginine, Histidine (at pH 6.0).

Another grouping may be those amino acids with phenyl groups: Phenylalanine, Tryptophan, Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |

-continued

| | |
|---|---|
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free NH$_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors, a person skilled in the art will be able to construct a variety of vector/expression control sequence/host combinations that will express the DNA sequences of this invention on fermentation or in large scale animal culture.

The present invention extends to the preparation of antisense oligonucleotides and ribozymes that may be used to interfere with the expression of the eEF-2 kinase gene at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into eEF-2 kinase-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, *Tetrahymena*-type and "hammerhead"-type. (Hasselhoff and Gerlach, 1988) *Tetrahymena*-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to *Tetrahymena*-type ribozymes for inactivating a specific mRNA species, and eighteen base recognition sequences are preferable to shorter recognition sequences.

Polypeptides

In a further aspect, the present invention includes an isolated protein characterized by the presence of at least two domains, one of the domains being an alpha-kinase catalytic domain and the other domain being an ion channel domain.

Thus, the present invention provides an isolated melanoma alpha kinase protein characterized by having an alpha-kinase catalytic domain and an ion channel domain. In particular, a melanoma alpha kinase protein is provided which comprises the amino acid sequence set out in SEQ ID NO: 27 and 29, and analogs, variants and fragments thereof.

The invention further provides an isolated kidney alpha kinase protein characterized by having an alpha-kinase catalytic domain and an ion channel domain. In particular, the kidney alpha kinase protein comprises the amino acid sequence set out in SEQ ID NO: 31 and 33, and analogs, variants and fragments thereof.

The present invention further provides an isolated heart alpha kinase protein. In particular, the heart alpha kinase protein comprises the amino acid sequence set out in SEQ ID NO: 35 and 37, and analogs, variants and immunogenic fragments thereof.

The present invention still further provides an isolated skeletal muscle alpha kinase protein. In particular, the skeletal muscle alpha kinase protein comprises the amino acid sequence set out in SEQ ID NO: 39, and analogs, variants and immunogenic fragments thereof.

The invention includes an isolated lymphocyte alpha kinase protein. In particular, the lymphocyte alpha kinase protein comprises the amino acid sequence set out in SEQ ID NO: 41, and analogs, variants and immunogenic fragments thereof.

Two amino acid sequences are "substantially homologous" when at least about 70% of the amino acid residues (preferably at least about 80%, and most preferably at least about 90 or 95%) are identical, or represent conservative substitutions.

Antibodies

In a further aspect, the invention provides a purified antibody to an alpha kinase protein selected from the group of melanoma alpha kinase, kidney alpha kinase, heart alpha kinase, skeletal muscle alpha kinase and lymphocyte alpha kinase.

A monoclonal antibody to an alpha kinase protein selected from the group of melanoma alpha kinase, kidney alpha kinase, heart alpha kinase, skeletal muscle alpha kinase and lymphocyte alpha kinase is still further provided. the invention includes an immortal cell line that produces a monoclonal antibody to an alpha kinase protein selected from the group of melanoma alpha kinase, kidney alpha kinase, heart alpha kinase, skeletal muscle alpha kinase and lymphocyte alpha kinase.

Any such contemplated antibody may be labeled with a detectable label. The label may be selected from the group consisting of an enzyme, a chemical which fluoresces, and a radioactive element.

The invention further includes an antibody to an alpha kinase protein selected from the group of melanoma alpha kinase, kidney alpha kinase, heart alpha kinase, skeletal muscle alpha kinase and lymphocyte alpha kinase, which recognizes the phosphorylated form of the alpha kinase or a phosphorylated fragment thereof.

The present invention likewise extends to antibodies against specifically phosphorylated alpha kinase targets, including naturally raised and recombinantly prepared antibodies. These antibodies and their labeled counterparts are included within the scope of the present invention for their particular ability in detecting alpha kinase activity via detection of the phosphorylated product by ELISA or any other immunoassay known to the skilled artisan.

In the instance where a radioactive label, such as the isotopes $^3H$, $^{14}C$, $^{32}P$, $^{33}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

In a particular embodiment, the present invention relates to phosphorylation target analogs, which are short peptide sequences derived from phosphorylation targets of this new superfamily of protein alpha kinases centered around the alpha kinases selected from the group of melanoma kinase, kidney kinase, heart kinase, skeletal muscle kinase and lymphocyte kinase. Specifically, it is contemplated that these peptide analogs will be instrumental in the development of high throughput screening assays to identify inhibitors of members of this new superfamily.

Also, antibodies including both polyclonal and monoclonal antibodies, and drugs that modulate the production or activity of alpha kinase may possess certain diagnostic applications and may, for example, be utilized for the purpose of detecting and/or measuring levels of alpha kinase. It is anticipated that further experimentation will reveal a prognostic correlation between alpha kinase levels and the prediction and or progression of certain malignancies associated with carcinoma. For example, alpha kinase may be used to produce both polyclonal and monoclonal antibodies to themselves in a variety of cellular media, by known techniques such as the hybridoma technique utilizing, for example, fused mouse spleen lymphocytes and myeloma cells.

Likewise, small molecules that mimic or antagonize the activity of alpha kinase of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against alpha kinase peptides can be screened for various properties; i.e., isotype, epitope, affinity, etc. Of particular interest are monoclonal antibodies that neutralize the activity of alpha kinase. Such monoclonals can be readily identified in alpha kinase activity assays. High affinity antibodies are also useful when immunoaffinity purification of native or recombinant alpha kinase is desired.

Preferably, the anti-alpha kinase antibody used in the diagnostic methods of this invention is an affinity purified polyclonal antibody. More preferably, the antibody is a monoclonal antibody (mAb). In addition, it is preferable for the anti-alpha kinase antibody molecules used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to alpha kinase, such as an anti-alpha kinase antibody, preferably an affinity-purified polyclonal antibody, and more preferably a mAb. In addition, it is preferable for the anti-alpha kinase antibody molecules used herein be in the form of Fab, Fab', F(ab')$_2$ or F(v) portions or whole antibody molecules. As previously discussed, patients capable of benefitting from this method include those suffering from cancer, a pre-cancerous lesion, a viral infection or other like pathological derangement. Methods for isolating the alpha kinase and inducing anti-alpha kinase antibodies and for determining and optimizing the ability of anti-alpha kinase antibodies to assist in the examination of the target cells are all well-known in the art.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with a particular kinase and of the present invention and their ability to inhibit specified alpha kinase activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mM glutamine, and 20% fetal calf serum. An exemplary inbred mouse strain is the Balb/c.

Methods for producing monoclonal anti-alpha kinase antibodies are also well-known in the art. See Niman et al., *Proc. Natl. Acad. Sci. USA*, 80:4949–4953 (1983). Typically, the present alpha kinase or a peptide analog is used either alone or conjugated to an immunogenic carrier, as the immunogen in the before described procedure for producing anti-alpha kinase monoclonal antibodies. The hybridomas are screened for the ability to produce an antibody that immunoreacts with the eEF-2 kinase peptide analog and the present alpha kinase.

Therapeutic Compositions and Methods

Therapeutic possibilities are raised by the knowledge of the alpha kinase sequences, melanoma kinase, kidney kinase, heart kinase, skeletal muscle kinase and lymphocyte kinase. Accordingly, it is contemplated that sequences that are derived from the complement to the alpha kinase mRNA sequence, and various modifications thereof, can act as potent antisense drugs that either inhibit expression in a competitive fashion, or, more effectively, by nuclease activity associated with the antisense drug that cleaves the alpha kinase mRNA sequence, thus rendering it irreversibly inactive. Alternative therapeutics are also contemplated that concern the use of peptides and peptide analogs representing portions of phosphorylation target amino acid sequences. It is envisioned that such peptide-based drugs would inhibit alpha kinase activity on its native target, thus bypassing the cascade of events that would lead to malignant transformation.

In a particular aspect, the present invention includes a pharmaceutical composition comprising one or more alpha kinase protein selected from the group of melanoma alpha kinase, kidney alpha kinase, heart alpha kinase, skeletal muscle alpha kinase and lymphocyte alpha kinase, and a pharmaceutically acceptable carrier.

The present invention provides a method for treating an animal in need of increased activity of melanoma alpha kinase which comprises administration of melanoma alpha kinase to the animal.

The present invention further provides a method for treating an animal in need of increased activity of melanoma alpha kinase which comprises administration of an antibody against melanoma alpha kinase to the animal.

The present invention also provides a method for treating an animal in need of increased activity of kidney alpha kinase which comprises administration of kidney alpha kinase to the animal.

The invention also includes a method for treating an animal in need of increased activity of kidney alpha kinase which comprises administration of an antibody against kidney alpha kinase to the animal.

The invention further provides a method for treating an animal in need of increased activity of heart alpha kinase which comprises administration of heart alpha kinase to the animal.

The present invention also contemplates a method for treating an animal in need of increased activity of heart alpha kinase which comprises administration of an antibody against heart alpha kinase to the animal.

In an additional aspect, the invention provides a method for treating an animal in need of increased activity of skeletal muscle alpha kinase which comprises administration of skeletal muscle alpha kinase to the animal.

A method for treating an animal in need of increased activity of skeletal muscle alpha kinase which comprises administration of an antibody against skeletal muscle alpha kinase to the animal is further provided.

The present invention includes method for treating an animal in need of increased activity of lymphocyte alpha kinase which comprises administration of lymphocyte alpha kinase to the animal.

The present invention further provides a method for treating an animal in need of increased activity of lymphocyte alpha kinase which comprises administration of an antibody against lymphocyte alpha kinase to the animal.

The therapeutic method provided herein could include the method for the treatment of various pathologies or other cellular dysfunctions and derangements by the administration of pharmaceutical compositions that may comprise effective inhibitors of alpha kinase activity, or other equally effective drugs developed for instance by a drug screening assay prepared and used in accordance with a further aspect of the present invention.

It is a still further object of the present invention to provide a method for the treatment of mammals to control the amount or activity of alpha kinase, so as to alter the adverse consequences of such presence or activity, or where beneficial, to enhance such activity.

It is a still further object of the present invention to provide a method for the treatment of mammals to control the amount or activity of alpha kinase, so as to treat or avert the adverse consequences of invasive, spontaneous or idiopathic pathological states.

The present invention further contemplates therapeutic compositions useful in practicing the therapeutic methods of this invention. A subject therapeutic composition includes, in admixture, a pharmaceutically acceptable excipient (carrier) and one or more of an anti-alpha kinase antibody, peptide analog capable of competing for phosphorylation of target by alpha kinase, antisense drug against alpha kinase mRNA, or any other compound that is found to inhibit alpha kinase activity. In a preferred embodiment, the composition comprises an antigen capable of modulating the activity of alpha kinase within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of eEF-2 kinase activity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Formulations

| Intravenous Formulation I | |
|---|---|
| Ingredient | mg/ml |
| cefotaxime | 250.0 |
| antibody, peptide, antisense drug, or other compound | 10.0 |
| dextrose USP | 45.0 |
| sodium bisulfite USP | 3.2 |
| edetate disodium USP | 0.1 |
| water for injection q.s.a.d. | 1.0 ml |

| Intravenous Formulation II | |
|---|---|
| Ingredient | mg/ml |
| ampicillin | 250.0 |
| antibody, peptide, antisense drug, or other compound | 10.0 |
| sodium bisulfite USP | 3.2 |
| disodium edetate USP | 0.1 |
| water for injection q.s.a.d. | 1.0 ml |

| Intravenous Formulation III | |
|---|---|
| Ingredient | mg/ml |
| gentamicin (charged as sulfate) | 40.0 |
| antibody, peptide, antisense drug, or other compound | 10.0 |
| sodium bisulfite USP | 3.2 |

-continued

Intravenous Formulation III

| Ingredient | mg/ml |
| --- | --- |
| disodium edetate USP | 0.1 |
| water for injection q.s.a.d. | 1.0 ml |

Intravenous Formulation IV

| Ingredient | mg/ml |
| --- | --- |
| antibody, peptide, antisense drug, or other compound | 10.0 |
| dextrose USP | 45.0 |
| sodium bisulfite USP | 3.2 |
| edetate disodium USP | 0.1 |
| water for injection q.s.a.d. | 1.0 ml |

As used herein, "pg" means picogram, "ng" means nanogram, "ug" or "µg" mean microgram, "mg" means milligram, "ul" or "µl" mean microliter, "ml" means milliliter, "l" means liter.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

Assays and Methods

The present invention also relates to a variety of diagnostic applications, including methods for detecting and quantifying the levels of alpha kinase. As mentioned earlier, alpha kinase can be used to produce antibodies to itself by a variety of known techniques, and such antibodies could then be isolated and utilized as in tests for the presence and levels of alpha kinase activity in suspect target cells.

The invention includes an assay system for screening of potential drugs effective at attenuating alpha kinase activity of target mammalian cells by interrupting or potentiating the phosphorylation of alpha kinase selected from the group of melanoma kinase, heart kinase, kdiney kinase, skeletal muscle kinase and lymphocyte kinase. In one instance, the test drug could be administered to a cellular sample along with ATP carrying a detectable label on its γ-phosphate that gets transferred to the kinase target, including the kinase itself, or a peptide substrate, by the particular alpha kinase. Quantification of the labeled kinase target or peptide substrate is diagnostic of the candidate drug's efficacy. A further embodiment would provide for the assay to be performed using a purely in vitro system comprised of the alpha kinase, ATP or labeled ATP, the kinase target or peptide substrate, appropriate buffer, and detection reagents and/or instrumentation to detect and quantify the extent of alpha kinase-directed phosphorylation activity.

The assay system could more importantly be adapted to identify drugs or other entities that are capable of binding to the alpha kinase and/or its cognate phosphorylation target, either in the cytoplasm or in the nucleus, thereby inhibiting or potentiating alpha kinase activity and its resultant phenotypic outcome. Such an assay would be useful in the development of drugs that would be specific against particular cellular activity, or that would potentiate such activity, in time or in level of activity. For example, such drugs might be used to treat various carcinomas or other hyperproliferative pathologies.

In an additional aspect, the present invention includes a method for detecting the presence or activity of an alpha kinase protein selected from the group of melanoma alpha kinase, kidney alpha kinase, heart alpha kinase, skeletal muscle alpha kinase and lymphocyte alpha kinase, wherein said alpha kinase is measured by:

A. contacting a biological sample from a mammal in which the presence or activity of said alpha kinase is suspected with a binding partner of said alpha kinase under conditions that allow binding of said alpha kinase to said binding partner to occur; and B. detecting whether binding has occurred between said alpha kinase from said sample and the binding partner;

wherein the detection of binding indicates that presence or activity of said alpha kinase in said sample.

The present invention further provides a method for detecting the presence of an alpha kinase protein selected from the group of melanoma alpha kinase, kidney alpha kinase, heart alpha kinase, skeletal muscle alpha kinase and lymphocyte alpha kinase, wherein the alpha kinase is measured by:

a. contacting a sample in which the presence or activity of an alpha kinase protein selected from the group of melanoma alpha kinase, kidney alpha kinase, heart alpha kinase, skeletal muscle alpha kinase and lymphocyte alpha kinase is suspected with an antibody to the said alpha kinase protein under conditions that allow binding of the alpha kinase protein to the binding partner to occur; and b. detecting whether binding has occurred between the alpha kinase protein from the sample and the antibody;

wherein the detection of binding indicates the presence or activity of the alpha kinase protein in the sample.

In a still further aspect, the invention provides a method of testing the ability of a drug or other entity to modulate the kinase activity of an alpha kinase protein selected from the group of melanoma alpha kinase, kidney alpha kinase, heart alpha kinase, skeletal muscle alpha kinase and lymphocyte alpha kinase which comprises:

A. culturing a colony of test cells containing the alpha kinase protein;

B. adding the drug or other entity under test; and

C. measuring the kinase activity of said alpha kinase protein in the test cells, wherein when the amount of kinase activity in the presence of the modulator is greater than in its absence, the modulator is identified as an agonist or activator of the alpha kinase protein, whereas when the amount of kinase activity in the presence of the modulator is less than in its absence, the modulator is identified as an antagonist or inhibitor of the alpha kinase protein.

It is a further object of the present invention to provide a method for detecting alpha kinase activity in mammals in which invasive, spontaneous, or idiopathic pathological states are suspected to be present.

As described in detail above, antibody(ies) to alpha kinase can be produced and isolated by standard methods including the well known hybridoma techniques. For convenience, the antibody(ies) to alpha kinase will be referred to herein as $Ab_1$ and antibody(ies) raised in another species as $Ab_2$.

The presence and levels of alpha kinase in cells can be ascertained by the usual immunological procedures applicable to such determinations. A number of useful procedures are known. Three such procedures which are especially useful, utilize either alpha kinase labeled with a detectable label, antibody $Ab_1$ labeled with a detectable label, or antibody $Ab_2$ labeled with a detectable label. The procedures may be summarized by the following equations wherein the asterisk indicates that the particle is labeled, and "~" stands for alpha kinase:

A. $\sim^* + Ab_1 = \sim^* Ab_1$
B. $\sim + Ab^* = \sim Ab_1^*$
C. $\sim + Ab_1 + Ab_2^* = \sim Ab_1 Ab_2^*$ The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, alpha kinase forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-alpha kinase antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

eEF-2 kinase can also be labeled with a radioactive element or with an enzyme. The radioactive label can be detected by any of the currently available counting procedures. The preferred isotope may be selected from $^{3}H$, $^{14}C$, $^{32}P$, $^{33}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the alpha kinase may be radiolabeled and combined, for example, with antibodies or other inhibitors thereto, after which binding studies would be carried out. Solutions would then be prepared that contain various quantities of labeled and unlabeled uncombined alpha kinase, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

In accordance with the above, an assay system for screening potential drugs effective to modulate the activity of alpha kinase may be prepared. The alpha kinase may be introduced into a test system, and the prospective drug may also be introduced into the resulting cell culture, and the culture thereafter examined to observe any changes in the alpha kinase activity of the cells, due either to the addition of the prospective drug alone, or due to the effect of added quantities of the known alpha kinase. Alternatively, these assays can be carried out in a purely in vitro fashion as discussed below.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Molecular Cloning of cDNAs Encoding *C. Elegans*, Mouse, Rat, and Human eEF-2 Kinases eEF-2 kinase from rabbit reticulocyte lysate was purified as described (Hait et al., (1996) *FEBS Lett.* 397:55–60). Peptides were generated from the nitrocellulose-bound 103-kDa eEF-2 kinase protein by in situ tryptic digestion (Erdjument-Bromage et al., (1994) *Protein Sci.* 3:2435–2446) and fractionated by reverse-phase HPLC (Elicone et al., (1994) *J. Chromatogr.* 676:121–137) using a 1.0 mm Reliasil C18 column. Selected peak fraction were then analyzed by a combination of automated Edman sequencing and matrix-assisted laser-desorption time-of-flight mass spectrometry (Erdjument-Bromage et al., (1994)). The peptide sequences provided an essential lead into the cloning of eEF-2 kinase from human, mouse, rat, and *Caenorhabditis elegans*.

To clone the cDNA for *C. elegans* eEF-2 kinase, oligonucleotide primers were designed based on the amino and carboxy termini of the predicted gene product from F42A10.4. Reverse transcriptase-PCR (RT-PCR) was performed using these primers and total RNA from *C. elegans*. A single PCR product of ~2.3 kb was obtained and gel-purified using a gel extraction kit (Qiagen, Chatsworth, Calif.). The fragment was ligated into vector pCR2.1 using the TA cloning kit (Invitrogen, Sorrento Valley, Calif.), and then transformed into *Escherichia coli*. Plasmid DNA was purified, and restriction analysis used to verify the orientation of the coding sequence with respect to the T7 promoter. Two clones (Cefk-1 and Cefk-2, *C. elegans* eEF-2 kinase isoforms 1 and 2) were chosen and sequenced using a Li-Cor (Lincoln, Nebr.) Long Read IR model 400L Automated DNA Sequencer. Analysis revealed that the two clones were identical except for a deletion of 24 bp in Cefk-2 which corresponds to exon 4 and probably represents an alternatively spliced form.

To clone the mouse eEF-2 kinase, degenerate primers were designed based on the amino acid sequence of two peptides from rabbit eEF-2 kinase (LTPQAFSHFTFER (SEQ ID NO: 15) and LANXYYEKAE (SEQ ID NO: 16)): primer A, CA(G/A)GC(C/G/T/A)TT(C/T)(T/A)(C/G)(T/CCA(C/T)TT(C/T)AC(C/G/T/A)TT(C/T)GA(G/A(C/A)G (SEQ ID NO: 17); and primer B, TC(C/G/T/A)GC(C/T)TT(C/T)TC(G/A)TA(G/A)TA(C/T)TT(G/A)TT(C/G/A/T)GC (SEQ ID NO: 18). RT-PCR was performed using primers A and B and poly(A)$^+$ RNA from mouse spleen (CLONTECH). A single PCR product (~1.6 kb) was cloned into pCR2.1 (Invitrogen) and sequenced. Using sequence information form these mouse eEF-2 kinase cDNA fragments, new primers were designed for 5' rapid amplification of cDNA ends (RACE) and 3' RACE to obtain full-length mouse eEF-2 kinase cDNA. 5' RACE and 3' RACE were performed using Marathon-Ready mouse spleen cDNA (CLONTECH). This was carried out according to the manufacturer's instructions using the primers AP1 and C kinase, suggested that this gene encoded eEF-2 kinase. We cloned the full-length cDNA by RT-PCR using *C. elegans* total RNA. Several clones were isolated and sequenced. Cefk-1 has six of the predicted exons and encodes 768 amino acids. Cefk-2 represents an alternatively spliced form that has five exons; it is missing amino acids 625–632 that correspond to exon four. Cefk-1 and Cefk-2 were found to have eEF-2 kinase activity when expressed in cell-free system using a wheat germ extract coupled transcription/translation system.

To determine the amino acid sequence of mammalian eEF-2 kinase, we cloned and sequenced the cDNA of mouse eEF-2 kinase. We reasoned that since the sequenced peptides from rabbit eEF-2 were 100% identical to *C. elegans* eEF-2 kinase, then the two peptides should also match the sequence of mouse eEF-2 kinase. Degenerate primers were designed based on the amino acid sequence of the peptides and were used to perform RT-PCR on mouse spleen poly(A)$^+$ mRNA. A single PCR product of ~1.6 kb was obtained and sequenced. To obtain the full-length cDNA, 5' RACE and 3' RACE were performed using mouse spleen cDNA. The full-length cDNA, which encodes 724 amino acids, was expressed in a cell-free coupled transcription/translation system. A single translation product with an apparent molecular weight of 100 kDa was obtained.

A cDNA for rat eEF-2 kinase was cloned and sequenced using a fragment of mouse eEF-2 kinase cDNA to probe a PC12 cDNA library. However, after this work was completed, a paper describing the cloning of eEF-2 from rat skeletal muscle was published (Redpath et al., (1996) J Biol. Chem. 271:17547–17554) and the reported sequence appears to be identical to the eEF-2 kinase sequence from PC12 cells. Like the mouse eEF-2 kinase, the rat eEF-2 kinase cDNA encodes a 724-amino acid protein.

```
(TACAATCAGCTGATGACCAGAACGCTC)  (SEQ ID NO: 19)  5'antisense, or D (GGATTTGGACTGGACAAGAACCCCC)   (SEQ ID NO: 20)  3'sense.
```

To clone rat eEF-2 kinases, PCR was performed on a rat PC12 cDNA library cloned in λGT10 (CLONTECH) using primer B and vector primers. A 700-bp fragment was specifically amplified. The fragment was cloned into pCR2.1 (Invitrogen) and sequenced. This 700-bp fragments was radiolabeled and used to probe the same PC12 cDNA library (600,000 plaques). Fourteen positives were obtained in the initial screening. Five plaques were chosen for further analysis and sequencing based on insert sizes that ranged from 1.4 to 2.0 kb.

Recently, eEF-2 kinase from rabbit reticulocyte lysate was purified to near homogeneity (Hait et al., (1996)). This enabled determination of its partial amino acid sequence as noted above. Two peptide sequences (LTPQAFSHFTFER (SEQ ID NO: 15) and LANXYYEKAE (SEQ ID NO: 16)) were compared with entries in a nonredundant database using the National Center for Biotechnology Information BLAST program (Altschul et al., (1990) *J. Mol. Biol.* 215:403–410). Matches were found with a *C. elegans* hypothetical protein (F42A10.4; GenBank accession number U10414). This sequence was obtained from the *C. elegans* genome sequencing project and is located on chromosome III (Wilson et al., (1994) *Nature* 368:32–38). The 100% identity between the sequenced peptides and the *C. elegans* protein, as well as the fact that the predicted molecular weight of the *C. elegans* protein is similar to that of eEF-2

The human eEF-2 kinase cDNA was cloned. RT-PCR was performed on poly(A)$^+$ mRNA from the human glioma cell line T98G using 20'mer primers corresponding to the 5' and 3' ends of the mouse eEF-2 kinase coding region. The human eEF-2 kinase cDNA encodes a 725 amino acid protein.

EXAMPLE 2

Figure 2A:
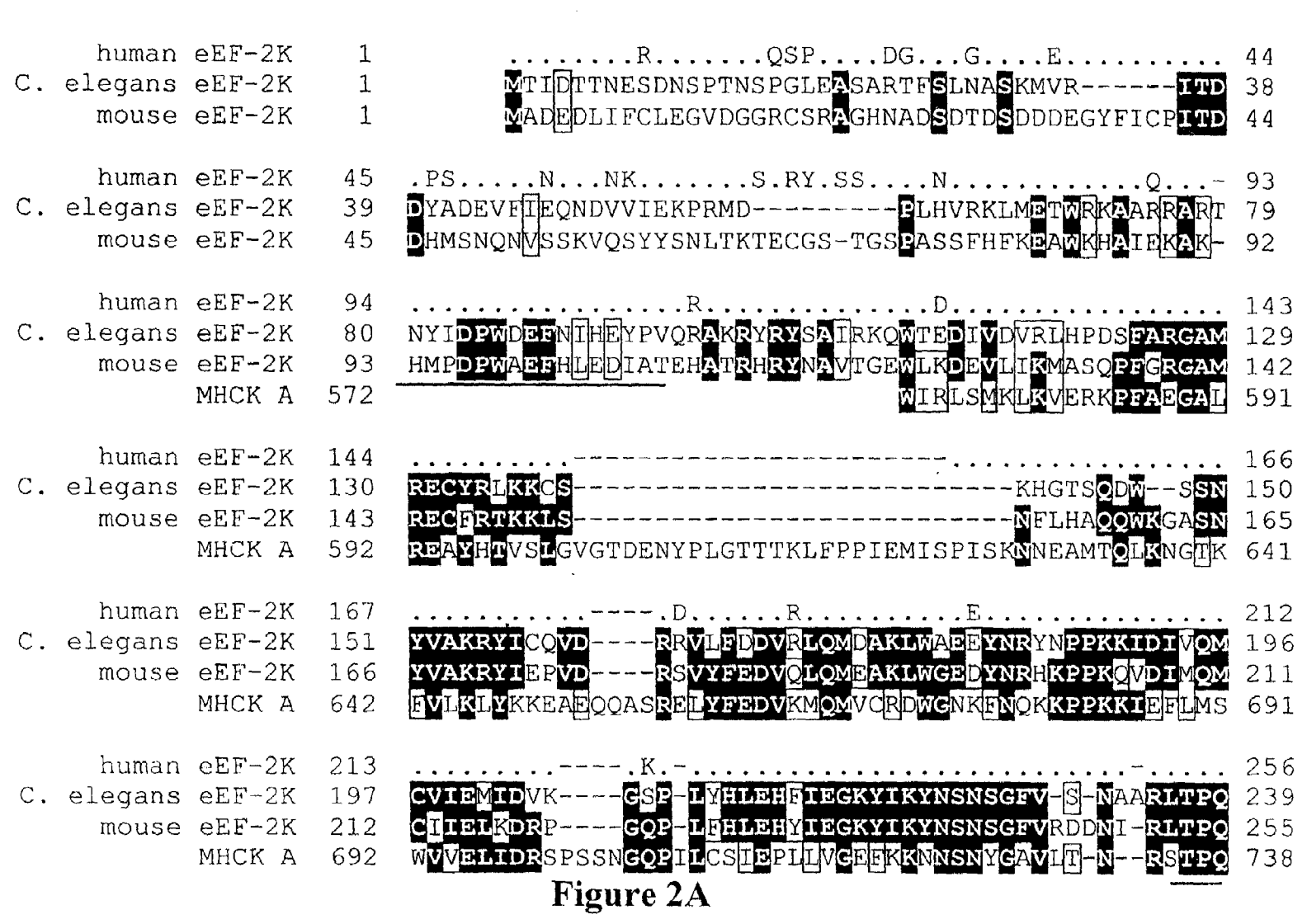

Lack of Homology of eEF-2 Kinase to Members of Eukaryotic Protein Kinase Superfamily The alignment of the amino acid sequences of *C. elegans* and mammalian eEF-2 kinases is shown in FIG. 2. Rat and mouse eEF-2 kinase are very similar being 97% identical and differing by only 23 amino acids. Human eEF-2 kinase is 90% identical to mouse and rat eEF-2 kinase. In contrast, *C. elegans* eEF-2 kinase is found to be only 40% identical to mammalian eEF-2 kinase.

According to the current classification, eEF-2 kinase belongs to the family of closely related calmodulin-dependent protein kinases. Surprisingly, upon analyzing eEF-2 kinase sequences, we did not find any homology to the other calmodulin-dependent kinases or to any other members of the protein kinase super-family. The only motif which it shares with all other protein kinases is the GXGXXG (SEQ ID NO: 21) motif (279–284 in *C. elegans* eEF-2 kinases; 295–300 in mouse eEF-2 kinase) which forms a glycine-rich loop and is part of the ATP-binding site. Comparison of mammalian and *C. elegans* eEF-2 kinase revealed only one extended region of homology that spans ~200 amino acids upstream of the GXGXXG motif. The high degree of similarity and the proximity to the nucleotide-binding site suggests that these 200 amino acids represent the catalytic domain. This region has a high degree of similarity and a portion of this region (amino acids 251–300 in mouse eEF-2 kinase) displays 75% identity to the catalytic domain of MHCKA (see below), which also suggests that this is the catalytic domain. In the recently published rat eEF-2 kinase sequence [Redpath et al., *J. Biol. Chem.* 271: 17547–17554 (1996)], the catalytic domain was predicted to reside between amino acids 288 and 554 based on the homology with the catalytic domain of cAMP-dependant protein kinase (PKA). Our results demonstrate that their prediction cannot be correct for several reasons. First, we find that the homology of this region with PKA is not statistically significant. Second, this region is the least conserved between mammalian and *C. elegans* eEF-2 kinase. Finally, according to secondary structure predictions [made by Alexei V. Finkelstein, Institute of Protein Research, Russia using the ALB-GLOBULE program [Ptitsyn and Finkelstein, *Biopolymers* 22:15–25 (1983)]], this region most likely has a distorted structure and contains almost no $\alpha$-helices or $\beta$-strands, which are characteristic of a catalytic domain.

Because eEF-2 kinase is $CA^{2+}$/calmodulin-dependant, it should contain a calmodulin-binding domain, which is usually represented by an amphipathic $\alpha$-helix. There are several regions that could possibly assume an amphipathic $\alpha$-helical conformation. Further biochemical analysis is required to determine which of these is the calmodulin-binding domain.

In the C-terminal region, there is a short stretch of 22 amino acids which is 86% identical between mammalian and *C. elegans* eEF-2 kinase and is preceded by a longer region of weak homology. We do not know the function of this conserved region at present. One of the possibilities is that it is that it is involved in oligomerization of the kinase. It was thought previously that eEF-2 kinase was an elongated monomer because it migrated during gel filtration as an ~150-kDa protein and migrated on SDS gels as a 105-kDa polypeptide [Ryazanov and Spirin, *Translational Regulation of Gene Expression*, Pienum, N.Y., Vol 2, pp 433–455 (1993); Abdelnajid et al., *Int. J. Dev. Biol.*, 37:279–290 (1993)]. However, the molecular weight of a monomer of mammalian eEF-2 kinase based on the predicted sequence is just 82 kDa. Thus, it is possible that eEF-2 kinase is not a monomer but a responsible for dimerization. Interestingly, according to computer prediction using the COIL program, this conserved region can form a coiled-coil. Formation of coiled-coil is often responsible for dimerization [Lupas, *Trends Biochem. Sci.*, 21:375–382 (1996)].

We found that eEF-2 kinases is homologous to the central portion of the recently described MHCKA from *Dictyostelium* [Futey et al., *J. Biol. Chem.* 270:523–529 (1995) see FIG. 2]. The kinase was biochemically identified as a 130-kDa protein and has a demonstrated role in myosin assembly, both in vitro and in vivo [Futey et al., 1995, supra]. As with eEF-2 kinase, MHCKA displays no region with detectable similarity to the conserved catalytic domains found in known eukaryotic protein kinases. Primary structure analysis of MHCKA revealed an amino-terminal domain with a probable coiled-coil structure, a central nonrepetitive domain, and a C-terminal domain consisting of seven WD repeats [Futey et al., 1995, supra]. A fragment of the central nonrepetitive domain of MHCKA containing amino acids 552–841 was recently shown to represent the catalytic domain [Cote et al., *J. Biol. Chem.* 272:6846–6849 (1997)].

Because the catalytic domain of MHCKA and eEF-2 kinase have a high degree of similarity, the substrate specificity of these two kinases was assayed. It was demonstrated that MHCK A cannot phosphorylate eEF-2, and likewise, rabbit eEF-2 kinase cannot use myosin heavy chains as a substrate. This demonstrated that each of these kinases is specific for their respective substrates.

EXAMPLE 3 eEF-2 Kinase and MHCKA Define A New Class of Protein Kinases

Figure 3:
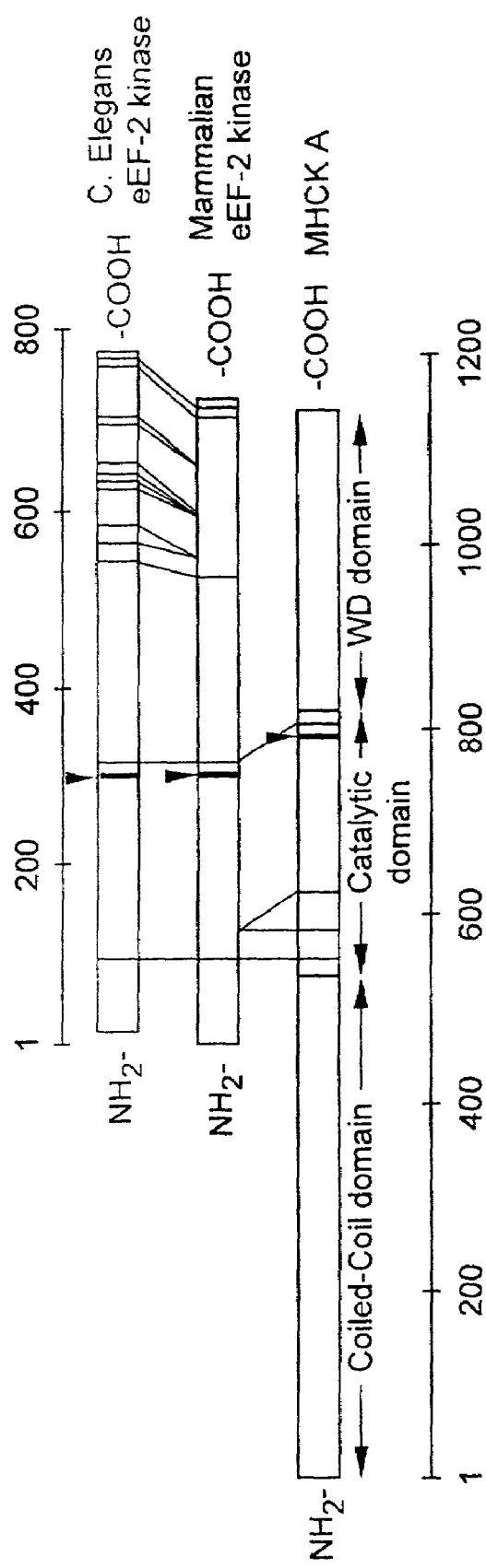
FIG. 3 depicts a schematic representation of the structure of mammalian and *C. elegans* eEF-2 kinases and MHCK A. The homologous regions are represented by dark shading. The regions of weak similarity are represented by light shading. The position of the GXGXXG (SEQ ID NO: 21) motif is indicated by vertical arrows.

Members of the eukaryotic protein kinase superfamily are characterized by a conserved catalytic domain containing approximately 260 amino acids and is divided into twelve subdomains [Hanks and Hunter, *FASEB J.*, 9:576–596 (1996); Hardie and Hanks, *The Protein Kinase Facts Book*, Academic, London (1995), Taylor et al., *Annu. Rev. Cell Biol.* 8:429–462 (1992) Johnson et al., *Cell.* 85: 149–158 (1996)]. The three-dimensional structure of several protein kinases revealed that the catalytic domain consists of two lobes. The smaller N-terminal lobe, which has a twisted $\beta$-sheet structure, represents the ATP-binding domain. The larger C-terminal lobe, which is predominantly $\alpha$-helical is involved in substrate binding. At the primary structure level, the only motif similar between eEF-2 kinase, MHCK A, and other protein kinases is the GXGXXG motif which forms the loop interacting directly with the phosphates of ATP [Hanks and Hunter, 1996, supra; Hardie and Hanks 1995, supra; Taylor et al., supra]. In eukaryotic protein kinases, this motif is located at the very N terminus of the ATP-binding lobe of the catalytic domain. In contrast, in a eEF-2 kinase and MHCK A, this motif is close to the C terminus of the catalytic domain (see FIG. 3). However, the overall topology of the ATP-binding subdomain of eEF-2 kinase and MHCK A can be similar to other protein kinases because the region upstream of the GXGXXG (SEQ ID NO: 21) motif is strongly predicted to contain four or five $\beta$-strands and thus can form a twisted $\beta$-sheet.

However, the mechanism of ATP-binding to eEF-2 kinase is probably quite different in comparison to other conventional members of the eukaryotic protein kinase superfamily. In protein kinases, there is a conserved lysine residue, corresponding to Lys-72 in cAMP-dependant protein kinases which binds to the $\beta$- and $\gamma$-phosphates of ATP and is located at about 20 amino acids downstream of the GXGXXG motif. Analysis of eEF-2 kinase and MHCK A sequences revealed that there are no conserved lysine residues in the vicinity of the GXGXXG motif. There is another atypical protein kinase, BCR-ABLE, which does not contain this conserved lysine and it is proposed that it interacts with ATP via two cysteine residues [Maro and Witte, *Cell*, 67:459–468 (1991)]. Interestingly, eEF-2 kinase and MHCK-A contain two conserved cysteine residues (Cys-313 and Cys-317 in mouse eEF-2 kinase) which are located near the GXGXXG motif and therefore might be involved in ATP binding. Thus the mechanism of ATP-binding of eEF-2 kinase and MHCK A is different from other members of the protein kinase superfamily, but may be similar to that of the BCR-ABLE protein kinase.

The overall catalytic mechanism of eEF-2 kinase and MHCKA is probably also very different from other eukaryotic protein kinases. All members of the eukaryotic protein kinase superfamily contain a DXXXN (SEQ ID NO: 22) motif in the catalytic loop and a DFG motif in the activation segment [Hanks and Hunter, 1996; supra, Hardie and Hanks 1995, supra; Taylor et al., supra; Johnson et al., 1996, supra]. These two motifs, which are directly involved in the catalysis of the protein phosphorylation reaction, are absent from the eEF-2 kinase and MHCK A catalytic domain.

We would predict that there are other protein kinases which are structurally similar to eEF-2 kinase and MHCK A. An extensive search of the entire nonrestricted database of the National Center for Biotechnology Information using the BLAST program did not reveal any protein with a significant homology to the catalytic domain of eEF-2 kinase and MHCKA. A search of the Expressed Sequence Tag (EST) database revealed several ESTs from *C. elegans*, mouse and human which are essentially identical to portions of eEF-2 kinase cDNA sequences reported here. Interestingly, a search of the recently completed genome database of *Saccharomyces cerevisiae* did not reveal any protein with homology to eEF-2 kinase despite the fact that eEF-2 phosphorylation was reported in yeast (41).

Conclusion.

Since the catalytic domains of eEF-2 kinase and MHCK A do not share homology with other known protein kinases, these two protein kinases establish the presence of a novel and widespread superfamily of eukaryotic protein kinases. Although the existence of several unusual protein kinases have been reported, to our knowledge, we demonstrate for the first time the existence of a biochemically well-characterized and ubiquitous protein kinase that is structurally unrelated to other serine/threonine/tyrosine kinases. Contrary to the widely accepted belief that all eukaryotic protein kinases evolved from a single ancestor, our results suggest that eukaryotic protein kinases appeared at least twice during the course of evolution. This also suggests that, in addition to the relatively well-characterized catalytic mechanism employed by members of eukaryotic serine/threonine/tyrosine protein kinase superfamily, there exists another mechanism of protein kinase superfamily, there exists another mechanism of protein phosphorylation. Further studies will reveal the molecular details of this mechanism and whether there are other protein kinases that phosphorylate their substrates using this mechanism.

EXAMPLE 4

Cloning and Analysis of Melanoma Alpha Kinase cDNA

Here, we describe cloning and sequencing of a novel protein entitled "melanoma alpha-kinase". This protein has two domains, one domain is the alpha-kinase catalytic domain and the other is an ion channel. This is the first example of an ion channel being covalently linked to a protein kinase. It is likely that this novel protein kinase can be regulated by ion flow through the membrane. Expression of this kinase was detected in all mouse tissues studied, including heart, skeletal muscle, brain, liver and lung. This kinase is the most abundant in the heart. The ion channel portion is very similar to (70% identical) to a previously identified protein called melastatin that is selectively down-regulated in metastatic tumors, and therefore is believed to be a metastasis suppressor gene. Melanoma alpha-kinase, as well as melastatin, belongs to the TRP family of ion channels. All TRP proteins function as tetramers, and various trp proteins can form tetramers in different combinations that results in ion channel with different properties. Considering the high degree of similarity between melanoma kinase and melastatin, it is likely that melanoma kinase can form tetrameric complexes with melastatin. In humans, melanoma kinase is located on chromosome 15q21.

Human EF-2 kinase amino acid sequence (Acc. No. AAB58270) was used to search for homologous sequences in the expressed sequence tag (EST) division of Genbank using the BLAST server and the tblastn program at the National Center for Biotechnology Information. One human EST (Acc. No. AA332887) that overlapped and displayed significant homology to the catalytic domain of EF-2 kinase was found. We used the nucleotide sequence of this EST to look for overlapping EST sequences. We identified mouse melanoma EST sequence (Acc. No. AA138771) that overlapped by 45 nucleotides with the human EST sequence. We obtained the mouse melanoma EST clone from Research Genetics and sequenced the entire clone. This clone represents the 3' end of melanoma alpha-kinase mRNA and includes the 3' untranslated region plus approximately 350 amino acids of the C-terminus of the protein.

To obtain the full-length cDNA for mouse melanoma alpha-kinase, we used a Marathon-ready mouse heart cDNA library from Clontech. To obtain the remaining sequence of melanoma alpha-kinase, we performed 5' rapid amplification of cDNA ends (RACE) using the following primers: MK1-R1 (5'-TGACCAGGTACACAGCACTTTGACT-GCTCT-3' (SEQ ID NO: 23)). PCR was performed under the following conditions: denaturation for 15seconds at 95° C.; annealing plus extension for 4 minutes at 68° C., 30 cycles. A single PCR product of approximately 4.0 kb was obtained and gel-purified using a gel extraction kit (Qiagen). The fragment was ligated into vector pCR2.1 using the TA cloning kit (Invitrogen), and then transformed into *Escherichia coli* TOP10F'. Plasmid DNA was purified, and restriction analysis used to verify the orientation of the coding sequence with respect to the T7 promoter. Three clones were chosen and sequenced using an ABI 377 sequencer (Applied BioSystems).

To obtain full-length human melanoma alpha-kinase cDNA, new primers were designed for 5' and 3' RACE using sequence information from mouse melanoma alpha kinase cDNA fragments, and full-length cDNA was obtained using a human leukocyte cDNA library (provided by Dr. S. Kotenko).

Mouse melanoma alpha kinase hybridizations were performed using EST 585207 DNA as a probe. The probe was labeled with [a-32P]dCTP using the random-primed DNA labeling method. A multiple tissue northern blot (CLONTECH) was prehybridized at 42° C. for 16 hours in a 50% formamide solution containing 10× Denhardt's solution, 5×SSPE, 2% SDS, and 100 μg/ml salmon sperm DNA. Hybridizations were completed in the same solution containing the 32P-labeled probe (1×106 cpm/ml; specific activity, 1×108 dpm/μg DNA) and 10% dextran sulfate at 42° C. for 16 hours. Blots were washed twice at room temperature (15 minutes) in 2×SSPE, 0.05% SDS, and once at 50° C. (15 minutes) in 0.5×SSPE, 0.5% SDS. RNA/cDNA hybrids were visualized by autoradiography.

EXAMPLE 5

A Novel Type of Signaling Molecule-Protein Kinases Covalently Linked to Ion Channels Abstract Recently we identified a new class of protein kinases with a novel type of catalytic domain structurally and evolutionarily unrelated to the conventional eukaryotic protein kinases. This new class, which we named alpha-kinases, is represented by eukaryotic elongation factor-2 kinase and the *Dictyostelium* myosin heavy chain kinases. Here we cloned and sequenced five other mammalian alpha-kinases. One of these proteins, which was initially identified as an EST from a mouse melanoma cDNA library, was named melanoma alpha-kinase (MK), and according to northern analysis, has a ubiquitous tissue distribution, being present in all mouse and human tissues studied. Four other alpha kinases have a more restricted tissue distribution and were named after the tissue in which they are predominantly expressed: kidney alpha-kinase (KK), heart alpha-kinase (HK), skeletal muscle alpha-kinase (SK), and lymphocyte alpha-kinase (LK). All these protein kinases are large proteins of more than 1000 amino acids with a typical alpha-kinase catalytic domain located at the very carboxyl-terminus. We expressed the catalytic domain of human MK in *Escherichia coli*, and found that it autophosphorylates on threonine residues, demonstrating that it is a genuine protein kinase.

Unexpectedly, we found that the long amino-terminal portions of melanoma and kidney α-kinases represent new members of the transient receptor potential (TRP) ion channel family, which are implicated in the mediation of capacitative $Ca^{2+}$ entry in non-excitable mammalian cells. This suggests that melanoma and kidney α-kinases, which represent a novel type of signaling molecule, are involved in the regulation of $Ca^{2+}$ influx into mammalian cells. It has also been implied that TRP channels may mediate the Ca2+-release-activated Ca2+ current (CRAC). The channel portions of KK and MK were highly similar to each other and highly similar to melastatin. Melastatin is a putative Ca2+ channel that was identified as a gene product specifically downregulated in metastatic melanoma. Phylogenetic analysis revealed that both KK and MK belong to the long TRP (LTRP) channel subfamily, which also includes melastatin, and several uncharacterized channel proteins from mammals, Caenorhabditis elegans and *Drosophila*. Among LTRP channels, only MK and KK possess an α-kinase domain.

Introduction

The vast majority of eukaryotic protein kinases have a typical catalytic domain structure consisting of twelve conserved subdomains (1). The existence of other protein kinases with a different structure was reported in eukaryotes (2–4). Recently we identified a new class of protein kinases with a novel type of catalytic domain, structurally and evolutionarily unrelated to the conventional eukaryotic protein kinases (5). This class, which we named alpha-kinases, is represented by eukaryotic elongation factor-2 (eEF-2) kinase and the *Dictyostelium* myosin heavy chain kinases A and B (MHCKA and B) (2,3,29). The catalytic domain of the alpha-kinases can be subdivided into eight domains (6). There is no significant homology between those eight domain and any of the twelve subdomains of the conventional protein kinases. We named this new class of protein kinases the alpha-kinases because the existing evidence suggests that they can phosphorylate amino acids located within a-helices (6).

In order to study how widespread the alpha-kinases are and to identify new members of the alpha-kinase family in mammals, we used a functional genomic approach. We performed an extensive expressed sequence tag (EST) database search for sequences homologous to the catalytic domain of human eEF-2 kinase. As a result of this screen, we obtained several partial sequences for putative alpha-kinases, which were subsequently used to clone the full-length cDNAs.

We cloned and sequenced and analyzed the tissue distribution of five new members of the alpha-kinase family. All these proteins contain the typical alpha-kinase catalytic domain. The expressed catalytic domain of MK was able to autophosphorylate, therefore demonstrating that it is a genuine protein kinase.

Unexpectedly, the amino-terminal portions of MK and KK appear to have a long amino-terminal portions highly homologous to a number of ion channel proteins that belong to transient receptor potential (TRP) family of Ca2+ channels. The ion channel portions of MK and KK are remarkably homologous to melastatin. Melastatin is a protein downregulated in metastatic melanoma, and is a newly discovered member of the TRP Ca2+ channel family (7, 8). TRP channels derive their name from a mutation in a *Drosophila* calcium channel that is involved in photoreception (30,31). This mutation caused an inability to maintain a sustained receptor potential, and was therefore named transient receptor potential (trp), and the channel was named the TRP channel (19,30,31). Several homologues of TRP channels in mammals have been identified (27,32,33). The recent interest in the TRP channel family is related to the fact that they may represent channels responsible for store-operated calcium influx—one of the major pathways of calcium entry into non-excitable mammalian cells (9,10,12,18,24,34).

TRP channels are Ca2+-permeable channels believed to be responsible for Ca2+ influx in response to depletion of internal Ca2+ stores (9–11). The ion channel portion of MK and KK, being highly similar to melastatin, makes MK and KK new member of the TRP family, in particular the LTRP family to which melastatin belongs.

Thus, in our work, we demonstrated a novel type of signaling molecule—an ion channel covalently linked to a protein kinase. We discuss the possibility that this hybrid ion channel/protein kinase is involved in the regulation of store-operated Ca2+ entry in non-excitable tissues.

Materials and Methods

Cloning of Melanoma Kinase

We searched the EST database, and identified several mouse and human ESTs homologous to the catalytic domain of human eEF-2 kinase. One of these EST clones was derived from a mouse melanoma cDNA library (IMAGE clone 585207; GenBank accession #AA138771). We sequenced this clone and found it encodes the C-terminus (approximately 300 amino acids) of a novel protein. We used 5' rapid amplification of cDNA ends (RACE) and a mouse heart Marathon-ready cDNA library (Clontech) to determine the full-length sequence. We used this sequence information to design primers and clone human melanoma kinase from a Hela cell cDNA library.

Cloning of Kidney Kinase

A further search in the EST database revealed an EST derived from a mouse kidney cDNA library encoding another protein homologous to the catalytic domain of eEF-2 kinase (IMAGE clone 656119; GenBank accession # AI390333). We used the sequence information to perform 5'RACE and 3'RACE using a mouse heart Marathon-ready cDNA library (Clontech). After partial sequencing of this clone, we used the new sequence information to design primers and clone human kidney kinase from a human kidney Marathon-ready cDNA library (Clontech).

Cloning of Heart Kinase

Database searches revealed another homologous EST clone approximately 2 kb in length (IMAGE clone #585879; GenBank accession #AA140393). To obtain the full length cDNA, we screened a mouse heart 5'-STRETCH PLUS cDNA lambda library (Clontech). A 32P-labeled 2 kb EST fragment was used as a probe for clone identification. Several clones gave positive signals, and were further analyzed by PCR. The largest of the clones (~5 kb) was sequenced. Subsequently we found a human EST in the EST database homologous to mouse heart kinase (IMAGE clone #843057; GenBank accession #AA485987). We sequenced this clone, and found it encodes a protein corresponding to the C-terminus of heart kinase. After partial sequencing of this clone, we used the new sequence information to design primers and clone human heart kinase from a human heart Marathon-ready cDNA library (Clontech).

Cloning of Skeletal Muscle Kinase

We searched the HTGS database for sequences homologous to mouse heart kinase, and found a clone containing the gene encoding a protein similar to heart kinase. We designed primers using the database sequence and performed PCR using a human placenta cDNA library to clone the catalytic domain of muscle kinase.

Cloning of Lymphocyte Kinase

By searching the non-restricted database, we found a genomic DNA clone derived from chromosome IV that encodes a protein containing the α-kinase catalytic domain. We used this sequence information to search for overlapping ESTs in order to reconstruct the full-length protein, and then to design primers for PCR to clone the full-length protein from a lymphocyte cDNA library.

Cloning of the Melanoma Kinase Catalytic Domain

The catalytic domain of melanoma kinase was cloned from a Hela cell cDNA library. Primers were designed based upon the sequence of melanoma kinase. The sequences of the primers are:

```
Forward: 5'-GTTAGTACACCATCTCAGCCAAGTTGCAAA-3',        (SEQ ID NO: 24)

Reverse: 5'-TTATAACATCAGACGAACAGAATTAGTTGATTCTGATTCT-3'    (SEQ ID NO: 25).
```

PCR conditions were as follows: 30 sec. at 94° C., 30 sec. at 58° C., 3 min. at 72° C. for 30 cycles, followed by a 10 min. final extension at 72° C. The PCR product was cloned into PCRII-TOPO vector (Invitrogen) as per manufacturer's instructions. The insert was then subcloned into the EcoRI site in pMAL-p2x (NEB) to tag the protein with maltose binding protein (MBP).

Expression and Purification of MBP-MK

E. coli strain DH5α carrying the pMALp2x-MK plasmid were grown to an OD1=600 0.5, then IPTG was added to a final concentration 0.3 mM. Cells were grown for additional 6 hours at 37° C. All following procedures were carried out at 4° C. Cells was resuspended in 20 mM Tris-HCl (pH 7.4), 200 mM NaCl, 1 mM EDTA, 10 mM b-mercaptoethanol and sonicated. Inclusion bodies were pelleted by centrifugation at 30,000× g for 30 min., dissolved in 6M urea, 20 mM Tris-HCl (pH 7.4), 200 mM NaCl, 1 mM EDTA, 10 mM b-mercaptoethanol, 20% (w/v) glycerol and centrifuged again at 30,000×g for 30 min. The supernatant was dialyzed overnight against the same buffer but without urea. After dialysis, the sample was centrifuged once again at 30,000×g for 30 min., and the supernatant was loaded onto an amylose column equilibrated with 20 mM Tris-HCl (pH 7.4), 200 mM NaCl, 1 mM EDTA, 10 mM b-mercaptoethanol, 20% (w/v) glycerol. Elution was performed by a step gradient of the same buffer plus 10 mM maltose.

Phosphorylation of MBP-MK

Assays for MBP-MK activity were performed at 30° C. in an assay buffer containing 50 mM Hepes-KOH (pH 6.6), 10 mM MgCl2, 1 mM DTT, 50 mM ATP, 20 mCi [g-32P]-ATP and 3mg MBP-MK. After incubation, Laemmli sample buffer was added, samples were boiled and 25 ml of each sample was loaded onto a 10% SDS-PAGE gel. The gel was stained with Coomassie Blue, dried and exposed to film for 16 hours.

Phosphoamino Acid Analysis

Phosphorylation of MBP-MK was done as described above, but the reaction volume was increased 5-fold. The incubation time was 2 hours. Samples were separated by 10% SDS-PAGE and transferred to an Immobilon-P membrane (Millipore). The portion of membrane with phospho-MBP-MK was excised and incubated in 6M HCl at 110° C. for 1 hour. After incubation, the mixture was dried, and the dried pellet was dissolved in 9 µl of water, with the addition of non-radioactive phosphoserine, phosphothreonine, and phosphotyrosine. Phosphoamino acids were separated by thin-layer chromatography on cellulose (cellulose on polyester; Aldrich) using a buffer consisting of isobutyric acid and 0.5M NH$_4$OH in a 5:3 ratio. The TLC plate was stained with 0.2% ninhydrin and exposed to film.

Northern Blot Analysis

Standard Multiple Tissue Northern (MTN) Blots (Clontech) were stained with DNA probes according to manufacturer's instructions. The probes were labeled with [α-$^{32}$P]-dCTP using the Megaprime DNA labeling system (Amersham) using specific DNA fragments as templates. The DNA fragments were obtained as follows.

A 430 bp DNA fragment of human melanoma kinase (corresponding to nucleotides 4331–4761) was obtained by PCR from a Hela cDNA library (Clontech). The following primers were used for PCR:

```
LMK2:   5'CTGCGACAGAGACTACATGGGGTAGAACTC 3'   (SEQ ID NO: 42)

LMK4:   5'TGAGTGTCTTCGGTAGATGGCCTTCTACTG 3'   (SEQ ID NO: 43)
```

A 741 bp DNA fragment of human kidney kinase was produced by PCR from a plasmid containing kidney kinase cDNA. The region corresponding to nucleotides 3721–4462 was amplified using the following primers:

KK-F1: 5'ATGGAGATTGCTGGAGAGAAG 3' (SEQ ID NO: 44) and

KK-R3: 5'ATTCACTACTCTGGGCCGATC 3' (SEQ ID NO: 45)

A 1.2 kb DNA fragment of human muscle kinase was obtained by EcoRI digestion of the human muscle kinase cDNA insert cloned in pCRII-TOPO (Invitrogen). The mouse melanoma kinase 2.2 kb DNA fragment was obtained from EST clone 585207. The fragment was cut out with BamHI and XhoI from pBluescript SK-vector (Stratagene). The mouse heart kinase 2 kb DNA fragment was produced by restriction with SmaI and KpnI from EST clone 585879.

Results

Figure 8A:
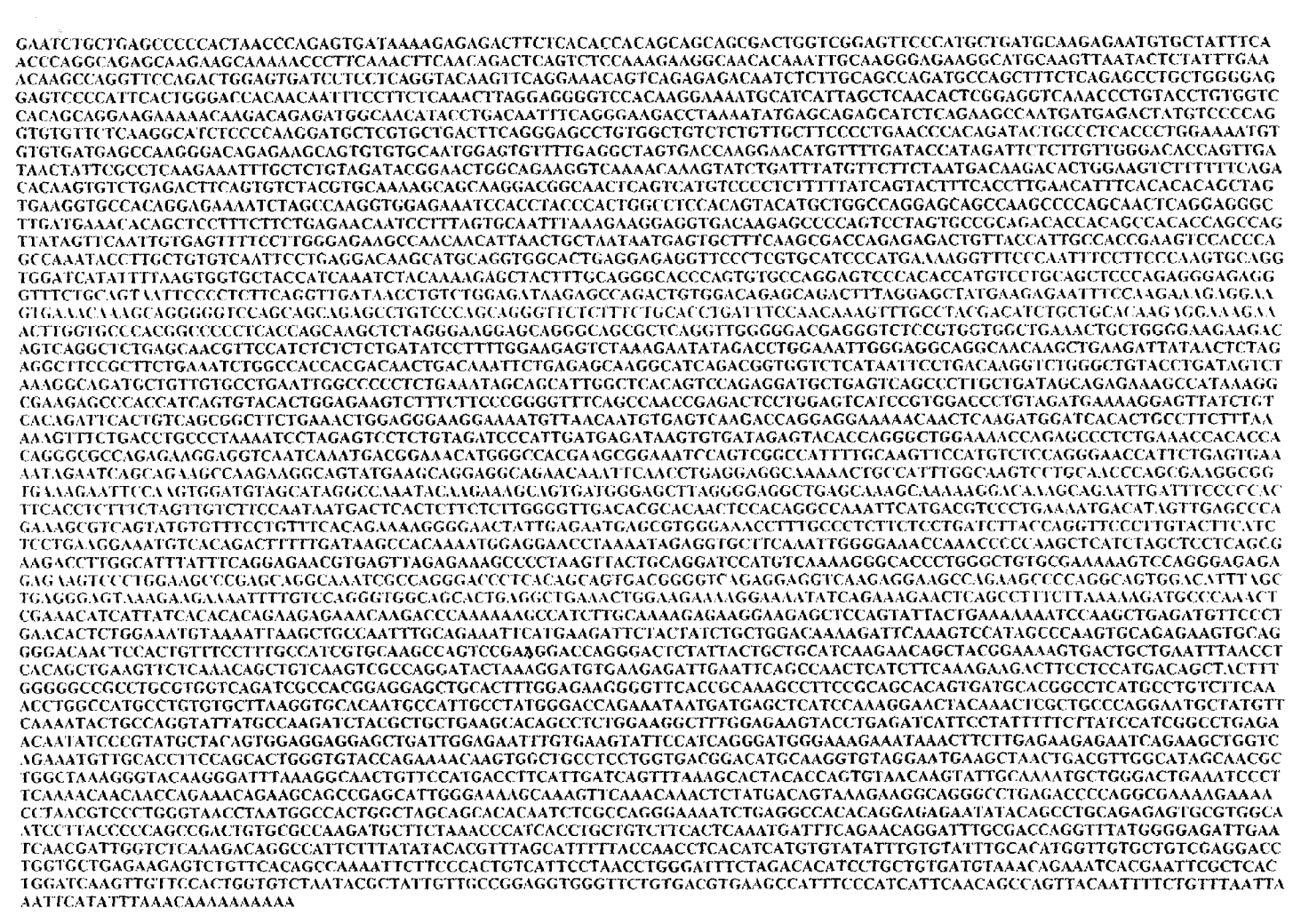
Figure 11A:
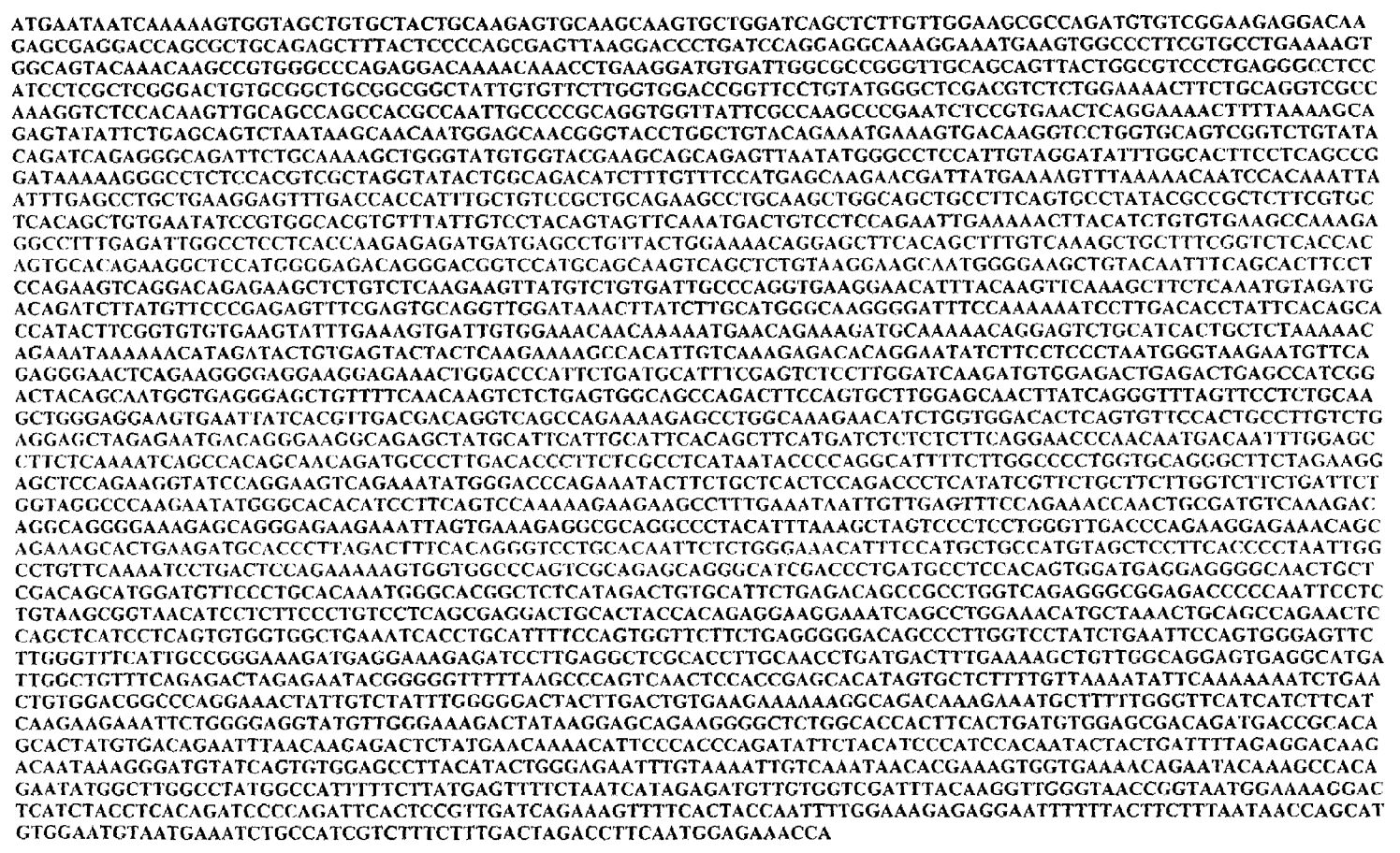
Figure 12:
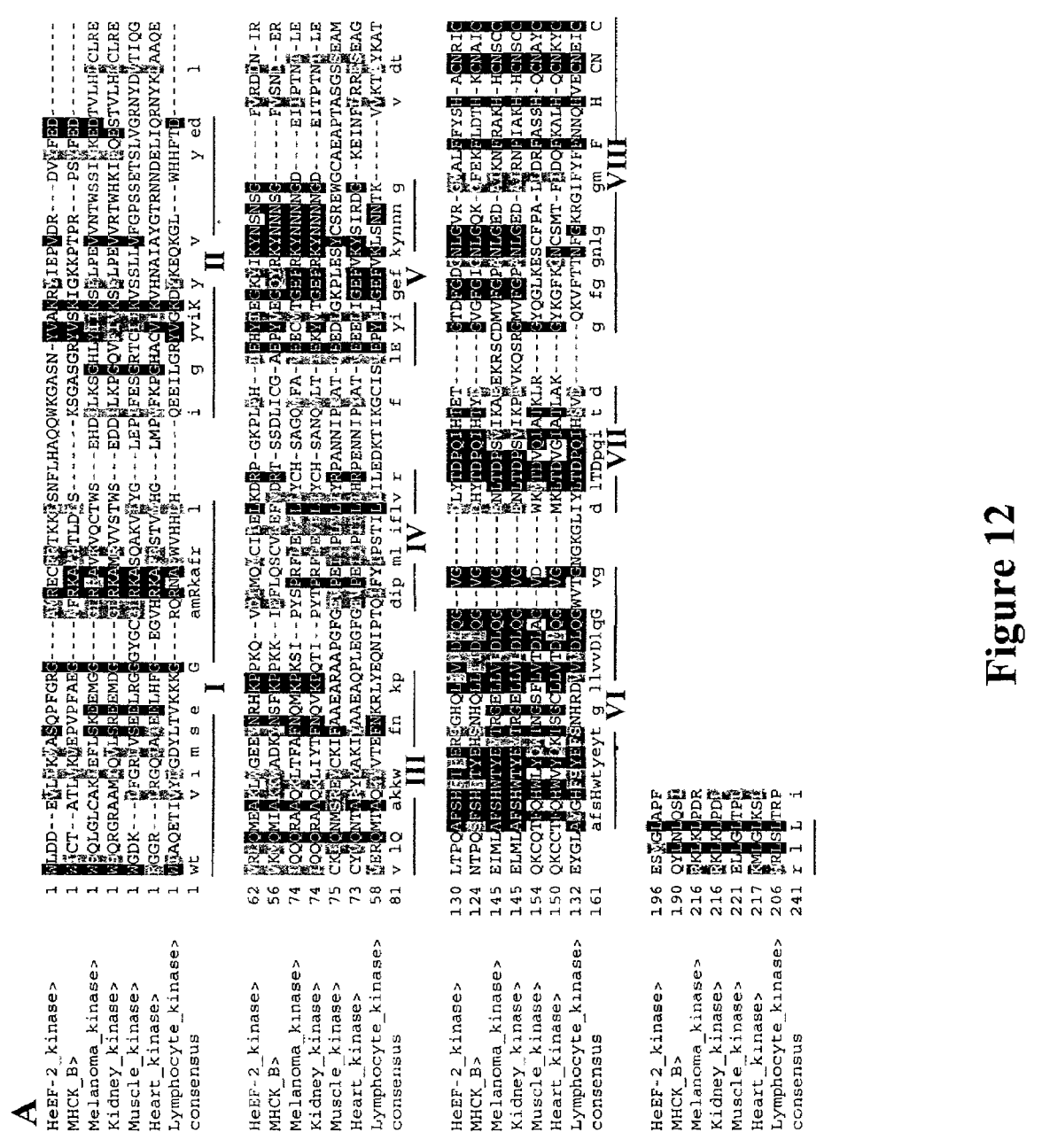

In our work we cloned and sequenced five new members of the alpha-kinase family. They are named according to their tissue distribution: heart alpha-kinase (HK), melanoma alpha-kinase (MK), kidney alpha-kinase (KK), skeletal muscle alpha-kinase (SK), lymphocyte alpha-kinase (LK). The nucleic acid sequence and predicted amino acid sequence of the human heart alpha-kinase (HK) are depicted in FIG. 8A and B (SEQ ID NO: 34 and 35, respectively). The nucleic acid sequence and predicted amino acid sequence of the mouse heart alpha-kinase (HK) are provided in SEQ ID NO: 36 and 37, respectively. The nucleic acid sequence (SEQ ID NO: 26) and predicted amino acid sequence (SEQ ID NO: 27) of the human melanoma alpha-kinase (MK) are depicted in FIG. 7A and B. The nucleic acid sequence (SEQ ID NO: 28) of mouse melanoma α-kinase is shown in FIG. 5. The predicted amino acid sequence (SEQ ID NO: 29) of mouse melanoma α-kinase is shown in FIG. 6. The nucleic acid and predicted amino and sequence of the human kidney alpha-kinase (KK) are depicted in FIG. 9A and B (SEQ ID NO: 30 and 31, respectively). The nucleic acid and predicted amino and sequence of mouse kidney alpha-kinase (KK) are provided in SEQ ID NO: 32 and 33, respectively. FIG. 10A and B depicts the nucleic acid sequence (SEQ ID NO: 38) and predicted amino acid sequence (SEQ ID NO: 39) of human skeletal muscle alpha-kinase (SK). The nucleic acid sequence (SEQ ID NO: 40) and predicted amino acid sequence (SEQ ID NO: 41) of the lymphocyte alpha-kinase (LK) are shown in FIG. 11A and B. All of these protein kinases are large proteins of more than 1000 amino acids with a typical alpha-kinase catalytic domain located at the very C-terminus. FIG. 12 shows the alignment of the catalytic domains of the cloned alpha-kinases. The catalytic domain sequence reveals 30–80% similarity between these alpha-kinases. It can be divided into several subdomains with no homology between these subdomains and any of the twelve subdomains of the conventional protein kinases. Altogether, there are sixteen positions in the alignment of the cloned proteins that are invariant among all the known alpha-kinases. All five new proteins are homologous to each other, as well as homologous to the eEF-2 kinase and MHCK B catalytic domains. A comparison of the five new α-kinases, eEF-2 kinase and MHCK B reveals sixteen invariant amino acids. We reported previously (6) that the α-kinase catalytic domain can be divided into eight subdomains, each having a characteristic sequence motif. Identification of new α-kinases allowed us to characterize these subdomains more precisely. In addition, we used the ALB secondary structure prediction service (http://indy.ipr.serpukhov.su/~rykunov/alb/) (35) to predict a consensus secondary structure of the α-kinase catalytic domain. Subdomain I begins with a conserved Trp residue present in all α-kinases with the exception of HK, which has a Phe in this position. Subdomain I is also characterized by an invariant Gly and an invariant Arg that are part of the conserved Arg-Lys-Ala motif. Subdomain II is characterized by an invariant Lys, that is part of an Hyd-Hyd-X-Lys motif (Hyd=hydrophobic). Subdomain III contains an invariant Gln, and is predicted to form an α-helix. Subdomain IV contains a stretch of hydrophobic amino acids and is predicted to form a β-sheet. Subdomain V is predicted to form an α-helix containing an invariant Glu, and is followed by a conserved Asn (an Arg in HK and SK). Subdomain VI is predicted to form a β-turn-β-turn structure with an invariant His in the first P-strand, and the conserved sequence, Leu-Leu-Val-Val-Asp-Leu-Gln-Gly, that forms the end of the second β-strand and second turn and also contains an invariant Asp and Gly. Subdomain VII is characterized by the conserved sequence, Leu-Thr-Asp-Pro-Gln-Ile, which contains an invariant Thr-Asp. Subdomain VIII begins with a Gly-rich region that is not predicted to have any regular secondary structure, followed by a sequence containing invariant Phe and His residues, an invariant Cys-Asn-X-X-Cys motif and an invariant Leu. The region containing the Cys-Asn-X-X-Cys motif is predicted to form a short α-helix.

Figure 13:
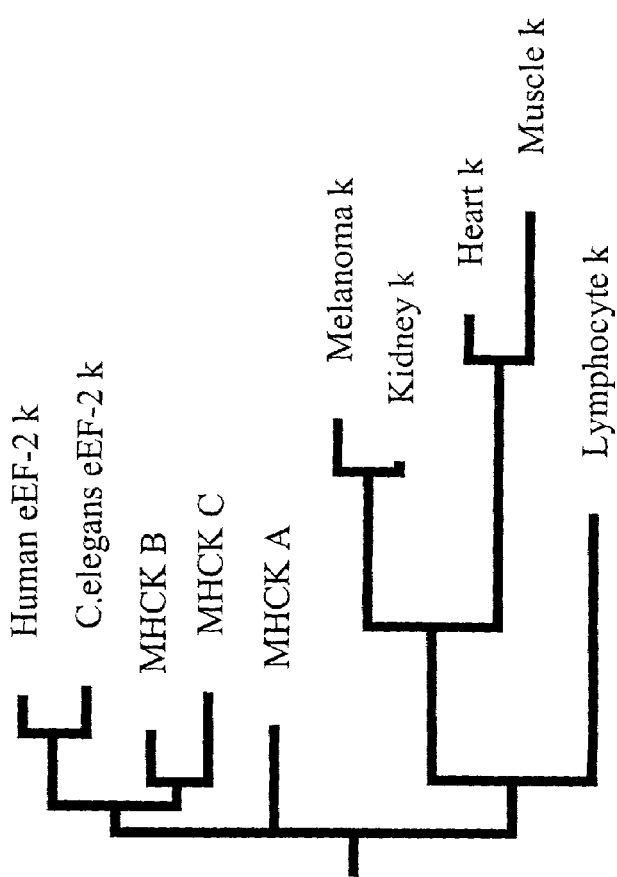
FIG. 13 depicts a phylogeneic analysis of the cloned alpha-kinases.

Phylogenetic analysis (FIG. 13) of the cloned alpha-kinases suggests that all five alpha-kinases are more closely related to each other than to eEF-2 kinase or the MHCKs, and form a separate subfamily. MK is closely related to KK (78% identity). HK is similar to SK (47% identity). LK has less similarity to the others, but they all form a distinctive separate subfamily of alpha-kinases, displaying various degrees of similarity to eEF-2 kinase.

Figure 14:
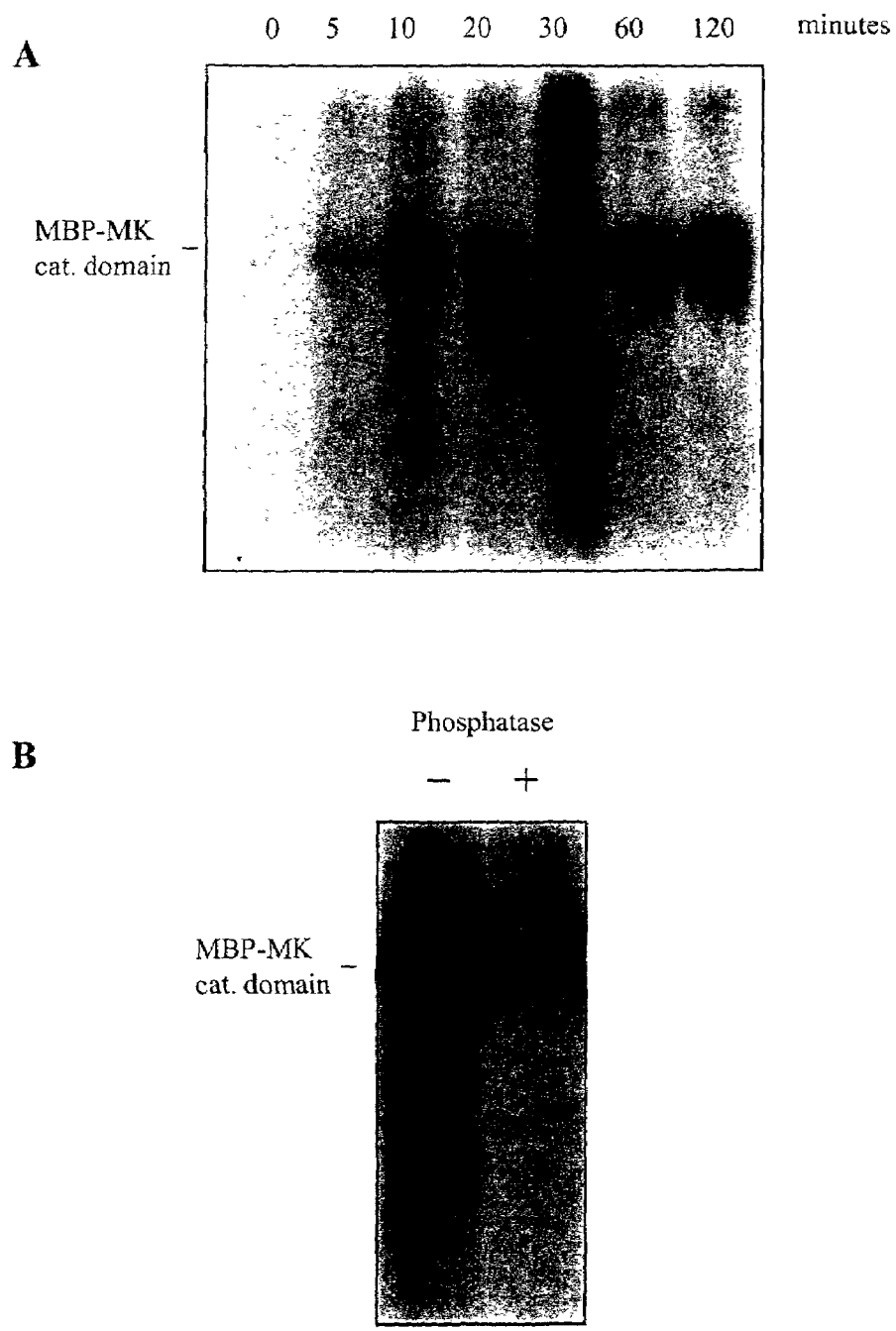
FIG. 14 shows the time course of $^{32}P$ incorporation into expressed maltose-binding protein-melanoma alpha-kinase fusion protein (MBP-MK).

In order to analyze kinase activity, we expressed the catalytic domain of MK as maltose-binding protein (MBP) fusion protein. Affinity-purified MBP-MK was able to autophosphorylate. FIG. 14 shows the time course of 32P incorporation into MBP-MK. This phosphorylation can be reversed by incubation with lambda phosphatase. Phosphoamino acid analysis revealed that MK is phosphorylated on a threonine residue.

Figure 15:
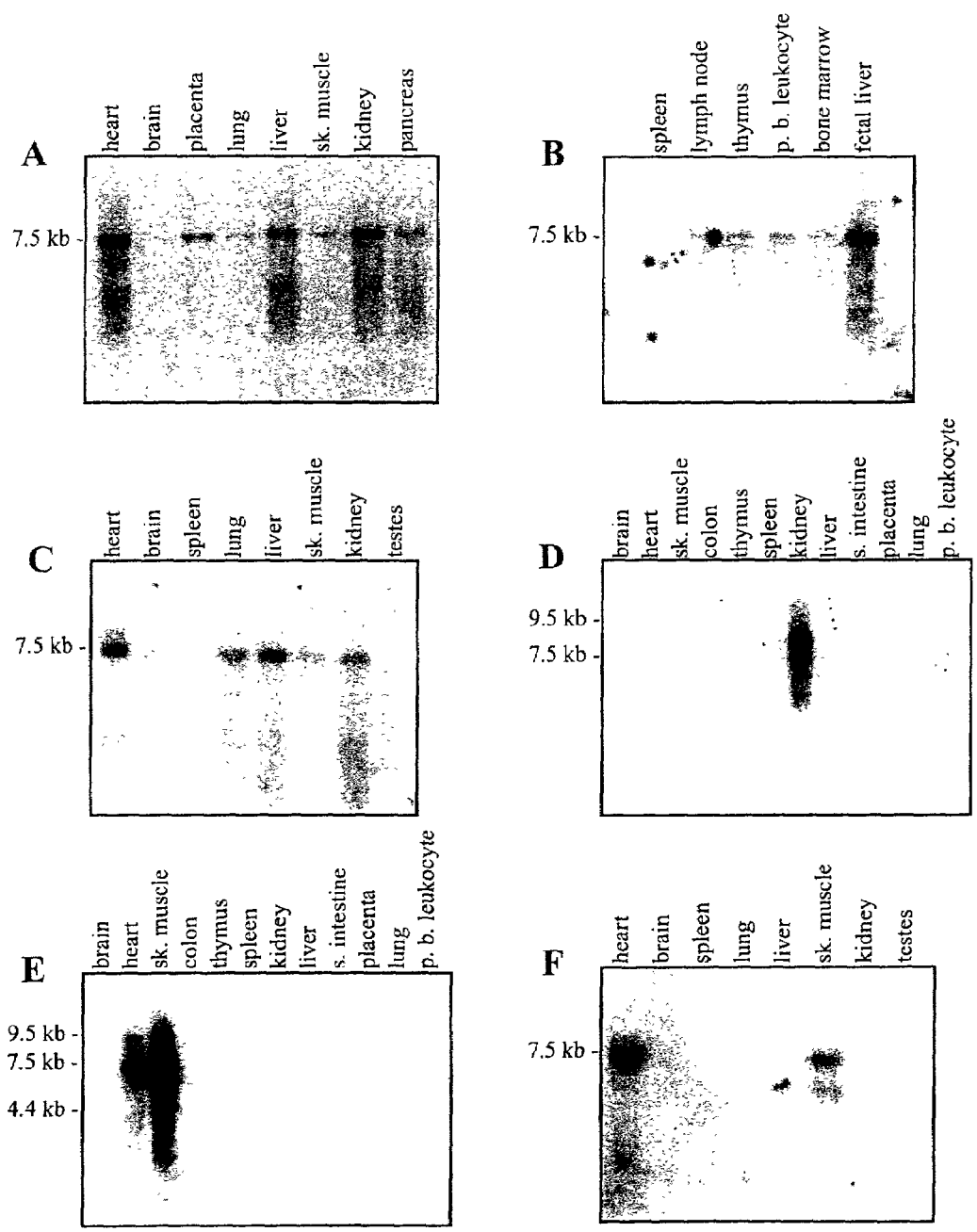
FIGS. 15A through F shows Northern Blot analysis of the tissue distribution of the alpha-kinases in human and mouse tissues. Standard Multiple Tissue Northern (MTN) blots (Clontech) were stained as described in Materials and Methods. A, B, C: Blots probed for Melanoma Kinase; A: Human MTN Blot B: Human Immune System MTN Blot II. C: Mouse MTN Blot. D: Human 12-Lane MTN Blot probed for Kidney kinase. E: Human 12-Lane MTN Blot probed for Muscle kinase. F: Mouse MTN Blot probed for Heart kinase. (abbreviations: sk. muscle—skeletal muscle, p.b. leukocyte—peripheral bood leukocyte, s. intestine—small intestine).

Using northern blot analysis, we analyzed the tissue distribution of the α-kinases in human and mouse tissues (FIG. 15). MK, KK, HK and SK are large proteins (corresponding cDNAs are 7.5kb). LK mRNA is represented by two bands, 5.5 and 7.5 kb. An additional minor band at 9.5 kb can be seen for SK. MK is ubiquitously expressed, being detected in every tissue tested. In human tissues, it is most abundant in the liver, kidney and heart, and in mouse tissues—heart, lung, liver and kidney. There were noticeable amounts in human lymphoid, bone marrow and thymus tissues. The least amount of MK mRNA, among human tissues, was observed in brain. LK mRNA can be detected by northern analysis in various human tissues. Its tissue distribution was virtually identical to MK, although it is much less abundant than MK since three weeks of exposure were required to visualize the bands. LK can be detected by reverse transcriptase-PCR (RT-PCR) in human fetal liver and placenta tissues, and lymphocyte libraries. A full-length clone was obtained from a lymphocyte cDNA library. KK is present almost exclusively in kidney tissue, with trace amounts in human lymphocyte, brain and bone marrow tissues. HK is found almost exclusively in mouse heart tissue, with a smaller amount in skeletal muscle tissue. It was not seen in any other tissues tested. SK is very abundant in human muscle tissues, with a considerable amount in human heart tissue. Trace amounts of SK can be seen in human lung, placenta and kidney tissues.

Figure 17A:
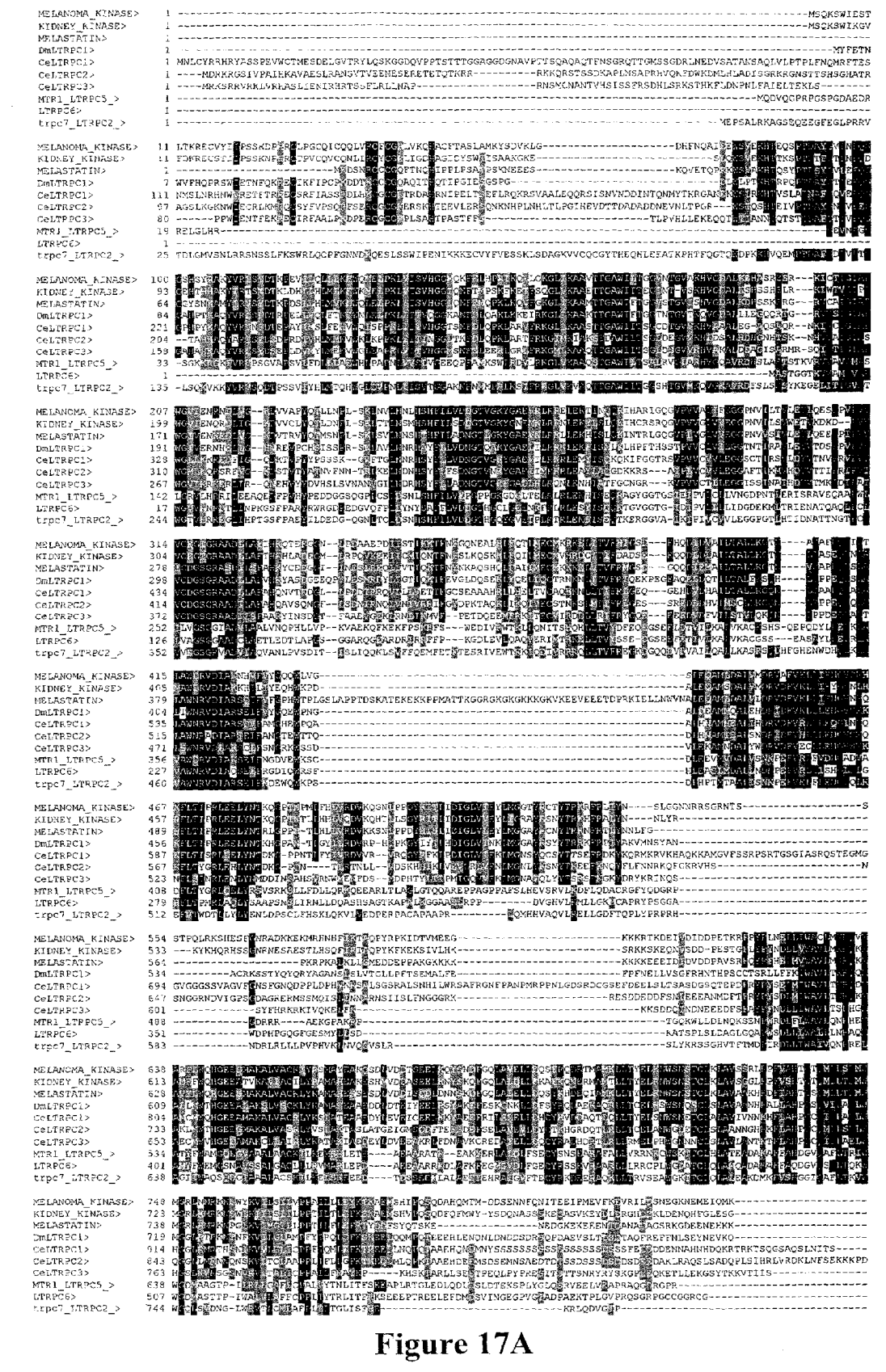
Figure 17B:
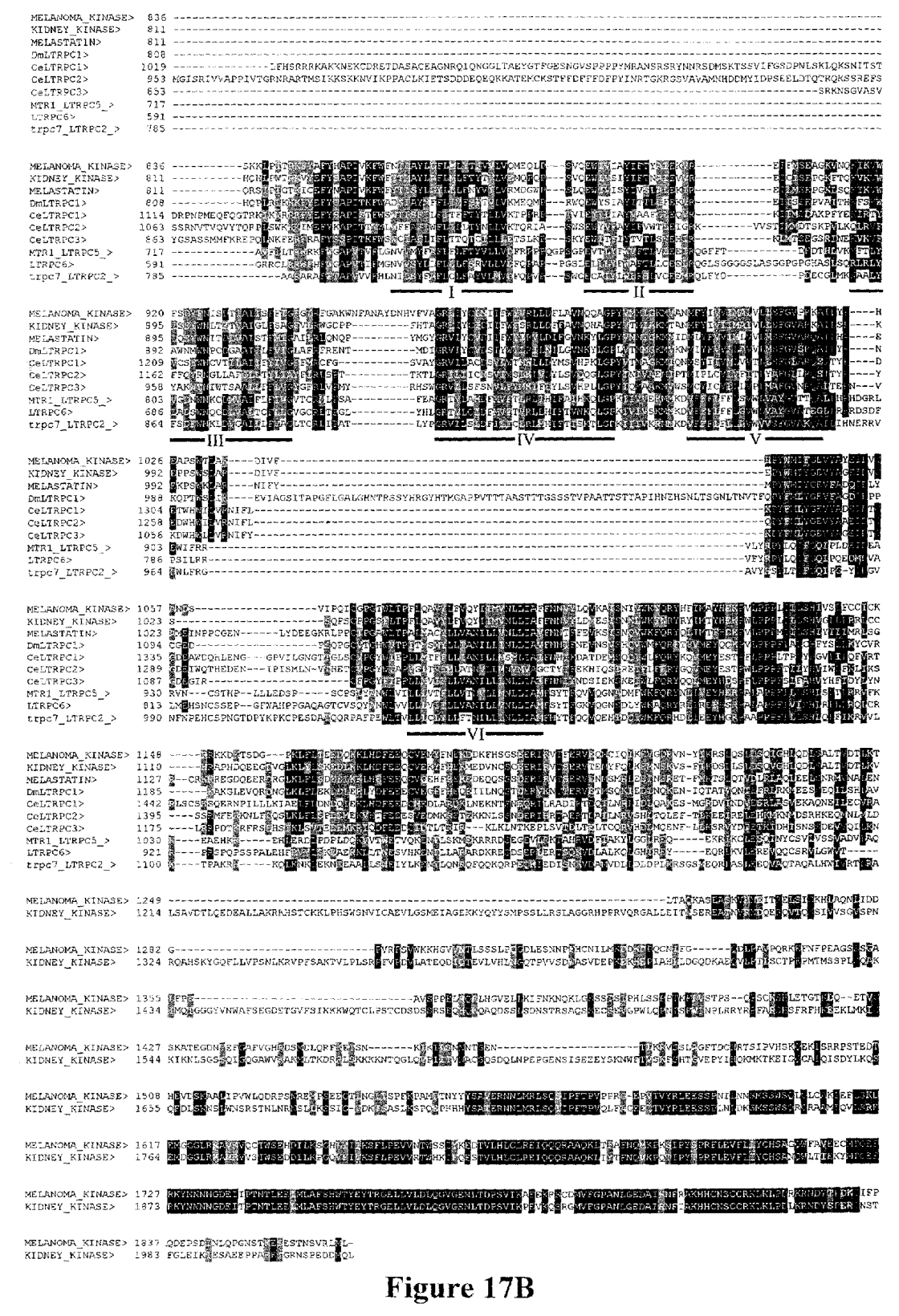

We cloned full-length cDNA for MK and KK. The long N-terminal portion of MK and KK display high similarity to ion channels homologous to TRP channel family. The MK sequence contained 1864 amino acids and the KK sequence contained 2011 amino acids. Unexpectedly, we found that the long amino terminal portions of MK and KK are homologous to ion channels. The approximately 1200 amino acid long N-terminal portions of MK and KK were similar to each other (59% identical) and homologous to melastatin (48% and 51% identical respectively; see FIG. 17). Melastatin is a putative $Ca^{2+}$ channel that belongs to the transient receptor potential (TRP) family of ion channels (8). Like melastatin, MK and KK contain all the sequence elements characteristic of the TRP channel family. These elements include six predicted transmembrane segments, a highly conserved sequence in the putative pore region between transmembrane segments 5 and 6, a highly conserved sequence at the end of transmembrane segment 6, and a Pro-Pro-Pro motif-containing sequence that immediately follows transmembrane segment 6 (FIG. 17). We found several human, mouse, *Caenorhabditis elegans* and *Drosophila* proteins in GenBank that are highly similar to the melastatin-like portions of MK and KK (FIG. 17). All these proteins belong to a subfamily of the TRP channels which were named long TRP channels (LTRPC), and are characterized by a long conserved N-terminal sequence that precedes the transmembrane segments (14). These proteins include a protein that was initially called TRPC7 (36), and was later renamed LTRPC2 (14), a protein named MTR1 or LTRPC5 (14,37), an unnamed human putative protein we named LTRPC6 (GenBank accession #AK000048), three *C. elegans* proteins (F54D1.5, T01H8.5, and C05C12.3) named respectively CeLTRPC1, CeLTRPC2 and CeLTRPC3 (14), and a *Drosophila* putative protein that we named DmLTRPC1 (GenBank accession #AE008311) (FIG. 17). Thus, MK and KK can be classified as members of the LTRPC subfamily, and we suggest they be designated LTRPC3 and LTRPC4, respectively. As can be seen in FIG. 17, MK and KK, like other LTRPC proteins, contain a long N-terminal sequence (approximately 600–800 amino acids) that has several conserved and unique motifs. The ALB program predicted several long α-helices in this region in all LTRPC proteins.

Figure 19:
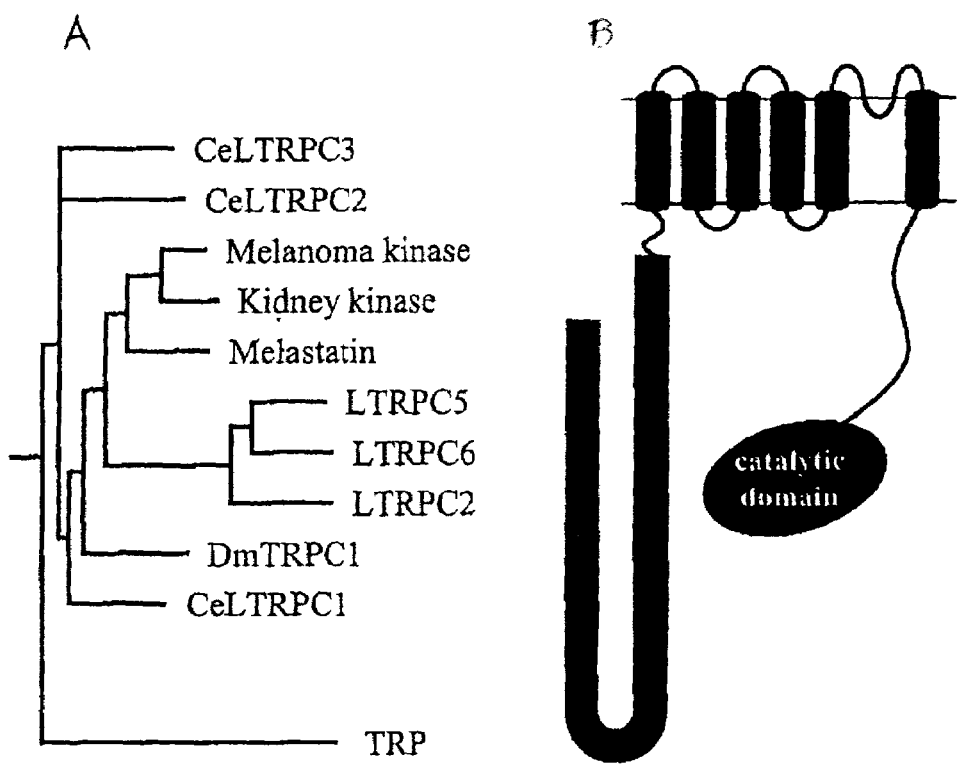
FIGS. 19. A and B. Phylogenetic tree of the LTRP channel subfamily. This tree was generated from the full-length protein sequences using the ClustalW program. B. The proposed structural model of MK and KK.

Phylogenetic analysis revealed that MK, KK as well as other LTRPC proteins are related to the prototypic *Drosophila* TRP protein, but are more similar to each other than to the prototypic TRP (FIG. 19).

We also determined the full-length sequence of LK cDNA that encodes a protein containing 1242 amino acids. The TMPred program predicts four transmembrane segments located close to the N-terminus.

HK and SK cDNAs encode proteins of 1531 and 1215 amino acids, respectively. Comparison of the predicted amino acid sequences of HK and SK with other proteins in GenBank using the BLAST program revealed that there is an approximately 100 amino acid motif located just N-terminal to the catalytic domain that displays sequence similarity to immunoglobulin-like domains of titin, myosin light chain kinase, and several other proteins. The same region in both kinases is identified as an immunoglobulin-like domain using the CD-Search program. The remainder of the HK amino acid sequence did not display any strong similarity to any known proteins. The N-terminal portion of SK displayed a weak similarity to collagen, which may be attributed to the high glycine and proline content.

Discussion

In our previous work, we discussed the unique structure of eEF-2 kinase and the *Dictyostelium* MHCKs, and suggested that they represent a new class of protein kinases, the α-kinases (5,6). In this work, we cloned and sequenced five new members of the α-kinase class. Thus, together with eEF-2 kinase, there are at least six distinct α-kinases in mammals. These six α-kinases encompass all sequences from vertebrate sources deposited in GenBank thus far with homology to the α-kinases. With approximately 90% of the human genome represented in GenBank to date, it is likely we cloned most, if not all, of the mammalian α-kinases. Interestingly, in the *C. elegans* genome there is only one α-kinase (eEF-2 kinase) while none have been identified in the *Drosophila*, yeast and plant genomes. However, the α-kinases appear to be widespread among the protozoa: sequences encoding proteins with a high similarity to the α-kinases are present in the genomes of *Trypanosoma*, *Leishmania*, and *Amoeba*.

We cloned and sequenced five new members of the alpha-kinase family. All of these kinases have a typical alpha-kinase catalytic domain located the very carboxyl-terminus. The alignment of the cloned alpha-kinase catalytic domains reveals eight subdomains characteristic of the alpha-kinases which have no significant homology to the conventional eukaryotic protein kinase catalytic domain. An alignment of the α-kinase catalytic domain revealed several characteristic motifs. These motifs are different from those that characterize the eukaryotic Ser/Thr/Tyr protein kinase superfamily, suggesting that the α-kinases and conventional eukaryotic protein kinases are structurally and evolutionarily unrelated. The expressed catalytic domain of MK is able to efficiently autophosphorylate. Tissue distribution of the new cloned proteins reveals that among the cloned alpha-kinases, MK has a wide tissue distribution, while the others (KK, HK, LK and SK) are specific for particular tissues. SK, which is specific to human skeletal muscle, is remarkably abundant. Phylogenetic analysis suggests that our cloned alpha-kinases are closely related to each other, and are distantly related to eEF-2 kinase and the MHCKs, forming a distinctive subfamily of alpha-kinases. All of the five new alpha-kinases probably evolved from a common ancestor during the evolutionary process. Therefore, the alpha-kinase family has been enlarged and now includes five new members.

Recently the structure of a novel type of protein kinase catalytic domain has been determined represented by the bacterial histidine kinases, EnvZ and CheA (38,39). The structure of the catalytic domain of the histidine kinases appears to be completely different from that of the Ser/Thr/Tyr protein kinase superfamily but utilizes a fold similar to Hsp90, DNA gyrase B, and MutL (Bergerat fold; 40). There are protein kinases that are highly similar to the bacterial histidine kinases, but phosphorylate their substrates on serine residues [for example, plant phytochromes (41) and animal pyruvate dehydrogenase kinase (42)] or on tyrosine residues [DivL (43)], suggesting that protein kinases with the Bergerat fold can phosphorylate amino acids other than histidine. Is it possible that the α-kinases also use a similar fold? We noticed that the distribution of consensus secondary structure elements predicted for the α-kinases using the ALB program is similar to the distribution of secondary structure elements in EnvZ as determined by NMR. Moreover, the conserved asparagine and invariant aspartic acid residues located in subdomains V and VI, respectively, may correspond to the invariant asparagine and aspartic acid residues located in the N and G1 boxes, respectively, of the histidine kinases. These residues play a crucial role in ATP binding (38,39,40). The glycine-rich region in subdomain VIII of the α-kinases may correspond to the G2 box of histidine kinases, which is a highly mobile region that forms part of the "lid" of the ATP binding site (38,39,40). In addition, the histidine residues phosphorylated by histidine kinases are located within α-helices (39,44,45), suggesting that the catalytic domain of these protein kinases is adapted to recognize α-helices. Finally, the overall topology of some α-kinases (MK, KK and LK) with several transmembrane segments in the N-terminal region of the molecule and catalytic domain located at the C-terminal region resemble the topology of many histidine kinases (46). All these facts raise the possibility that the α-kinases and the histidine kinases may be evolutionarily related.

The expressed catalytic domain of MK is able to autophosphorylate, demonstrating that it is a genuine protein kinase. Phosphoamino acid analysis revealed that MK autophosphorylates exclusively on a threonine residue. Interestingly, the only two other α-kinases for which the substrates have been identified, eEF-2 kinase and MHCK A, both phosphorylate their substrates on threonine residues. Therefore, it is possible that the α-kinases in general are specific for phosphothreonine.

Northern analysis reveals that MK and LK have a wide tissue distribution suggesting a general function for these kinases, while KK, HK and SK are expressed primarily within specific tissues, suggesting they have tissue-specific functions. Interestingly, the tissue distribution patterns of MK and LK were virtually identical, suggesting that these two proteins are similarly regulated and may have similar functions.

Remarkably, two of the new members, MK and KK, appeared to have ion channels at the very amino-terminus that are highly homologous to the TRP channel family. TRP channels are Ca2+-permeable channels that are believe to be responsible for Ca2+ influx in response to depletion of internal Ca2+ stores (9–11). Such a depletion of intracellular Ca2+ stores followed by activation of the Ca2+ entry mechanism at the plasma membrane is called capacitative Ca2+ entry (CCE).

CCE is loosely defined as an influx of Ca2+ from the extracellular space following inositol 1,4,5-triphosphate (IP3) or other Ca2+-mobilizing agent-induced depletion of internal Ca2+ from the ER and SR. CCE plays a central role in many aspects of cell signaling, and is present in many types of cells. It is an essential component of the cellular response to many hormones and growth factors. (12, 13). The TRP gene of Drosophila (19, 20) and its homologue, TRP-like (TRPL; 21)together with recently-discovered mammalian homologues (22–25) were suggested to encode the CCE channels (26, 27). The family of known TRPs and their homologues are conserved from worms to humans. All show the same basic channel subunit structure with six putative transmembrane helices, and a range of motifs in the amino- and carboxyl-terminal regions (14).

It was recently suggested that by their functional properties and structure, the TRP channel family can be subdivided into three subfamilies: short TRP (STRP), osmoTRP (OTRP) and long TRP (LTRP) (14). MK and KK display similarity to melastatin, which, by its structure and function, can be classified as an LTRP (14). Melastatin is a putative Ca2+ channel identified recently as a gene specifically downregulated in metastatic melanoma (8). Sequence analysis of the ion channel region of MK and KK reveals a typical structure of LTRPs. The function of STRP including Drosophila TRP and many mammalian homologs is to mediate Ca2+ influx subsequent to activation of phospholipase C. The OTRP subfamily is Ca2+-permeable channels involved in pain transduction, chemo-, mechano- and osmoregulation. The function of the LTRP subfamily channels is not yet well characterized.

Figure 18:
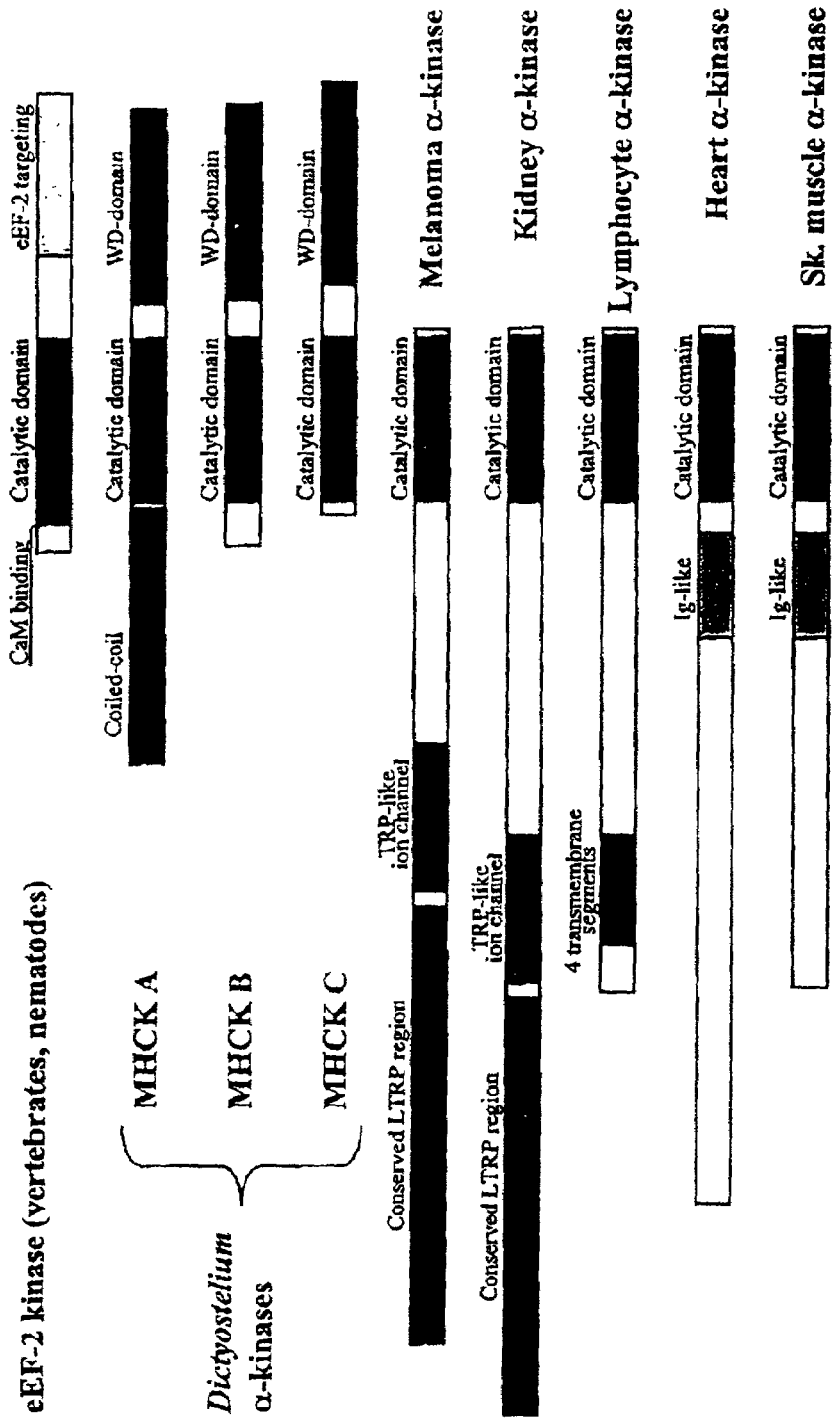
FIG. 18. Schematic representation of five new α-kinases described in this paper together with eEF-2 kinase and the *Dictyostelium* MHCKs.

LTRP channels have longer coding sequences than STRP and OTRP, particularly at their amino-termini. All TRP channels share similar structure: they have six transmembrane segments and a pore-forming loop between the fifth and sixth segments (reviewed in 24,9,14,47). The same conserved sequences are present in MK and KK (FIG. 4). The Pro—Pro—Pro motif that follows the sixth transmembrane segment in MK and KK is characteristic for STRP and LTRP channels. LTRPs do not have the ankyrin repeats characteristic of the STRPs and OTRPs (14). Instead, they have a long N-terminus with a unique and highly-conserved sequence. As can be seen in FIG. 17, the long N-terminal portion of MK and KK also has this highly conserved sequence. This region in MK and KK is predicted to form several long α-helices. In addition to MK and KK, we identified eight other LTRP channels among the sequences deposited in GenBank: four in mammals, three in C. elegans, and one in Drosophila. The first LTRP to be identified was melastatin, a putative $Ca^{2+}$ channel whose mRNA is specifically downregulated in metastatic melanoma (7,8). MK and KK are particularly similar to melastatin (more than 48% and 51% identity) suggesting that MK and KK may be a product of a recent evolutionary event—a fusion between the α-kinase catalytic domain and a melastatin-like ion channel. Thus, considering the striking similarity of MK and KK to LTRP channels, we suggest that MK and KK are ion channels with a unique molecular structure—ion channels covalently linked to a protein kinase. FIG. 18 and FIG. 19 show a schematic representation of the major domains of MK, KK as well as other α-kinases, a phylogenetic tree of LTRP channels, and a proposed structural model of MK and KK. Thus, MK and KK, having ion channel part with the typical structure of LTRPs, can be considered a new member of the LTRP family. To date, MK and KK are the only known channels covalently linked to a protein kinase catalytic domain.

It is possible that the other three α-kinases may also have regions homologous to ion channels. LK has four predicted transmembrane segments near its N-terminus, although this region is not similar to the TRP channels. We did not find sequences homologous to ion channels at the N-termini of HK and SK, however, it is likely that we did not obtain the very N-terminal regions of these proteins. TRP channels are Ca2+-permeable channels believed to be responsible for Ca2+ influx in response to depletion of internal Ca2+ stores (9–12,18,24,27,32,34). The TRP gene of Drosophila (19,31) together with recently-discovered mammalian homologues (27,32,33) were suggested to encode store-operated $Ca^{2+}$ channels, also known as capacitative $Ca^{2+}$ entry channels (9,10,12,18,24,27,31,32,34).

The first of the $Ca^{2+}$-permeable store-operated channels to be characterized in detail were those mediating $Ca^{2+}$-release-activated current ($I_{CRAC}$) (16,48,51). CRAC channels are highly $Ca^{2+}$ selective, low conductance channels that mediate $Ca^{2+}$ entry in response to depletion of $Ca^{2+}$ from intracellular stores in various non-excitable cells, and play a central role in activation of lymphocytes, degranulation of mast cells, and possibly mitogenic stimulation of various cells (16,48,51,54,55). The molecular identity of CRAC channels has not yet been determined. It has been suggested that members of the TRP channel family may underlie $I_{CRAC}$ (9,10,12,18,24,27,32,34,55). However, none of the TRP channels studied to date have all the properties of CRAC channels (14). Nevertheless, TRP proteins are currently the most likely candidates for CRAC channels, and it has been suggested that the CRAC channels may be hidden in the LTRP family whose function is largely unknown (14).

It is possible that MK and KK are indeed the "hidden" members of the LTRP channel family mediating $I_{CRAC}$. The tissue distribution of MK (which is ubiquitously expressed in all tissues tested, and predominant in non-excitable tissues such as liver and lymphocytes) is consistent with this idea. Moreover, the protein kinase domain can be part of the signaling mechanism that modulates channel function. There is evidence that protein phosphorylation is involved in both the activation of the store-operated $Ca^{2+}$ channels as well as in the regulation of channel closure (54,56–59).

The conserved location of the transmembrane domain and catalytic domains linked together reveals a new structure for a novel type of protein. What is the role of such an unusual protein structure? There are a number of reports indicating a role for protein phosphorylation in CCE. There are indications that protein phosphatases may regulate the responsiveness of the entry channel to hypothetical diffusible component of the entry, implying that the latter may act by promoting channel phosphorylation (34). It has been proposed that the endoplasmic reticulum might possess protein kinases or phosphatases capable of altering the phosphorylation state of the entry channel (12). Phosphatase inhibitors will enhance Ca2+ entry by serine/threonine phosphorylation (52). Tyrosine phosphorylation has been implicated in coupling store depletion of Ca2+ entry, but there are inconsistencies in overall information and a possible explanation is that separate kinases phosphorylate different components of the entry mechanism. Different kinases may be involved in the process of CCE, one of the consistent implications is that protein kinases possibly phosphorylate the IP3 receptor, but the CRAC channel is the likely target for protein phosphorylation (12). It was also shown that phosphatase inhibitors can inhibit ICRAC. The tissue distribution of MK is consistent with its being a CRAC since it is present in all tissues and is most prominent in non-excitable, while barely detectable in the brain. We suggest that we discovered a new type of molecule—a protein kinase covalently linked to an ion channel—represents a new signaling molecule which underlies CRAC channels. The placement of a kinase and channel on a single molecule is particularly interesting and suggests a self-regulated molecule, whereby the phosphorylation/autophosphorylation of these unique alpha kinases controls or contributes to the open or closed state of the channel. In addition, such an unusual molecular structure may be a part of a signal transduction mechanism that links depletion of internal Ca2+ stores to channel opening.

In summary, our discovery of five new members has broadened the class of α-kinases. Two of the new α-kinases represent a novel type of signaling molecule—a TRP-like ion channel covalently linked to a protein kinase suggesting that one of the functions of the α-kinases is to regulate $Ca^{2+}$ influx in mammalian cells. It is also possible that MK and KK are CRAC channels and play a central role in the immune response.

REFERENCES

1. Hanks, S. K, & Hunter, T., (1995) FASEB J., 9, 576–596.
2. Côté, G. P., Luo, X., Murphy, M. B., and Egelhoff, T. T. (1997) J. Biol. Chem. 272, 6846–6849.
3. Futey, L. M., Medley, Q G., Côté, G. P., and Egelhoff, T. T. (1995) J. Biol. Chem. 270, 523–529.
4. Redpath, N. T., Price, N. T., and Proud, C. G. (1996) J. Biol. Chem. 271, 17547–17554.
5. Ryazanov, A. G. et al. (1997) Proc. Natl. Acad. Sci. USA 94, 4884–4889.
6. Ryazanov, A. G., Pavur, K. S., and Dorovkov, M. V. (1999) Curr. Biol. 9, R43-R45.
7. Duncan, L. M., Deeds, J., Hunter, J., Shao, J., Holmgren, L. M., Woolf, E. A., Tepper, R. I., & Shyjan, A. W. (1998) Cancer Res. 58, 1515–1520.
8. Hunter, J. J., Shao, J., Smutko, J. S., Dussault, B. J., Nagle, D. L., Woolf, E. A., Holmgren, L. M., Moore, K. J., &Shyjan, A. W. (1998) Genomics 54, 116–123.
9. Putney, J. W., Jr., & McKay, R. R. (1999) Bioessays 21, 38–46.
10. Hardie, R. C. (1996) Curr. Biol. 6,1371–1373.
11. Friel, D. D. (1996) Cell 85, 617–619.
12. Berridge, M. J. (1995) Biochem. J. 312, 1–11.
13. Putney, J. W., Jr. (1990) Cell Calcium 11, 611–624.
14. Harteneck, C., Plant, T. D., & Schultz, G. (2000) Trends Neurosci. 23,159–163.
15. Putney, J. W., Jr. (2000) Calcium Signaling (CRC Press, New York, N.Y.).
16. Hoth, M., & Penner, R. (1993) J. Physiol. 465, 359–386.
17. Garcia R L, Schilling W P. Biochem Biophys Res Commun. 1997 October 9;239(1):279–83.
18. Parekh A B, Penner R. Store depletion and calcium influx. Physiol Rev. 1997 October;77(4):901–30.
19. Montell C, Rubin G M. Molecular characterization of the Drosophila trp locus: a putative integral membrane protein required for phototransduction. Neuron. 1989 April; 2(4):1313–23.
20. Wong F, Schaefer E L, Roop B C, LaMendola J N, Johnson-Seaton D, Shao D. Proper function of the Drosophila trp gene product during pupal development is important for normal visualtransduction in the adult. Neuron. 1989 Jul;3(1):81–94.
21. Phillips A M, Bull A, Kelly L E. Identification of a Drosophila gene encoding a calmodulin-binding protein with homology to the trp phototransductiongene. Neuron. 1992 Apr;8(4):631–42.
22. Philipp S, Cavalie A, Freichel M, Wissenbach U, Zimmer S, Trost C, Marquart A, MurakamiM, Flockerzi V. A mammalian capacitative calcium entry channel homologous to Drosophila TRP and TRPL. EMBO J. 1996 Nov. 15;15(22):6166–71.
23. Zitt C, Zobel A, Obukhov A G, Harteneck C, Kalkbrenner F, Luckhoff A, Schultz G. Cloning and functional expression of a human Ca2+-permeable cation channel activated by calcium store depletion. Neuron. 1996 June; 16(6):1189–96.
24. Bimbaumer L, Zhu X, Jiang M, Boulay G, Peyton M, Vannier B, Brown D, Platano D, Sadeghi H, Stefani E, Bimbaumer M. On the molecular basis and regulation of cellular capacitative calcium entry: roles for Trp proteins. Proc Natl Acad Sci USA. 1996 Dec. 24;93(26):15195–202.
25. Sinkins, W. G. & Schilling, W. P. (1997) Biophys. J. 72, A271.
26. Hardie R C, Minke B. Novel Ca2+ channels underlying transduction in Drosophila photoreceptors: implications forphosphoinositide-mediated Ca2+ mobilization. Trends Neurosci. 1993 Sep;16(9):371–6.
27. Zhu X, Jiang M, Peyton M, Boulay G, Hurst R, Stefani E, Bimbaumer L. trp, a novel mammalian gene family essential for agonist-activated capacitative Ca2+ entry. Cell. 1996 May 31;85(5):661–71.

28. Hoth M, Penner R. Depletion of intracellular calcium stores activates a calcium current in mast cells. Nature. 1992 Jan 23;355(6358):353–6.
29. Clancy, C. E., Mendoza, M. G., Naismith, T. V., Kolman, M. F., and Egelhoff, T. T. Identification of a protein kinase from *Dictoyostelium* with homology to the novel ctalytic domain of myosin heavy chain kinase A. (1997) J. Biol. Chem. 272, 11812–11815.
30. Cosens, D. J., and Manning, A. (1969) Abnormal electroretinogram from a *Drosophila* mutant. Nature 224, 285–287.
31. Hardie, R. C., and Minke, B. (1992) The trp gene is essential for a light-activated $Ca^{2+}$ channel in *Drosophila* photoreceptors. Neuron 8, 643–651.
32. Wes, P. D., Chevesich, J., Jeromin, A., Rosenberg, C., Stetten, G., and Montell, C. (1995) TRPC1, a human homolog of a *Drosophila* store-operated channel. Proc. Natl. Acad. Sci. USA 92, 9652–9656.
33. Zhu, X., Chu, P. B., Peyton, M., and Birnbaumer, L. (1995) Molecular cloning of a widely expressed human homologue for the *Drosophila* trp gene. FEBS Lett. 373, 193–198.
34. Barritt, G. J. (1999) Receptor-activated $Ca^{2+}$ inflow in animal cells: a variety of pathways tailored to meet different intracellular $Ca^{2+}$ signalling requirements. Biochem. J 337, 153–169.
35. Ptitsyn, O. B., and Finkelstein, A. V. (1983) Theory of protein secondary structure and algorithm of its prediction. Biopolymers 22, 15–25.
36. Nagamine, K., Kudoh, J., Minoshima, S., Kawasaki, K., Asakawa, S., Ito, F., and Shimizu, N. (1998) Molecular cloning of a novel putative $Ca^{2+}$ channel protein (TRPC7) highly expressed in brain. Genomics 54, 124–131.
37. Prawitt, D., Enklaar, T., Klemm, G., Gartner, B., Spangenberg, C., Winterpacht, A., Higgins, M., Pelletier, J., and Zabel, B. (2000) Identification and characterization of MTR1, a novel gene with homology to melastatin (MLSN1) and the trp gene family located in the BWS-WT2 critical region on chromosome 11p15.5 and showing allele-specific expression. Hum. Mol. Gen. 9, 203–216.
38. Tanaka, T., et al. (1998) NMR structure of the histidine kinase domain of the *E. coli* osmosensor EnvZ. Nature 396, 88–92.
39. Bilwes, A. M., Alex, L. A., Crane, B. R., and Simon, M. I. (1999) Structure of CheA, a signal-transducing histidine kinase. Cell 96, 131–141.
40. Dutta, R., and Inouye, M. (2000) GHKL, an emergent ATPase/kinase superfamily. Trends Biochem. Sci. 25, 24–28.
41. Yeh, K. C., and Lagarias, J. C. (1998) Eukaryotic phytochromes: light-regulated serine/threonine protein kinases with histidine kinase ancestry. Proc. Natl. Acad. Sci. USA 95, 13976–13981.
42. Bowker-Kinley, M., and Popov, K. M. (1999) Evidence that pyruvate dehydrogenase kinase belongs to the ATPase/kinase superfamily. Biochem. J 344, 47–53.
43. Wu, J., Ohta, N., Zhao, J. L., and Newton, A. (1999) A novel bacterial tyrosine kinase essential for cell division and differentiation. Proc. Natl. Acad. Sci. USA 96, 13068–13073.
44. Zhou, H., Lowry, D. F., Swanson, R. V., Simon, M. I., and Dahlquist, F. W. (1995) NMR studies of the phosphotransfer domain of the histidine kinase CheA from *Escherichia coli*: assignments, secondary structure, general fold, and backbone dynamics. Biochemistry 34, 13858–13870.
45. Tomomori, C., et al. (1999) Solution structure of the homodimeric core domain of *Escherichia coli* histidine kinase EnvZ. Nat. Struct. Biol. 6, 729–734.
46. Hoch, J. A., and Silhavy, T. J., eds., (1995) Two-component signal transduction (Washington, D.C.: ASM Press).
47. Philipp, S., Wissenbach, U., and Flockerzi, V. (2000) Molecular Biology of Calcium Channels. In *Calcium Signaling*, ed. Putney, J. W., Jr. (CRC Press, New York, N.Y.), pp. 321–342.
48. Zweifach A, Lewis R S. Mitogen-regulated Ca2+ current of T lymphocytes is activated by depletion of intracellular Ca2+ stores. Proc Natl Acad Sci USA. 1993 Jul. 1;90 (13):6295–9.
49. McDonald TV, Premack B A, Gardner P. Flash photolysis of caged inositol 1,4,5-trisphosphate activates plasma membrane calcium current in human T cells. J Biol Chem. 1993 Feb. 25;268(6):3889–96.
50. Fasolato C, Hoth M, Penner R. A GTP-dependent step in the activation mechanism of capacitative calcium influx. J Biol Chem. 1993 Oct. 5;268(28):20737–40.
51. Hoth M, Penner R. Calcium release-activated calcium current in rat mast cells. J Physiol (Lond). 1993 June; 465:359–86.
52. Medley, Q. G., Gariepy, J., Côté, G. P. *Dictyostelium* myosin II heavy-chain kinase A is activated by autophosphorylation: studies with *Dictyostelium* myosin II and synthetic peptides. (1990) Biochem. 29, 8992–8997.
53. Kolman, M. F., and Egelhoff, T. T. *Dictoyostelium* myosin heavy chain kinse A subdomains. Coiled-coil and wd repeat roles in oligomerization and substrate targeting. (1997) J. Biol. Chem. 272, 16904–16910.
54. Parekh, A. B., and Penner, R. (1995) Depletion-activated calcium current is inhibited by protein kinase in RBL-2H3 cells. Proc. Natl. Acad. Sci. USA 92, 7907–7911.
55. Lewis, R. S. (1999) Store-operated Calcium Channels. In *Advances in Second Messenger and Phosphoprotein Research*, eds. Armstrong, A. L., and Rossie, S. (Academic Press, New York, N.Y.), pp. 279–307.
56. Parekh, A. B., Terlau, H., and Stuhmer, W. (1993) Depletion of InsP3 stores activates a $Ca^{2+}$ and $K^+$ current by means of a phosphatase and a diffusible messenger. Nature 364, 814–818.
57. Koike, Y., Ozaki, Y., Qi, R., Satoh, L., Kurota, K., Yatomi, Y., and Kume, S. (1994) Phosphatase inhibitors suppress $Ca^{2+}$ influx induced by receptor-mediated intracellular $Ca^{2+}$ store depletion in human platelets. Cell Calcium 15, 381–390.
58. Thomas, D., and Hanley, M. R. (1995) Evaluation of calcium influx factors from stimulated Jurkat T-lymphocytes by microinjection into *Xenopus* oocytes. J. Biol. Chem. 270, 6429–6432.
59. Hahn, J., Jung, W., Kim, N., Ulhm, D. Y., and Chung, S. (2000) Characterization and regulation of rat microglial $Ca^{2+}$ release-activated $Ca^{2+}$ (CRAC) channel by protein kinases. Glia 31, 118–124.

This invention may be embodied in other forms or carried out in other ways without departing from the spirit or essential characteristics thereof. The present disclosure is therefore to be considered as in all aspects illustrate and not restrictive, the scope of the invention being indicated by the appended claims, and all changes which come within the meaning and range of equivalency are intended to be embraced therein.

Various references are cited throughout this Specification, each of which is incorporated herein by reference in its entirety.

What is claimed is:

1. An isolated nucleic acid encoding a mammalian alpha kinase expressed in the heart and having alpha kinase activity, wherein the nucleic acid is selected from the group consisting of:
   a. the DNA sequence of SEQ ID NO: 34; and
   b. DNA sequences capable of encoding the amino acid sequence encoded by the DNA sequences of subpart (a).

2. An isolated nucleic acid encoding human alpha kinase, expressed in the heart and having alpha kinase activity, wherein the nucleic acid comprises the DNA sequence of SEQ ID NO: 34.

3. A recombinant DNA expression vector comprising the nucleic acid of claim 1, wherein the DNA encoding the alpha kinase is operatively associated with an expression control sequence.

4. An isolated transformed host cell transfected with the DNA vector of claim 3.

5. A unicellular host transformed with a recombinant DNA molecule comprising a DNA sequence which encodes a mammalian alpha kinase selected from the group consisting of:
   a. the DNA sequence of SEQ ID NO: 34;
   b. DNA sequences that encoding the amino acid sequence encoded by the DNA sequence of subpart(a)and
   c. a fragment of SEQ ID NO: 34 wherein said fragment has alpha kinase activity;
   wherein said DNA sequence is operatively linked to an expression control sequence.

6. The unicellular host of claim 5 wherein the unicellular host is selected from the group consisting of *E. coli, Pseudomonas, Bacillus, Streptomyces*, yeasts, CHO, R1.1, B-W, L-M, COS 1, COS 7, BSC1, BSC40, and BMT10 cells, plant cells, insect cells, mouse cells and human cells in tissue culture.

7. An isolated nucleic acid encoding a mammalian alpha kinase comprising the amino acid sequence set out in SEQ ID NO: 35, expressed in the heart and having alpha kinase activity.

* * * * *